US011352666B2

(12) United States Patent
Kim et al.

(10) Patent No.: US 11,352,666 B2
(45) Date of Patent: Jun. 7, 2022

(54) METHOD FOR DETECTING OFF-TARGET SITES OF PROGRAMMABLE NUCLEASES IN A GENOME

(71) Applicant: INSTITUTE FOR BASIC SCIENCE, Daejeon (KR)

(72) Inventors: Jin Soo Kim, Seoul (KR); Dae Sik Kim, Incheon (KR); Sang Su Bae, Seoul (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 465 days.

(21) Appl. No.: 15/526,528

(22) PCT Filed: Nov. 13, 2015

(86) PCT No.: PCT/KR2015/012255
§ 371 (c)(1),
(2) Date: May 12, 2017

(87) PCT Pub. No.: WO2016/076672
PCT Pub. Date: May 19, 2016

(65) Prior Publication Data
US 2019/0153530 A1 May 23, 2019

Related U.S. Application Data

(60) Provisional application No. 62/079,945, filed on Nov. 14, 2014.

(30) Foreign Application Priority Data

Sep. 24, 2015 (KR) .......................... 10-2015-0135702

(51) Int. Cl.
| C12Q 1/6874 | (2018.01) |
| C12N 9/22 | (2006.01) |
| C12Q 1/686 | (2018.01) |
| C12Q 1/6806 | (2018.01) |
| G16B 30/00 | (2019.01) |
| G16B 30/10 | (2019.01) |

(52) U.S. Cl.
CPC ............ *C12Q 1/6874* (2013.01); *C12N 9/22* (2013.01); *C12Q 1/686* (2013.01); *C12Q 1/6806* (2013.01); *G16B 30/00* (2019.02); *G16B 30/10* (2019.02)

(58) Field of Classification Search
None
See application file for complete search history.

(56) References Cited

U.S. PATENT DOCUMENTS

| 6,479,626 B1 | 11/2002 | Kim |
| 6,903,185 B2 | 6/2005 | Kim |
| 7,153,949 B2 | 12/2006 | Kim |

| 2005/0064474 A1 | 3/2005 | Urnov |
| 2006/0188987 A1 | 8/2006 | Guschi |
| 2013/0217131 A1 | 8/2013 | Kim |
| 2014/0295556 A1 | 10/2014 | Joung et al. |
| 2015/0132821 A1 | 5/2015 | Fine et al. |

FOREIGN PATENT DOCUMENTS

| CN | 103492578 | 1/2014 |
| KR | 10-1656237 | 9/2016 |
| WO | 2012/093833 | 7/2012 |
| WO | 2013/169398 | 11/2013 |
| WO | 2014/065596 | 5/2014 |

OTHER PUBLICATIONS

S. W. Cho et al, "Analysis of off-target effects of CRISPR/ Cas-derived RNA-guided endonucleases and nickases", Genome Research, vol. 24, No. 1, Nov. 19, 2013, pp. 132-141.
Viviana Cobos Jimenez et al, "Next-generation sequencing of microRNAs in primary human polarized macrophages", Genomics Data, vol. 2, Jun. 27, 2014, pp. 181-183.
Seung Woo Cho et al., "Targeted genome engineering in human cells with the Cas9 RNA-guided endonuclease", Nature Biotechnology Mar. 2013, vol. 31, No. 3, p. 230-232.
Hye Joo Kim et al., "Targeted genome editing in human cells with zinc finger nucleases constructed via modular assembly", Genome Res (2009), vol. 19, p. 1279-1288.
Thomas J. Cradick et al., "CRISPR/Cas9 systems targeting b-globin and CCR5 genes have substantial off-target activity", Nucleic acids research, Published online Aug. 11, 2013, 41 (20): 9584-9592.
Erika Brunet et al., "Chromosomal translocations induced at specified loci in human stem cells", Proc Natl Acad Sci, Jun. 30, 2009, 106: 10620-10625.
Raymond J. Monnat, Jr. et al., "Generation of Highly Site-Specific DNA Double-Strand Breaks in Human Cells by the Homing Endonucleases I-PpoI and I-CreI", Feb. 5, 1999, Biochem. Biophysics Res. Common., 255: 88-93.
Roger R. Beerli et al., "Engineering polydactyl zinc-finger transcription factors", Feb. 2002, Nature Biotechnol., 20: 135-141.
Carl O. Pabo et al., "Design and Selection of Novel Cys2His2 Zinc Finger Proteins", Jul. 2001, Ann. Rev. Biochem., 70: 313-340.
Mark Isalan., "A rapid, generally applicable method to engineer zinc fingers illustrated by targeting the HIV-1 promoter", Jul. 2001, Nature Biotechnol., 19: 656-660.

(Continued)

*Primary Examiner* — Joseph Woitach
(74) *Attorney, Agent, or Firm* — Lex IP Meister, PLLC

(57) ABSTRACT

The present disclosure relates to a method for detecting off-target sites of a programmable nuclease in a genome, and specifically, to a method for detecting off-target sites through data analysis by subjecting the genome isolated in vitro to programmable nucleases to cleave the genome and then performing whole genome sequencing or deep sequencing, and to a method for selecting on-target sites of a programmable nuclease, which minimizes the off-target effect, using this method. The Digenome-seq of the present disclosure can detect the off-target sites of a programmable nuclease on the genomic scale at a high degree of reproducibility, and thus can be used in the manufacture of programmable nucleases having high target specificity and the study thereof.

19 Claims, 55 Drawing Sheets

Specification includes a Sequence Listing.

(56) References Cited

OTHER PUBLICATIONS

David J Segal et al., "Custom DNA-binding proteins come of age: polydactyl zinc-finger proteins", Dec. 1, 2001, Curr. Opin. Biotechnol., 12: 632-637.
Yen Choo et al., "Advances in zinc finger engineering", Aug. 1, 2000, Curr. Opin. Struct. Biol., 10: 411-416.
Bernd Zetsche et al., "Cpf1 is a single RNA-guided endonuclease of a Class 2 CRISPR-Cas system", Cell, Oct. 22, 2015, 163 (3): 759-71.
D. Kim et al., "Digenome-Seq: Genome-Wide Profiling of CRISPR-Cas9 Off-Target Effects in Human Cells", Nature Methods, vol. 12, No. 3, Mar. 2015, pp. 237-243, XP055287797.
C. Kuscu et al., "Genome-Wide Analysis Reveals Characteristics of Off-Target Sites Bound by the Cas9 Endonuclease", Nature Biotechnology, vol. 32, No. 7, Jul. 2014, pp. 677-683, XP055382577.
V. Pattanayak et al., "High-Throughput Profiling of Off-Target DNA Cleavage Reveals RNA-Programmed Cas9 Nuclease Specificity", Nature Biotechnology, vol. 31, No. 9, 2013, pp. 839-843, XP055294934.
B. Shen et al., "Efficient Genome Modification by CRISPR-Cas9 Nickase with Minimal Off-Target Effects", Nature Methods, vol. 11, No. 4, Apr. 2014, pp. 399-402, XP055227888.
Sangsu Bae et al., "Cas-OFFinder: a fast and versatile algorithm that searches for potential off-target sites of Cas9 RNA-guided endonucleases", Bioinformatics, vol. 30 No. 10, Jan. 24, 2014, pp. 1473-1475. doi:10.1093/bioinformatics/btu048.
Yanni Lin et al., "CRISPR/Cas9 systems have off-target activity with insertions or deletions between target DNA and guide RNA sequences", Nucleic Acids Research, May 16, 2014, vol. 42, No. 11, pp. 7473-7485. doi: 10.1093/nar/gku402.
SIPO, Search Report of CN CN 201580067606.X dated Apr. 21, 2020 (English translation only).
SIPO, Office Action of CN 201580067606.X, dated Apr. 24, 2020 (translation from the Chinese Patent Office).

Indel frequencies (%)

Indel frequencies (%)

Fig. 4b
OT1
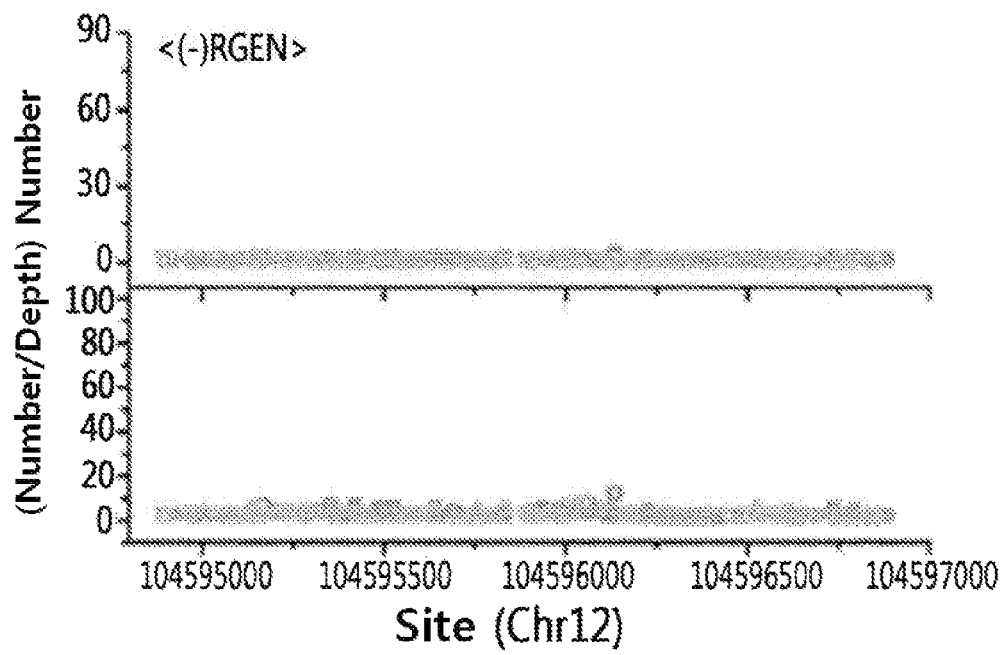
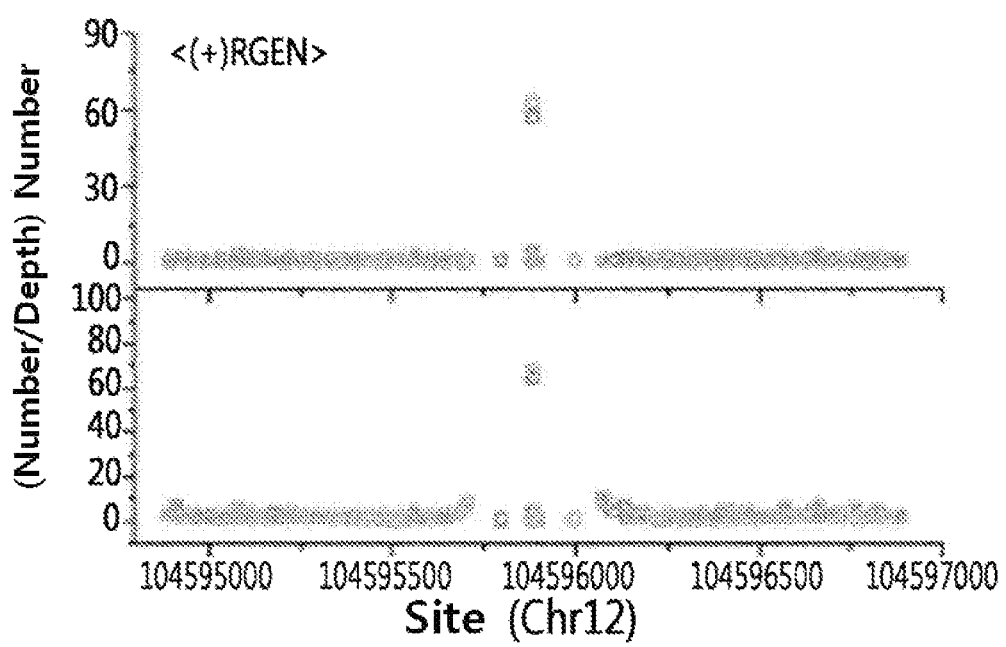

Fig. 4c
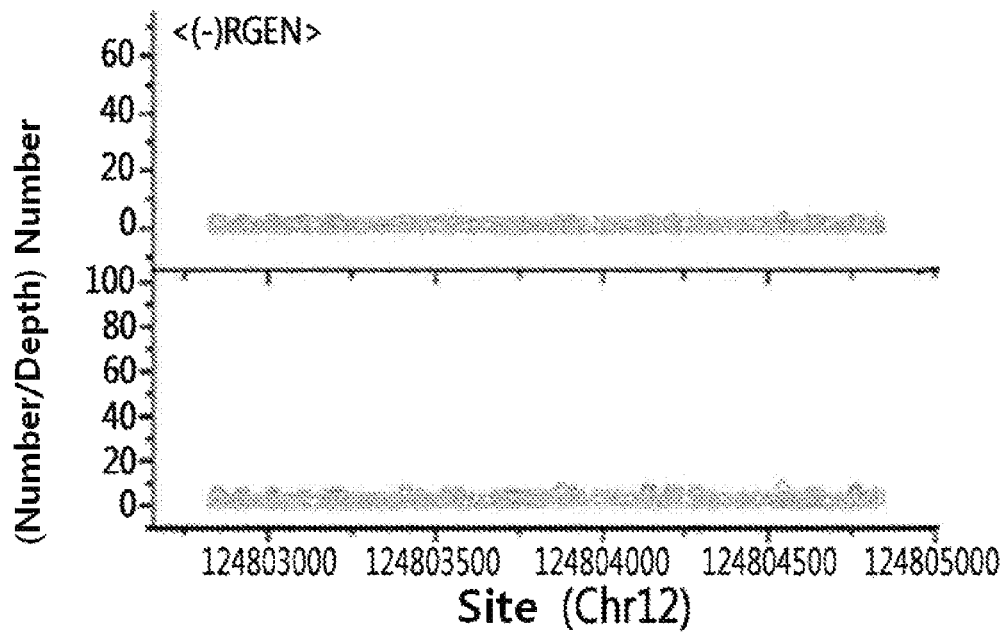
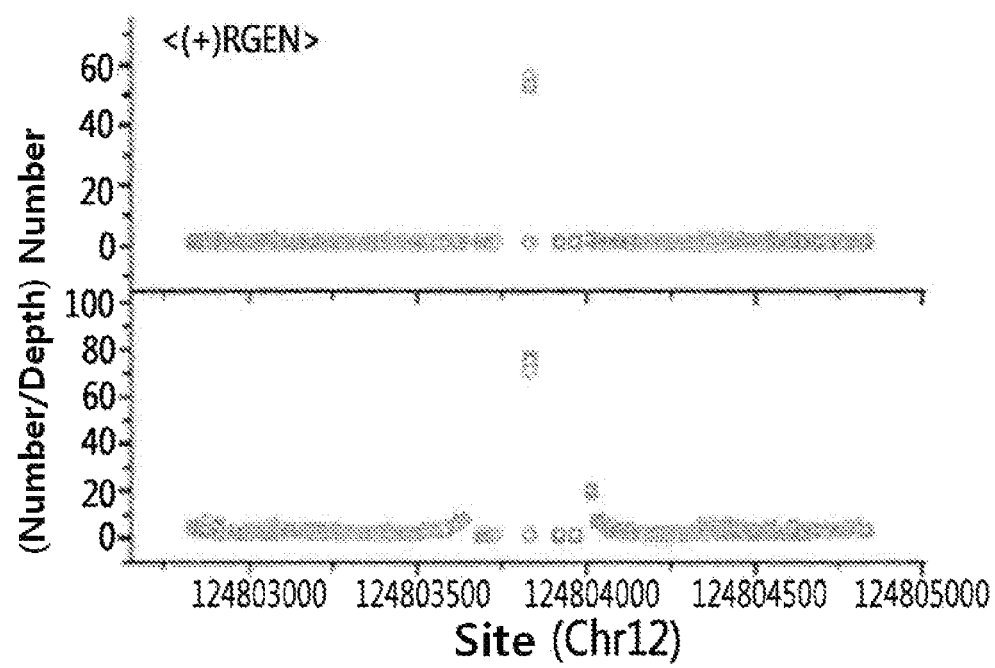

| Total | | Site detected by Digenome | | Site not-detected by Digenome | |
|---|---|---|---|---|---|
| Number of mismatch | Number of sites | Total number | Validated number of sites | Total number | Validated number of sites |
| 0 | 1 | 1 | 1 | 0 | 0 |
| 1 | 0 | 0 | 0 | 0 | 0 |
| 2 | 0 | 0 | 0 | 0 | 0 |
| 3 | 15 | 7 | 4 | 8 | 0 |
| 4 | 142 | 14 | 0 | 128 | N.D. |
| 5 | 1,191 | 15 | 0 | 1,176 | N.D. |
| 6 | 7,896 | 1 | 0 | 7,895 | N.D. |

Fig. 6
a Non-transformed HAP1
(chr17:20,082,220-20,082,620)
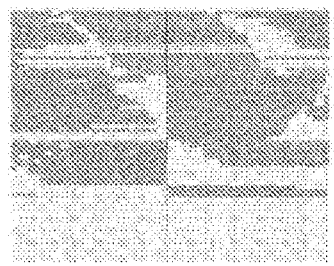
▲
10-bp insertion
hg19 : TGGCT----------AATAA
HAP1 : TGGCTTAGGAAGAAAAATAA
b RGEN-transformed HAP1
(chr15:86,453,445-86,453,845)
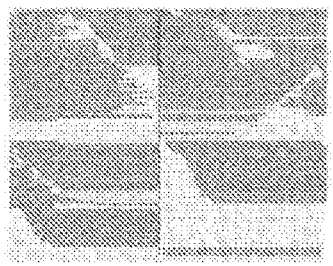
▲
32-bp insertion
hg19 : AGT--------------------------------TCT
HAP1 : AGTACTGCTCAGCATTACGTGGAGGAACAGCTGAATCT
c Cas9 only treated HAP1
(chr17:21,251,293-21,251,493)
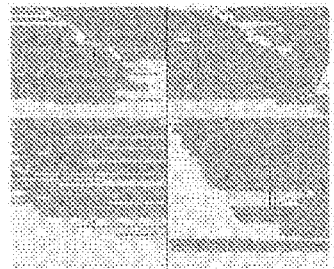
▲
10-bp insertion
hg19 : AGCAC----------AATAA
HAP1 : AGCACTGTAAAGAAAAATAA

Fig. 7 a  *HBB_48*
```
GCTATTGCCCCACGGGGCAG-TGACGGTAC    WT
GCTATTGCCCCACGGGGCAG------GGTAC   -4
GCTATTG-------------------ACGGTAC -15
GCTATTGCCCCACGG------------TAC    -11
GCTATTGCCCCACGGGGCAGTTGACGGTAC    +1
GCTATTGCCCCACGGGGCAGATGACGGTAC    +1
``` b  *HBB_75*
```
GTTGTGGCCCCACAGGGCAG-GAATGGCAGCG   WT
GTTGTGGCCCCACAGGGCAG-----------CG  -9
GTTGTGGCCCCACAGGGCAGGGAATGGCAGCG   +1
GTTGTGGCCCCACAGGGCAG--AATGGCAGCG   -1
GTTGTGGC----------------------AGCG -19
GTTGTGG-----------------AATGGCAGCG -14
```

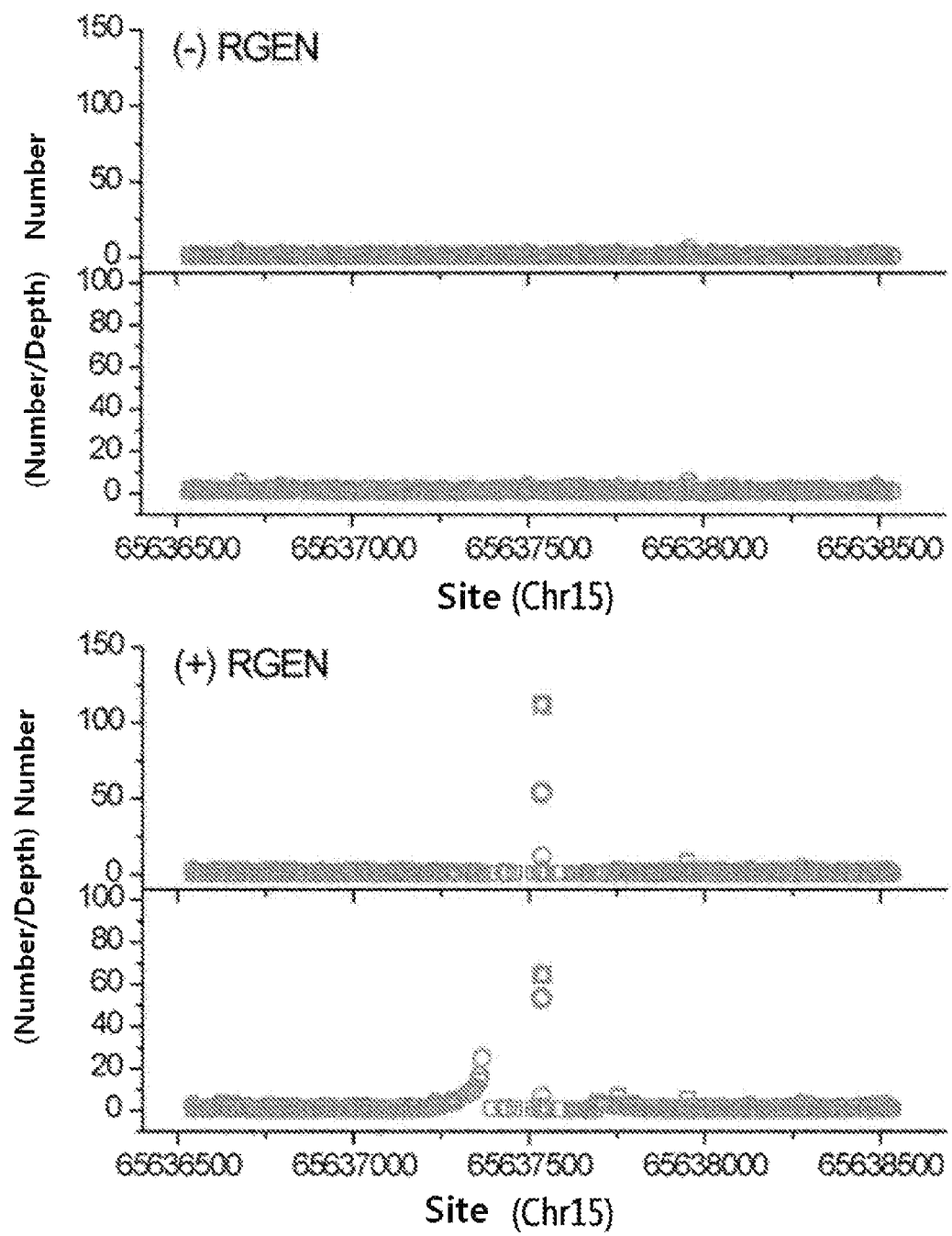

Fig. 8d

| Total | | Site detected by Digenome | | Site not-detected by Digenome | |
|---|---|---|---|---|---|
| Number of mismatch | Number of sites | Total number | Validated number of sites | Total number | Validated number of sites |
| 0 | 1 | 1 | 1 | 0 | 0 |
| 1 | 1 | 1 | 1 | 0 | 0 |
| 2 | 4 | 3 | 3 | 1 | 0 |
| 3 | 32 | 5 | 2 | 27 | 0 |
| 4 | 283 | 12 | 1 | 271 | N.D. |
| 5 | 2,176 | 7 | 0 | 2,169 | N.D. |
| 6 | 13,892 | 6 | 1 | 13,886 | N.D. |

Fig. 9c
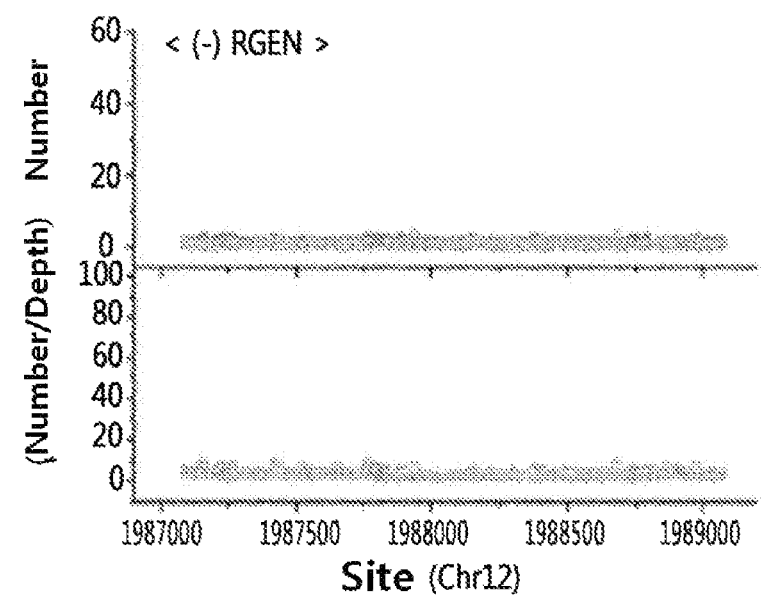
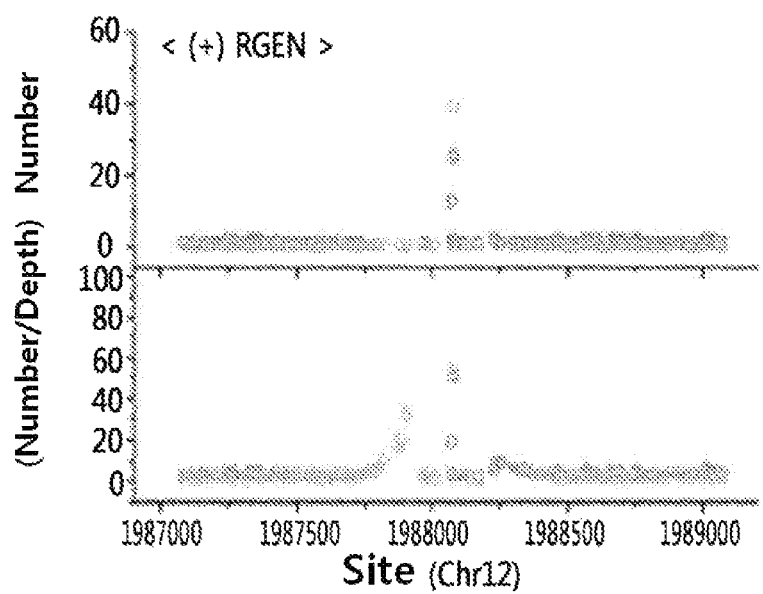

Fig. 10 a *VEGF-A* 26

```
TATGCGTGGGGGGTGTTTGC-TCCCGGGCA        WT
AG----------(-37bp)----------GT       -37
TATGCGTGGG---(-29bp)---------AG       -29
TATGCGTGGGGGGTGTTTGCTTCCCGGGCA        +1
TATGCGTCCCGGG----------------CA       -14
TATGCGTGGGGGGTGTTTGC----------A       -8
``` b *VEGF-A* 76

```
CAGCCAGGA-GCAAGCTCCCTCCACTAAAC        WT
CAGCCAGGAGGCAAGCTCCCTCCACTAAAC        +1
--------------AAGCTCCCTCCACTAAAC      -11
CA----------(-25bp)------CTAAAC       -25
CAGC-------------TCCCTCCACTAAAC       -11
CAGC----------AAGCTCCCTCCACTAAAC      -7
``` c *VEGF-A* 35

```
CTGCCTGGA-GCAAGCTTCCCCCCGGGCCC        WT
CTGCCTGGAAGCAAGCTTCCCCCCGGGCCC        +1
CTGCCTGGAGGCAAGCTTCCCCCCGGGCCC        +1
CTGCCTGA--GCAAGCTTCCCCCCGGGCCC        -1
------------GAATTCCCCCCGGGCCC         -15, +3
``` d *VEGF-A* 84

```
CGGTGGGTGGGGGAGTTTGCCCCAGGCCA         WT
AC-----------(-42bp)----------GA      -42
CGGTGGGTGGGG----------------GA        -33
AG-----------(-36bp)--------GCCA      -36
CGGTGGGTGGGGGAGTTTGCC--------A        -7
CGGTGGGTG-------------------CC        -23
```

Fig. 11

Score at the $i$ site =

$$\sum_{a=1}^{5}\frac{C(F_i-1)}{D_i}\gamma\frac{C(R_{i-4+a}-1)}{D_{i-4+a}}\times(F_i+R_{i-4+a}-2)$$

$$+\sum_{a=1}^{5}\frac{C(R_{i-1}-1)}{D_{i-1}}\gamma\frac{C(F_{i-3+a}-1)}{D_{i-3+a}}\times(R_{i-1}+F_{i-3+a}-2)$$

$F_i$ : Number of forward sequence reads starting at the $i$ site
$R_i$ : Number of reverse sequence reads starting at the $i$ site
$D_i$ : Sequencing depth at the $i$ site Example: 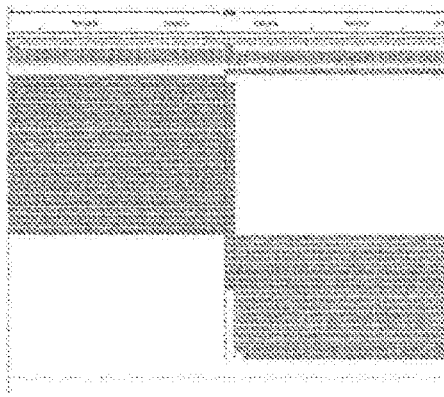

| | | 75006253 | 75006254 | 75006255 | 75006256 | 75006257 | 75006258 | 75006259 |
|---|---|---|---|---|---|---|---|---|
| Number | Reverse | 0 | 0 | 1 | 22 | 0 | 0 | 0 |
| | Forward | 0 | 0 | 0 | 9 | 9 | 1 | 0 |
| Depth | | 23 | 23 | 23 | 31 | 18 | 19 | 19 |

Score at 75006256 site

= 10000 * (22-1)/31 * [(0-1)/23 * (22+0-2) + (9-1)/31 * (22+9-2) + (9-1)/18 * (22+9-2) + (1-1)/19 * (22+1-2) + (0-1)/19 * (22+0-2)]

+ 10000 * (9-1)/18 * [(0-1)/23 * (9+0-2) + (1-1)/23 * (9+1-2) + (22-1)/31 * (9+22-2) + (0-1)/18 * (9+0-2) + (0-1)/19 * (9+0-2)]

= 206,900

Fig. 12c
Oligonucleotide template
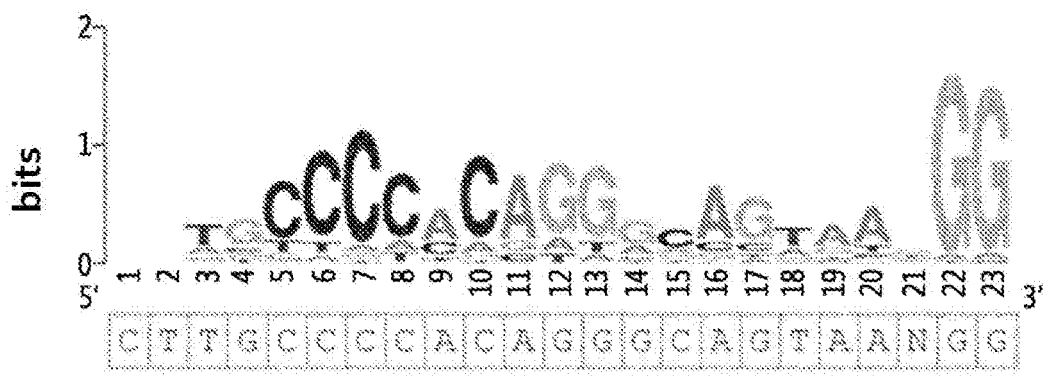
Plasmid template
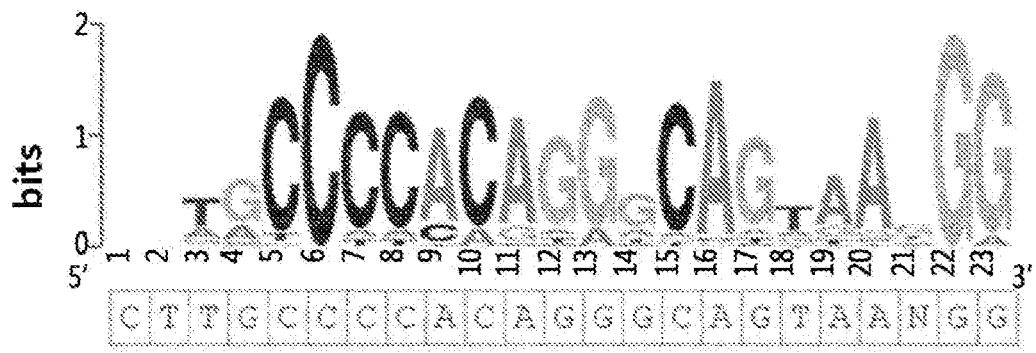

```
5'- GTTACCCC-CAGGGAAGTATAGG -3'  Off-target 1
5'- CTTGCCCCACAGGGCAGTAACGG -3'  Target sequence 5'-CGTGCCCCACAGGG-AGTGAGGG -3'   Off-target 3
5'-CTTGCCCCACAGGGCAGTAACGG -3'   Target sequence 5'-TGTGCCCCACA-GGCAGTACATG -3'   Off-target 2
5'-CTTGCCCCACAGGGCAGTAACGG -3'   Target sequence 5'-CTT-CCCCAATATCC-AGTAGGG -3'   Off-target 4
5'-CTTGCCCCACAGGGCAGTAACGG -3'   Target sequence
```

Fig. 16b
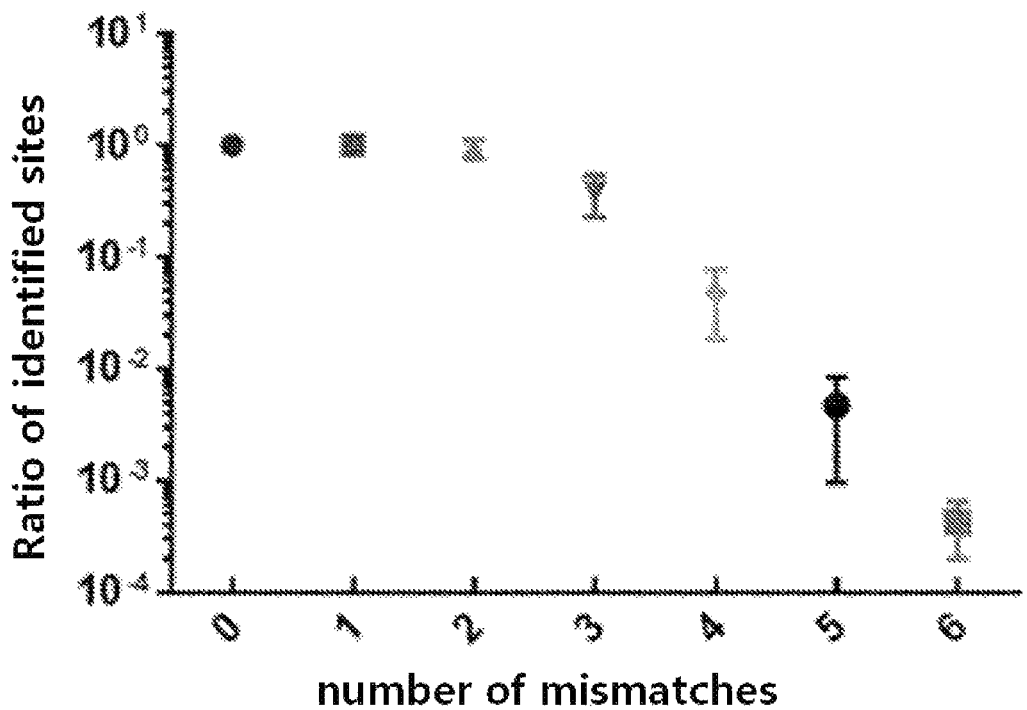
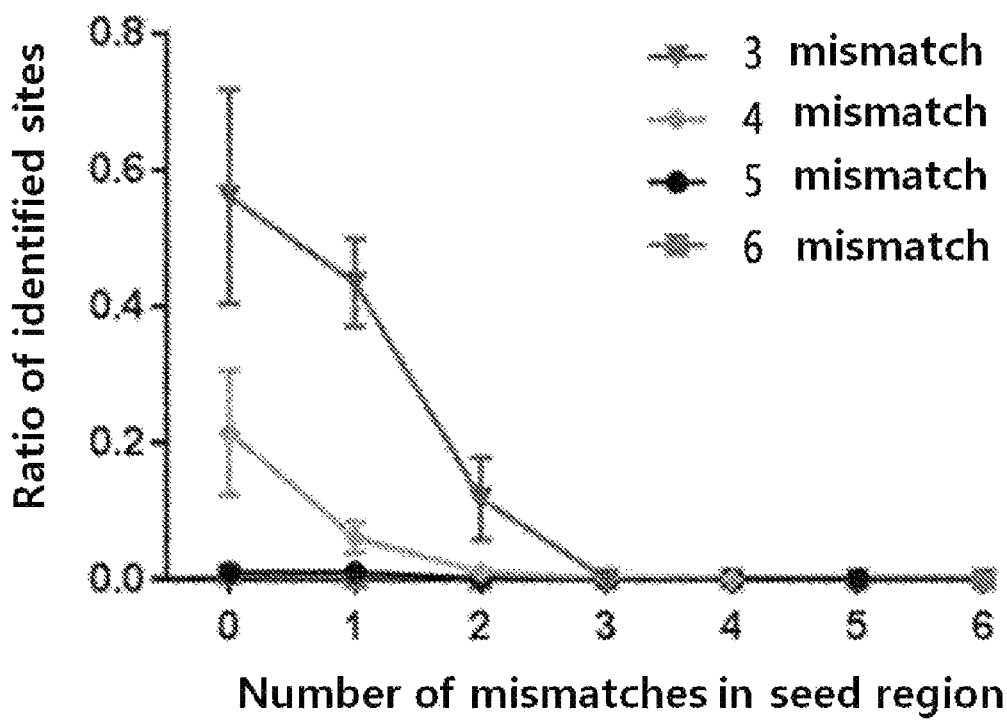

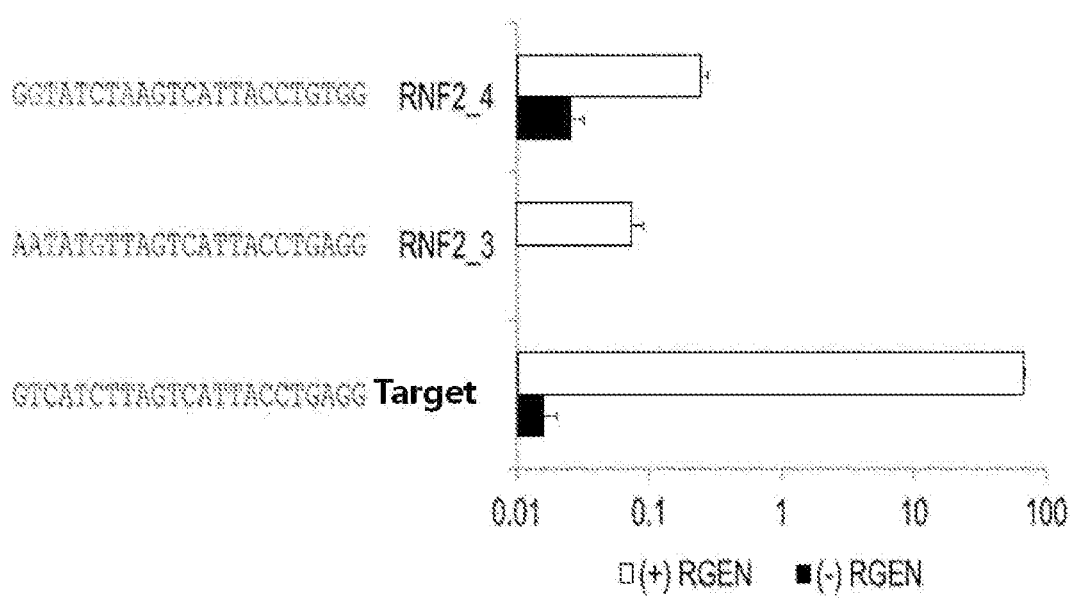

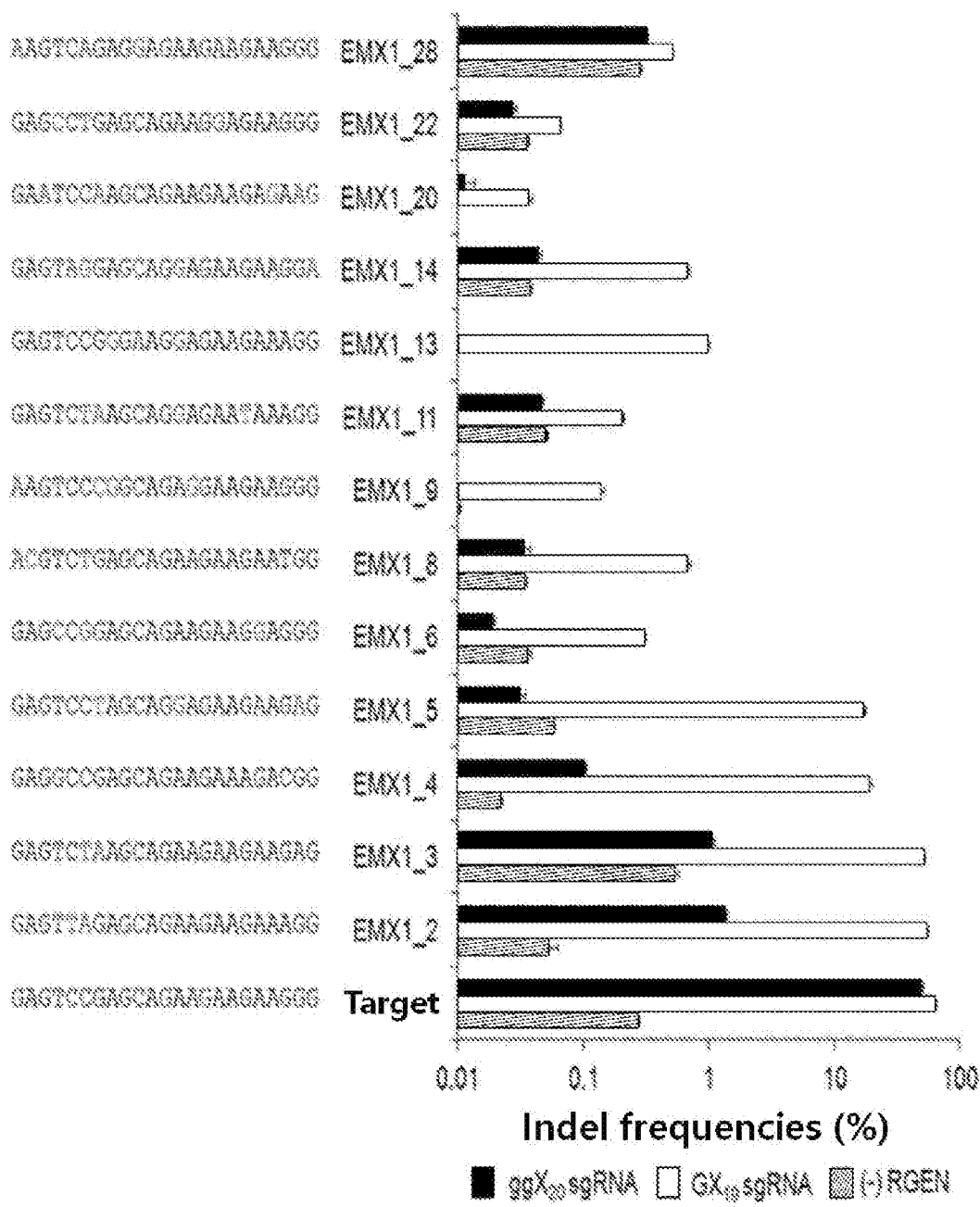

Fig. 21e

*EMX1*

| Target | Ratio of specificity (on-target/off-target) | | |
|---|---|---|---|
| | GX19 | ggX20 | ggX20/GX19 |
| EMX1_2 | 1.2 | 36.0 | 31.2 |
| EMX1_3 | 1.2 | 46.0 | 37.7 |
| EMX1_4 | 3.4 | 477.0 | 142.0 |
| EMX1_5 | 3.7 | 1543.4 | 420.1 |
| EMX1_6 | 208.7 | 2560.4 | 12.3 |
| EMX1_8 | 92.9 | 1454.4 | 15.6 |
| EMX1_9 | 461.2 | 5157.4 | 11.2 |
| EMX1_11 | 308.7 | 1055.8 | 3.4 |
| EMX1_13 | 65.6 | 5406.6 | 82.4 |
| EMX1_14 | 94.1 | 1125.4 | 12.0 |
| EMX1_20 | 1750.7 | 4313.0 | 2.5 |
| EMX1_22 | 982.2 | 1760.9 | 1.8 |
| EMX1_28 | 125.0 | 155.3 | 1.2 |

Fig. 21f

*HEK293-3*

| Target | Ratio of specificity (on-target/off-target) | | |
|---|---|---|---|
| | GX19 | ggX20 | ggX20/GX19 |
| HEK3_2 | 240.0 | 3220.9 | 13.4 |
| HEK3_4 | 3.8 | 2264.1 | 597.9 |
| HEK3_5 | 36.9 | 8716.1 | 236.3 |
| HEK3_6 | 2.1 | 54.8 | 26.0 |
| HEK3_8 | 475.5 | 5618.8 | 11.8 |
| HEK3_9 | 628.8 | 2803.3 | 4.5 |

Fig. 21g

*RNF2*

| Target | Ratio of specificity (on-target/off-target) | | |
|---|---|---|---|
| | GX19 | ggX20 | ggX20/GX19 |
| RNF2_3 | 1985.1 | 5312.7 | 2.7 |
| RNF2_4 | 234.9 | 4749.7 | 20.2 |

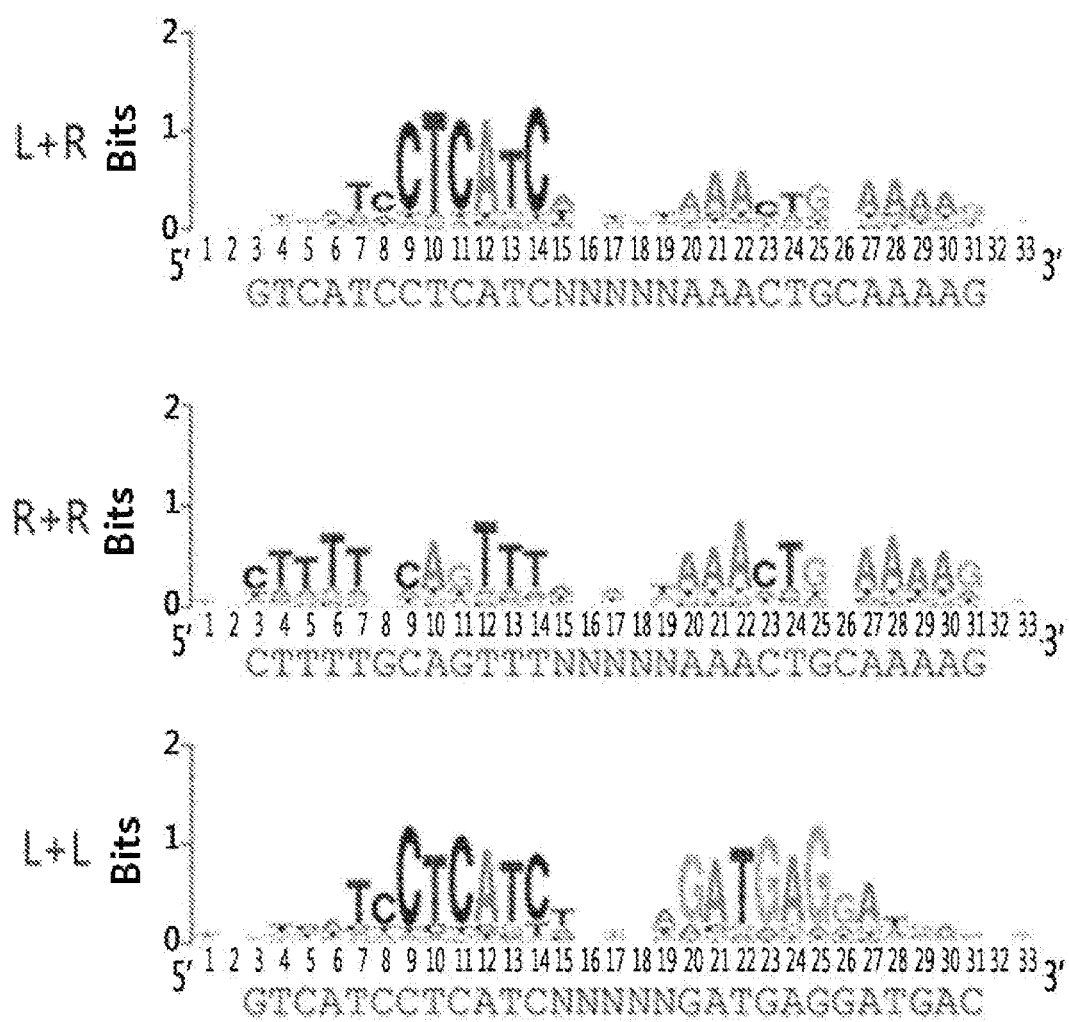

METHOD FOR DETECTING OFF-TARGET SITES OF PROGRAMMABLE NUCLEASES IN A GENOME

TECHNICAL FIELD

The present disclosure relates to a method for detecting off-target sites of a programmable nuclease in a genome, and specifically, to a method for detecting off-target sites through data analysis comprising cleaving genome by treating the genome (cell-free genomic DNA) isolated in vitro with programmable nucleases, and then performing whole genome sequencing, and to a method for selecting on-target sites of a programmable nucleases, which minimizes the off-target effect, using this method.

BACKGROUND ART

Programmable nucleases such as ZFNs (zinc finger nucleases), TALENs (transcriptional activator-like effector nucleases), and RGENs (RNA-guided engineered nucleases) derived from the type II CRISPR/Cas (clustered regularly interspaced repeat/CRISPR-associated) prokaryotic adaptive immunity system, etc. are widely used for genome editing in cultured cells and whole organisms. The genome editing technology using programmable nucleases is very useful technology that can be used for various purposes in life science, biotechnology, and medicine fields. For example, gene/cell therapy for diverse genetic or acquired diseases has become possible by causing targeted genetic modifications in stem cells or somatic cells. However, the programmable nucleases can mutate not only on-target sites but also off-target sites that are homologous thereto (Nucleic acids research, 2013, 41 (20): 9584-9592).

As a representative example, RGENs, which comprise the Cas9 protein derived from S. pyogenes and small guide RNA (sgRNA) recognize 23-bp (base pair) target DNA sequences composed of a 20-bp (base pair) sequence that hybridizes with the sgRNA and a 5'-NGG-3' protospacer-adjacent motif (PAM) sequence recognized by Cas9, but can tolerate mismatches at up to several nucleotide sequences (Genome Res, 2014, 24: 132-141). Furthermore, RGENs can also cleave off-target DNA sequences harboring an extra base sequence (DNA bulge) or lacking a base (RNA bulge) compared to the sgRNA sequences. Likewise, both ZFNs and TALENs can also cleave sequences that differ in some bases. This suggests that there might be vast numbers of off-target sites in addition to on-target sites in case where programmable nucleases are applied to a genome.

Off-target DNA cleavages can lead to mutations at unintended gene such as proto-oncogenes and tumor suppressor genes, as well as gross genome recombination such as translocations, deletions, and inversions, and raise serious concerns about the use of programmable nucleases in research and medicine (Proc Natl Acad Sci, 2009, 106: 10620-10625). In this regard, various strategies have been reported to reduce off-target effects of programmable nucleases, the programmable nucleases specifically working at on-target sites without off-target effects in the entire genomic scale have not yet been reported. To address this issue, it is imperative to develop methods to interrogate the specificities of programmable nucleases on a genomic scale.

DISCLOSURE

Technical Problem

As a result that the present inventors did their best to develop a system capable of detecting and analyzing the target and off-target sites of programmable nucleases on a genomic scale, it has been developed to complete the present invention that a method for detecting off-target sites of programmable nucleases by performing next generation sequencing (NGS) after cleaving a genome with a programmable nuclease (Digenome-seq, nuclease-cleaved genomic DNA sequencing).

Technical Solution

It is an object of the present disclosure to provide a method for detecting an off-target sites of a programmable nuclease, comprising: (a) cleaving an isolated genomic DNA with a target-specific programmable nuclease; (b) performing next generation sequencing of the cleaved DNA; and (c) determining a cleaved site in a sequence read obtained by the sequencing.

It is another object of the present disclosure to provide a method for reducing off-target effects in genome editing, comprising: introducing in vitro transcribed guide RNA into a cell using a plasmid as a template.

Effect

Digenome-seq of the present disclosure can detect off-target sites of a programmable nuclease on a genomic scale with high reproducibility, and thus can be used for the production and study of programmable nucleases with high target specificity.

DESCRIPTION OF DRAWINGS

FIG. 6 illustrates false positive positions identified in the intact genome sequence. (a-c) It is the representative IGV data around false positive sites that resulted from naturally occurring indels in HAP1 cells.

FIG. 7 illustrates indel sequences induced by the HBB RGEN at newly validated off-target sites. (a, b) Off-target indels were detected by targeted deep sequencing. Inserted nucleotides are shown in red and the PAM sequence is shown in blue.

FIG. 10 illustrates indel sequences induced by the VEGF-A RGEN at newly validated off-target sites. (a-d) Off-target indels were detected by targeted deep sequencing. Inserted nucleotides are shown in red and the PAM sequence is shown in blue.

FIG. 11 illustrates an in vitro DNA cleavage scoring system for Digenome-seq analysis.

FIG. 20 illustrates the indel frequencies at on-target and off-target sites in RNF2-specific sgRNA-transformed HeLa cells in a log scale.

BEST MODE

Figure 1A:
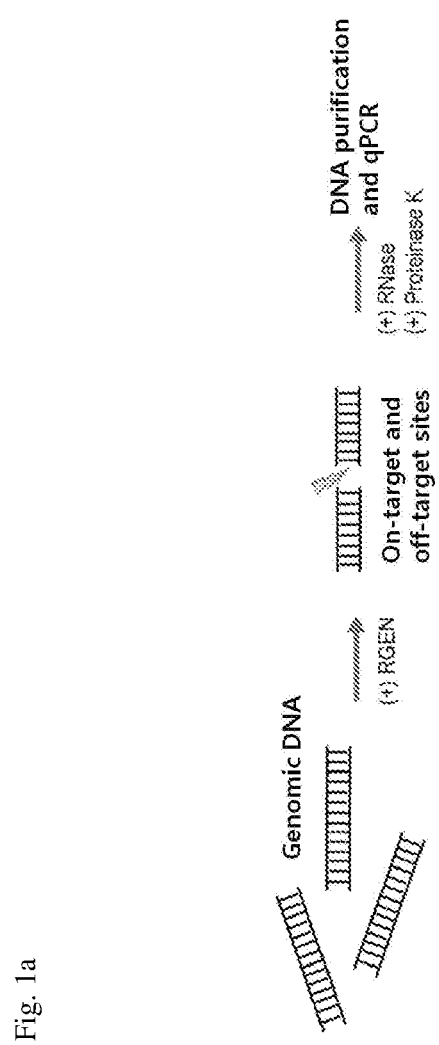
FIG. 1 relates to an RGEN-mediated genomic DNA cleavage in vitro. (a) It is a mimetic diagram of RGEN-mediated genomic DNA cleavage in vitro. (b) It identifies whether genomic DNA is cleaved by the HBB-targeting RGEN at on-target and four potential off-target sites. For the 1× reaction, Cas9 protein (40 μg, 300 nM) and sgRNA (30 μg, 900 nM) were reacted with 8 μg of HAP1 genomic DNA for 8 hours. Cas9 and sgRNA were serially diluted by 10-fold to 10,000-fold. The uncleaved DNA was measured by qPCR. (Bottom) It illustrates DNA sequences of the on-target and the four potential off-target sites. Mismatched nucleotides are shown in red and the PAM sequence is shown in blue. (c) It measures the mutation frequencies by RGEN with the T7E1 assay at the on-target and potential off-target sites. (d) It performs targeted deep sequencing to measure indel frequencies.

According to one aspect in order to achieve this object of the present disclosure, there is provided a method for detecting off-target sites in a genome comprising: (a) cleaving an isolated genomic DNA with a target-specific programmable nuclease; (b) performing next generation sequencing of the cleaved DNA; and (c) determining a cleaved site in a sequence read obtained by the sequencing. The present inventors named said method "Digenome-seq," which refers to nuclease-cleaved genomic DNA sequencing.

Genome editing/gene editing technology are the technologies that can introduce a target-directed mutation into the genomic base sequence of animal and plant cells including human cells. It can knock-out or knock-in specific genes, or can introduce a mutation into non-coding DNA sequences that do not produce proteins. The method of the present disclosure detects the off-target site of programmable nucleases used in this genome editing/gene editing technology, which can be usefully used to develop programmable nucleases that specifically work only at on-target sites.

The step (a) is a step of cleaving the isolated genomic DNA with a target-specific programmable nuclease, that is, a step of cleaving the isolated genomic DNA in vitro with the programmable nucleases specifically working at on-target sites. However, even if the programmable nucleases are produced specifically for the target, other sites, that is, off-target sites, can also be cleaved depending on the specificity. Accordingly, as a result, by the step (a), the used target specific programmable nucleases cleaves a on-target site position which may has an activity with respect to the genomic DNA and a plurality of off-target sites, thereby obtaining genomic DNA whose specific site is cleaved. The type of the genomic DNA is not particularly limited, and may be a genomic DNA of a wild-type cell or a transformed cell. In addition, the transformed cell may be transformed to express specific programmable nucleases depending on the purpose of Digenome-seq.

The term "programmable nuclease" used in the present disclosure refers to all forms of nuclease that is capable of recognizing and cleaving a specific site on a desired genome. In particular, it may include, but is not limited to, a transcription activator-like effector nuclease (TALEN) fused with a transcription activator-like effector (TAL) domain derived from a plant pathogenic gene, which is a domain recognizing a specific target sequence on a genome, and a cleavage domain, zinc-finger nuclease, meganuclease, RGEN (RNA-guided engineered nuclease) derived from CRISPR, which is a microbial immune system, Cpf1, Ago homolog (DNA-guided endonuclease), etc.

The programmable nucleases recognize specific base sequences in the genome of animal and plant cells, including human cells, to cause double strand breaks (DSBs). The double strand breaks include both the blunt end or the cohesive end by cleaving the double strands of DNA. DSBs are efficiently repaired by homologous recombination or non-homologous end-joining (NHEJ) mechanisms within the cell, which allows researchers to introduce desired mutations into on-target sites during this process. The programmable nucleases may be artificial or manipulated non-naturally occurring.

The term "on-target site" used in the present disclosure means a site to which a mutation is to be introduced by using programmable nucleases, and may be selected arbitrarily depending on the purpose thereof. It may be a non-coding DNA sequence that can be present within a specific gene and does not produce a protein.

The programmable nucleases have sequence specificity, and thus work at an on-target site, but may work at an off-target site depending on the target sequence. The term "off-target site" used in the present disclosure refers to a site where the programmable nucleases have activity at a site having a sequence that is not identical to the target sequence of the programmable nucleases. That is, it refers to a site other than an on-target site that is cleaved by the programmable nucleases. In particular, the off-target site in the present disclosure includes not only the actual off-target site for a specific programmable nuclease but also the site where it is likely to become an off-target site. The off-target site may be, but is not limited to, a site cleaved by programmable nucleases in vitro.

The fact that programmable nucleases have activity even at sites other than on-target sites may be due to a phenomenon that can be caused by various causes. However, in particular, in the case of off-target sequences with high sequence homology to on-target sites having a target sequence designed for the on-target site and a nucleotide mismatch, there is a possibility that the programmable nucleases would work. The off-target site may be, but is not limited to, a site with a target sequence and one or more nucleotide mismatches.

It can lead to mutations of unintended gene in a genome, and raises serious concerns about the use of the programmable nucleases. In this regard, the process of accurately detecting and analyzing off-target sites as well as the activity at on-target sites of gene programmable nucleases may also be very important, and can be usefully used for developing programmable nucleases that specifically work only at on-target sites without off-target effects.

The programmable nucleases may be selected from the group consisting of meganuclease, ZFN (zinc finger nuclease), TALEN (transcription activator-like effector nuclease), RGEN (RNA-guided engineered nuclease), Cpf1, and Ago homolog. It may be included, but is not limited to, in the scope of the present disclosure as long as it recognizes a specific sequence of a target gene and has a nucleotide-cleaving activity and can cause insertion and deletion (indels) in a target gene.

The meganuclease may be, but is not limited to, a naturally-occurring meganuclease, which recognizes 15 to 40 base pair cleavage sites, which are usually classified into four families: LAGLIDADG family, the GIY-YIG family, His-Cyst box family, and HNH family. The exemplary meganuclease includes I-SceI, I-CeuI, PI-PspI, PI-SceI, I-SceIV, I-CsmI, I-PanI, I-SceII, I-PpoI, I-SceIII, I-CreI, I-TevI, I-TevII, and I-TevIII.

Site-specific genomic modifications have been promoted in plants, yeast, Drosophila, mammalian cells and mice using DNA binding domains derived from naturally-occurring meganuclease, mainly from LAGLIDADG family. This approach is based on the modification of the homologous gene in which the meganuclease target sequence is conserved (Monet et al. (1999) Biochem. Biophysics Res. Common. 255: 88-93), and there was a limit to the modification of the pre-engineered genome into which the target sequence is introduced. Accordingly, there has been an attempt to engineer meganuclease to exhibit novel binding specificities at medically or biotechnologically relevant sites. In addition, the naturally-occurring or engineered DNA binding domain derived from meganuclease is operably linked to a cleavage domain derived from a heterologous nuclease (e.g., Fok1).

The ZFN comprises a selected gene and a zinc-finger protein engineered to be bound to a cleavage domain or an on-target site of a cleavage half-domain. The ZFN may be an artificial restriction enzyme comprising a zinc-finger DNA binding domain and a DNA cleavage domain. Here, the zinc-finger DNA binding domain may be engineered to be bound to the selected sequence. For example, Beerli et al. (2002) Nature Biotechnol. 20: 135-141; Pabo et al. (2001) Ann. Rev. Biochem. 70: 313-340; Isalan et al., (2001) Nature Biotechnol. 19: 656-660; Segal et al. (2001) Curr. Opin. Biotechnol. 12: 632-637; Choo et al. (2000) Curr. Opin. Struct. Biol. 10: 411-416 may be included as reference material in the present specification. In comparison of naturally-occurring zinc finger proteins, the engineered zinc finger binding domains may have novel binding specificities. The engineering method includes, but is not limited to, a rational design and a selection of various types. The rational design includes the use of databases containing, for example, triple (or quadruple) nucleotide sequences, and individual zinc finger amino acid sequences, wherein each triple or quadruple nucleotide sequence is associated with one or more sequences of zinc fingers that bind to a particular triple or quadruple sequence.

The selection of target sequences and the design and construction of fusion proteins (and polynucleotide encoding thereon) are well known to those skilled in the art, and are described in detail in the full text of U.S. Patent Application Publication Nos. 2005/0064474 and 2006/0188987. The entire disclosure of said publications is included in the present specification as reference of the present disclosure. In addition, as disclosed in these references and other references in the pertinent art, zinc finger domains and/or multi-finger zinc finger proteins may be linked together by a linker comprising any suitable linker sequence, such as a linker of five or more amino acids in length. Examples of linker sequences of six or more amino acids in length are disclosed in U.S. Pat. Nos. 6,479,626; 6,903,185; 7,153,949. The proteins explained herein may include any combination of suitable linkers between each zinc finger of the protein.

In addition, nuclease such as ZFN contains a nuclease active portion (cleavage domain, cleavage half-domain). As is well known, the cleavage domain may be heterologous to the DNA binding domain, such as, for example, a cleavage domain from a nuclease that is different from a zinc finger DNA binding domain. The heterologous cleavage domain may be obtained from any endonuclease or exonuclease. The exemplary endonuclease from which the cleavage domain may be derived include, but is not limited to, restriction endonuclease and meganuclease.

Similarly, a cleavage half-domain may be derived from any nuclease, or a portion thereof, that requires dimerization for cleavage activity, as indicated above. Where the fusion protein comprises a cleavage half-domain, generally two fusion proteins require cleavage. Alternatively, a single protein comprising two cleavage half-domains may be used. The two cleavage half-domains may be derived from the same endonuclease (or functional fragments thereof), or each cleavage half-domain may be derived from a different endonuclease (or functional fragments thereof). In addition, the on-target site of the two fusion proteins is located in such a way that the cleavage half-domains are spatially oriented to each other by the binding of the two fusion proteins and their respective on-target sites. Thus, it is preferable to arrange the cleavage half-domains to be able to form a functional cleavage domain by dimerization. Accordingly, in one embodiment, neighboring edges of the on-target site are isolated by 3 to 8 nucleotides or 14 to 18 nucleotides. However, nucleotides or nucleotide pairs of any integer may be interposed between two on-target sites (e.g., 2 to 50 nucleotide pairs or more). Generally, the cleavage site lies between on-target sites.

Restriction endonucleases (restriction enzymes) are present in many species, may be sequence-specifically bound to DNA (at an on-target site), and cleave DNA directly at or near a binding site. Some restriction enzymes (e.g., Type IIS) cleave DNA at sites removed from a recognition site and have separable binding and cleavable domains. For example, the Type IIS enzyme FokI catalyzes double strand breaks of DNA at 9 nucleotides from a recognition site on one strand and 13 nucleotides from a recognition site on the other one strand. Accordingly, in one embodiment, the fusion protein comprises a cleavage domain (or cleavage half-domain) from at least one Type IIS restriction enzyme and one or more zinc-finger binding domains (which may or may not be engineered).

The term "TALEN" used in the present disclosure refers to a nuclease capable of recognizing and cleaving a target region of DNA. TALEN refers to a fusion protein comprising a TALE domain and a nucleotide cleavage domain. In the present disclosure, the terms "TAL effector nuclease" and "TALEN" are interchangeable. TAL effectors are known as proteins that are secreted by their type III secretion system when Xanthomonas bacteria are infected with a variety of plant species. The protein may be combined with a promoter sequence in a host plant to activate the expression of a plant gene that aids bacterial infection. The protein recognizes plant DNA sequences through a central repetitive domain consisting of various numbers of amino acid repeats of 34 or fewer. Accordingly, TALE is expected to be a novel platform for tools in genome engineering. However, in order to construct a functional TALEN with genomic-editing activity, a few key parameters that have not been known thus far should be defined as follows. i) The minimum DNA-binding domain of TALE, ii) the length of the spacer between the two half-digits constituting one target region, and iii) the linker or fusion junction that links the FokI nuclease domain with dTALE.

The TALE domain of the present disclosure refers to a protein domain that binds nucleotides in a sequence-specific manner via one or more TALE-repeat modules. The TALE domain includes, but is not limited to, at least one TALE-repeat module, and more specifically, 1 to 30 TALE-repeat modules. In the present disclosure, the terms "TAL effector domain" and "TALE domain" are interchangeable. The TALE domain may include half of the TALE-repeat module. The entire contents disclosed in International Patent Publication No. WO/2012/093833 or U.S. Patent Application Publication No. 2013-0217131 in relation to this TALEN are included in the present specification as reference.

The term "RGEN" used in the present disclosure means a nuclease comprising a target DNA-specific guide RNA and Cas protein as a component.

In the present disclosure, the RGEN may be, but is not limited to, applied to a genomic DNA isolated in vitro in the form of a target DNA-specific guide RNA and an isolated Cas protein.

The guide RNA may be transcribed in vitro, and in particular, it may be, but is not limited to, transcribed from an oligonucleotide double strand or a plasmid template.

In the present disclosure, the term "Cas protein" is a major protein component of the CRISPR/Cas system, and is a protein capable of forming an activated endonuclease or nickase.

The Cas protein may form a complex with crRNA (CRISPR RNA) and tracrRNA (trans-activating crRNA) to exhibit its activity.

Cas protein or gene information may be obtained from the known database such as GenBank of National Center for Biotechnology Information (NCBI). Specifically, the Cas protein may be a Cas9 protein. In addition, the Cas protein may be a *Streptococcus* genus, more specifically, a Cas protein derived from *Streptococcus pyojens*, and more specifically, a Cas9 protein. In addition, the Cas protein may be a *Neisseria* genus, more specifically, a Cas protein derived from *Neisseria meningitidis*, and more specifically, a Cas9 protein. In addition, the Cas protein may be a *Pasteurella* genus, more specifically, a Cas protein derived from *Pasteurella multocida*, and more specifically, a Cas9 protein. In addition, the Cas protein may be a *Francisella* genus, more specifically, a Cas protein derived from *Francisella novicida*, and more specifically, a Cas9 protein. In addition, the Cas protein may be a *Campylobacter* genus, more specifically, a Cas protein derived from *Campylobacter jejuni*, and more specifically, a Cas9 protein. However, the present disclosure is not limited to the examples described above.

In addition, the Cas protein is used in the present disclosure as a concept including both native proteins as well as variants capable of acting as an endonuclease or nickase activated in cooperation with a guide RNA. The variant of the Cas9 protein may be a mutated form of Cas9 in which a catalytic aspartate residue is changed to any other amino acid. Specifically, the other amino acids may, but is not limited to, be alanine.

In the present disclosure, the Cas protein may be a recombinant protein.

When used in reference to, for example, a cell, nucleic acid, protein or vector, etc., the term "recombinant" refers to the introduction of a heterologous nucleic acid or protein or a modification of a native nucleic acid or protein, or a cell, a nucleic acid, a protein, or a vector modified by a cell derived from a modified cell. Thus, for example, the recombinant Cas protein may be made by reconstructing a sequence encoding the Cas protein using a human codon table.

The Cas protein or a nucleic acid encoding it may be a form that allows the Cas protein to work in the nucleus.

The isolated Cas protein may also be a form that is easy to be introduced into cells. For example, Cas proteins may be linked to cell penetration peptides or protein transduction domains. The protein transduction domain may be, but is not limited to, poly-arginine or a TAT protein derived from HIV. In addition to the above-described examples, various types of cell penetrating peptide or protein transduction domain are well known in the pertinent art, so that a person skilled in the art may, but is not limited to, apply various examples to the present disclosure.

In addition, the nucleic acid encoding the Cas protein may further include a nuclear localization signal (NLS) sequence. Accordingly, the expression cassette containing the nucleic acid encoding the Cas protein may, but is not limited thereto, include an NLS sequence in addition to a regulatory sequence such as a promoter sequence, etc. for expressing the Cas protein.

The Cas protein may be linked to a tag advantageous for isolation and/or purification. For example, a small peptide tag such as a His tag, a Flag tag, or an S tag, etc., or a Glutathione S-transferase (GST) tag or a Maltose binding protein (MBP) tag may be, but is not limited to, linked depending on the purpose.

The term "guide RNA" used in the present disclosure means a target DNA-specific RNA, which may be bound to a Cas protein and guides a Cas protein to a target DNA.

In the present disclosure, the guide RNA is a dual RNA comprising two RNAs, that is, a crRNA (CRISPR RNA) and a tracrRNA (trans-activating crRNA) as components; or a form comprising a first site comprising a sequence complementary to a sequence in the target DNA and a second site comprising a sequence interacting with a Cas protein, and more specifically, a single chain guide RNA (sgRNA), which is a form of fusion of the major portions of crRNA and tracrRNA.

The sgRNA may include a portion having a sequence complementary to the sequence in the target DNA (also referred to as a Spacer region, a target DNA recognition sequence, a base pairing region, etc.) and a hairpin structure for Cas protein binding. More specifically, it may include a portion having a sequence complementary to a sequence in the target DNA, a hairpin structure for Cas protein binding, and a terminator sequence. The structures described above may, but is not limited to, be sequentially present in the order of 5' to 3'.

Any type of guide RNA can also be used in the present disclosure if the guide RNA comprises a major portion of the crRNA and tracrRNA and a complementary portion of the target DNA.

The crRNA may be hybridized with the target DNA.

RGEN may be composed of Cas protein and dual RNA, or may, but is not limited to, be composed of Cas protein and sgRNA.

The guide RNA, specifically, the crRNA or sgRNA, may comprise a sequence complementary to a sequence in the target DNA, and may comprise one or more additional nucleotides at the upstream region of crRNA or sgRNA, specifically, the 5' end of crRNA of sgRNA or dual RNA. The additional nucleotide may be, but is not limited to, guanine (G).

For the purposes of the present disclosure, the RGEN may have nuclease activity in vivo and in vitro. Accordingly, it can be used to detect the off-target site of genomic DNA in vitro, and when it is applied in vivo, it can be expected to have activity even at the same site as the detected off-target site.

The genomic DNA may be isolated from a transformed cell so that a non-transfomed cell or a target specific programmable nuclease has a nuclease activity, and may be used without limitation of its origin depending on the purpose of detecting the off-target sites of programmable nucleases.

In the present disclosure, the term "Cpf1" is a programmable nuclease of a new CRISPR system which is distinct from the CRISPR/Cas system, and the role of Cpf1 as a programmable nuclease has recently been reported (Cell, 2015, 163 (3): 759-71). The Cpf1 is a programmable nuclease driven by a single RNA, does not require tracrRNA and is relatively small in size compared to Cas9. In addition, it uses a thymine-rich protospacer-adjacent motif (PAM) sequence and cleaves the double chain of DNA to form a cohesive end. The Cpf1 may be, but is not limited to, derived from *CandidatusPaceibacter, Lachnospira* genus, *Butyrivibrio* genus, *Peregrinibacteria, Acidominococcus* genus, *Porphyromonas* genus, *Prevotella* genus, *Francisella* genus, *Candidatus methanoplasma*, or *Eubacterium* genus.

In a specific embodiment of the present disclosure, on-target sites and some off-target predicted sites are cleaved as a result that the HBB gene-targeted RGEN is treated with genomic DNA isolated in vitro. In vivo, indels (insertion and deletion) were induced at the site (FIG. 1). However, not all off-target predicted positions were cleaved.

The step (b) is a step of performing a next generation sequencing (NGS) using the DNA cleaved through the step (a). Unlike the indirect method of finding a sequence that has a homology with a sequence at on-target sites and predicting it to be off-target sites, it is performed to detect off-target sites that are substantially cleaved by a programmable nuclease on the entire genomic scale.

In the present disclosure, the term "whole genome sequencing" means a method of reading the genome by many multiples in 10×, 20×, and 40× formats for whole genome sequencing by next generation sequencing. "Next generation sequencing" means a technology that sculpts the whole genome or targeted region of genome in a chip-based and PCR-based paired end format and performs sequencing at a super high speed based on chemical reaction (hybridization) of the fragment.

The step (c) is a step of determining a site where the DNA is cleaved in the sequence reading obtained by the next generation sequencing (NGS), and on-target sites and off-target sites of a programmable nuclease may be easily detected by analyzing the sequencing data. Determining a specific site at which the DNA is cleaved from the sequence read may be performed in a variety of approaches, and the present disclosure provides many reasonable methods for determining the site. However, this is merely an example included in the technical idea of the present disclosure, and the scope of the present disclosure is not limited by these methods.

For example, as an example for determining a cleavage site, when the sequence read obtained through the whole genome sequencing is aligned according to the site in a genome using an analysis program (for example, BWA/GATK or ISAAC), the site where 5' end is vertically aligned may mean the site at which DNA is cleaved. In other words, in the present disclosure, the term "vertical alignment" means an arrangement in which the 5' end of two or more sequence reads starts at the same site (nucleotide position) of the genome when the whole genome sequencing results are analyzed with a program such as BWA/GATK or ISAAC, for each of the neighboring Watson strand and Crick strand. This is shown because each of the DNA fragments that are cleaved by programmable nucleases and thus have the same 5' end is sequenced.

That is, when the programmable nucleases have nuclease activity at on-target sites and off-target sites and cleave said sites, if the sequence read is aligned, the common cleaved sites are vertically aligned because each of their sites start at the 5' end. However, the 5' end is not present in the uncleaved sites, so that it can be arranged in a staggered manner in alignment. Accordingly, the vertically aligned site may be regarded as a site cleaved by programmable nucleases, which means on-target sites or off-target sites of the programmable nucleases.

The alignment means mapping the sequence read to the reference genome and then aligning the bases having the same site in a genome to fit for each site. Accordingly, any computer program may be used as long as the sequence read can be arranged in the same manner as described above, which may be a known program already known in the pertinent art, or a program tailored to the purpose. In one embodiment of the present disclosure, alignment is performed using ISAAC, but is not limited thereto.

As a result of the alignment, the site at which the DNA is cleaved by programmable nucleases may be determined by a method such as finding a site where the 5' end is vertically aligned as described above, and the cleaved site may be determined as an off-target site if it is not an on-target site. In other words, the sequence that is identical to the base sequence designed with an on-target site of programmable nucleases is an on-target site, and the sequence that is not identical to the base sequence is regarded as a off-target site. This is obvious according to the definition of an off-target site described above. The off-target site may, in particular, be composed of a sequence having a homology to the sequence of an on-target site, specifically, include a sequence having an on-target site and one or more nucleotide mismatches, and more specifically, an on-target site and 1 to 6 nucleotide mismatches, but is not particularly limited thereto. It may be included in the scope of the present disclosure if it is the site that programmable nucleases can cleave. At this time, the on-target site may be a 15-30 nucleotide sequences complementary to a guide RNA, and may further include a sequence recognized by a nuclease (for example, a PAM sequence recognized by Cas9 in the case of Cas9).

In addition to a method of finding the site where the 5' end is vertically aligned, the off-target site may be determined as an off-target site if the site is not an on-target site when the dual peak pattern is seen in the 5' end plot. When a graph is drawn by counting the number of nucleotides constituting the 5' end of the same base at each site in a genome, a dual peak pattern appears at a specific site. It is because that the dual peak is indicated by each of the double stands cleaved by programmable nucleases.

In a specific embodiment of the present disclosure, the genomic DNA was cleaved into RGEN, and after the whole genome analysis, it was aligned with ISAAC, and the patterns aligned vertically at the cleavage site and the staggered pattern at the uncleaved site were identified. It was identified that a unique pattern of double peaks appears at the cleavage site when represented by a 5 'end plot (FIGS. 2 to 4).

Moreover, it is not limited thereto, but as a specific example, the site where two or more sequence reads corresponding to Watson strand and Crick strand are aligned vertically may be determined as an off-target site. In addition, the site where 20% or more of sequence reads is vertically aligned and the number of sequence reads having the same 5' end in each of the Watson and Creek strands is 10 or more is determined as an off-target site position, that is, a cleavage site.

In a specific embodiment of the present disclosure, the site where the number of sequence reads having the same 5' end at both strands is 10 or more, and at least 19% of the sequence reads are vertically aligned was searched. As a result, it was identified that Digenome-seq has a high reproducibility by detecting 125 sites including on-target and off-target sites that had been previously validated (FIGS. 5 to 7).

Figure 8B:
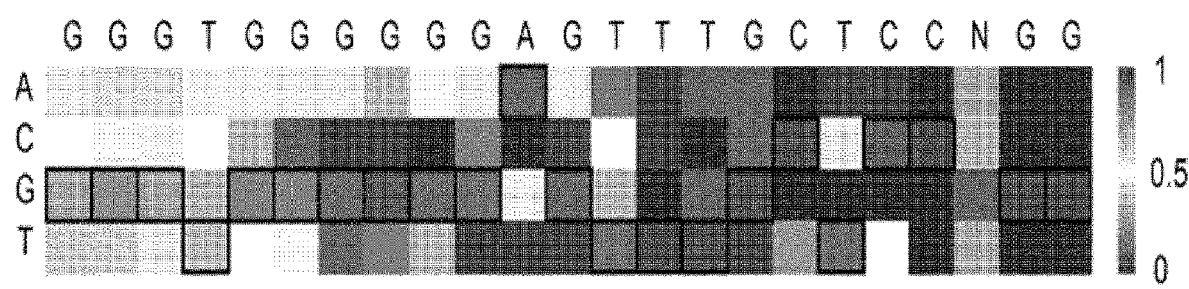
FIG. 8 illustrates off-target sites of the VEGF-A RGEN identified by Digenome-seq. (a) It illustrates a plot of the number of 5' ends at one of the VEGF-A off-target sites. (b) It is a heatmap comparing the site identified by Digenome-seq with the on-target site. Dark red and dark blue correspond to 100% and 0% match at a given position. (c) It illustrates sequence logo obtained by WebLogo using DNA sequences at the site identified by Digenome-seq. (d) It is a summary of the result of Digenome-seq and targeted deep sequencing. N.D. means that nothing is determined. (e) It illustrates off-target sites validated by targeted deep sequencing. Blue and red bars represent indel frequencies obtained using non-transformed HAP1 cells and the VEGF-A RGEN-transformed HAP1 cells. (Left) It illustrates DNA sequences of on-target and off-target sites. Mismatched bases are shown in red, and the PAM sequence is shown in blue. (Right) P value was calculated by the Fisher exact test.
Figure 8C:
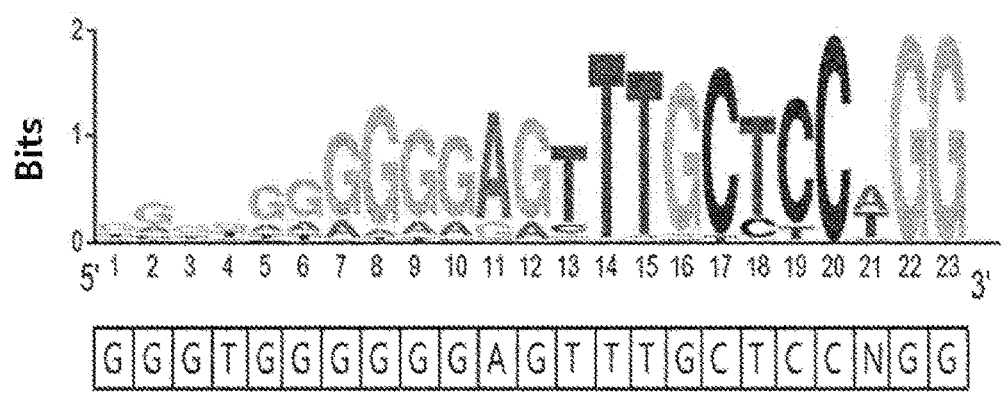
Figure 8E:
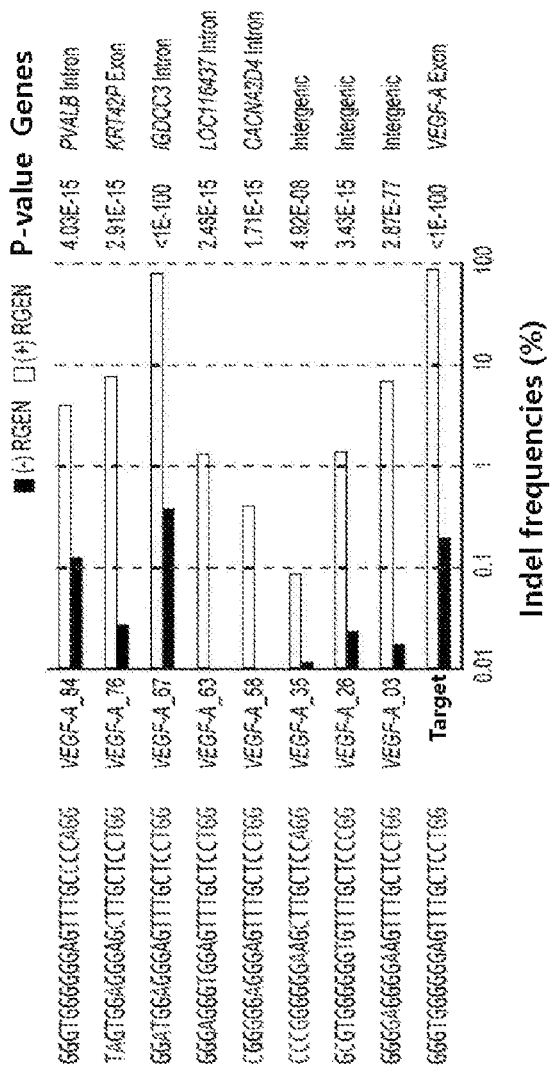
Figure 9A:
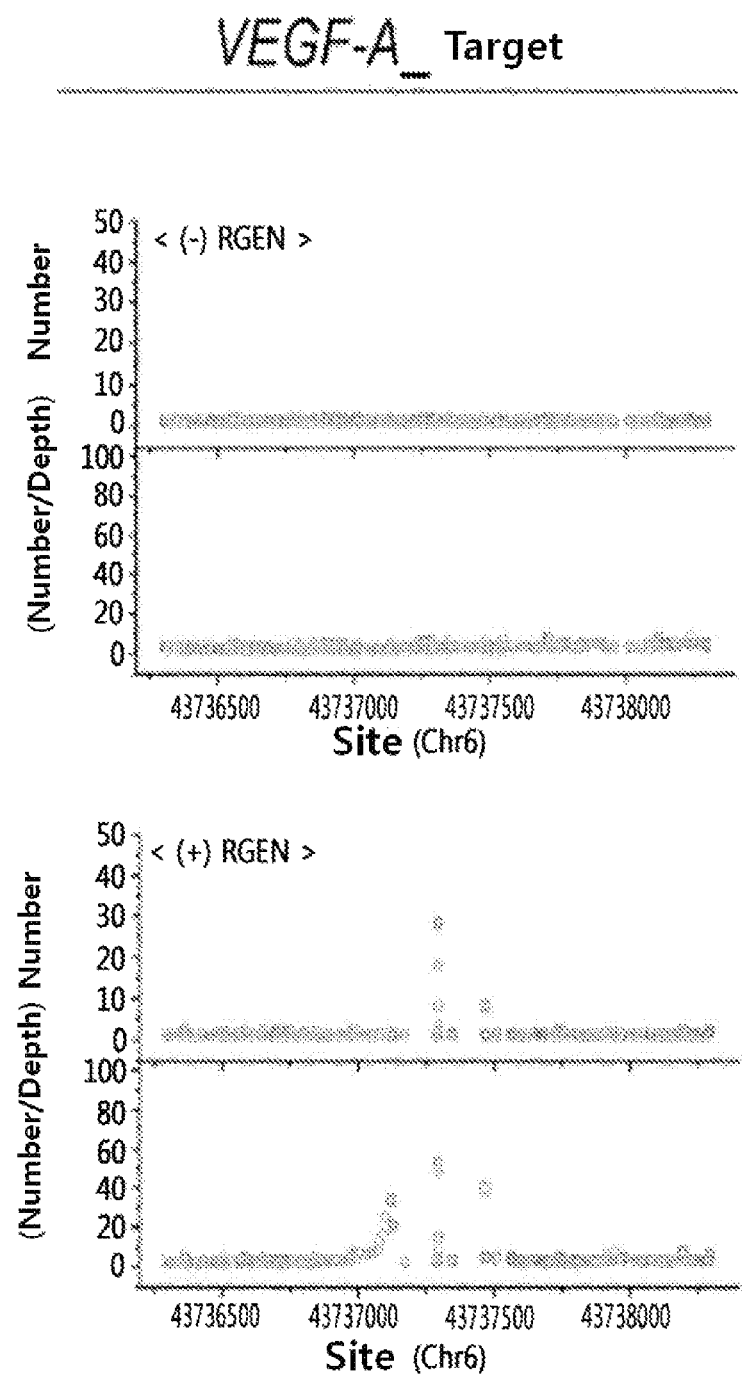
FIG. 9 illustrates an RGEN-induced Digenome-seq to identify off-target sites of the VEGF-A RGEN. (a-d) It illustrates 5' end plots showing the absolute and relative number of sequence reads with the same 5' end according to nucleotide positions in on-target (a) and off-target sites (b-d).
Figure 9B:
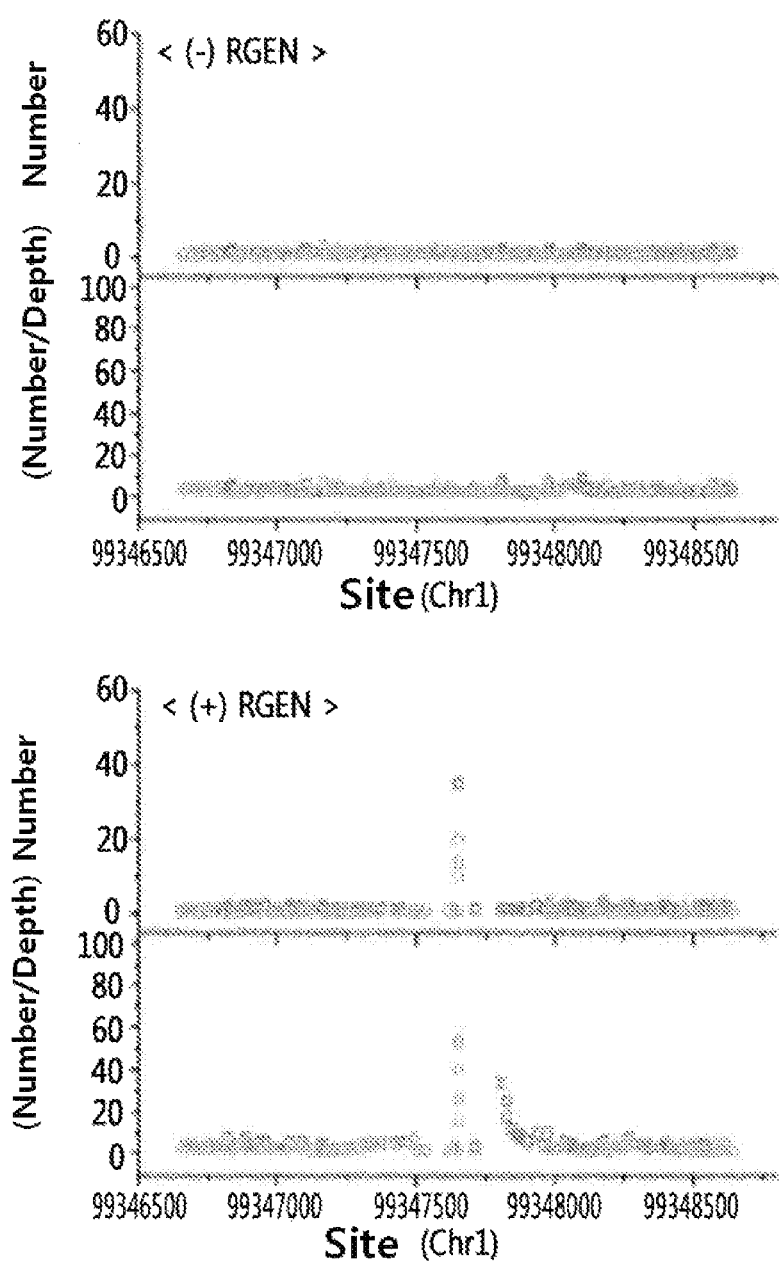
Figure 9D:
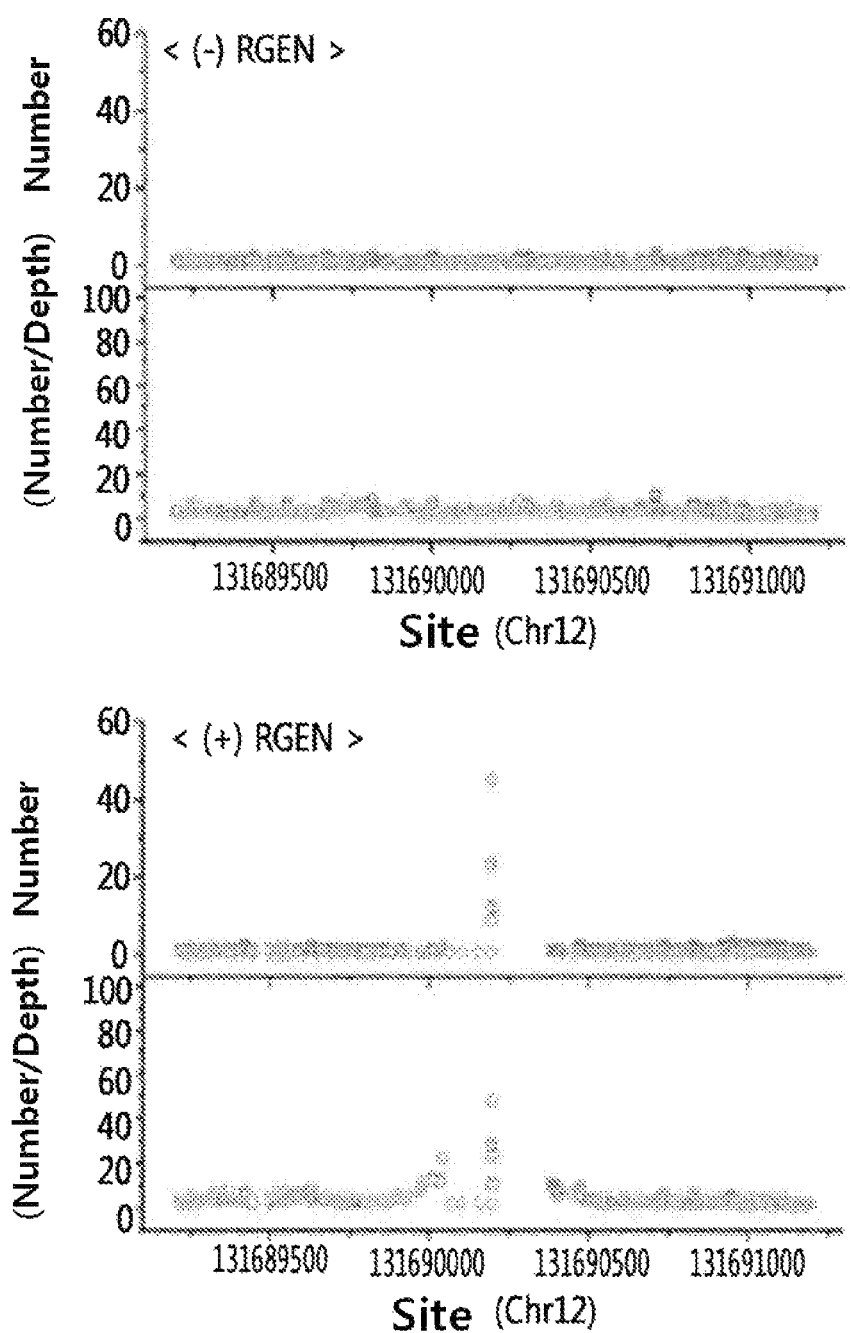

In another specific embodiment of the present disclosure, it was identified that off-target sites may be detected with Digenome-seq for another target gene, VEGF-A (FIGS. 8 to 10). In another specific embodiment, it was identified that Digenome-seq may also detect off-target sites of ZFN other than RGEN (FIG. 24). In conclusion, it can be seen from these results that Digenome-seq of the present disclosure is a method for detecting off-target sites of programmable nucleases without being limited to the types of on-target sites and programmable nucleases.

The off-target site is performed in vitro by processing programmable nucleases in a genomic DNA. Thus, it can be identified whether off-target effects are actually produced also in vivo in the off-target site detected by this method. However, this is merely an additional verification process, and thus is not a step that is essentially accompanied by the scope of the present disclosure, and is merely a step that can be additionally performed according to the needs. In the present disclosure, the term "off-target effect" is a concept that is distinct from an off-target site. That is, as described above, in the present disclosure, the concept of an off-target site means a site other than the on-target sites among the sites where programmable nucleases can work, and is referenced as a site cleaved by nuclease. The off-target effect refers to an effect showing indels (insertion and deletion) by programmable nucleases at an off-target site in cells. In the present disclosure, the term "indel" is a generic term for a mutation in which some bases are inserted or deleted in the middle of a base sequence of DNA. In addition, the off-target site at which the indel caused by programmable nucleases is also referred to as an off-target indel site. In conclusion, the off-target site of the present disclosure is deemed as a concept of including an off-target indel site, and it is sufficient if it is a site where programmable nucleases have a possibility of having an activity, and indels do not necessarily have to be identified by programmable nucleases. Meanwhile, the off-target site in the present disclosure is referred to as a candidate off-target site, and the off-target indel site is also referred to as a validated off-target site.

Specifically, the verification process may include, but is not limited to, isolating genomic DNA from cells expressing the programmable nucleases for the off-target site, identifying indels at the off-target site of DNA, and identifying the off-target effect at the off-target site. The off-target effect may be identified by a method of analyzing a mutant detection using T7E1 analysis and Cel-I enzyme and identifying indels known in the pertinent art such as targeted deep sequencing. The step of identifying the off-target effect may be a direct confirmation on whether indels occur at an off-target site. However, even if indels do not occur during the in vivo verification process, it should be regarded as an auxiliary means because it does not identify the case that indels occur at a frequency below the detectable level.

By identifying the vertically aligned site as described above, or by identifying the double peak in the 5' end plot, the off-target site may sufficiently be detected, which can be highly reproducible. However, there is a problem that some sites having a heterogeneous cleavage pattern or a low sequencing depth may be missing. Based on the alignment pattern of the sequence reads, the present inventors developed a formula for calculating the DNA cleavage score at each nucleotide site (FIG. 11) as follows:

$$\text{Score at the } i \text{ site} = \sum_{a=1}^{5} \frac{C(F_i-1)}{D_i} \times \frac{C(R_{i-4+a}-1)}{D_{i-4+a}} \times (F_i + R_{i-4+a} - 2) +$$

$$\sum_{a=1}^{5} \frac{C(R_{i-1}-1)}{D_{i-1}} \times \frac{C(F_{i-3+a}-1)}{D_{i-3+a}} \times (R_{i-a} + F_{i-3+a} - 2)$$

$F_i$: Number of forward sequence reads starting at the $i$ site $R_i$: Number of reverse sequence reads starting at the $i$ site $D_i$: Sequencing depth at the $i$ site $C$: Arbitrary constant Through this formula, a plurality of additional sites that were not detected in the existing Digenome-seq could be detected, thereby allowing easy filtering of false-positive sites. The C value in this formula is not limited by the examples of the present disclosure, as a person skilled in the art can apply arbitrary constants. In particular, it is not limited thereto, but for example, when the C value is 100 and the calculated score is 25,000 or more, it may be determined as an off-target site. However, the criteria of the score may be appropriately adjusted or changed by a person skilled in the art depending on the purpose.

Figure 12A:
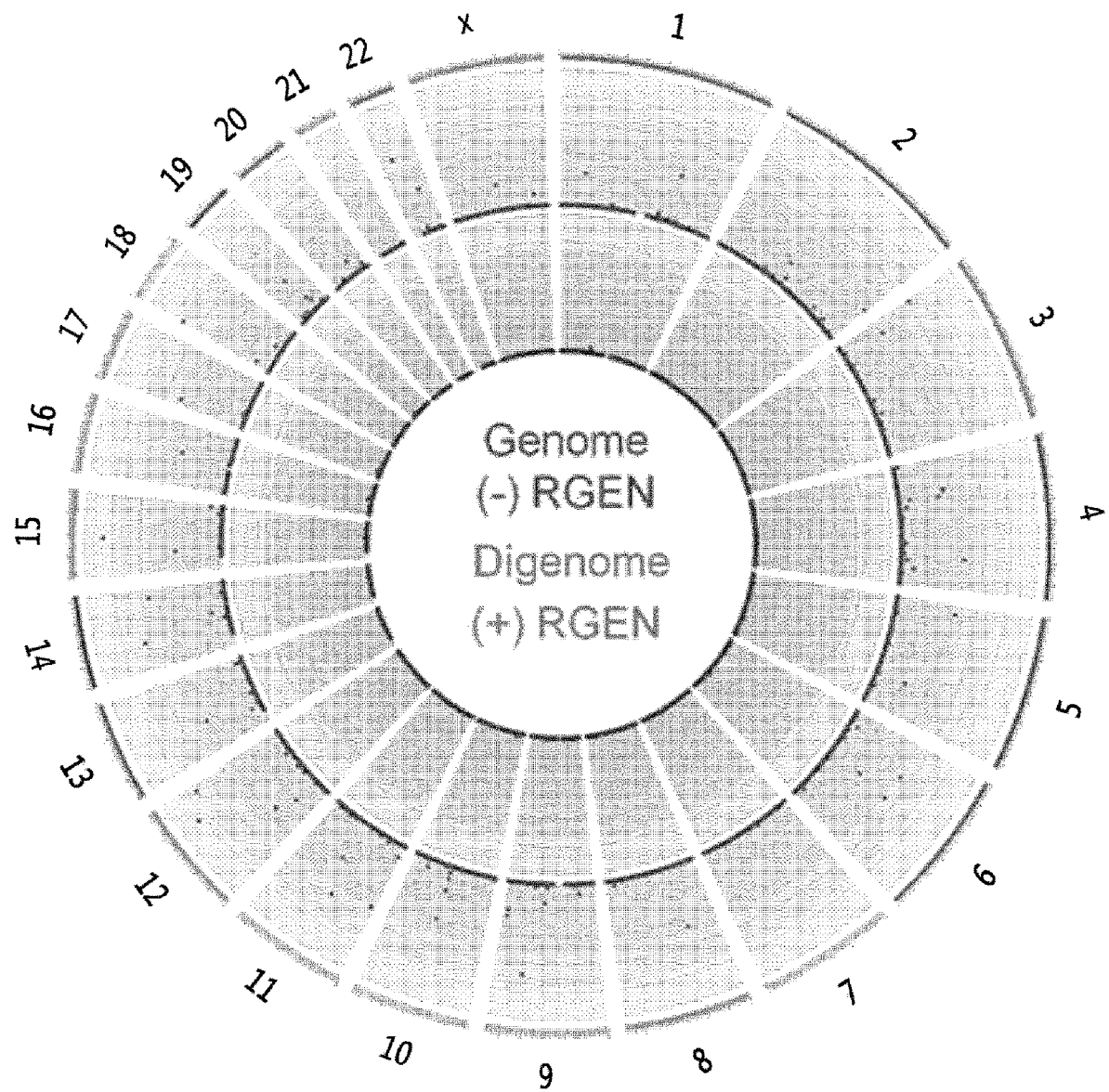
FIG. 12 illustrates an improved Digenome-seq analysis. (a) It illustrates genomic scale Circos plot of in vitro DNA cleavage score. Whole genome sequencing (WGS) was performed using human genomic DNA (red) and genomic DNA (green) cleaved with RGEN. (b) It illustrates a mimetic diagram of Digenome-seq using oligonucleotide double strand or sgRNA transcribed from a plasmid. (C) It illustrates a sequence logo obtained using an oligonucleotide double strand or sgRNA transcribed from a plasmid.

In a specific embodiment of the present disclosure, the off-target site was detected by introducing the DNA cleavage score into the existing Digenome-seq method. As a result, an additional position could be detected as compared with a method of merely finding a vertical alignment site, and it has a high reproducibility (FIGS. 12 and 13). In another specific embodiment of the present disclosure, in the sgRNA of RGEN, the off-target site detected when the sgRNA transcribed from the plasmid template was used as compared with the one transcribed from a plasmid template and one transcribed from the oligonucleotide double strand has a high homology as compared with the on-target site (FIG. 14, Table 1 and Table 2).

Further, the Digenome-seq of the present disclosure may be performed using a plurality of programmable nucleases, and the present inventors have named this "multiplex digenome-seq". In this case, the programmable nucleases may be a mixture of programmable nucleases for 2 or more, specifically 2 to 100 targets, but is not limited thereto.

In the case of the multiplex Digenome-seq, it is important to check whether a cleavage site is cleaved by programmable nucleases because genomic DNA is cleaved by each of programmable nucleases. This can be achieved by classifying the off-target site according to the edit distance to the on-target site and is based on the assumption that the base sequence at the off-target site is homologous to the on-target site. This allows a clear distinction between on-target and off-target sites for each programmable nuclease.

In a specific embodiment of the present disclosure, a multiplex Digenome-seq using sgRNA for 11 different on-target sites in Digenome-seq was performed, and 964 positions identified were classified according to edit distance with an on-target site to identify the off-target site for each on-target site (FIGS. 15-19).

Figure 23A:
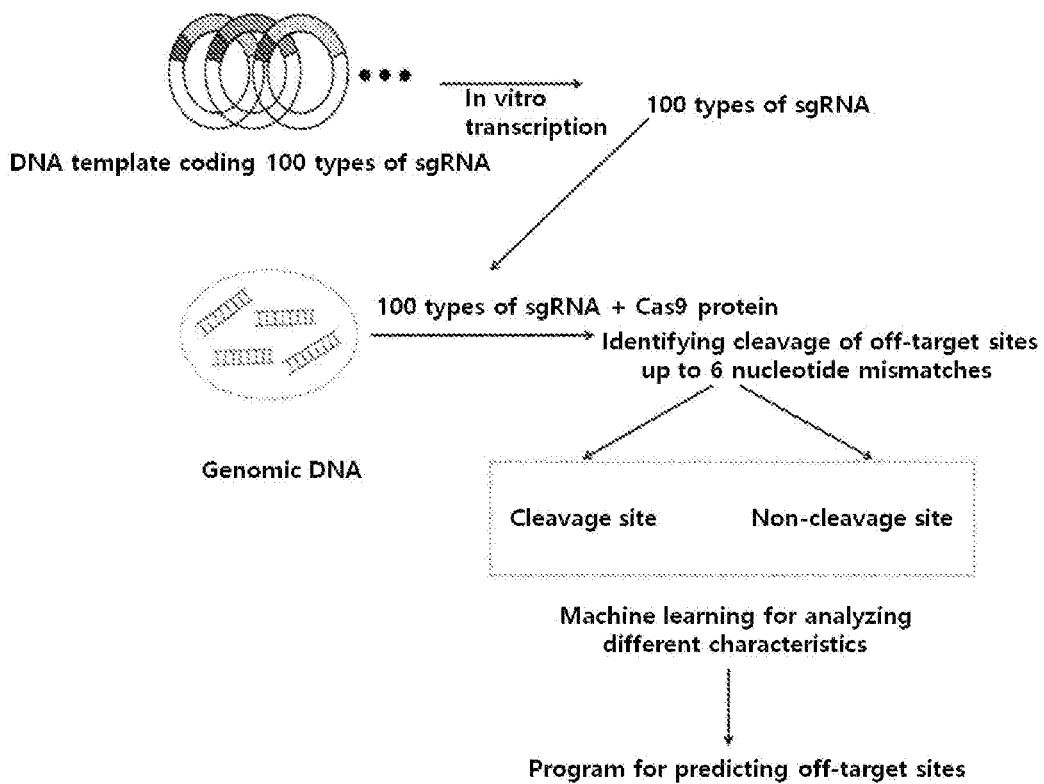
FIG. 23 illustrates the results of Digenome-seq performed on 100 on-target sites. (a) It mimetically illustrates a test process, and (b) it illustrates the results of comparing programs that predict off-target sites based on Digenome-seq with the other programs (Crop-it).
Figure 23B:
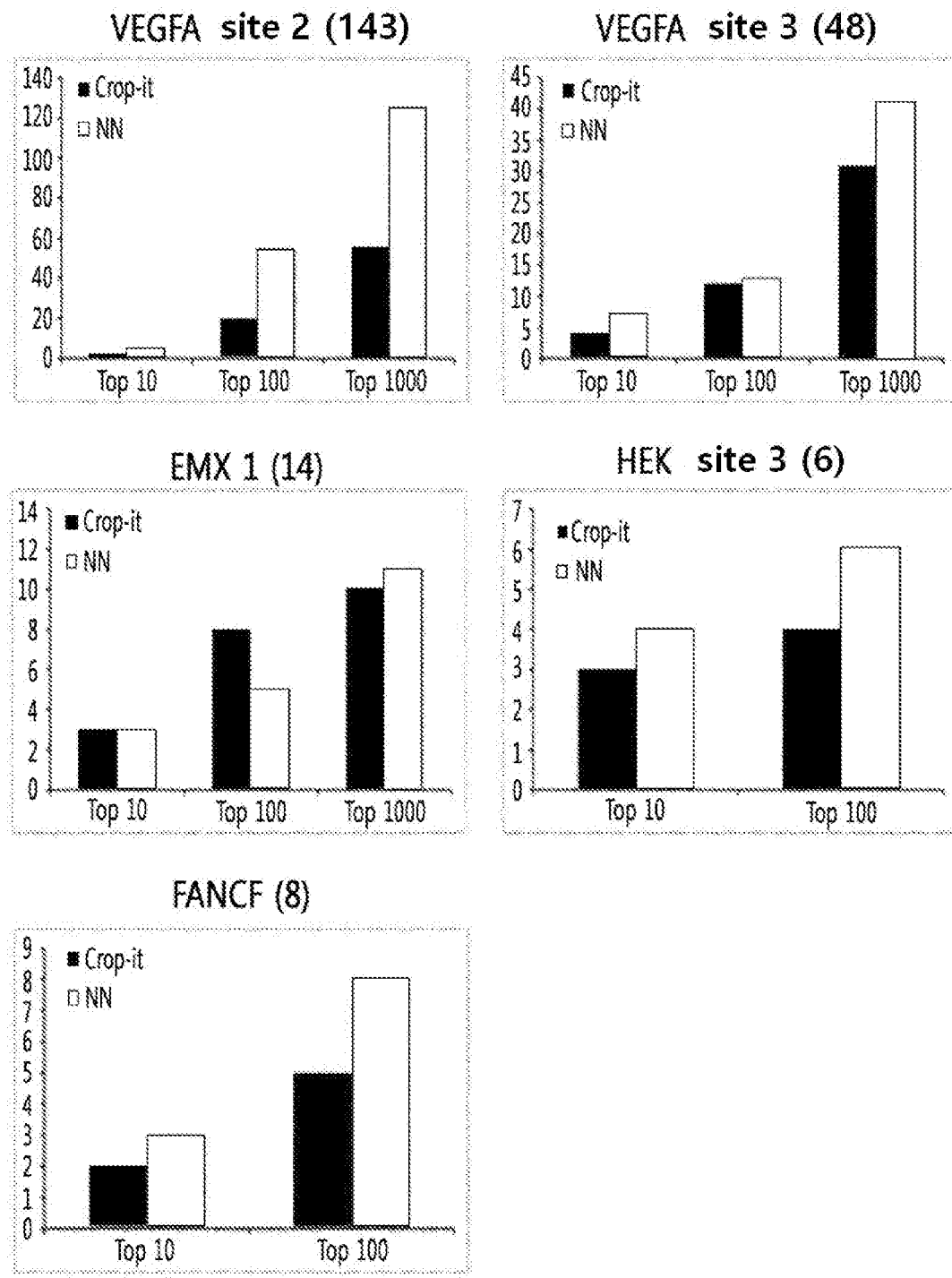

In another specific embodiment, a multiplex Digenome-seq was performed using sgRNA for 100 different on-target sites, and also in this case, off-target sites could be identified without particular limitation (FIG. 23). It was identified that the Digenome-seq of the present disclosure can be applied to any number of on-target sites without limitation.

In a specific embodiment of the present disclosure, for RNA-guided engineered nuclease (RGEN) targeting a specific site, among the off-target sites detected by Digenome-seq in the whole genome, when the homology site with a nucleotide mismatch to an on-target site of 6 or less is 13,000 or less and they do not have a homology site with a nucleotide mismatch of 2 or less, it was identified that the off-target effect can be minimized by selecting the specific site as the on-target site of the RGEN. This is an example showing a process of establishing a preferable criterion for selecting on-target sites using the Digenome-seq of the present disclosure, and it is expected that the off-target effect of programmable nucleases can be minimized through Digenome-seq.

In another specific embodiment of the present disclosure, it was identified that the number of sites having homology with the sequence at an on-target site was detected at a small rate by Digenome-seq as the nucleotide mismatch level increased (FIG. 16).

This is because the smaller the nucleotide sequence having homology in the target sequence and the genome in the selection of the on-target site of RGEN, the more specific the nucleotide sequence having a high homology. The on-target site of the selected RGEN through this may be that the of-target effect is minimized In another aspect, the present disclosure provides a method for reducing off-target effects in genome editing, comprising introducing in vitro transcribed guide RNA into cells having a plasmid as a template.

This off-target effect reduction is attributed to the prevention of indels at bulge-type off-target sites when the plasmid is used as a template. That is, when the guide RNA is prepared through in vitro transcription process, a large number of bulge-type off-target sites are detected when the oligonucleotide double strand is used as a template, but most of the bulge-type off-target sites disappear when the plasmid template is used. In addition to Digenome-seq, RGEN can be used to cleave genomic DNA and induce indels, which can use the plasmid as a template instead of an oligonucleotide double strand to reduce off-target effects. This is because oligonucleotides contain failed sequences, which are called (n-1)mer.

[Best Mode]

Hereinafter, the present disclosure will be described in detail with reference to examples. However, these examples of the present disclosure have been described herein for purposes of illustration only, and the scope of right of the present disclosure is not limited by these examples.

EXAMPLE 1

Cas9 and in vitro sgRNA

Recombinant Cas9 protein was purified from *E. coli* or purchased from ToolGen (South Korea). sgRNAs were synthesized by in vitro transcription using T7 RNA polymerase. Specifically, sgRNA templates were mixed with T7 RNA polymerase in a reaction buffer (40 mM Tris-HCl, 6 mM MgCl$_2$, 10 mM DTT, 10 mM NaCl, 2 mM spermidine, NTP, and RNase inhibitor) at 37° C. for 8 hours. Transcribed sgRNAs were purified using PCR purification kits (Macrogen) after being incubated with DNaseI to remove the template DNA.

EXAMPLE 2

Cell Culture and Transformation Conditions

HeLa cells were cultured in a DMEM medium containing 10% FBS. A Cas9 expression plasmid (500 ng) and a plasmid (500 ng) encoding sgRNA were introduced into 8×10$^4$ HeLa cells using lipofectamine 2000 (Life Technologies). After 48 hours, the genomic DNA was isolated with DNeasy Tissue kit (Qiagen) according to the manufacturer's instructions.

EXAMPLE 3

In vitro Cleavage of Genomic DNA

Genomic DNA was purified from HAP1 cells using DNeasy Tissue kit (Qiagen). In vitro cleavage of the genomic DNA was performed for Digenome-seq. Specifically, Cas9 protein and sgRNA were incubated at room temperature for 10 minutes to form RNP (ribonucleoprotein). Next, the RNP complex and the genomic DNA were reacted in the reaction buffer (100 mM NaCl, 50 mM Tris-HCl, 10 mM MgCl$_2$, and 100 μg/ml BSA) for 8 hours at 37° C. The genomic DNA cleaved during this process to decompose sgRNA was treated with RNase A (50 ug/mL), and purified again with DNeasy Tissue kit (Qiagen).

EXAMPLE 4

Whole Genome Sequencing and Digenome-seq (Cleaved Genome Sequencing)

For whole genome sequencing (WGS), the cleaved DNA was disrupted with a sonicator and ligated with an adapter to make a library. WGS was performed on the Illumina HiSeq X Ten Sequencer from Macrogen (South Korea) using this library. Then, Isaac was used to align the sequence file for the human reference genome hg19. The cleavage scoring system was used to identify the DNA cleavage site.

For multiplex Digenome-seq, the detection site results were classified into 11 groups according to edit distance. The computer program used to detect the in vitro RGEN cleavage site and the computer program used for Digenome detection site classification were generated separately.

EXAMPLE 5

Targeted Deep Sequencing

On-target sites and potential off-target sites were amplified using Phusion polymerase (New England biolabs). PCR amplification products were denatured with NaOH, paired-end sequencing was performed using Illumina MiSeq, and then the frequency of insertion and deletion (indels) was calculated.

EXPERIMENTAL EXAMPLE 1

Cleavage of Genomic DNA using RGEN in vitro

In order to develop a method for detecting off-target sites of programmable nucleases, the present inventors have conducted experiments using RGEN (RNA guided engineered nuclease) as a representative. However, this is only an example for explaining the technique of the present disclosure, and the kind of programmable nucleases that can be applied is not limited to RGEN. A method for detecting off-target sites of programmable nucleases in a genome of the present disclosure is characterized in that a genome is cleaved into programmable nucleases for a specific target in vitro, and then off-target sites of programmable nucleases was detected by performing and analyzing the whole genome sequencing (WGS). The present inventors named it Digenome-seq (nuclease-cleaved genomic DNA sequencing).

The present inventors reasoned that they could identify off-target mutations induced by programmable nucleases in a bulk population of cells by Digenome-seq.

It should be possible to cleave off-target DNA sequences efficiently at high RGEN concentration in vitro, producing many DNA fragments with identical 5' ends. These RGEN-cleaved DNA fragments would produce sequence reads that are vertically aligned at nuclease cleavage sites. In contrast, the sequence reads that were not cleaved by RGEN would be aligned in a staggered manner A computer program was developed to search for sequence reads with vertical alignment that correspond to off-target sites.

First, the present inventors tested whether RGENs could cleave potential off-target DNA sequences efficiently in a genome in vitro. For this, a HBB gene-specific RGEN that had been shown to induce off-target mutations at an on-target site of RGEN and a highly homologous site (refereed to as OT1 site) was chosen. In addition to this site, three other potential off-target sites (referred to as OT3, OT7 and OT12 sites) that differed from the on-target site of the RGEN by three nucleotides were analyzed.

Figure 1B:
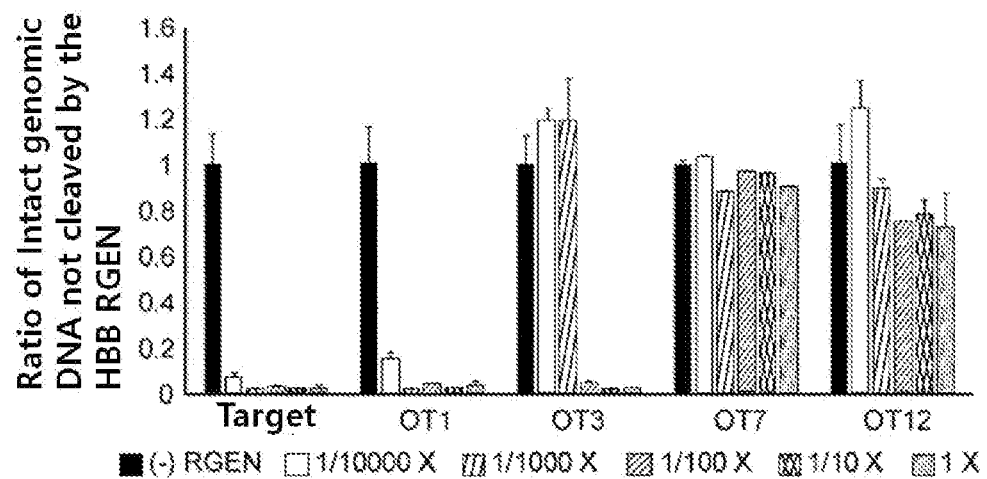

Genomic DHA isolated from wild-type HAP1 cells was cleaved using Cas9 protein pre-incubated with the HBB-specific sgRNA at concentrations that ranged from 0.03 nM to 300 nM (FIG. 1a). Then, quantitative PCR was used to measure DNA cleavage at these sites. Both the HBB on-target and OT1 sites were cleaved almost completely even at a very low RGEN concentration (FIG. 1b). By contrast, the OT3 site was cleaved completely only at high RGEN concentrations. The other two sites, OT7 and OT12, were cleaved poorly even at the highest concentration.

Next, this RGEN was transformed into HAP1 cells and used T7 endonuclease I (T7E1) and targeted deep sequencing were used to detect indels (insertion and deletion) induced at these sites.

For T7E1 assay, genomic DNA was isolated using DNeasy Tissue kit (Qiagen) according to the manufacturer's instructions. The on-target site was amplified by PCR. Next, amplified PCR products were denatured by heating and cooled slowly using a thermocycler. The cooled products were incubated with T7 endonuclease I (ToolGen) for 20 minutes at 37° C., and size-separated by agarose gel electrophoresis.

For targeted deep sequencing, genomic DNA segments spanning the on-target and off-target sites were amplified using Phusion polymerase (New England biolabs). The PCR amplicons were subjected to paired-end sequencing using Illumina MiSeq.

Figure 1C:
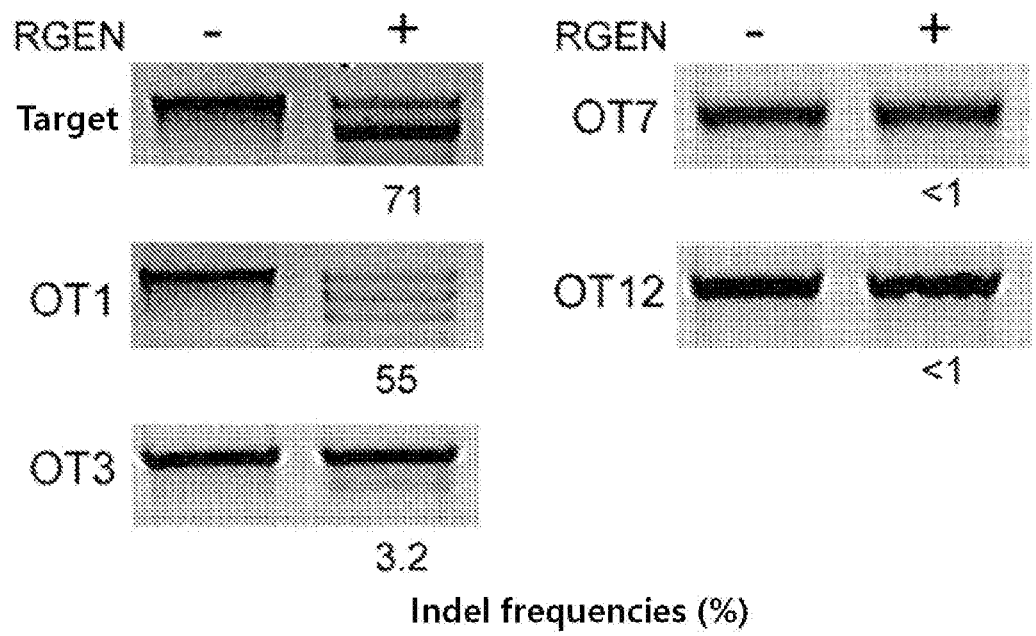
Figure 1D:
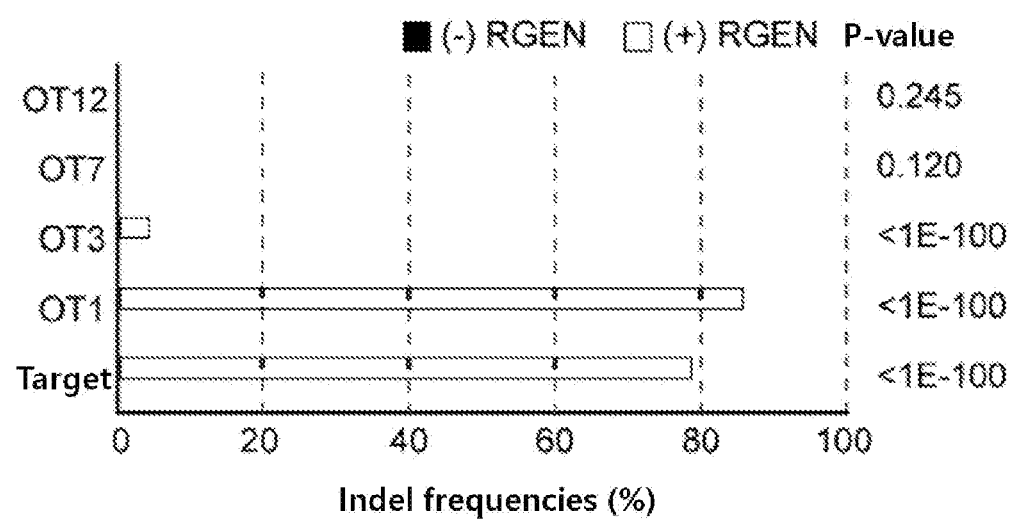

In interpreting the results, indels located 3-bp upstream of the PAM (protospacer-adjacent motif) were considered to be the mutations induced by RGENs. As expected, the HBB RGEN was highly active at both the HBB on-target and the OT1 off-target sites, producing indels at frequencies of 71% and 55% (T7E1), respectively (FIG. 1c). Off-target indels were also induced at the OT3 site with a frequency of 3.2% (T7E1) or 4.3% (deep sequencing) (FIGS. 1c, d). Meanwhile, at the other two potential off-target sites that were poorly cleaved in vitro, no indels were detected using T7E1 (detection limit, ~1%) and deep sequencing (detection limit, ~0.1%). Note that the OT7 site had no nucleotide mismatches in the seed region (10- to 12-nt sequence upstream of the PAM) but was not cleaved either in vitro or in cells, identifying the importance of the PAM-distal region.

These results are consistent with our previous finding that RGENs can cleave off-target DNA sequences in vitro but often cannot induce indels at the same sties in cells. Accordingly, RGENs appear much more promiscuous in vitro than in cells in terms of target specialty. Perhaps, most DNA double strand breaks (DSBs) generated by RGENs are repaired in cells by non-homologous end-joining (NHEJ) or homologous recombination (HR).

EXPERIMENTAL EXAMPLE 2

Sequence Read Analysis

Four different sets of genomic DNA were subjected to whole genome sequencing (WGS) to investigate whether in vitro cleavage of genomic DNA using RGENs can produce sequence reads with vertical alignment at cleavage sites.

Figure 2A:
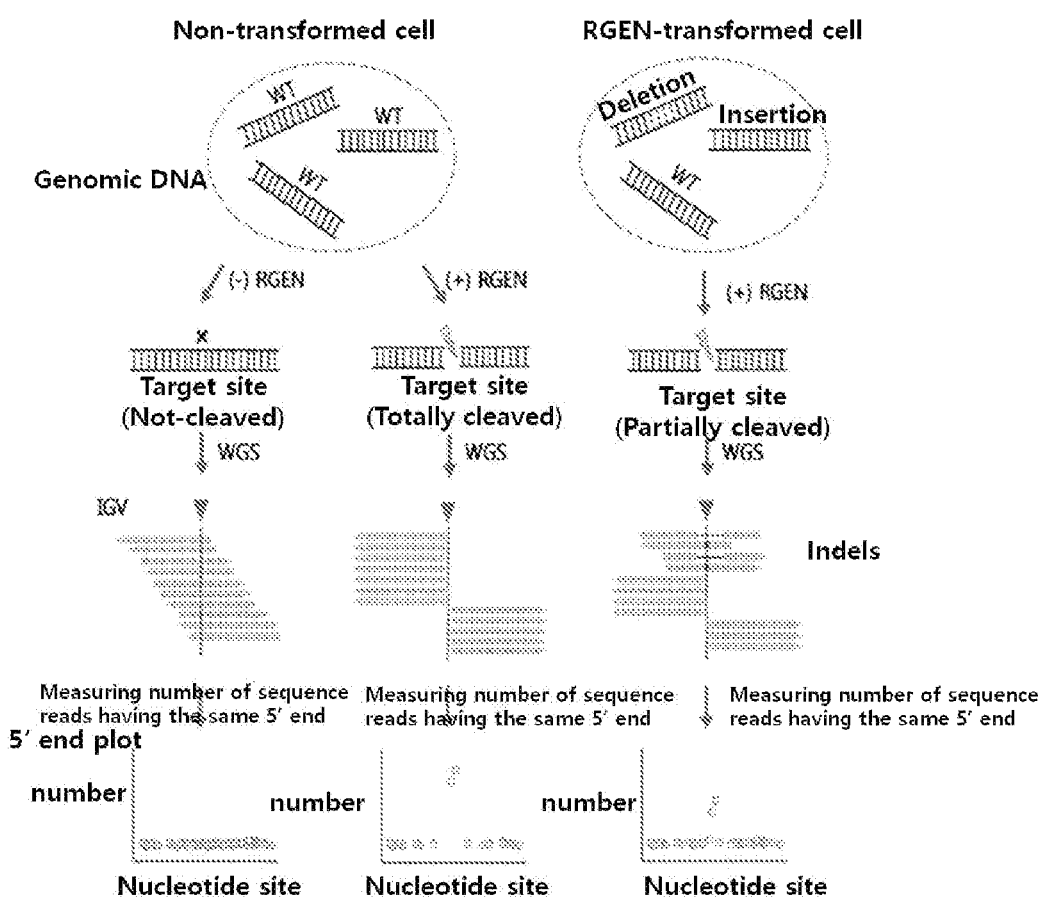
FIG. 2 relates to an RGEN-induced Digenome-seq to identify off-target sites. (a) It is a mimetic diagram of nuclease-cleaved whole genome sequencing (WGS) for the identification of off-target sites. Genomic DNA isolated from non-transfomed or RGEN-transfomed cells is cleaved by the RGEN, and subjected to WGS. Sequence reads are aligned to the reference genome (hg19) and visualized using the IGV program. Forward and reverse sequence reads are shown in orange and sky-blue, respectively. Red triangles and vertical dotted lines indicate cleavage positions. (b) It is the representative IGV data obtained using the HBB-specific RGEN at the on-target site. An indel is indicated by an arrow. (c) It shows the absolute and relative number of sequence reads with the same 5' end according to nucleotide positions.

Genomic DNA isolated from RGEN- and non-transformed HAP1 cells was completely cleaved in vitro with 300 nM Cas9 and 900 nM sgRNA targeting HBB genes. In parallel, WSG was performed without RGEN cleavage in vitro by using the genomic DNA isolated from these cells (FIG. 2a). After mapping sequence reads into the reference genome, IGV (intergrative genomics viewer) was used to observe patterns of sequence alignments at the on-target and the four homologous sites.

Figure 2B:
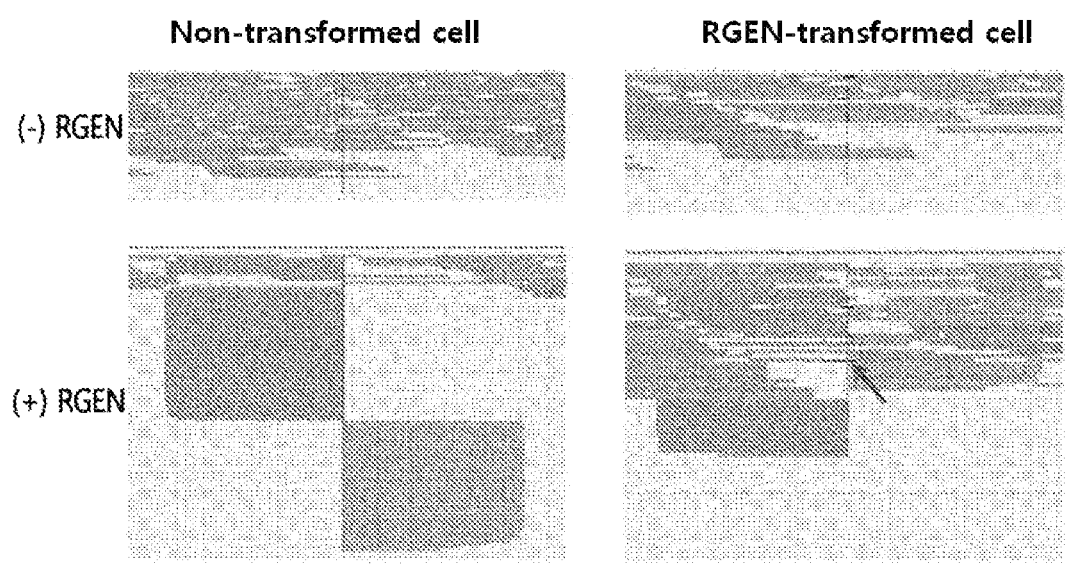
Figure 3A:
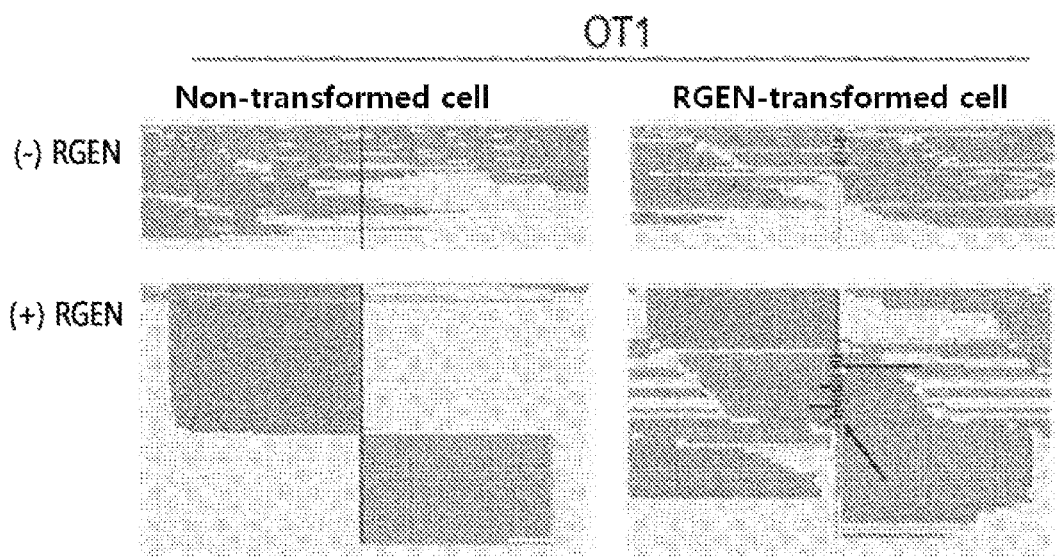
FIG. 3 relates to an RGEN-induced Digenome-seq to identify off-target sites. (a-d) It is the representative IGV data obtained using the HBB-specific RGEN at the potential off-target sites OT1 (a), OT3 (b), OT7 (c), and OT12 (d). An indel is indicated by an arrow (a) or shown in a box (b).
Figure 3B:
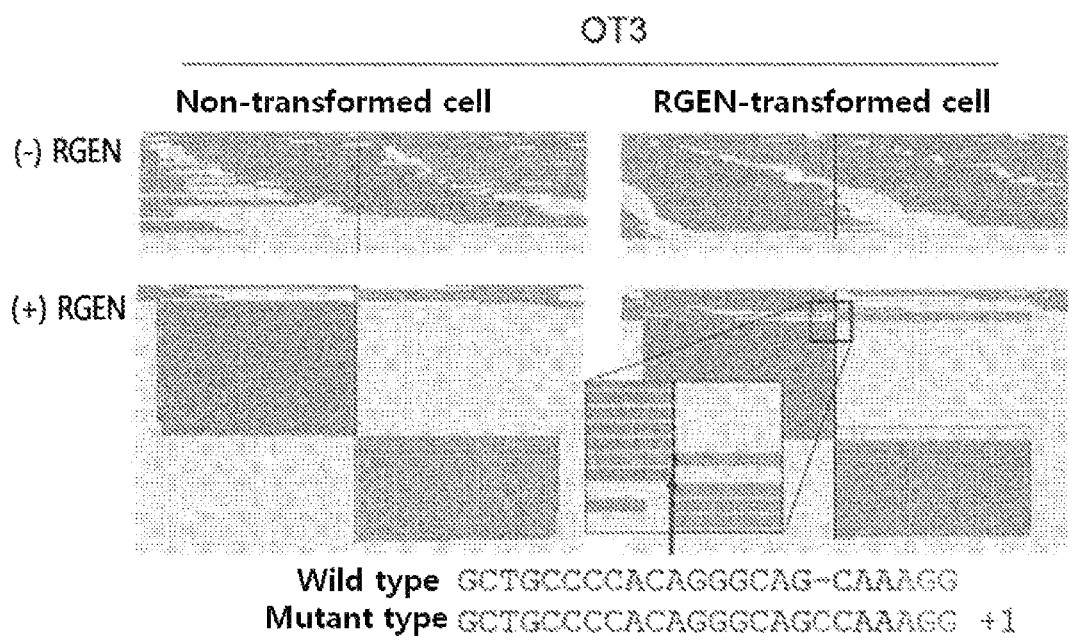
Figure 3C:
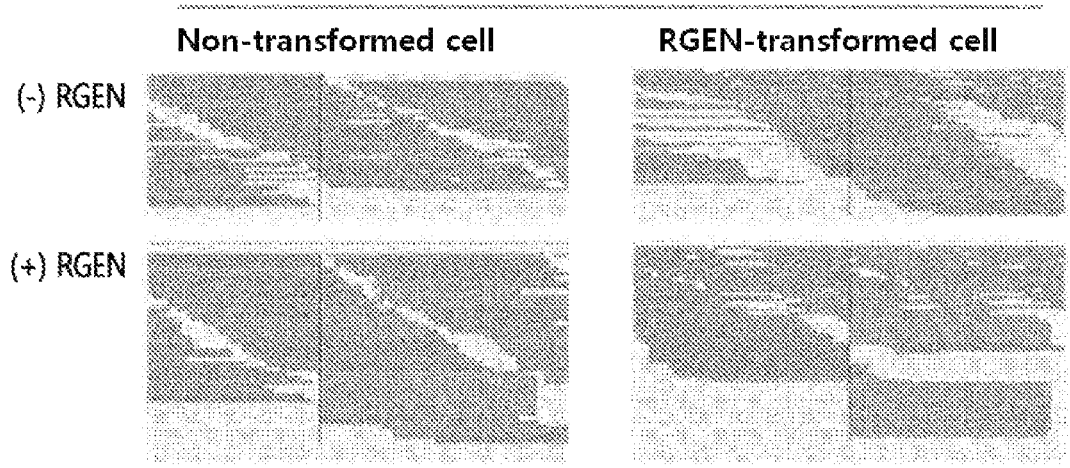
Figure 3D:
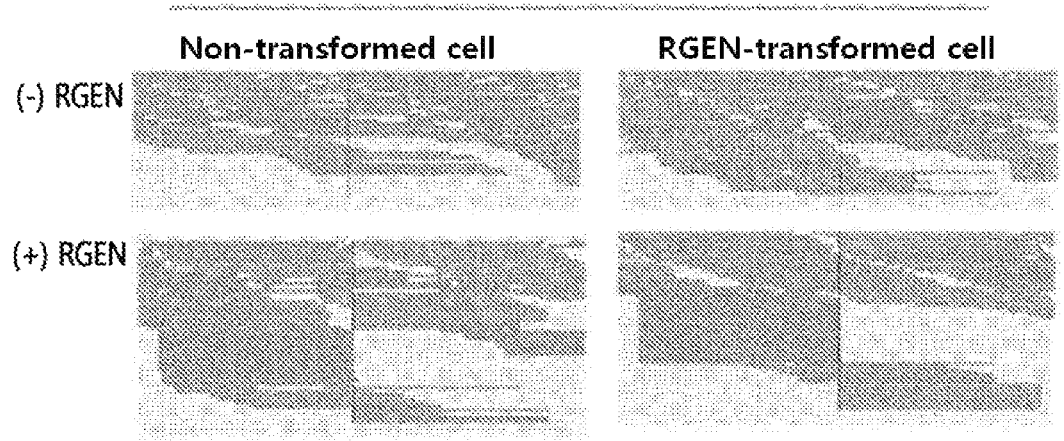

First, the Digenome (cleaved genome) isolated from control group HAP1 cells were examined. At the on-target, OT1, and OT3 sites, unusual patterns of vertical alignments were observed (FIG. 2b and FIG. 3a, b). Sequence reads that spanned the cleavage sites were very rare. In contrast, no such vertical alignments were observed at these sites when the intact genome that had not been treated with the RGEN was analyzed. At the OT7 and OT12 sites, most sequence reads spanned the potential cleavage site (3-bp upstream of the PAM), resulting in a staggered alignment (FIG. 3c, d).

Second, the Digenome isolated from RGEN-transformed cells was compared with the corresponding intact genome. At all five sites, the intact genome gave rise to typical patterns of staggered alignments (FIG. 2b and FIG. 3). In contrast, the Digenome showed both vertical and staggered alignments at the on-target and OT1 sites. At these two sites, almost all sequence reads corresponding to staggered alignments contained indels (FIG. 2b and FIGS. 3a and 3b). That is, note that RGENs cannot cleave indel sequences induced by themselves. Meanwhile, no indels were found with sequence reads that spanned the OT7 and OT12 cleavage sites, in line with the T7E1 and deep sequencing results. At the OT3 site, the Digenome showed a straight alignment pattern with a few sequence reads that spanned the cleavage sites. In particular, one sequence read contained an indel, induced by the RGEN (FIG. 3b).

These results suggest that Digenome-Seq is sensitive enough to allow identification of rear off-target mutations and that a vertical alignment of sequence reads is a unique signature of RGEN cleavage in vitro.

EXPERIMENTAL EXAMPLE 3

5' End Plot at Signal Nucleotide Scale

Figure 2C:
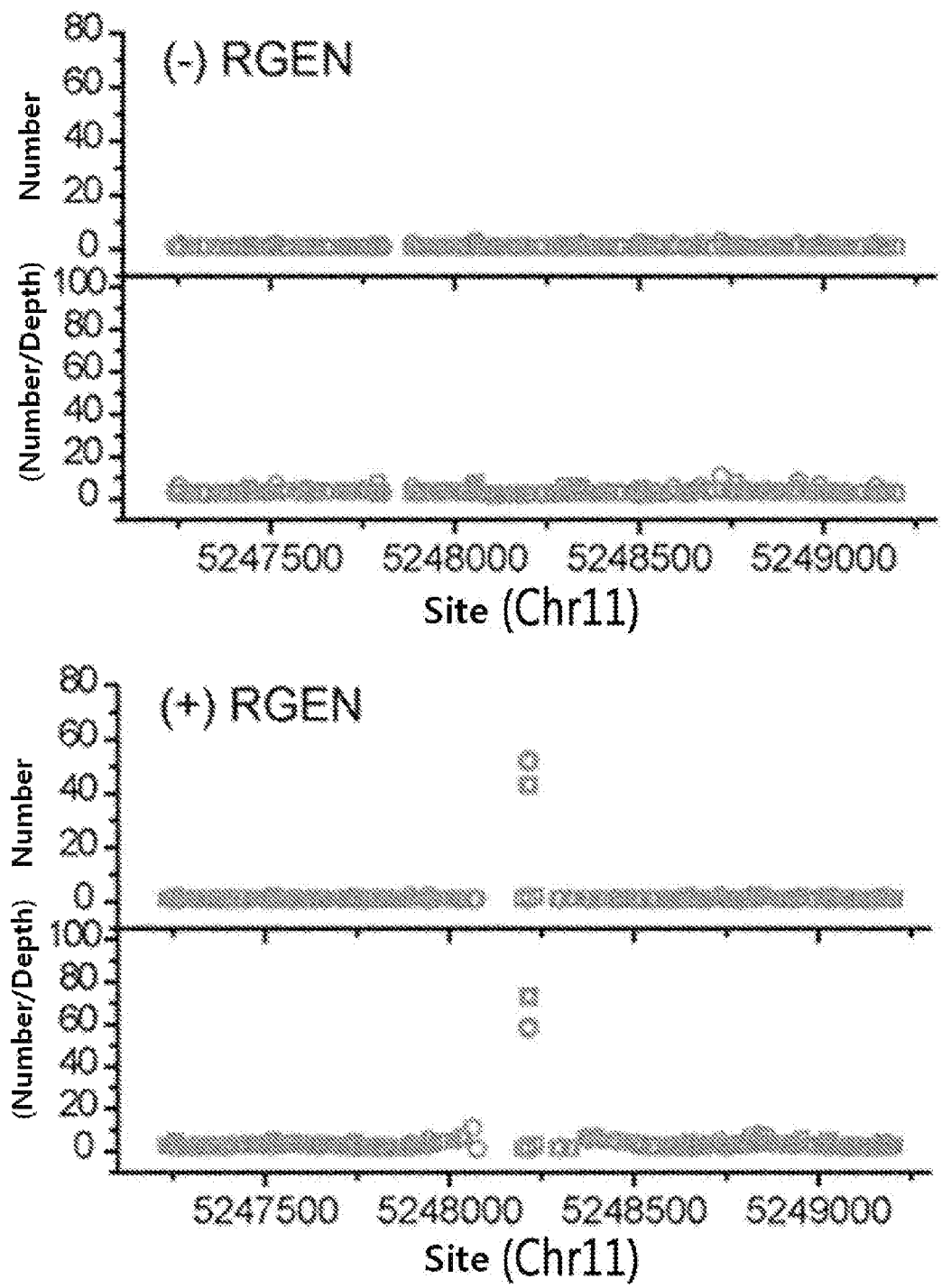
Figure 4A:
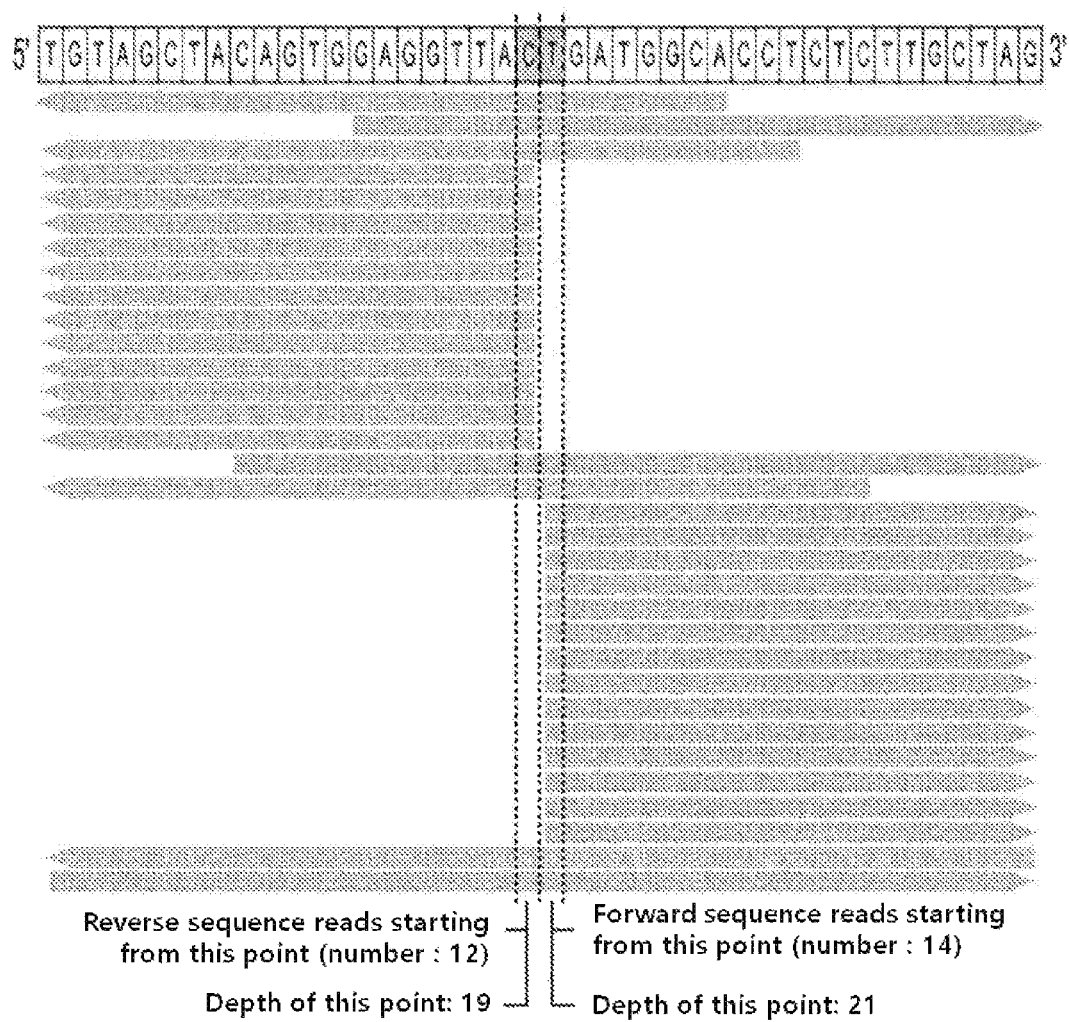
FIG. 4 illustrates a plot of the number of 5' ends at a particular location on a genome. (a) It shows IGV data at a nuclease cleavage site. (b, c) It illustrates 5' end plots showing the absolute and relative number of sequence reads with the same 5' end according to nucleotide positions at the OT1 (b) and OT3 (c) sites.

To identify potential RGEN off-target sites on a genomic scale, a computer program that searched for straight alignments of sequence reads was developed. First, the count of sequence reads whose 5' ends started at the nucleotide position near the HBB on-target and two validated off-target sites (OT1 and OT3) at single nucleotide scale (FIG. 4a) was plotted. Because both Watson and Crick strands were sequenced, it was assumed that almost an equal number of sequence reads, corresponding to each strand, should be observed right next to each other at a cleavage site, producing double peaks. As expected, the digenome gave rise to double peaks at the three cleavage sites (on-target site, OT1 and OT3) (FIG. 2c and FIG. 4b, c). The intact genome that had been undergone RGEN treatment in vitro did not produce such double-peak patterns at these sites.

Figure 5A:
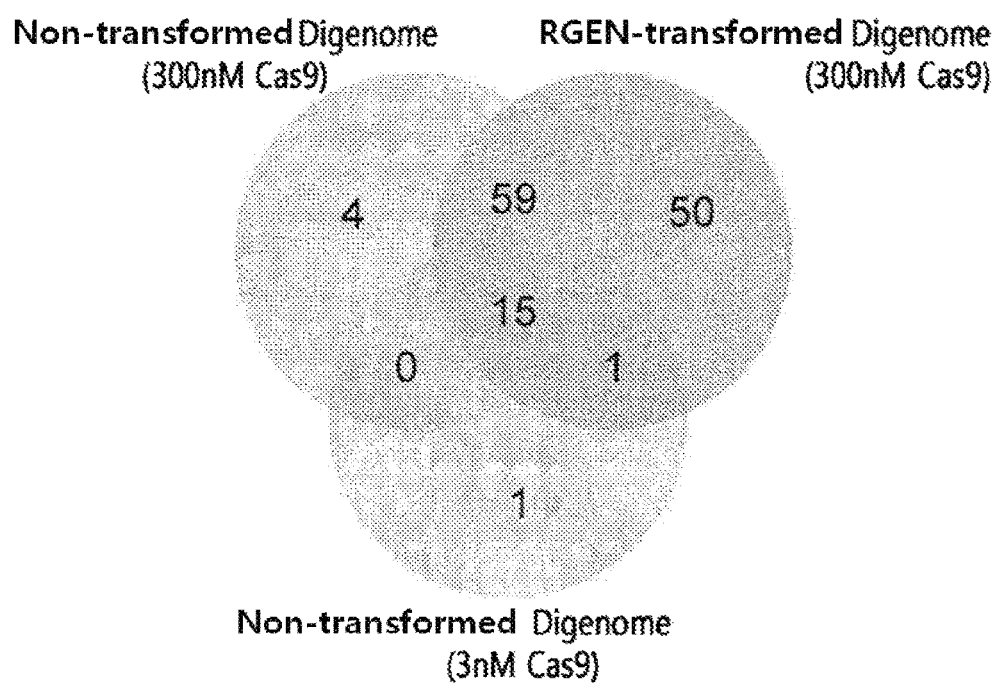
FIG. 5 illustrates off-target sites of the HBB RGEN identified by Digenome-Seq and validated by targeted deep sequencing. (a) It is a Venn diagram showing the number of on-target sites and off-target sites identified by Digenome-seq using the HBB RGEN in non-transformed or RGEN-transformed cells. (b) It illustrates a heatmap comparing sites identified by Digenome-seq with the on-target site. (c) It illustrates a sequence logo obtained by WebLogo using DNA sequences at sites identified by Digenome-seq. (d) It is a summary of the results of Digenome-seq and targeted deep sequencing. N.D. means that nothing is determined. (e) It illustrates off-target sites validated by targeted deep sequencing. Blue and red bars represent indel frequencies obtained using non-transformed HAP1 cells and the HBB RGEN-transformed HAP1 cells. (Left) It illustrates DNA sequences of on-target and off-target sites. Mismatched bases are shown in red, and the PAM sequences are shown in blue. (Right) P value was calculated by the Fisher exact test.

Next, this approach was applied to the entire RGEN-transformed Digenome, non-transformed Digenome, intact RGEN-transformed genome, and intact non-transformed genome. In addition, non-transformed genomic DNA was treated with Cas9 protein in vitro in the absence of sgRNA or with a 100-fold lower concentration of RGEN (3 nM Cas9) and subjected to WGS and Digenome analysis. The search was conducted for sites where the count of sequence reads with the same 5' end was greater than 10 in both strands and where at least 19% of sequence reads were aligned vertically. A total of 17 and 78 sites, including the on-target and two validated off-target sites, were identified in the non-transformed digenome treated with 3 nM and 300 nM RGEN (FIG. 5a), which showed double-peak patterns in a 5' end plot and straight alignments in a nIGV image. Among these sites, one and two sites in the digenomes treated with 3 nM and 300 nM RGEN were false positives that resulted from naturally-occurring indels. In addition, such patterns were observed at a total of 125 sites, including the three validated on- and off-target sites in the RGEN-transformed Digenome. Meanwhile, the invalidated OT7 and OT12 sites did not show double-peak patterns in these three digenomes. Moreover, most sites were commonly identified in the three Digenomes, demonstrating the high reproducibility of Digenome-seq. Specifically, 15 (94%) of the 16 candidate sites (excluding the one false positive site) found in the non-transformed Digenome (3 nM RGEN) were also identified in the other two Digenomes. 74 (97%) of 76 candidate sites found in the non-transformed Digenome (300 nM) were also identified in the RGEN-transformed digenome (FIG. 5a). Other than the three validated cleavage sites, none of the other 122 sites were accompanied by indels in the RGEN-transformed Digenome, suggesting that mutations at these candidate sites occurred rarely. Meanwhile, such double-peak patterns were observed at only two positions in the intact genome, three positions in the intact RGEN-transformed genome, and one position in the Cas9 (300 nM) alone-treated, non-transformed genome. All of these positions identified in the three intact genomes were false positive that resulted from naturally-occurring indels in the HAP1 genome relative to the reference genome (FIGS. 6a to 6c). Accordingly, double-peak patterns or vertical alignments of sequence reads were unique features found in the Digenomes.

Figure 5B:
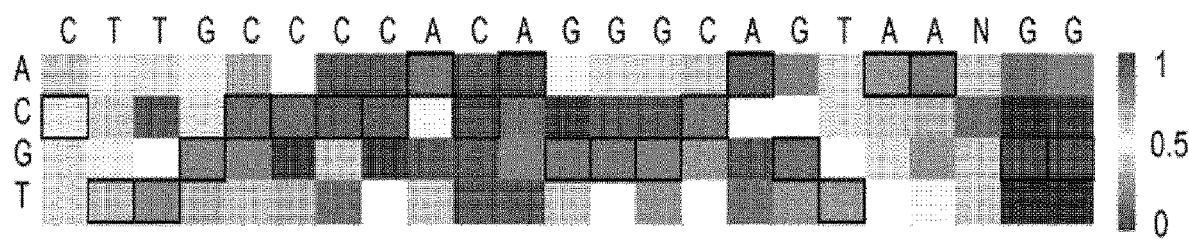
Figures 5C, 5D:
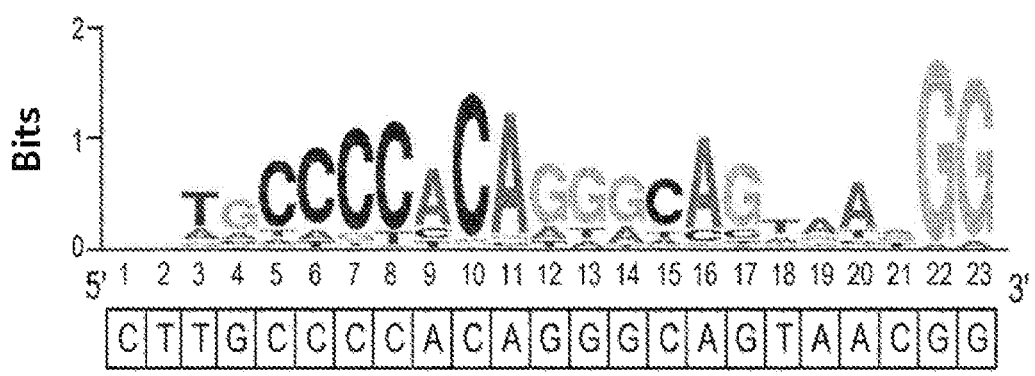

Next, DNA sequences at the 74 common sites identified in the RGEN-transformed and non-transformed Digenomes were compared with the 20 bp on-target site and it was found that of the 20 nucleotides, all but the one at the 5' end were conserved (FIG. 5b). Furthermore, the sequence logo or de novo motif obtained by comparing the DNA sequences at the 74 sites with one another rather than with the on-target sequence clearly showed matches with the on-target sequence at all positions other than the first two nucleotides (FIG. 5c). In addition, 70 (95%) of these double-peak positions were accompanied by the 5'-NAG-3'PAM exactly 3 nucleotides downstream from the expected cleavage position. Only 6.25% (=1/16) of sites are expected to be accompanied by a PAM by chance. Two sites contained the 5'-NAG-3'PAM. Some sites were matched to the on-target site by allowing a DNA or RNA bulge or assuming 5'-NGA-3' as a non-canonical PAM. It is questionable whether 5'-NGA-3' can function as a PAM in cells, but, under our extreme in vitro cleavage conditions, RGENs may cleave these sites. The other sites had no sequence homology with the on-target sequence, suggesting that they could be false positives.

In addition, the fewer nucleotide mismatches there were in homologous sites, the more likely they were to be detected by Digenome-seq. That is, 7 out of 15 (47%) and 14 out of 142 (10%) homologous sites that differed by 3 and 4 nucleotides from the on-target site were detected, but only 15 out of 1,191 sites (1.2%) and one out of 7,896 sites (0.013%) that differed by 5 and 6 nucleotides were detected (FIG. 5d).

Taken together, these results indicate that most of the double-peak patterns are caused by RGEN cleavage in vitro and that Digenome-seq can find nuclease cleavage sites on a genomic scale.

EXPERIMENTAL EXAMPLE 4

Deep Sequencing to Identify Off-Target Effect at Candidate Sites

Figure 5E:
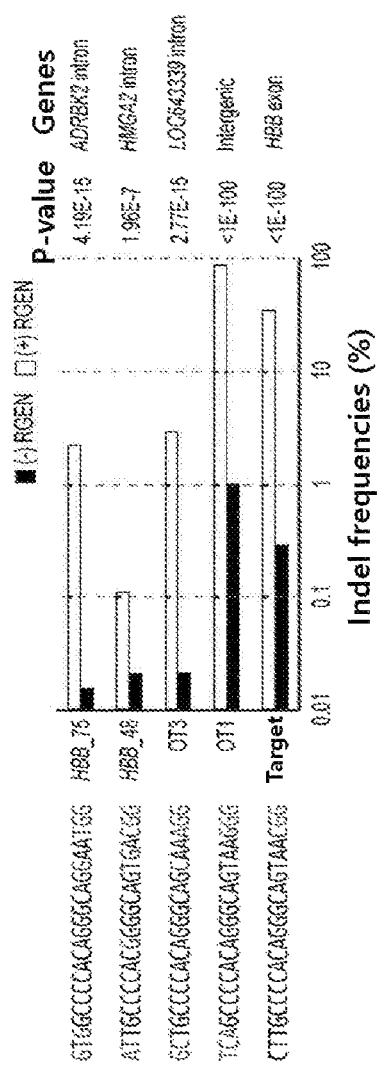

Deep sequencing was performed to validate off-target effects at the 74 common sites identified in the two Digenomes (FIG. 5e). Moreover, the other 8 sites that differed from the on-target site by three nucleotides but were not detected by Digenome-seq was also tested. No off-target indels were detected at these 8 sites with a frequency of at least 0.1% and greater than that of negative control group (Fisher exact test, p<0.01) (FIG. 5d). Indels were observed at a total of 5 sites including already-validated on-target, OT1, and OT3 sites, among the 74 sites, with frequencies ranging from 0.11% to 87% (FIG. 5e and FIG. 7a, b). At the other two newly-validated off-target sites, termed HBB_48 and HBB-75, indels were detected with a frequency of 0.11% and 2.2%. These two sites differed from the on-target site by three nucleotides. There were three nucleotide mismatches at the HBB_48 site and two mismatches at the HBB_75 site, relative to the 20-nt sgRNA sequence, which differed from the on-target site by one nucleotide at the 5' end. None of these validated off-target sites harbored a DNA or RNA bulge compared to the 20-nt sgRNA sequence, nor were they accompanied by a non-canonical PAM such as 5'-NGA-3' or 5'-NAG-3'. Note that these two new off-target sites and the other three sites were identified independently in each of the three Digenomes. These results show that Digenome-seq is a sensitive and reproducible method to identify nuclease off-target effects on a genomic scale.

EXPERIMENTAL EXAMPLE 5

Digenome Sequencing for VEGF-A Specific RGEN

Next, the present inventors tried to identify whether Digenome-seq is applicable to the other genes other than the HBB genes. Digenome-seq was performed with another RGEN that had been shown to induce on-target mutations at a VEGF-A locus and additionally, off-target mutations at four homologous sites. A total of 81 sites, including the on-target and four already validated off-target sites, were identified that showed double-peak patterns (FIG. 8a and FIG. 9). All of the DNA sequences at these 81 sites contained the canonical 5'-NGG-3' PAM sequences. Comparison of these sequences with the on-target sequences showed matches at every nucleotide site. Moreover, these sequences were also compared with one another to obtain a de novo motif: The resulting sequence logo also showed matches with the target sequence at almost every nucleotide position, suggesting that every nucleotide in the 20-nt sgRNA sequence contributed to the specificity of RGEN (FIGS. 8b and 8c).

Next, targeted deep sequencing was used to identify on-target and off-target effects at the 81 sites identified by Digenome-seq and 28 sites that differed by 3 or fewer nucleotides from the on-target site but were not identified by Digenome-seq. This RGEN was highly active in HAP1 cells, producing indels at the on-target site with a frequency of 87% and at the four previously-validated off-target sites with frequencies that ranged from 0.32% to 79%. In addition, four off-target sites were additionally identified at which indels were induced with frequencies that ranged from 0.065 ±0.021% to 6.4 ±1.2% (FIG. 8e and FIG. 10). The indel frequency at these sites obtained using the RGEN was significantly greater than that obtained using an empty vector control group (Fisher exact test, p<0.01). These off-target sites contained one to six nucleotide mismatches with the 20-nt target sequence and at least one mismatch in the PAM-proximal seed region. There are 13,892 sites with 6-nt mismatches in the human genome but only 6 sites (0.043%) were identified by Digenome-seq and, among them, only one site was validated by deep sequencing (FIGS. 8d and 8e). Thus far, an RGEN off-target site with 6-nt nucleotide mismatches with on-target sites had never previously been identified. None of these off-target sites contained a DNA or RNA bulge, although 40 out of 81 sites identified by Digenome-seq contained a missing or extra nucleotide compared to the 20-nt target sequence. At all the other sites, including those not identified by Digenome-seq, indel frequencies obtained using the RGEN were 0.05% or less, or were smaller than or not statistically different from those obtained using an empty vector control group.

It can be seen from these Experimental examples 1 to 5 that the Digenome-seq of the present disclosure is a very highly reproducible method for detecting off-target sites of programmable nucleases.

EXPERIMENTAL EXAMPLE 6

Improved Digenome-seq

First, the present inventors developed a scoring system capable of identifying an in vitro cleavage site using the whole genome sequencing (WGS) data on a human genome. The Digenome-seq analysis identified in these Experimental examples 1 to 5 has a high reproducibility, but there is a problem that some sites having a heterogeneous cleavage pattern or a low sequencing depth may be missing. The present inventors have found that these sites can be identified by estimating the case where the Cas9 protein makes one or two nucleotide overhangs at the blunt end. Based on the alignment pattern of the sequence read, a DNA cleavage score was assigned to each nucleotide site (FIG. 11).

Through this program, a number of additional sites that were not detected in the existing Digenome-seq were detected. A genomic scale plot of the cleavage score shows that few false positive sites are found in the uncleaved genomic DNA (FIG. 12a):

A small number of false positive sites identified in the whole genome include indels (insertion and deletion), which occurs naturally in genomic DNA, which can be easily screened. As can be seen in two independent Digenome-seq analyses, the cleavage score for the human genome has a high reproducibility (R2=0.89) (FIG. 13).

Figure 12B:
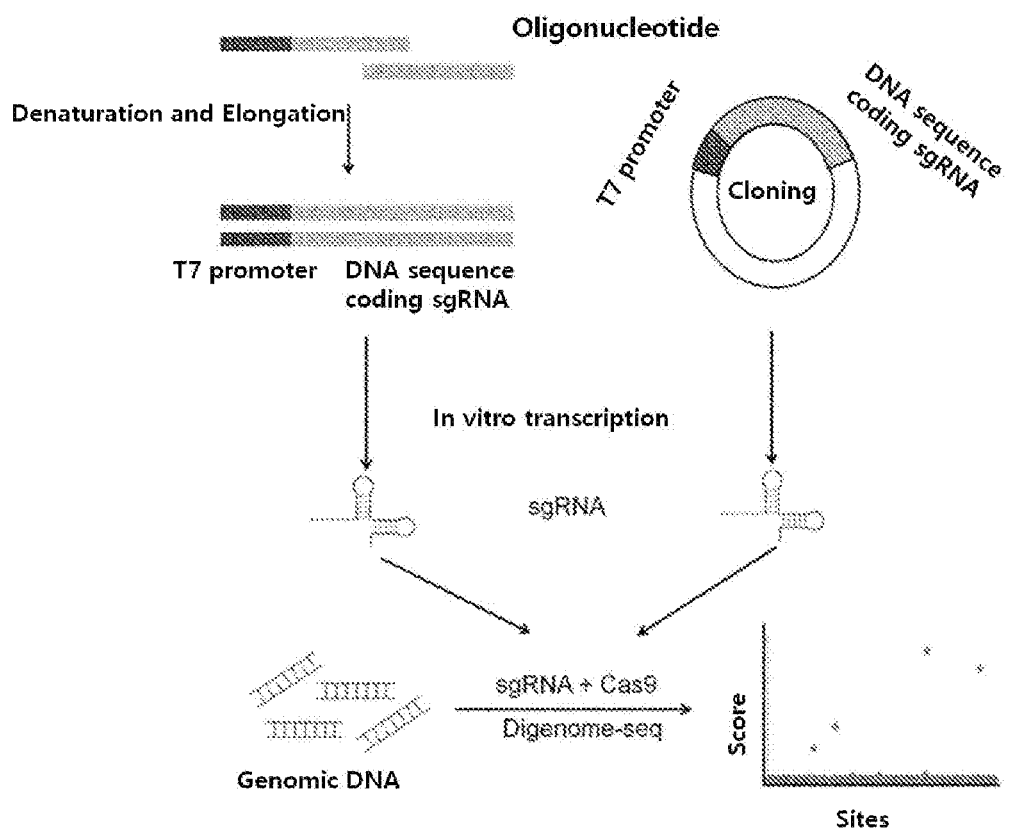
Figures 13, 14:
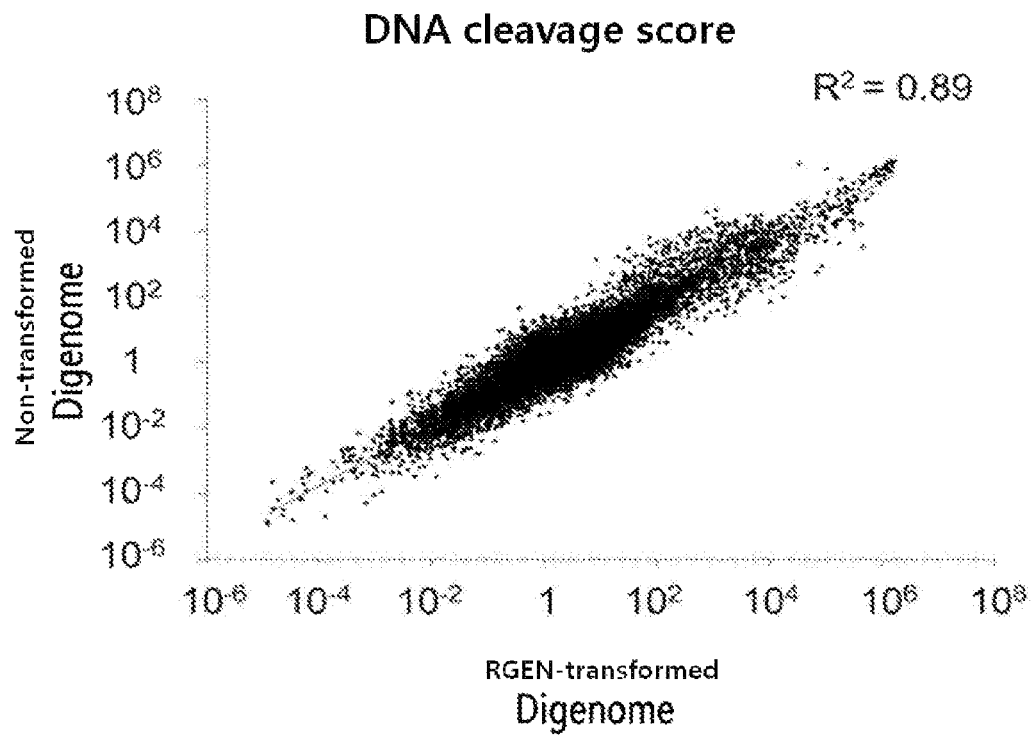
FIG. 13 illustrates the reproducibility of the in vitro DNA cleavage scoring system.
FIG. 14 illustrates a bulge-type off-target site identified by Digenome-seq using sgRNA transcribed from an oligonucleotide double strand.

The present inventors also found that the sgRNA transcribed through the plasmid template in the Digenome-seq analysis does not cleave even a bulge-type off-target site of any nucleotide-deficient false positive at an on-target site where it was detected with transcribed one using oligonucleotide double strand (FIG. 12b and FIG. 14).

This is because sgRNA transcribed from the oligonucleotide double strand is not a homogeneous component, including incomplete molecules transcribed from oligonucleotides that failed to synthesize. As a result, the cleavage sites identified using the sgRNA transcribed from the plasmid template are more highly homologous to the on-target site than those identified using the sgRNA transcribed from the oligonucleotide template (Table 1 and Table 2). The DNA sequences surrounding the cleavage site can be identified from a sequence logo obtained by comparing them (FIG. 12c).

TABLE 1

| Oligonucleotide template | | | |
|---|---|---|---|
| Chromosome | location | DNA sequence at cleavage site | Bulge |
| chr11 | 5248215 | CTTGCCCCACAGGGCAGTAACGG | x |
| chr1 | 38230668 | CTCTGTCTCGCGCTGCTTTTGGG | x |
| chr1 | 177593980 | TCTACCCCACATGGCAGTAATGG | x |
| chr2 | 112686732 | GGTCCCGGGAATAGCGGGTAAGG | x |
| chr2 | 240591539 | ACAGCCCCACAGGGCACTAGAGG | x |
| chr3 | 3662556 | AAAGCCCCACAGGGTAGTAGAGG | x |
| chr3 | 19957634 | GCTACCCCACAGGGCATTAGGGG | x |
| chr4 | 45763604 | GCTGCCCCACATGACAGAAATGG | x |
| chr4 | 48091817 | ACTCGTCTCCGATATCCAGTTGG | x |
| chr4 | 55979545 | GGTGTAACCCGGAGTGACCAAGG | x |
| chr4 | 55979546 | GGTGTAACCCGGAGTGACCAAGG | x |
| chr4 | 148531374 | GTTACCTCACAGAGCAGAAAGGG | x |
| chr4 | 165593737 | TATGCTCCAGAGGGTAGTAATGA | x |
| chr5 | 14347051 | CATACCCCACAGGTCAGTAAGGA | x |
| chr5 | 131423385 | TCTGCCCCACAGGCCAGGAAGGG | x |
| chr6 | 50041372 | TCTGCCCCACATGGCAGTAATGA | x |
| chr6 | 80093919 | TGAGTTCTCCAATATCCAGTTGG | x |
| chr6 | 85738203 | ACTGCCCCACAGGGAAGTAATAG | x |
| chr8 | 41296595 | TCAGCCCCACAGGTCAGCAATGG | x |
| chr9 | 24439672 | GGACTCCTCCAATATCCTGTTGG | x |

TABLE 1-continued

Oligonucleotide template

| Chromosome | location | DNA sequence at cleavage site | Bulge |
|---|---|---|---|
| chr9 | 78341070 | GTTACCCC-CAGGGAAGTATAGG | RNA Bulge |
| chr9 | 104595883 | TCAGCCCCACAGGGCAGTAAGGG | x |
| chr9 | 134609673 | TTTGCCCCTCAGGGCAGCTAAGG | x |
| chr9 | 134994964 | CCTGCCCCACAGGGCAATTATGG | x |
| chr10 | 71843328 | CATGGCCAGGAAGAGAAGGCTGG | x |
| chr10 | 72286450 | CAAGCCCCACAGGGCAGACAGGG | x |
| chr10 | 73555691 | CAGGCCCCACAGGACAGGAAGGG | x |
| chr11 | 3125346 | AGCCCCCACAGGGCAGGTAGGGG | x |
| chr11 | 59611432 | CGGCCAGATTCATGGCAATCAGG | X |
| chr11 | 76387498 | CTGCCCCTCAGGGACAGTATGGG | x |
| chr12 | 27234755 | GATGCCTCACAGGACAGGAAGGG | x |
| chr12 | 40327469 | GCTATGGTTCCTGAACGGCCTGG | x |
| chr12 | 93549202 | ATTGCCCCACGGGSCAGTGACGG | x |
| chr12 | 124803834 | GCTGCCCCACAGGGCAGCAAAGG | x |
| chr13 | 29005426 | TTGGTCAATTCGTCGCCTTACGG | x |
| chr13 | 44886376 | GGAGCCCCACAGGGCAGAGAGGG | x |
| chr14 | 36889538 | GTTATCCCACAGGACAGTGAGGG | x |
| chr14 | 59445901 | CTT-CCCCAATATCCAGT-AGGG | RNA Bulge |
| chr14 | 94585327 | ATGGCCCCACAAGGCAGAAATGG | x |
| chr15 | 29983547 | CCAGCCCCACAGGGCAGTAAAGC | x |
| chr15 | 46598129 | GTTGCCCCTCAGGACAGTACAGG | x |
| chr15 | 99709337 | TGTGCCCCACAGG-AGTGAGGG | RNA Bulge |
| chr16 | 49082904 | GCAGCCCCACAGGTCAGTGAGGG | x |
| chr17 | 8370253 | TGCTCCCACAGGGCAGTAAACGG | x |
| chr18 | 745994 | AAAATACCTCGTTGATTTCCAGG | x |
| chr18 | 6663844 | GTTGCCCCACTGGGGAGAAAAGG | x |
| chr19 | 29880768 | TGTGCCCCACAGG-CAGTAGATG | RNA Bulge |
| chr19 | 34262013 | CTGCTCCACAGGGCAGGTATGGG | x |
| chr19 | 37539042 | CTTGCACCACAGAGCACTAAGGG | x |
| chr20 | 39992928 | AGTGGCCCCAGGGCAGTGAGGG | x |
| chr22 | 17230623 | TGTGCCCCACAGAGCACTAAGGG | x |
| chr22 | 35537395 | AGTGCCCCACAGGGGAGAAATGG | x |
| chrX | 75006257 | GTGGCCCCACAGGGCAGGAATGG | x |
| chrX | 132429379 | GCATCCCCACAGGGCAGTATGTG | x |

TABLE 2

Plasmid template

| Chromosome | location | DNA sequence at cleavage site | Bulge |
|---|---|---|---|
| chr11 | 5248215 | CTTGCCCCACAGGGCAGTAACGG | x |
| chr1 | 17346702 | GGTCCCCACAGGGTCAGTAAGGG | x |
| chr1 | 177593980 | TCTACCCCACATGGCAGTAATGG | x |
| chr3 | 3662556 | AAAGCCCCACAGGGTAGTAGAGG | x |
| chr3 | 19957634 | GCTACCCCACAGGGCATTAGGGG | x |
| chr4 | 148531374 | GTTACCTCACAGAGCAGAAAGGG | x |
| chr5 | 14347051 | CATACCCCACAGGTCAGTAAGGA | x |
| chr5 | 131423385 | TCTGCCCCACAGGCCAGGAAGGG | x |
| chr6 | 23709579 | GAAGCCCTACAGGGCAGCAATGG | x |
| chr6 | 50041372 | TCTGCCCCACATGGCAGTAATGA | x |
| chr8 | 24931381 | AGTGCCACACACAGCAGTAAGGG | x |
| chr9 | 104595883 | TCAGCCCCACAGGGCAGTAAGGG | x |
| chh9 | 134994964 | CCTGCCCCACAGGGCAATTATGG | x |
| chr10 | 72286450 | CAAGCCCCACAGGGCAGACAGGG | x |
| chr10 | 73555691 | CAGGCCCCACAGGACAGGAAGGG | x |
| chr11 | 76387498 | CTGCCCCTCAGGGACAGTATGGG | x |
| chr12 | 27234755 | GATGCCTCACAGGACAGGAAGGG | x |
| chr12 | 93549202 | ATTGCCCCACGGGGCAGTGACGG | x |
| chr12 | 124803834 | GCTGCCCCACAGGGCAGCAAAGG | x |
| chr13 | 44886376 | GGAGCCCCACAGGGCAGAGAGGG | x |
| chr14 | 36889538 | GTTATCCCACAGGACAGTGAGGG | x |
| chr14 | 94585327 | ATGGCCCCACAAGGCAGAAATGG | x |
| chr15 | 34059408 | GTTACCACACAGAGCAGTTAAGG | x |
| chr15 | 46598129 | GTTGCCCCTCAGGACAGTACAGG | x |
| chr16 | 49082904 | GCAGCCCCACAGGTCAGTGAGGG | x |
| chr17 | 8370253 | TTGCTCCCACAGGGCAGTAAACG | x |
| chr19 | 8560462 | AAATCCCCACAGGGCAGTAAGGC | x |
| chr20 | 39992928 | AGTGGCCCCAGGGCAGTGAGGG | x |
| chr22 | 17230623 | TGTGCCCCACAGAGCACTAAGGG | x |
| chrX | 75006257 | GTGGCCCCACAGGGCAGGAATGG | x |

Accordingly, the number of false negative sites can be significantly reduced using the cleavage scoring system of the present disclosure, and the number of false positive sites can be significantly reduced using the sgRNA transcribed in the plasmid template.

EXPERIMENTAL EXAMPLE 7

Multiplex Digenome-Seq

Figure 15A:
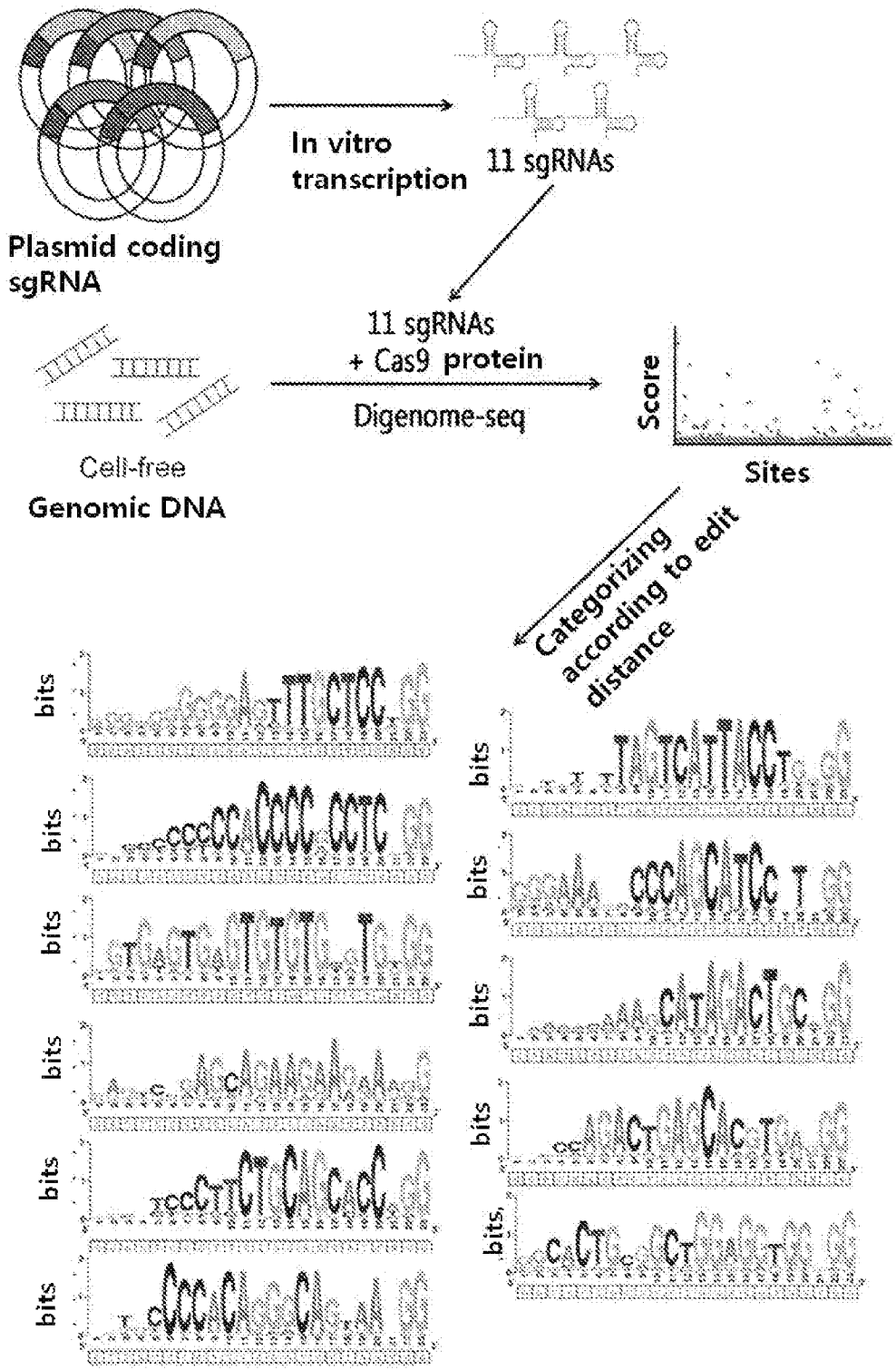
FIG. 15 illustrates a multiplex Digenome-seq. (a) It illustrates a mimetic diagram of a multiplex Digenome-seq. (b) It illustrates a Venn diagram showing the number of in vitro cleavage sites identified by single and multiplex Digenome-seq analyses. (c) It illustrates an in vitro DNA cleavage score on the X-chromosome obtained by single or multiplex Digenome-seq.

Unlike the other methods, Digenome-seq can be used in combination without increasing sequencing depth proportional to the number of nuclease. The present inventors selected 10 sgRNAs that were individually analyzed using GUIDE-seq, which is more sensitive than IDLV detection and other methods. The present inventors cleaved human genomic DNA with a mixture of one additional sgRNA targeting Cas9 protein, 10 sgRNA, and HBB gene, and performed two independent WGS analyses (FIG. 15a).

Next, the scoring system was used to investigate in vitro cleavage sites on a genomic scale. As a result, a total of 964 sites were identified in the human genome (Tables 3 to 12). Next, the site was then classified according to the edit distance to the on-target site (FIG. 15a and Tables 3 to 12).

TABLE 3

| VEGFA1 | | | |
|---|---|---|---|
| Chr | Position | DNA cleavage Score | DNA seq at a cleavage sites |
| Chr6 | 43737290 | 389070 | GGGTGGGGGAGTTTGCTCCAGG |
| Chr15 | 65637537 | 255675 | GGATGGAGGGAGTTTGCTCCTGG |
| Chr5 | 7067159 | 221853 | GAGGGTGGGGAGTTTACTCCTGG |
| Chr1 | 99347651 | 212884 | GGGGAGGGGAAGTTTGCTCCTGG |
| Chr12 | 1988077 | 206789 | CGGGGGAGGGAGTTTGCTCCTGG |
| Chr22 | 37215276 | 204286 | GGGTGGGGGAGTTTGCCCCAGG |
| Chr17 | 32986325 | 177694 | GGGGGTGGGGACTTTGCTCCAGG |
| Chr1 | 82627648 | 185975 | GGGTGCTGGCACAGTGCTCCTGG |
| Chr12 | 26841302 | 164500 | AGTTTGGGGGAGTTTGCCCCAGG |
| Chr1 | 233157354 | 156007 | GGAGGAGGGAGTCTGCTCCAGG |
| Chr10 | 124731416 | 153228 | AGCTGGAGGGAGTTTGCCCCAGG |
| Chr12 | 131690199 | 143751 | GGGAGGGTGGAGTTTGCTCCTGG |
| Chr11 | 71497119 | 143413 | AGGAAGGAGGAGTTAGCTCCTGG |
| Chr20 | 7836107 | 142045 | CAGGTGGGAGAGTTTGCTCCCAG |
| Chr17 | 39796328 | 140863 | TAGTGGAGGGAGCTTGCTCCTGG |
| Chr4 | 8453803 | 140625 | GAGTGGGTGGAGTTTGGTACAGG |
| Chr9 | 88657759 | 140587 | GGATGGAGGTAGTTTGTTCCTGG |
| Chr9 | 93925190 | 140509 | GGGGGTGGGGAGCATGCTCCAGG |
| Chr3 | 125633992 | 137819 | AGGAAGGAGGAGTTAGCTCCTGG |
| Chr16 | 8763213 | 134448 | AAGTAAGGGAAGTTTGCTCCTGG |
| Chr8 | 140714327 | 131288 | GGGAGGAGAGAGTTTGCTCTCTG |
| Chr20 | 56175356 | 130037 | AGGGAGGAGGAATTTGCTCCAGG |
| Chr15 | 93140401 | 126800 | GGGGGAGGGAAGTTTCCTCCAGG |
| Chr2 | 209437600 | 115754 | AGGGAGGGAGAATTTGCTCCTGG |
| Chr3 | 128284321 | 115556 | AGGTGGTGGGAGCTTGTTCCTGG |
| Chr5 | 32945275 | 115513 | GCGTGGGGGGTGTTTGCTCCCGG |
| Chr6 | 14316373 | 114987 | GTGGGGGTAGAGTTTGCTCCAGG |
| Chr13 | 26202812 | 113722 | GGTTGAGGGGAGTCTGCTCCAGG |
| Chr5 | 156390 | 112828 | TGCTCGGGGGAGTTTGCACCAGG |
| Chr21 | 43889878 | 106684 | GGCCCAGGGGAGTTTGCTCCCAG |
| Chr19 | 51310920 | 106639 | GTGCAGGGGGAATTTGCTTCCGG |
| Chr5 | 139263024 | 106310 | TTGGGGGGGCAGTTTGCTCCTGG |
| ChrX | 82127748 | 104937 | AGAGGGGGAGAGTTTGCCCCTGG |
| Chr7 | 17819097 | 101772 | ACAACTGGGGAGTTTGCTCCTGG |

TABLE 3-continued

VEGFA1

| Chr | Position | DNA cleavage Score | DNA seq at a cleavage sites |
|---|---|---|---|
| Chr22 | 41676762 | 100633 | AGTGCAGGGGAGCTTGCTCCTGG |
| Chr2 | 96056645 | 98836 | GGGTGGGGAGAGTTTCTTCCTGG |
| Chr3 | 195671264 | 97500 | GGTGGGGGAGAGCTAGCTCCGGG |
| Chr11 | 3445204 | 97065 | AGGAAGGAGGAGTTAGCTCCTGG |
| Chr6 | 45554056 | 96928 | GGGGTGGGAGAGTTTGCTCTCTG |
| Chr18 | 366714 | 94490 | GGGGGCAGGGAGATTGCTCCTGG |
| Chr3 | 13580170 | 91496 | ATGGGGAGAAACTTGCTCCTGG |
| ChrX | 19185601 | 89375 | GGGAGGGGAGAGTTTGTTCCAGG |
| Chr11 | 67574262 | 86762 | AGGAAGGAGGAGTTAGCTCCTGG |
| Chr17 | 47317539 | 85047 | CTGGTGGGGAGCTTGCTCCAGG |
| Chr6 | 91365256 | 83954 | CCCGGGGGAAGCTTGCTCCAGG |
| Chr22 | 16454323 | 83642 | GGAAAGGAGGAGCTTGCTCCAGG |
| Chr22 | 19698463 | 83277 | GAGGGGGAGCAGTTTGCTCCAGG |
| Chr3 | 36358934 | 82931 | AGTGGGGGAGAGTATGCTCCGGG |
| Chr21 | 37116659 | 77154 | AAGTGGGAAGAGTTTGTTCCAGG |
| Chr11 | 117481208 | 75392 | GGGCAAGGGGAGGTTGCTCCTGG |
| Chr7 | 29081029 | 74507 | GGAGTGGGTGAGCTTGCTCCTGG |
| Chr17 | 63035708 | 73840 | AGGAGGGGAAGAATGCTCCAGG |
| Chr2 | 181170961 | 67144 | TGGGGAGGGAAATTGCTCCTGG |
| Chr6 | 109284989 | 66994 | TGGAGAGGGGAGTTGCTCCTGG |
| Chr11 | 122583511 | 66565 | AGAAGAGGGGATTTGCTCCTGG |
| Chr5 | 56172079 | 66003 | GGTGGGGGTGGGTTTGCTCCTGG |
| Chr1 | 33643286 | 64800 | GGGTGGGTGGAGTTTGCTACTGG |
| Chr8 | 28483353 | 63725 | AAGTGGGAGGAGACTGCTCCAGG |
| Chr22 | 38219333 | 60450 | AGGTCGGGGAGTTAGATCCCGG |
| Chr15 | 29263777 | 59556 | GGGATGGGAGAGTCTGCTCCTGG |
| Chr2 | 30430777 | 57143 | AGGGAGAGGGAGCTTGCTCCCAG |
| Chr12 | 107832636 | 54149 | TCTTGGGGGGAAGTTGCTCCAGG |
| Chr4 | 185246171 | 53058 | GGAGGGGGGCTTTTGCTCCAGG |
| Chr8 | 10804669 | 48246 | GAGTGAGGAGAGCTTGCTCCATG |
| Chr5 | 95220670 | 46459 | GGGAGCAGGGAATTTGCTCCAGG |
| Chr2 | 129199817 | 44575 | TCCTGAGGGCAGTTTGCTCCAGG |
| Chr13 | 31251013 | 43669 | TGTAGAGGGAGTTTTGCTCCCGG |
| Chr16 | 89679839 | 43503 | GGAGGAGGGAACTTTGCTCCAGG |
| Chr1 | 20166440 | 42581 | GTGGGAGGATAGCTTGCTCCTGG |
| Chr18 | 1383474 | 37242 | GGGTGAAAGAAGTTTACTCCTGG |
| Chr6 | 50485682 | 36345 | ATGTGTGGGAATTTGCTCCAGG |
| Chr1 | 205484156 | 34692 | GTGTGAGTGGAGTTTGCTCTGGG |

TABLE 3-continued

VEGFA1

| Chr | Position | DNA cleavage Score | DNA seq at a cleavage sites |
|---|---|---|---|
| Chr6 | 109070771 | 35169 | GGTGGGGGAAAGTTTGCTCCTGA |
| Chr15 | 101813024 | 34008 | AAGGAGGCGGAGCTTGCTCCTGG |
| Chr11 | 11823598 | 31395 | GGCTGGAGGGGATTTGCTCCTGG |
| Chr9 | 5336085 | 31120 | TCGTGGTGGGAATTTACTCCTGG |
| Chr4 | 116853325 | 29172 | AAAGGGGGAACTTTGCTCCAGG |
| Chr11 | 86695106 | 28100 | AGGGAAGGGGAATTTGCACCTGG |
| Chr5 | 57030871 | 27679 | CTCTGAGGGGAGTTTGCTCTGGG |
| Chr15 | 84047385 | 26663 | GGAGTCAGGGAATTTGCTCCTGG |

TABLE 4

VEGFA2

| Chr | Position | DNA cleavage Score | DNA seq at a Cleavage sites |
|---|---|---|---|
| Chr2 | 242214607 | 1670405 | ATTCCCCCCCACCCCGCCTCAGG |
| Chr9 | 103599649 | 1051618 | ACACCCCCCACCCCGCCTCAGG |
| Chr14 | 75098723 | 1009605 | CCTCACCCCCACCCCACCTCTGG |
| ChR11 | 31817468 | 952389 | GGGCCCCTCCACCCCGCCTCTGG |
| Chr17 | 4356752 | 726896 | TACCCCCCACACCCGCCTCTGG |
| Chr16 | 56983429 | 579579 | TGCCCCCCCACCCCACCTCTGG |
| Chr12 | 25025095 | 561897 | CATTCCCCCACCCCACCTCAGG |
| Chr1 | 111680603 | 445046 | TAAATCCTCCACCCCACCTCAGG |
| Chr18 | 21359559 | 407413 | GCCCCCACCCACCCCGCCTCTGG |
| Chr6 | 43738562 | 362168 | GACCCCCTCCACCCCGCCTCCGG |
| Chr10 | 116294256 | 353588 | CCCCACCCCCACCCCGCCTCAGG |
| Chr22 | 32532961 | 351783 | GAGCCACTGCGCCCGGCCCCCGG |
| Chr9 | 27338815 | 339351 | GACCCCTCCACCCCGACTCCGG |
| Chr17 | 40044757 | 334353 | TGCCCCTCCACCCCGCCTCTGG |
| Chr12 | 31812350 | 318535 | GATCGACTCCACCCCGCCTCTGG |
| Chr13 | 100546989 | 300000 | CCCCCCCCCCCCCCGCCTCAGG |
| Chr19 | 13122189 | 299926 | GCCCCCCACCACCCCACCTCGGG |
| Chr5 | 8715119 | 294250 | CTACCCCTCCACCCCGCCTCCGG |
| Chr10 | 72538218 | 293269 | CAGTCCCCCACCCCACCTCTGG |
| Chr16 | 13492458 | 286462 | TCCGCCCCCACCCCACCTCCGG |
| Chr4 | 38537628 | 280706 | CTCCCCACCCACCCCGCCTCAGG |
| Chr6 | 160552566 | 278603 | TCAGACCTCCACCCCGCCTCAGG |
| Chr16 | 81442194 | 261364 | TTCACCATCAACCCCACTTCAG |
| Chr4 | 182638032 | 250540 | TCCTTTCTCCACCCCACCTCTGG |
| Chr10 | 135149946 | 247222 | CGCCCTCCCCACCCCGCCTCCGG |

TABLE 4-continued

| | | VEGFA2 | |
|---|---|---|---|
| Chr | Position | DNA cleavage Score | DNA seq at a Cleavage sites |
| Chr11 | 2686249 | 231975 | CTCACCCCCACCCCACCTCTGG |
| Chr11 | 83433600 | 193501 | GTCACTCCCCACCCCGCCTCTGG |
| Chr4 | 148977716 | 167619 | TCCCGCCCCCACCCCACCTCCGG |
| Chr1 | 196124848 | 187500 | TGCAACCTCCTCCCCGCCTCGGS |
| Chr9 | 131766552 | 185503 | AGCCAACCCCACCCCGCCTCTGG |
| Chr17 | 29983010 | 158558 | CATCTTCCCCACCCCGCCTCTGG |
| ChrX | 70597842 | 142798 | CTACGCTCCACCACCACCTCCAG |
| Chr16 | 69188711 | 130118 | AGTAGCCCCCACCCCGCCTCGGG |
| Chr4 | 1496258 | 121825 | AGGCCCCCACACCCCGCCTCAGG |
| Chr4 | 160033153 | 121760 | TCACTCCCCACCCCACCTCTGG |
| Chr11 | 71948805 | 113590 | GCTTCCCTCCACCCCGCATCCGG |
| Chr18 | 19751064 | 106648 | CGTCTCCCCCACCCCACCTCAGG |
| Chr11 | 374667 | 92770 | AGGCCCCCCCGCCCCOCCTCAGG |
| Chr14 | 19361511 | 87124 | GTCGAGGTCCACCCCGCCTCAGG |
| Chr5 | 139028257 | 85248 | CTCCCCCCCCTCC6CGCCTCTGG |
| Chr9 | 140428961 | 86077 | CTCCCAGACTCCTCCCCCTCCTC |
| Chr3 | 140398801 | 81467 | CAACCCCCCCACCCCGCTTCAGG |
| Chr20 | 25240252 | 80973 | CCCACACCCCACCCCACCTCCGG |
| Chr8 | 122367964 | 70587 | CCACCATCCCACCCCGCCTCTGG |
| ChrX | 118665483 | 60675 | GTCCTCCACCACCCCGCCTCTGG |
| Chr1 | 5477153 | 60344 | CTGCCTCCTCACCCCGCCTCAGG |
| Chr6 | 10882454 | 56969 | CCCTCTCCACCCCCACCCTCTGG |
| Chr13 | 107367839 | 55772 | TCTCCCCTGTACCCCGCCTCTGG |
| Chr11 | 14596970 | 44608 | CCCTACCCCCACCCCACCTCAGG |
| Chr17 | 48624779 | 36894 | CCCTTCCCCCACCCCACCTCCGG |
| Chr19 | 42806601 | 36547 | TTCTCCCTCCTCCCCGCCTCGGG |
| Chr2 | 225762279 | 38133 | CTCCCCTCCACCCCAGCCTCCGG |
| Cht12 | 101603788 | 37584 | GCCAGCCCTCACCCCGCCTCGGG |
| Chr2 | 12744776 | 36920 | GACACACCCCACCCCACCTCAGG |
| Chr11 | 45402251 | 33163 | CGATCCTCTTACCCCGCCTCCGG |
| Chr6 | 187929403 | 32814 | GCTGTCTCCCACCCCGCCTCAGG |
| Chr21 | 37111654 | 31086 | TCTTCTTTCCACCCCGCCTCAGG |
| Chr17 | 41797972 | 29279 | TCCCCTTCCCACCCCACCTCCGG |
| Chr9 | 13973961 | 29086 | CAAGTAATCCACCCCACCTCAGG |
| Chr1 | 112708281 | 28448 | GCCACCTTCCACCCCACCTCAGG |
| Chr5 | 58336894 | 27731 | CTTCCTCCACCCCGCAGTCTATG |
| Chr17 | 58404889 | 26399 | CGCCCACCCCACCCCACCTCAGG |
| Chr4 | 84744222 | 25794 | CCAGCTCCOCACCCCACCTCAGG |

TABLE 5

| | | VEGFA3 | |
|---|---|---|---|
| Chr | Position | DNA cleavage Score | DNA seq at at cleavage sites |
| Chr20 | 2650069 | 500934 | GGTGTATGAGTGTGTGCGTCGGA |
| Chr2 | 177463426 | 450296 | GGTGAGTGTGTGTGTGCATGTGG |
| Chr5 | 89440969 | 437216 | AGAGAGTGAGTGTGTGCATGAGG |
| Chr5 | 98946319 | 431533 | GGTGTAGTGGTGTGTGCTTGTGG |
| Chr6 | 39028642 | 412319 | GGTGTGTGAGTGTGTGCATTGGG |
| Chr4 | 58326608 | 395166 | AGTGAGTGAGTGAGTGAGTGAGG |
| Chr19 | 1716792 | 367812 | CATGAGTGAGTGTGTGGGTGGGG |
| Chr16 | 74898121 | 311776 | GGTGAGAGAGTGTGTGCGTAGGA |
| Chr7 | 152671378 | 309713 | AGTGAGTGAGTGAGTGAGTGAGG |
| Chr4 | 89935133 | 298318 | TCTGAGTGAGTGTGGGCATGGGG |
| Chr16 | 84032646 | 287579 | GGTGAATGAGTGTGTGCTCTGGG |
| Chr22 | 37662824 | 277795 | GCTGAGTGAGTGTATGCGTGTGG |
| Chr20 | 50724405 | 270841 | CGTGAGTGAGTGTGTACCTGGGG |
| Chr6 | 157078327 | 269512 | GATGAGTGAGTGAGTGAGTGGGG |
| Chr11 | 79178523 | 268949 | AGTGAGTGAGTGAGTGGGGTTGG |
| Chr14 | 65569159 | 247298 | AGTGAGTGAGTGTGTGTGTGGGG |
| Chr20 | 20178284 | 240641 | AGTGTGTGAGTGTGTGCGTGTGG |
| Chr17 | 33323269 | 238213 | TGTGAGTGAGTATGTACATGTGG |
| Chr7 | 23792987 | 227214 | TATGAGTGAGTGTGTGGATGAGG |
| Chr5 | 34452076 | 220662 | TGTGTGAGTGTGTGTGTGCGTGG |
| Chr5 | 29367379 | 213110 | TGTGAGTGAGTGTGTGTATGGGG |
| Chr14 | 98442534 | 205743 | GGTGAGTGTGTGTGTGAGTGTGG |
| Chr15 | 29699015 | 204548 | GGAGAGCGAGTGTGTGCATTTGG |
| Chr8 | 143890827 | 204401 | GGTGTATGAGTGTGTGTGTGAGG |
| Chr3 | 10723187 | 203640 | AGCGAGTGAGTGAGTGCATTGGG |
| Chr2 | 230506241 | 196805 | GGTGAGCAAGTGTGTGTGTGTGG |
| Chr2 | 199628306 | 188735 | TGTGAGTGAGTGTGTGCAGAAGG |
| Chr10 | 109378067 | 180328 | GGTGAGTGAGTGAGTGAGTGAGG |
| Chr18 | 43287997 | 178553 | TGAGAGTGTGTGTGTGTATATGG |
| Chr2 | 183092036 | 176699 | GATGTGTGAGTGTGTGCCTGTGG |
| Chr15 | 92864212 | 168436 | TGTGAGTGAGTGTGTGTGTGTGA |
| Chr5 | 115434676 | 161900 | TGTGGGTGAGTGTGTGCGTGAGG |
| Chr9 | 18733635 | 156191 | AGCGAGTGAGTGTGTGTGTGGGG |
| Chr17 | 79111961 | 153074 | GGTAAGTGTGTGTGTGCATGTGG |
| Chr3 | 10403702 | 150578 | CATGAGTGGGTGTGTGCATTGGG |
| Chr8 | 48997806 | 147492 | GTAGAGTGAGTGTGTGTGTGTGG |
| Chr20 | 21927847 | 145142 | GAAGAATGAGTGTGTGCTTGTGG |
| Chr10 | 87387984 | 141970 | GGTGTGTGAGTGTGTGCATGTTG |
| Chr10 | 1684972 | 140632 | TGTGAGTGGGTGTGTGAGTGAGG |
| Chr11 | 7625795 | 134588 | GGTGAGTAGGTGTGTGTGTGGGG |
| Chr18 | 75912617 | 134342 | GGAGAGTGTGTGTGTGAGTGTGG |
| Chr6 | 24224744 | 129788 | GGTGAGCGTGTGTGTGCATGTGG |
| Chr2 | 18696225 | 129667 | AGTGAGAAAGTGTGTGCATGCGG |
| Chr1 | 203434970 | 129446 | CATAAGTGAGTGTGTGCGAGTGG |
| Chr10 | 130228354 | 127783 | AGGGAGTGACTGTGTGCGTGTGG |
| Chr1 | 152925734 | 124308 | TGTGAGTGTGTGTGTGCATCTGG |
| Chr3 | 14430297 | 124127 | GGTGAAGTGGTGTGTGCCTGTGG |
| Chr1 | 116485644 | 124043 | AATGAGTGAGTGTGTGAGTGAAG |
| Chr6 | 144458291 | 122623 | AGGGAGTGAGTGTGAGAGTGCGG |
| Chr1 | 32738764 | 120061 | GGGGTGAGTGTGTGTGTGGGGGG |
| Chr8 | 145090503 | 119609 | TGTGAGTGAATGTGTGCATATGG |
| Chr21 | 26653015 | 119496 | GGTGTGTGTGTGTGTGCATGTGG |
| Chr22 | 49740001 | 118564 | GGTGTGTGAGTGTGTGTGTGTGG |
| Chr19 | 47732492 | 116403 | CTGGAGTGAGTGTGTGTGTGTGG |
| Chr1 | 181204797 | 115862 | GGAGAGTGAGTGTGTTTGTGTGG |
| Chr16 | 49384711 | 114011 | TGTGTATGAGTGTGTGCGTTGGG |
| Chr17 | 47051410 | 113965 | AATGGGTGAGTGTGTGGGTGGGG |
| Chr15 | 71796660 | 113213 | AATGAATGAATGTGTGCATGTGG |
| Chr7 | 158305228 | 112748 | TGTGTGTGAGTGTGTGCATGTGG |
| Chr1 | 47690894 | 111112 | TGTGAGAGAGAGTGTGCGTGTGG |
| Chr8 | 128556646 | 109297 | TGTGAGTATGTGTGTGCATGTGG |
| Chr6 | 1587476 | 107804 | TGTGCATGAGGGTGTGTGTTGGG |
| Chr2 | 74655959 | 107266 | GGTAAGTATGTGTGTGCATGGGG |
| Chr7 | 51294279 | 106266 | AGTGAGTAAGTGAGTGAGTGAGG |
| Chr2 | 10373473 | 105950 | TGTGAGTGAATGAGTGCATGTGG |
| Chr11 | 63366342 | 105655 | AGTGAGTATGTGTGTGAGGGTGG |
| Chr21 | 44179977 | 104795 | TGTGAGTGGGTGTGTGCATGTGG |
| Chr4 | 168168030 | 104058 | GGT GTGTGTGTGTGTGTGTGTGG |
| Chr19 | 16569487 | 103866 | TGTGTGAGTGAGTGTGTGTGTGG |
| Chr16 | 87047314 | 103772 | AGTGAATGAGTGAGTGAGTGAGG |
| Chr3 | 193993884 | 103526 | AGTGAAGTGTGTGTGTGTGTGGG |
| Chr8 | 92645411 | 103384 | GATGTGTGAGTGTGTACATGAGG |
| Chr11 | 78871125 | 103076 | AATGAGTGAGTGAGTGCATGGAG |
| Chr17 | 64940809 | 102789 | AGTGAATGAGGCTGTGCTTCGGG |
| ChrX | 56327306 | 101167 | TGTGAGTGTGTGTGTGCATGTGG |
| Chr22 | 43939297 | 100509 | GGTGAGAGAGTGTGTGCACGGGG |

TABLE 5-continued

| | | VEGFA3 | |
|---|---|---|---|
| Chr | Position | DNA cleavage Score | DNA seq at at cleavage sites |
| Chr4 | 154005628 | 99910 | TGTGAGTGTGTGTGTGCATGCAG |
| Chr21 | 43375271 | 98094 | GTGATGTGAGCGTGTGTGTGTGG |
| Chr16 | 46642109 | 98037 | AGAGAGTGAGTGAGTGAGTGTGG |
| Chr3 | 55318919 | 97636 | AGTGAGTGAATGAGTGCATAGTG |
| Chr3 | 10207131 | 96875 | GGTGTGTGTGTGTGTGTGTGTGG |
| Chr11 | 68851139 | 95585 | GGTGAGTGAGTGCGTGCGGGTGG |
| Chr1 | 212639778 | 95559 | GGGGAATGAGTGTGTGCATGGAG |
| Chr3 | 43415188 | 95395 | TCAGAATGAGTGTGCCTGGGG |
| Chr8 | 140710467 | 92344 | GGGAGGTGAGTGCATGCGTGTGG |
| Chr12 | 133361327 | 90593 | GGGGTGTGAGCATGTGCGTGTGG |
| Chr17 | 74046702 | 89136 | CGTGAGTGAGTGTGTGGTTGGGG |
| Chr18 | 6130265 | 88536 | TGTGAGTGAATGTGTGTGTGTGG |
| Chr14 | 106029032 | 87987 | GGTGAGTGAGTGTGTGTGTGAGG |
| Chr19 | 47787100 | 86825 | GATGAGTGTGTCTGTGCATGAGG |
| Chr3 | 1831002 | 86791 | ACTGAGTGGGTGTGTGCCTGAGG |
| Chr14 | 62078773 | 86236 | TGTGAGTAAGTGTGTGTGTGTGG |
| Chr1 | 48691305 | 85819 | ATGTGTGAGAGTGTGCATGTGG |
| Chr19 | 40561867 | 83975 | ACTGTGTGAGTGTGTGCGTGAGG |
| Chr20 | 39096994 | 83171 | TGTATGTGAGTGTGTGCGTGTGG |
| Chr10 | 45209678 | 82764 | AGGTAGTGAGTGTGTGCATGGGT |
| Chr14 | 76750082 | 79866 | TGTGAGTGCGTGTCTGTGTGTGG |
| Chr16 | 84532 | 79700 | TATGAGTGTGTGTGTGAGTGTGG |
| Chr19 | 6660674 | 79444 | TGTGAGTGAGTGAGTGAATGTGG |
| Chr22 | 29329724 | 79139 | AGTGTGTGTGTGTGTGTGTGGGG |
| Chr4 | 5844313 | 78441 | TGTGAGAGAGTGTGTGAGTGTGG |
| Chr1 | 22117219 | 78182 | AGTGATGGAGTGTGTGCCTGTGG |
| Chr12 | 5100948 | 77679 | TGCATGTGAGTGTGTGTGCGTGG |
| Chr11 | 115758116 | 76545 | AGAGAGTGTGTGTGTGCTTGGGG |
| Chr18 | 73286082 | 76468 | CATGAGTGGGTGTGTGCGTGGAG |
| Chr1 | 236264583 | 76389 | TATGAGTGTGTGTGTGAATGTGG |
| Chr6 | 101025624 | 73050 | AGAGAGTGTGTGTGTGTGTGTGG |
| Chr7 | 101077901 | 71834 | TGTGAGTGAGTGTGTTGGTGAGG |
| ChrX | 38624688 | 71296 | TATGAGTGTATGTGTGCATAGGG |
| Chr5 | 22787253 | 70950 | GGTGTGTGTGTGTGTGTGTGTGG |
| Chr17 | 66592348 | 70915 | GGTGTGTGTGTGTGTGTGTGTGG |
| Chr10 | 5749657 | 70553 | AGTGAGTATGTGTGTGTGTGGGG |
| Chr2 | 217617270 | 70535 | AGGGAGTGAGTGTGTAAGTGTGG |
| Chr7 | 20263523 | 69959 | TGTGAGTGTATGTGTGTGTGTGG |
| Chr9 | 96679964 | 69839 | TGTGAGTGTGTGTGTGCATGTGA |
| Chr3 | 30904559 | 69551 | AGAGAGTGAGTGTGTGAGTGTGA |
| Chr4 | 62067619 | 69092 | GATGAGTGTGTGTGTGTGTGAGG |
| Chr17 | 72614843 | 68998 | GGGTGAGGAAGGTGTGCGTGGTG |
| Chr13 | 30280840 | 68632 | GATAAGTGAGTATGTGTGTGTGG |
| Chr20 | 62468987 | 67982 | AGTGAGTGAGTGAGTGAATGAGG |
| Chr11 | 83585151 | 67687 | AGAGAGAGAGTGTGTGCGTGTGA |
| Chr14 | 74353497 | 67524 | AGCGAGTGGGTGTGTGCGTGGGG |
| Chr3 | 150919004 | 67276 | AGAGAGAGAGTGTGTGCACGTGG |
| Chr3 | 38182513 | 66357 | TGTGAGTGAATGTGTGCCAGGGG |
| Chr16 | 23981202 | 66336 | GGTGTGTGTGTGTGTACGTGGGG |
| Chr11 | 12159168 | 66034 | TGTGTGAGTGTGTGTGTGGGGGG |
| Chr12 | 113240368 | 65974 | TGTGCGTGAGTGTGTGTATGTGG |
| Chr12 | 57612417 | 65969 | CTTGAGTGAGAGTGAGCGTGAGG |
| Chr3 | 80057064 | 65928 | GGTGTGTGTGTGTGAGTGTGTGG |
| Ch10 | 107867379 | 65724 | AGAGAGTGAGTGTGTGTGTTGGG |
| Chr21 | 39875948 | 65333 | AGTGTGTGAGTGTGTGTATGAGG |
| Chr10 | 105307473 | 65196 | TGAGTGTGAGTGTGTGCGTGGGG |
| Chr2 | 126931490 | 64648 | TGTGTGTGAGTGTGTGTGTGTGG |
| Chr9 | 23824554 | 64347 | TGTGGGTGAGTGTGTGCGTGAGA |
| Chr1 | 48305038 | 63571 | TGTGGGTGAGTGTGTGTGTGTGG |
| Chr22 | 33161120 | 61767 | AGCGAGAGAGTGTGTGAGTGTGG |
| Chr10 | 130236827 | 61760 | GGTGTGTGTGTGTGTGCGTGCGG |
| Chr6 | 54584099 | 61560 | GGTGTGTGTGTGTGTGTGTGTGG |
| Chr1 | 59847610 | 61476 | ACAGAGTGAGTGTATGTGTGGGG |
| Chr3 | 58727139 | 61458 | TGGTGATGAGTGTGTGTGTGTGG |
| Chr2 | 765652 | 61000 | TATGAATGTGTGTGTGCATGTGG |
| Chr18 | 50274481 | 60745 | GGTGTGTGAGTGAGTGAGTGCGG |
| Chr11 | 41554134 | 60452 | GGTGTGTGTGTGTGTGTGTGTGG |
| Chr5 | 21934229 | 59877 | TGTGTGTGAGTGTGTGTGTGTGG |
| Chr1 | 208239410 | 59583 | TGTGTGAGTGAGTGTGTGTGTGG |
| Chr5 | 150224721 | 59559 | AGTGAGAGTGTGTGTGTGGGGGG |
| Chr10 | 99685339 | 59057 | TGAGAGTGAGTGTGAGAGTGGGG |
| Chr6 | 89076647 | 58986 | TGTGAGTGTGTATGTGTGTGGGG |

TABLE 5-continued

| VEGFA3 | | | |
|---|---|---|---|
| Chr | Position | DNA cleavage Score | DNA seq at at cleavage sites |
| Chr12 | 592739 | 58963 | GGTGTAGTGGTGTGTGCCTGTGG |
| Chr13 | 90418142 | 58280 | TGTGTGTGTGAGTGTGTGTATGG |
| Chr11 | 40324874 | 58268 | TGTGTGTGAGTGTGTGCATGTGA |
| Chr18 | 23286405 | 57990 | CGTGAGTGTGTGTATGCGTGTGG |
| Chr4 | 7430877 | 57892 | CATGCGTGAGTGTGTGCATGGGG |
| Chr12 | 114752937 | 57500 | TGTGAGTGAGTGTGTGCATGTGA |
| Chr17 | 1178800 | 57499 | AGTGTGTGAGTGTGTGTGTGAGG |
| Chr3 | 194073652 | 57337 | ACTGAGTGAGTGTGAGTGTGAGG |
| Chr14 | 84459815 | 56913 | GGGTGAGATGTGTGTGCATGTGG |
| Chr20 | 25612568 | 56877 | GGTGTAGTGGTGTGTGCCTGTGG |
| Chr15 | 85046541 | 56714 | TGTGTGTGAGTGTGTGCATGTGG |
| Chr3 | 169379105 | 56450 | AGAGAGAGAGAGTGTGTGTGG |
| Chr2 | 238409544 | 56372 | GAAGAGTAAGTGTGTGTGTGGGG |
| Chr2 | 236425371 | 56133 | AGTGGATGAGTGAGTGCATGCGG |
| Chr11 | 8794152 | 55741 | GTAGAGTGAGTGTGAGAGTGTGG |
| ChrX | 42430834 | 55717 | AGTGAGTGAGTGTGAGCGTGAAG |
| Chr2 | 121087513 | 55543 | AGAGTGTGAGTGTGTGTGTGGGG |
| Chr16 | 86214365 | 55396 | GGGGTGTGAGTGTGGTGCGTGTG |
| Chr6 | 43737471 | 54966 | GGTGAGTGAGTGTGTGCGTGTGG |
| Chr1 | 238722563 | 54429 | GGTGTGTGTGTGTGTGCGTGTGG |
| Chr17 | 78954441 | 54363 | TGTGAGTGAGTGTGTGTGTGTGA |
| Chr8 | 20109735 | 53794 | AGTGTGTAAGTGTGTGAGTGGGG |
| Chr7 | 23276732 | 53659 | AGTGAGTGTGTGTGTGTGTTGGG |
| Chr2 | 124275984 | 53635 | AGTGAATGTGTGTGTGCATGTGG |
| Chr11 | 131931836 | 53621 | TGTGAGTGCGTGTGTGTGTGTGG |
| Chr5 | 139122257 | 53371 | TGTGAGTGCGTGTGTGAGTGTGG |
| Chr5 | 155118304 | 53029 | TGTGAGAGAGTGTGTGCATGTGA |
| Chr5 | 159012346 | 52995 | TGTGTGTGAGTGTGTGTATGTGG |
| Chr11 | 78932523 | 52603 | GGTGAGTTTGTGTGTGGGTGTGG |
| Chr13 | 60101377 | 52367 | GGTAAATGAGTGTGAGGCATGGG |
| Chr1 | 18868939 | 52267 | GGAGTGTGAGTGTGTGAGTGCGG |
| Chr5 | 178746539 | 51744 | TGTGAGTGAGTGCATGTGTGTGG |
| Chr6 | 129056545 | 51217 | TGTGTGTGAGTGTGTGTGTGTGG |
| ChrX | 99664994 | 50909 | GAAGAGTGAGTGTGTGGTGTGGG |

TABLE 5-continued

| VEGFA3 | | | |
|---|---|---|---|
| Chr | Position | DNA cleavage Score | DNA seq at at cleavage sites |
| Chr11 | 61485469 | 50776 | GCAGAGTGAGTGTGTGTGTTGGG |
| Chr4 | 187327499 | 50405 | CATGAGTGTGTGTGTGAGTGTGG |
| Chr9 | 95974277 | 50327 | TGTGAATGAGTGCGTGAATGGGG |
| Chr13 | 91706956 | 50092 | AGTGTGTGAGTGTGTGAGTGAGG |
| Chr2 | 73317050 | 49126 | GGTGAGTCAGTGTGTGAGTGAGG |
| Chr12 | 6937056 | 48851 | GGTGGATGAGTGTGTGTGTGGGG |
| Chr5 | 132802864 | 48840 | TGAGAGTGAGTGTATGAGTGTGG |
| Chr1 | 229141145 | 48503 | TGTGTGTGAGTGTGTACATGAGG |
| Chr2 | 123052110 | 48485 | GGTATTTGAGTGTGTACATGTGG |
| Chr2 | 171597348 | 48413 | ACTGACTGAGTGTGAGCATGTGG |
| Chr5 | 56989649 | 48026 | AATGAGTGTGTGTGTGTATGGGG |
| Chr7 | 117741100 | 47875 | GGTGTGTGTGTGTGTGCGTGTGG |
| Chr1 | 207097588 | 47546 | GTAGAGTGTGTGAGTGTGTGGCG |
| Chr10 | 28251664 | 46622 | GATGAGTGTGCGTGTGCATGAGG |
| Chr11 | 74904632 | 46613 | ACCAGGTGAGTGTGTGCGTGGGC |
| Chr14 | 28518304 | 46479 | TGTGAGTATGTGTGTGTGTGTGG |
| Chr10 | 95051225 | 45827 | CCTGAGCGAGTATGTGCATGTGG |
| Chr1 | 181557204 | 45772 | GGAGAGTGAGTGTGTGCATGTGC |
| Chr10 | 120245284 | 45770 | GGTGTGTGAATGTGTGTGTGTGG |
| Chr7 | 87667089 | 44986 | AGAAAGTGAGTGTGTGTATAAGG |
| Chr3 | 155092668 | 44566 | AGTGCATGAGTGTGTATGTGAGG |
| Chr12 | 31106567 | 43922 | GCTGAGTGTGTGTGTGCGTGTAG |
| Chr20 | 2780911 | 43695 | GGTGAGTGAGCGAAGGAGTAGGG |
| Chr8 | 107510883 | 43442 | TGTGAGTGTGTGTGTGAGTGTGG |
| Chr2 | 81220097 | 43319 | TGTGAGTGTATGTGTGTGTGTGG |
| Chr20 | 36039815 | 43235 | TATGAGTGTGTGTGTGCACGTGG |
| Chr1 | 4770493 | 43006 | TGGGTGTGAGTGTGTGCGTGTGG |
| Chr14 | 102953779 | 42717 | TGTGAGTGTGTGTGTGCGTGCGC |
| Chr5 | 23562308 | 42040 | AGAGAGAGAGTGTGTGTGTGTGG |
| Chr11 | 62781473 | 41850 | CATGAGTGACTGTGTGTGTGTGG |
| Chr21 | 30993730 | 41270 | GGTGTGTGTGTGTGTGTGTGGGG |
| Chr19 | 56497640 | 41146 | TGTGAGTGTGAGTGTGTGTTGGG |
| Chr15 | 37202049 | 41005 | TGTGTGTGGGGGTGGGGGTGGGG |
| Chr19 | 41713254 | 40809 | AGTGAGTGTGTATGTGTGTGTGG |
| Chr3 | 184590078 | 40193 | AATGAGTGTGTATGTGTGTGTGG |
| Chr13 | 101257208 | 40117 | TTTGAGTGTGTGTGTGCATGAGG |
| Chr11 | 133611177 | 39673 | TGCGTGTGAGTGTGTGCGTAGGT |
| Chr10 | 99306651 | 39637 | AGAGAGAGAGTGTGTGTGAGGG |
| Chr10 | 61044507 | 39573 | GGGGTAAGGGTGTGTGTGTGTGG |
| Chr17 | 10029642 | 39200 | TGTGTGTGAGCGTGTGTGTGTGG |
| Chr5 | 149501694 | 39132 | GATGAGTGAGTGTGTGAGTGAGA |
| Chr2 | 174931405 | 39132 | GGTGTGAGAGTGTGTGCGGAGGC |
| Chr4 | 168057437 | 39128 | TGTGTGTGAGTGTGTGTGTGTGG |
| Chr2 | 88996016 | 39077 | GATGAGTTTGTGTGTGTGTGGGG |
| Chr11 | 44999873 | 38823 | TGTGAGAGAATGTGTGCGTGTGA |
| Chr8 | 135523492 | 38820 | TGAGAGTGAGAGTGTGTGTGGGG |
| Chr19 | 40596585 | 38681 | GGACTGTGAGTGTGTGCGTGAGG |
| Chr18 | 60759565 | 38462 | TGTGAGTGGGTGTGTGTGTGTGG |
| Chr19 | 48782757 | 38450 | TGTGAGTGTGTGTGTGGGTGGGG |
| ChrX | 41726218 | 38335 | GGTGAGTGAGTGAGTGAGTGAGG |
| Chr11 | 1004348 | 38204 | GGTGTAGTGGTGTGTGCCTGTGG |
| ChrX | 105614415 | 37642 | AGTGAATGAGTGTGTGCATGTGA |
| Chr7 | 77128126 | 37477 | TGTGTATGAGTGTGTGTATGCGG |
| Chr2 | 16837556 | 37405 | TGTGAGTGGGTGTGGGTGTGG |
| Chr8 | 121823447 | 37394 | TGAGTGTGAGTGTGAGCGTGCGG |
| Chr7 | 31100113 | 37187 | TGTGAAGGAGTGTGTGTGTGTGG |
| Chr16 | 88218507 | 37056 | ATTGTGTGAGTGTGTGCATGTGG |
| Chr4 | 7132480 | 36475 | TGTGGGTGTGGATGTGTGTGTGG |
| Chr12 | 129149692 | 36397 | TATGTGTGAGTGTGCATATGGG |
| Chr4 | 183729842 | 36229 | TGTGGGTGGGTGTGTGCGTGTGG |
| Chr10 | 98760588 | 36228 | GTTGAGTGAATGTGTGCGTGAGG |
| Chr3 | 172121469 | 36168 | GGGAAGGGAGTGTGTGCATGGGG |
| Chr2 | 4734730 | 36144 | GGGGAATGAGTGTGTATGTGAGG |
| Chr5 | 31640966 | 35357 | AGTGAGTGTGTGTGTTGCGGGGG |

TABLE 5-continued

| | | VEGFA3 | |
|---|---|---|---|
| Chr | Position | DNA cleavage Score | DNA seq at at cleavage sites |
| Chr10 | 107228008 | 35025 | GGTGTGTGTGTGTGTGTGTGG |
| Chr16 | 23869051 | 34306 | AGAGAGTGTGTGTGTGTGTGG |
| Chr19 | 54524100 | 34299 | TGAGTGTGTGTGTGTGCGTGTGG |
| Chr5 | 134817941 | 34058 | CATGAGTGTGTGTGTGCTTGTGG |
| Chr17 | 50130332 | 33753 | GTGAGTGATGTGTGTGTGTGTGG |
| Chr11 | 75330150 | 33458 | TGTGTGTGAGTGTGTGCATGAGG |
| Chr13 | 110882529 | 33303 | TGTGTGTGAGTGTGTGCCCGTGG |
| Chr5 | 84905674 | 32861 | TGTGTGTGAGTGTGAGTGTGTGG |
| Chr8 | 9768212 | 32615 | AGAGAGAGAGTGTGTGTGTGTGG |
| Chr12 | 124763151 | 32224 | TGTGAGTGTGTGTGTACCTGGGG |
| Chr6 | 43905520 | 32218 | GGTGTAGGAGTGTGTGTGTGGGG |
| Chr20 | 31382040 | 31490 | GGTGAGGTGGTGTGTGCCTGTGG |
| Chr16 | 73585926 | 31285 | AATGAGTGAGTGTGTGTGTGTGA |
| Chr11 | 69518904 | 31172 | GGGGTGTGAGTGGGTGTGTGCGG |
| Chr12 | 131196667 | 31067 | GGTGGGTGAGTGAGTGAGTGAGG |
| Chr4 | 158621598 | 31029 | AGTGTATGAGTGTTTGCATGGGG |
| Chr7 | 134234248 | 30738 | AGTGAGTGAGTGAGTGAATGTGG |
| ChrX | 30439128 | 30450 | TGTGAGTGTGTGTGTGTATGTGG |
| Chr5 | 73855632 | 30379 | GGTGTGTGAGAGTGTGTATGTGG |
| Chr5 | 146520400 | 30071 | GGTGTGTGGGTGTGTGTGTGGGG |
| Chr12 | 125156261 | 29909 | GATGAGTGTGTGTGTGTGTGCGG |
| Chr15 | 80907957 | 29859 | TGTGAGTGTGTATGTGTGTGTGG |
| Chr14 | 78443706 | 29808 | TGTGTGTGTGTGTGTGTGTGTGG |
| Chr1 | 18837923 | 29595 | GGTGTGTGTGTGTGTGTGTGTGG |
| Chr1 | 35189392 | 29530 | TGTGTGTGAGTGTGTGTGTGGGG |
| Chr18 | 6110703 | 29521 | AGGATGTGAGTGTGTGCATGTGG |
| Chr12 | 33270666 | 29418 | GGAGAATAGGTGTGTGCGTGGGG |
| Chr8 | 141037928 | 29408 | AGTGAGTGTGTGTGTGAAGGAGG |
| Chr16 | 26809933 | 29366 | GATGAGTAAGTGTCTGAGTGGGG |
| Chr8 | 21494640 | 29292 | TGTGAGTGTGTGTATGCGTGTGA |
| Chr7 | 121687676 | 29255 | TGTGTGTGAGTGTGTGTGTGTGG |
| Chr9 | 29602720 | 29089 | GGGGTGTGTGTGTGTGTGTGTGG |
| Chr6 | 105265269 | 29056 | AGAGAGAGAGTGTGTGCAAGGGG |
| Chr10 | 43251651 | 29026 | GTAGGGTGGGAGTGTGTGTGTGG |
| Chr8 | 139883090 | 28455 | TGTGAGTGGGTGTGTATGTGAGG |
| Chr16 | 10276764 | 28379 | GGCGAGTGTGTGTGTGAGTGTGG |
| Chr14 | 90885641 | 28211 | GATGTGTGTGTGTGTGCGTGTGG |
| Chr6 | 33999846 | 27544 | TGTTAGTGAGTGTGTGCAGGTGG |
| ChrX | 39606149 | 27511 | GATGAGCGAGTGTGTGTGTATGG |
| Chr17 | 6891149 | 27499 | GGTGAAAGAGTATGTGTGTGTGG |
| Chr2 | 240564198 | 27202 | GGTGTGTATGTGTGGGGGTGTGG |
| Chr1 | 3325807 | 27195 | GGTGTGAGAGTGTGTGAGTGGGG |
| Chr12 | 2469347 | 27066 | GGGGTGTGTGTGTGTGTGTGTGG |
| Chr6 | 24574540 | 27056 | GGTGTAGTGGTGTGTGCCTGTGG |
| Chr1 | 175049116 | 26933 | TGTGAGTGTGTGTGTGTGTGTGG |
| Chr3 | 3697106 | 26689 | GGTGTGTGTGTGTGTGTGTGTGG |
| Chr7 | 39341125 | 26138 | GGTGTGTGAGTGTGTGTGTGTGA |
| Chr20 | 23960933 | 26077 | GGTATGTGAGTGTGAGTGTGGGG |
| Chr19 | 54375904 | 26077 | GGTGTGGTGGTGTGTGCGTGTGG |
| Chr7 | 31353825 | 25742 | CCAGAATGAGTGTGTGTGTGTGG |
| Chr3 | 79455732 | 25729 | TGTGTGTGAGTATGTGTGTGTGG |
| Chr2 | 126515435 | 25686 | TGTGAGTGAATATGTGTATGTGG |
| Chr4 | 82574191 | 25545 | GGTATGTGAGTGTGTGTATATGG |
| Chr1 | 3002774 | 25443 | GGTGAGCTCGTGAGTGCGTGAGG |
| Chr17 | 43132890 | 25361 | AAGTGAGGAGTGTGTGCCTGTGG |
| Chr18 | 74103175 | 25153 | GGTGAGTAAGTGTGAGCGTAAGG |

TABLE 6

| | EMX1 | | |
|---|---|---|---|
| Chr | Position | DNA cleavage Score | DNA seq at a cleavage sites |
| Chr11 | 62365273 | 772387 | GAATCCAAGCAGAAGAAGAGAAG |
| Chr19 | 1438827 | 597313 | GAAGTAGAGCAGAAGAAGAAGCG |
| Chr2 | 73160999 | 589285 | GAGTCCGAGCAGAAGAAGAAGGG |
| Chr1 | 234492864 | 494830 | GAAGTAGAGCAGAAGAAGAAGCG |
| Chr2 | 172374203 | 403017 | GAAGTAGAGCAGAAGAAGAAGCG |
| Chr2 | 219845073 | 382588 | GAGGCCGAGCAGAAGAAAGACGG |
| Chr1 | 23720618 | 374603 | AAGTCCGAGGAGAGGAAGAAAGG |
| Chr12 | 106646091 | 294995 | AAGTCCATGCAGAAGAGGAAGGG |
| Chr15 | 44109764 | 284237 | GAGTCTAAGCAGAAGAAGAAGAG |
| Chr8 | 128801260 | 279063 | GAGTCCTAGCAGGAGAAGAAGAG |
| Chr15 | 22366622 | 233100 | GGAGTAGAGCAGAGGAAGAAGGG |
| Chr9 | 127309505 | 222741 | AAGCCCAAGCAAATGAAGAATGG |
| Chr11 | 43747949 | 217179 | AAGCCCGAGCAAAGGAAGAAAGG |
| Chr5 | 9227163 | 213293 | AAGTCTGAGCACAAGAAGAATGG |
| Chr10 | 128080196 | 196235 | GAGTACAAGCAGATGAAAAACGG |
| Chr1 | 33606480 | 192057 | GAGCCTGAGCAGAAGGAGAAGGG |
| Chr3 | 34042974 | 178213 | GAGTTCAAGCAGAGAAGAAAGGG |
| Chr21 | 24667742 | 166991 | CCCTCCAAGCAGAAGAAGATGAG |
| Chr14 | 38654666 | 164832 | AAGTCTGAGAAGAAGAAGACATG |
| Chr5 | 45359067 | 163490 | GAGTTAGAGCAGAAGAAGAAAGG |
| Chr18 | 68861321 | 160118 | AGAGTAGAACAGAAGAAGGAAAG |
| Chr4 | 87256692 | 159096 | GAGTAAGAGAAGAAGAAGAAGGG |
| Chr10 | 58848729 | 156786 | GAGCACGAGCAAGAGAAGAAGGG |
| Chr8 | 74634212 | 155436 | AAGTCCAAAAAGAAGAAAAAAGG |
| Chr19 | 24250503 | 146744 | GAGTCCAAGCAGTAGAGGAAGGG |
| Chr8 | 105164126 | 143429 | GAGCCCAAGAAGAAGAAGAAGGA |
| Chr14 | 43156807 | 141435 | GAGGCCAAGCAGAAAAAAAATGG |
| Chr11 | 30301809 | 140265 | CAGTCTGAGTACAACAAAAAGGG |
| Chr4 | 58838593 | 138462 | AAGTCCCAGAAGAAGAAATATGG |
| Chr15 | 65614525 | 136049 | GAGAGGGAGCAGGGAGAAGAAGG |
| ChrX | 149010707 | 135051 | GGAGTCAAGGAGAAGAAGAAGAG |
| Chr7 | 111475449 | 130150 | GAGCCCAAGCACAAAAAGAATGG |
| Chr14 | 48932120 | 129466 | GAGTCCCAGCAAAAGAAGAAAAG |
| Chr10 | 91416162 | 127813 | ATGTCCAAGCAGAAGAAGTCTGG |
| Chr12 | 102743729 | 121776 | TAGTCAGAGCAGATGAAGGAAAG |
| Chr3 | 95690186 | 117619 | TCATCCAAGCAGAAGAAGAAGAG |

TABLE 6-continued

| | | | |
|---|---|---|---|
| Chr3 | 16077518 | 117265 | GAGGCAGAGAGAAAGAAGAAAGG |
| Chr12 | 73504675 | 105719 | GAGTTAGAGCAGAAAAAAAATGG |
| Chr6 | 9118799 | 104220 | ACGTCTGAGCAGAAGAAGAATGG |
| Chr5 | 141129457 | 103516 | AAGTCACAGGAGCAGAAAGAAGA |
| Chr7 | 31901077 | 103321 | GAGGCCAAGCAGAAAGAAAAAGG |
| Chr1 | 209931600 | 102834 | TTATCCGAGAAGAAGAAGTAAGG |
| Chr6 | 106901799 | 102469 | GAGCCGGAGCAGGGAGAAGAAGG |
| Chr22 | 34858917 | 102348 | GAGCCTGAGCAGGAAGAAGAAGA |
| Chr6 | 29806752 | 102267 | TGTCCAAGGCAGGAGAAGAAGGG |
| Chr15 | 36939471 | 99856 | CAGAGAGAGGAGCAGAAAAAAGA |
| Chr5 | 134375867 | 96143 | CAGGCTGAGCAGAAAGAAGAAAG |
| Chr2 | 199919487 | 95742 | GAGTCAGAGCAGAACTAGAAGGG |
| Chr20 | 6653999 | 95723 | AAGTCCAGACAGAAGAAGAAGGA |
| Chr8 | 135098073 | 94515 | CAGTCCAGCAGGAAGAAGAGAGG |
| Chr11 | 131106371 | 90172 | GCCTCCAAGCAGAAGGAGAAATG |
| Chr9 | 2513258 | 90018 | GAGAGAGAGCAAAAGGAAGAATG |
| Chr17 | 72057114 | 89855 | GAGGAGAGCAGAAAGAAGAAGGG |
| Chr16 | 56184077 | 88757 | AAGTCAGAGAAGGAAGAAGAAAG |
| Chr5 | 146833190 | 88608 | GAGCCGGAGCAGAAGAAGGAGGG |
| Chr5 | 120294736 | 83489 | ATGTCCAAGCACAAGAGGAATGG |
| Chr1 | 113741471 | 87189 | GAGGTAGAGCAGAAGAAGAAGCG |
| ChrX | 38971206 | 86924 | GAGTCCCAGAAGAAGAAAGAAAG |
| Chr4 | 2181662 | 86342 | CCTCTCGAGCAAAAGGAAGAAGG |
| Chr14 | 75723908 | 78355 | AGTTCCAAGCAGAGGAAGAAGGG |
| Chr4 | 155734338 | 77475 | TGCTTTGAGCAGAAAGAAGAAAG |
| Chr4 | 122686219 | 76915 | AAGTAAGAAGAGCAGGAAGAAGA |
| Chr12 | 4927416 | 75200 | TAGTCCTAGCAAGAATAAGAATG |
| Chr3 | 5031614 | 73504 | GAATCCAAGCAGGAGAAGAAGGA |
| Chr2 | 106719739 | 73041 | TAATGAGAGCAGAAAGAAGAATG |
| Chr7 | 142597224 | 72663 | GACAGAGAAGAGAAGAAGGAAGA |
| Chr1 | 27913391 | 72320 | AGGTCAGAGCAGAAGAAAAGAGG |
| Chr7 | 73602675 | 71804 | GCAAAGAGCAGGAAGAAGAAGGG |
| Chr18 | 34906762 | 71062 | GAGCCTGAGCGGAAGAGGAAAGG |
| Chr2 | 45607957 | 69584 | TAATCCCAGAGCAGGAAGAAGAA |
| Chr18 | 1677040 | 69087 | AGTCCAGAGCAAAATAAGAAGGG |
| Chr4 | 44622977 | 68873 | AAGTCTGAGAAGAAGAAGAAAGA |
| Chr12 | 2873991 | 68800 | GCTAAAGAGCAGAAGGAAGAAGG |
| Chr2 | 239393515 | 68020 | CAGTACGAGCAGAGGAAGGAAGA |
| Chr8 | 102244552 | 66479 | AGTTCCAAGCAGAAGAAGCATGG |
| Chr2 | 66582071 | 66179 | ATGGCAGAGCAGAAAGAAGAAAG |
| Chr11 | 69660352 | 62977 | CAGTCCATGCAGAGGGAAGAAGG |
| Chr11 | 130764292 | 62968 | GCATTAGAGCAGAAGGAAGAAGG |
| Chr1 | 231750743 | 61748 | GAGTCAGAGCAAAAGAAGTAGTG |
| Chr6 | 36604882 | 60741 | GGCAGAGAGCAGAAGGAAGAAAG |
| Chr15 | 61646878 | 60004 | AAGTCAGAGGAGAAGAAGAAGGG |
| Chr7 | 141972562 | 58917 | AAGTCCGGGCAAAAGAGGAAAGG |
| Chr12 | 111418051 | 58806 | GAGAGGGAGCAAAAGAAGGAAGG |
| Chr9 | 72899757 | 57967 | CAGAATGAGCAGGAAGAAGAACA |
| Chr17 | 8640231 | 56884 | GAGACTGAGAAGAAGAAGAAAGG |
| Chr1 | 84869216 | 56816 | GAGTCAGCTGAGCAGAAGGAAGA |
| Chr4 | 41187173 | 56700 | GAAGGAGAGCAGAAAGAAGAAAG |
| Chr9 | 130107853 | 53625 | GTTTGAGAGCAGAAGGAAGAAGA |
| Chr11 | 118816273 | 53228 | ATTTCCAAGCAGAGAAGAATG |
| Chr8 | 72482455 | 52761 | GAGTCCGAGAAGAAGAAAGAAAA |
| Chr1 | 221522625 | 50986 | GAGTTTGAGTAGAAGAAGAAGAG |
| Chr21 | 37132446 | 49332 | TGGCCAGAGCAGAAGGAAGAAGG |
| Chr2 | 217972073 | 49031 | TGTCCGAGGCAGTAGAAAGAACG |

TABLE 6-continued

| Chr | Position | Score | Sequence |
|---|---|---|---|
| Chr5 | 35927682 | 48391 | AAGCCCGAGCTAGAAGAAATAGG |
| Chr3 | 157623637 | 46601 | AAGGGGAGCAGGAAGAAGAAAGG |
| Chr20 | 14924870 | 46219 | AAGAAGGAGCAGGAAGAAGAAAG |
| Chr4 | 48639408 | 44366 | CACTCCAAGTAGAAGAAGAAAAG |
| Chr9 | 91487902 | 43847 | GAGGCAGAGAGAAGAAAGAAGGG |
| Chr2 | 105425353 | 43348 | AGATCCAAACAGAAGGAAGAATG |
| Chr7 | 100895242 | 43128 | CGCTCCGAGCAGAAGAAAAGTGG |
| Chr7 | 93390477 | 42514 | AGTCCTGAGCAGAGGAAGGAATG |
| Chr1 | 179024805 | 42398 | GAGTCCAAGAAGAAGAAGCCAGG |
| Chr7 | 54421043 | 42361 | GAGTCCCAGGAGAAGAAGAGAGG |
| Chr8 | 108409228 | 42088 | TGTTGAGAGCAGAAAGAAGAAAG |
| Chr15 | 68455211 | 42027 | GTCCAAAGGCAGGAGAAGAAGGG |
| Chr14 | 88550473 | 41703 | GAGGGAGAGAGCAGGAAGAAGAA |
| Chr12 | 124551806 | 41457 | TTGTTGAGCAGGAAGAAGAATGG |
| Chr18 | 32722290 | 41419 | TGTCCAGAGCAGATGAAGAATGG |
| Chr7 | 97319990 | 41090 | GAATCCAAGCAGAAGAAAATGGA |
| Chr7 | 3812761 | 40762 | GAGTCCTAGAAAAAGAAGAGAGG |
| Chr11 | 36270410 | 39031 | GAGAGAGAGCAGAAGAAGTAGAG |
| Chr18 | 25950253 | 38508 | AGGCCTGAGCAGAAGGAAGAAGG |
| Chr15 | 100292479 | 38402 | AAGTCCCGGCAGAGGAAGAAGGG |
| Chr3 | 169381222 | 38279 | GAGGGAGAGCAAAAGAAGGAAAG |
| Chr5 | 74513307 | 37749 | GTCCATAGCAAGAAAAAGAAGGG |
| Chr2 | 238373187 | 37583 | AGTGCAGAGCAGAAGAAGGAAAG |
| Chr7 | 70109967 | 37116 | GAATCAGAGCAAAAGGAGAAAGG |
| Chr6 | 110491414 | 36961 | AAGTCAGAGCAGAAAAAGAGAGG |
| Chr1 | 151027598 | 36487 | TTCTCCAAGCAGAAGAAGAAGAG |
| Chr9 | 135663404 | 35979 | CAGTCCAAACAGAAGAGGAATGG |
| Chr6 | 147955462 | 35474 | TGGCCAGAGCAGAAGGAAGAAAG |
| Chr9 | 140936012 | 34365 | GAGTCAAAGCAGAAGAAAGAACG |
| Chr14 | 35092801 | 33826 | TATCCAAGCAGGAAGAAGCAAGG |
| Chr17 | 73339913 | 33391 | TGCACGAGCAGGGAGAAGAAAGG |
| Chr4 | 82567700 | 33038 | TATTTACAGAGCAGGAAGAAGAG |
| Chr14 | 98020018 | 32807 | CATTCCAAGCAGAAGGAAGAGAG |
| Chr9 | 119853407 | 32546 | TACCAGGAGCAGGAAAAAGAAGG |
| Chr7 | 29268537 | 31836 | GAGCGGGAGCAAAAGGAAGAATG |
| Chr3 | 9802191 | 30997 | GTACCCAAGCAGAAGGAAGAAGG |
| Chr18 | 24570836 | 30752 | CCTGAAGAGCAGAAGGAGGAAGG |
| Chr13 | 101018849 | 27972 | GTCTGAGCAGAAAGGAAGAAGGG |
| Chr10 | 8337281 | 27943 | GAAGTCAGACAGAAGAAGAAGAG |
| Chr15 | 68619369 | 27871 | GAGAAAGAGCAGAAGGAAGAAGT |
| Chr2 | 218378108 | 27737 | GAGTCTAAGCAGGAGAATAAAGG |
| Chr1 | 2744291 | 27717 | GGTCCAGAGAGAAAGAAGAAAGG |
| Chr16 | 78848850 | 27402 | AAATCCAACCAGAAGAAGAAAGG |
| Chr10 | 5401788 | 27266 | TAATCCAATCAGAAGAAGAAGGG |
| Chr11 | 30490142 | 26821 | GAGAGAAGCAGAAAGAAGAAAGG |
| Chr17 | 21133222 | 26641 | GAATCCCAGCAGAAAGGAAGAAA |
| Chr6 | 12210833 | 26330 | ATGAATGAGCAGAAGGAGGAAAG |
| Chr7 | 43259054 | 26202 | GATACCGAGCTAAAGAAGGAAGG |
| Chr22 | 47725583 | 25746 | GAAGAGGAGCAGAAGGAGGAAGG |
| Chr11 | 56910170 | 25694 | ACCTGGGAGCAGGAAAAAGAAGG |

TABLE 7

FANCF

| Chr | Position | DNA cleavage Score | DNA seq at a cleavage sites |
|---|---|---|---|
| Chr7 | 102131659 | 1143904 | GTCTCCCCTTCTGCAGCACCAGG |
| Chr11 | 22647338 | 880988 | GGAATCCCTTCTGCAGCACCTGG |
| Chr10 | 73463136 | 820158 | TGAATCCCATCTCCAGCACCAGG |
| Chr10 | 37953200 | 740976 | GGAGTCCCTCCTACAGCACCAGG |
| Chr10 | 43410031 | 602472 | GGAGTCCCTCCTACAGCACCAGG |
| Chr7 | 44076497 | 564535 | GTCTCCCCTTCTGCAGCACCAGG |
| Chr18 | 8707528 | 471495 | GGAACCCGTCTGCAGCACCAGG |
| Chr16 | 49671025 | 438282 | GGAGTCCCTCCTGCAGCACCTGA |

TABLE 7-continued

| Chr3 | 35113165 | 408220 | TGAATCCTAACTGCAGCACCAGG |
|---|---|---|---|
| Chr7 | 102230832 | 340386 | GTCTCCCTTCTGCAGCACCAGG |
| Chr20 | 44903573 | 337872 | TCCATCCCTACTGCCAGCACCAG |
| Chr11 | 66475045 | 330843 | GGAACACCTTCTGCAGCTCCAGG |
| Chr3 | 10885901 | 3106520 | ACCCTCCCTTCTGCAGGCACCGG |
| Chr10 | 3151994 | 278757 | CTCTGTCCTTCTGCAGCACCTGG |
| Chr17 | 39675789 | 367600 | GGGAGTCCATCTGCAGCACCAGG |
| Chr11 | 47554037 | 192902 | GGAATCCCTTCTACAGCATCCTG |
| Chr2 | 54853314 | 174124 | GGAATATCTTCTGCAGCCCCAGG |
| Chr12 | 115467808 | 171967 | AGGGTCCCTTCTGCAGCCCCTGG |
| ChrX | 86355180 | 161944 | ACCATCCCTCCTGCAGCACCAGG |
| Chr2 | 35692938 | 130816 | ACTTTATCTTCTGCAGCACCTGG |
| Chr2 | 133174786 | 114095 | ATCCTTTCTTCTGCAGCACCTGG |
| Chr12 | 2719895 | 106450 | ACACTCCCTTCTGCAGCACCATG |
| Chr16 | 28615201 | 99927 | GGCTTCCCTTCTGCAGCCCCAGG |
| ChrX | 97566910 | 97653 | TGTATTCCTTCTGCAGGCACCAG |
| Chr17 | 30452575 | 89120 | CCTGCTGCTTCTGCAGCACCTGG |
| Chr9 | 113162294 | 88941 | AAAATCCCTTCCGCAGCACCTAG |
| Chr4 | 53092937 | 71120 | AATATTCCCTCTGCAGCACCAGG |
| Chr3 | 97725864 | 69246 | ACCATTTCTTCTGCAGCACCTGG |
| Chr17 | 34985068 | 67667 | GGGTCCGCTTCTGCAGCACCTGG |
| Chr9 | 111467809 | 52903 | AGGAATCCTACTGCAGCACCCAG |
| Chr4 | 76159966 | 48719 | TTACTCACTTCTGCAGGCACCTG |
| Chr5 | 68338523 | 47347 | CCACTCCTTCTGCAGCACCCGG |
| Chr17 | 3980376 | 46215 | GGAACCCCTCTGCAGCTTCTGG |
| Chr20 | 19790626 | 41979 | CATTTTCTTTCTGCAGCACCTGG |
| Chr17 | 78923978 | 41804 | AGAGGCCCCTCTGCAGCACCAGG |
| Chr8 | 71384404 | 40000 | TTTCCTGCTTCTGCAGCACCAGG |
| Chr17 | 39655735 | 37576 | GCCCCCTCCTCTGCAGCACCTGG |
| Chr6 | 41457565 | 33918 | CTCCTCCCTCCTGCAGCACCTGG |
| Chr13 | 109802140 | 32087 | AAAATACCTTCTGCAGTACCAGG |

TABLE 7-continued

| Chr | Position | | DNA seq at a cleavage sites |
|---|---|---|---|
| Chr5 | 85696042 | 30501 | CTACTGACTTCTGCAGCACCTGG |
| Chr4 | 7336836 | 30249 | AGCTCCCATTCTGCAGCACCCGG |
| Chr9 | 139891539 | 29763 | AGTTCCCATCTGCAGCACCAGG |
| Chr10 | 13436789 | 28672 | CTCATCCCTTCTGCAGCCCCAGG |
| Chr2 | 176121765 | 26781 | GCCCCCTGCTCTGCAGCACCCGG |
| Chr13 | 100011450 | 26724 | ACCTGCCTTCTGGCAGCACCAGG |
| Chr17 | 8432606 | 25254 | ACTGTCATTTCTGCAGCACCTGG |

TABLE 8

| RNF2 | | | |
|---|---|---|---|
| Chr | Position | DNA cleavage Score | DNA seq at a cleavage sites |
| Chr1 | 185056773 | 695836 | GTCATCTTAGTCATTACCTGAGG |
| Chr12 | 131619805 | 123134 | ATCACCTTAGCCATTACCAGGGG |
| Chr18 | 62061226 | 98156 | ATTATTTAGTCATTACCTTTGG |
| Chr8 | 99451745 | 82293 | CGTGCATTAGTCATTACCTGAGG |
| Chr7 | 43967267 | 70140 | ACTTATTTAGTCATTACCTGTAG |
| Chr6 | 143212079 | 67376 | GTAATATTAGTCATTACCGGTGG |
| Chr4 | 171989625 | 59218 | TAACACATAGTCACTACCTGGTG |
| Chr8 | 5745882 | 57546 | AATATGTTAGTCATTACCTGAGG |
| Chr4 | 189725512 | 34869 | ATGCTTCTTGTCATTACCTTGGG |
| Chr9 | 138721895 | 31931 | ACTTCAGTAGTCATTACCTAGGG |
| Chr5 | 92036966 | 29732 | GGTATCTAAGTCATTACCTGTGG |
| Chr15 | 25135467 | 35423 | CATCTAATAGTAATTACCTGGGG |
| Chr17 | 53928586 | 32362 | GTCATCTTAGTCATTAC-TGAGG |

TABLE 9

| HEK293-1 | | | |
|---|---|---|---|
| Chr | Position | DNA cleavage Score | DNA seq at a cleavage sites |
| Chr1 | 201992441 | 982832 | GGGAAAGTCCCAGCATCCTTTGG |
| Chr9 | 110103705 | 840188 | GGGAAAGACCCAGCATCCGTGGG |
| Chr22 | 47970525 | 773256 | GGAAAAGACCAAGCATCAGTGGG |
| Chr8 | 21121524 | 663039 | GGGAAGGACCCAGCATCCTGGGG |
| Chr9 | 129621088 | 618782 | GGGAAATACCCAGCATCCAATGG |
| Chr10 | 123094947 | 317069 | GGGAAAAGCCCAGCATCCCTTGG |
| Chr10 | 86303625 | 261270 | TGGAAAGAAACAGCATCCGTACG |
| Chr11 | 75956264 | 204471 | TTATAAGACCCAGCATCCGTAAG |
| Chr12 | 5555206 | 197869 | GGAGAAAGACCAGCATCCATAGG |
| Chr4 | 8541711 | 115848 | GGGAAATCCCCAGCATCTCTAGG |
| Chr5 | 65217522 | 89183 | GGAAAGTACACAGCATCCATCGG |
| Chr1 | 3488120 | 79221 | GGGGAAGACCCAGCACCCTTGGG |
| Chr13 | 31633478 | 74016 | ATGAAAGACCCAGCATCCATTGA |
| Chr19 | 30027761 | 30728 | AGGATTCCCCAAGCATCCGTGGG |
| Chr8 | 48879627 | 28382 | GAGAAAAGCCCAGCATCCTTAGG |
| Chr2 | 85388185 | 25657 | GGGAATACACCAGCATCCGTAGA |

TABLE 10

| | HEK293-2 | | |
|---|---|---|---|
| Chr | Position | DNA cleavage Score | DNA seq at a cleavage sites |
| Chr5 | 87240614 | 486955 | GAACACAAAGCATAGACTGCGGG |
| Chr4 | 90522184 | 377451 | GAACACAATGCATAGATTGCCGG |
| Chr10 | 43159340 | 336031 | AACACAAAGACATAGACCACTGG |
| Chr1 | 40461425 | 300007 | TACACACAAGCACAGACTGCAGG |
| Chr2 | 19844956 | 252268 | AACTCCAAAGCATATACTGCTGG |
| Chr15 | 93557679 | 248075 | AGAACACATGCATAGACTGCTAG |
| Chr11 | 128508577 | 243706 | GAATTCAAAGCATAGATTGCAGG |
| Chr5 | 131174461 | 212455 | AAATACAATGCATACACTGCTAG |
| Chr19 | 30112719 | 209645 | TACACAAAACATAAGACTGCTGG |
| Chr20 | 97641 | 192351 | GAATTCAAAGCATAGATTGCAGG |
| Chr4 | 53536210 | 179748 | GAATACTAAGCATAGACTCCAGG |
| Chr13 | 113428467 | 171254 | CAATACAAAGGATAGACTGCAGG |
| Chr18 | 22360702 | 167163 | GGAATCAAAGCACAGACTGCAGG |
| ChrX | 36949815 | 154618 | GAAAACAAAACATAGAGTGCTGG |
| Chr7 | 83764327 | 113259 | ACTATATAAGCATAGACTGTTGG |
| Chr5 | 126385455 | 107283 | CCACACCAAGCATAGACTTCTGG |
| Chr5 | 142142325 | 106923 | TAAACACTAACATAGACTGCAGG |
| Chr18 | 56307003 | 85167 | AAGAACAAAACATAGACTGCAGG |
| Chr1 | 36097073 | 85043 | GTAAACAAAGCATACACTGAGGG |
| Chr3 | 81710854 | 85027 | CTCCTAAAGCATTAGACTGCAGG |
| Chr5 | 7625837 | 63687 | GGTACACAATAATAGACTGCAGG |
| Chr18 | 5596266 | 58941 | CCTACAGAAGCATAGACTGCAGG |
| Chr6 | 139353018 | 58275 | CCAAACAAAACATAGACTGCTGG |
| Chr22 | 28895718 | 51098 | ATTAAGATAGCATAGACTGCAGG |
| Chr1 | 77190607 | 50766 | TCACACAACCATAGACTGAGGG |
| Chr6 | 40925010 | 46749 | AACAAGTATGCATAGACTGCTGG |
| Chr9 | 97332609 | 39286 | GTAATTAAAGCACAGACTGCTGG |
| Chr18 | 68431104 | 35875 | TGTGTAAGAGCATAGACTGCTGG |
| Chr20 | 23101380 | 34207 | ATACACAGAGCAAAGACTGCAGG |
| Chr8 | 97317605 | 30476 | GAACACAGTACATAGACTGGCAG |
| Chr9 | 290168 | 30365 | AAACATAAAGAATAGACTGCAAG |
| Chr6 | 152710071 | 30053 | TACTCTATATCATAGACTGCTGG |
| Chr4 | 31157435 | 28353 | TGATTGAGTGCATAGACTGCTGG |
| Chr1 | 108869935 | 28244 | AGTATAGCAGCATAGACTGCAGG |
| Chr15 | 65377019 | 26457 | GAGCGATAAGCACAGACTGCTGG |

TABLE 11

| Chr | Position | DNA cleavage Score | DNA seq at a cleavage sites |
|---|---|---|---|
| HEK293-3 | | | |
| Chr15 | 79749931 | 658647 | CACCCAGACTGAGCACGTGCTGG |
| Chr10 | 131593121 | 497117 | GAGCCAGAATGAGCACGTGAGGG |
| Chr1 | 47005705 | 473980 | AGCTCAGACTGAGCAAGTGAGGG |
| Chr7 | 66968042 | 471010 | GACACAGACCGGGCACGTGAGGG |
| Chr9 | 110184637 | 465474 | GGCCCAGACTGAGCACGTGATGG |
| Chr11 | 134582415 | 445120 | GGCGCAGACAGAGCACGTGACGA |
| ChrX | 114764149 | 271791 | AGACCAGACTGAGCAAGAGAGGG |
| Chr4 | 72203005 | 230364 | ATATCAGACTGAGCACCGTGAGG |
| Chr6 | 103918240 | 230024 | AAATAAGACTGAGCACGTGGTGG |
| Chr17 | 7594610 | 229698 | AGCCAGACTGAGGCAAGTGAGGG |
| Chr3 | 160129761 | 183487 | AGGCCAGACTGAACACGATGAGG |
| Chr15 | 35402774 | 163023 | CCTAAAGACTGAGCAAGTGAAGG |
| Chr9 | 137039236 | 159048 | CAGCCAGACAGAGCACGTGGAGG |
| Chr6 | 79958440 | 147188 | AACAAAGACTGAGCACGTTAGGG |
| Chr2 | 130402896 | 104759 | GACCCAGAATGAGCACAAAAGGG |
| Chr1 | 34163192 | 99903 | ATTCTAGACTGAGCACGTGCAAG |
| Chr2 | 97163211 | 92744 | CCCATGGGACTGAGCACATGAAGG |
| Chr17 | 79043523 | 71767 | TGGCCAGACTGAGCTCGTGAGTG |
| Chr10 | 22896606 | 64963 | GAAGGAGACTGAGCATGTGAGGG |
| Chr8 | 20947876 | 57273 | TCTCCAGACTGAGCCCATGAGGG |
| Chr19 | 19169358 | 51573 | GGACCAGGCTGAGCACATGGAGG |
| Chr6 | 112273496 | 51305 | AAGCCAGACTGAGCACGTTCAGG |
| Chr1 | 229294224 | 45946 | GGTCATCACTGAGCACGTGAGGT |
| Chr2 | 240026760 | 43234 | GGCTCAGACTGAGCACCTGAGAG |
| Chr15 | 94188821 | 42943 | ATTCCAGAATGAGCACATGAAGG |
| Chr2 | 131090691 | 41142 | ACCCAAGACAGAGCACGTGGAGG |
| Chr11 | 60830962 | 38724 | TCCCAGAACTAAGCACGTGAATG |
| Chr14 | 102917106 | 37462 | CTCTGGAGACTGACCACGTGAGGG |
| Chr10 | 231355036 | 32499 | ACTCCAGACTGAGCAACTGAGGG |
| ChrX | 16606309 | 31195 | TTCCCAGACAAAGCACGCGAAGG |
| Chr14 | 78070357 | 25732 | AACCAGACTGGAGCACGTGGTGG |

TABLE 12

| Chr | Position | DNA cleavage Score | DNA seq at a cleavage sites |
|---|---|---|---|
| HEK293-4 | | | |
| Chr15 | 75632142 | 795491 | GCACCTGCGGCTGGAGGTGGCAG |
| Chr1 | 201067376 | 656701 | GGCACTGCTGCTAGAGGTGCAGG |
| Chr16 | 50300347 | 649176 | AGCACTGTGGCTGGGGGAGGGGG |
| Chr4 | 56815199 | 648870 | GGCAATGCGGCTGGAGGCGGAGG |
| Chr11 | 528949 | 647145 | GGCTCTGCGTCCGGAGGTGAGAG |
| Chr9 | 139522901 | 644731 | GCCACAGCGGCCGGAGGTGGCAG |
| Chr20 | 60895671 | 643148 | GGCACAGCAGCTGGAGGTGCTGG |
| Chr16 | 28266968 | 617861 | GGCTCTTCGGCTGGAGGTAGCGG |
| Chr15 | 41044242 | 612537 | GGCGCTGCGGCGGGAGGTGGAGG |

TABLE 12-continued

| | | | |
|---|---|---|---|
| Chr7 | 134872032 | 592761 | AGCACTGTGGCTGGGGGAGGCGG |
| Chr14 | 21993455 | 579921 | GGTACAGCGGCTGGGGGAGGCGG |
| Chr5 | 141232854 | 577115 | GGCACTGCGGCAGGGAGGAGGGG |
| Chr12 | 113935461 | 571487 | GGCCCTGCGGCTGGAGATATGGG |
| Chr7 | 1397399 | 562494 | AGCACTGCAGCTGGGAGTGGAGG |
| Chr18 | 37194558 | 558246 | GGCACTGCGGGTGGAGGCGGGGG |
| Chr10 | 126694875 | 557909 | GGCACGACGGCTGGAGGTGGGGG |
| Chr3 | 51725452 | 545918 | GGCTCTGTGGCTGGAGGAGGTGG |
| Chr22 | 23284036 | 517249 | GGCCCTGCTGCTGGAGGTGCTGG |
| Chr15 | 80601340 | 503910 | GACACCTCGGCTGGAGGTGCAGG |
| Chr13 | 39262929 | 502808 | AGCAGTGCGGCTAGAGGTGGTGG |
| Chr19 | 33382081 | 502713 | GGCTCTGCGGCTGGAGGGGGTGG |
| Chr20 | 1151854 | 496956 | GGCACTGTGGCTGCAGGTGGAGG |
| Chr17 | 16982366 | 494752 | CAGACTGCGGCAGGGGGTGGCGG |
| Chr7 | 139244407 | 493992 | GCCACTGCGACTGGAGGAGGGGG |
| Chr7 | 54561438 | 490603 | AGGACTGCGGCTGGGGGTGGTGG |
| Chr1 | 32471660 | 484475 | GGCACTTCAGCTGGAGGCAGAGG |
| Chr19 | 1295087 | 474612 | GACACTGAGGCAGGAGGTGGGGG |
| Chr20 | 31349773 | 464930 | GGCACTGCGGCTGGAGGTGGGGG |
| Chr1 | 17108460 | 459439 | GCCACTGGGGCTGGGGGTGGGGG |
| Chr10 | 52054245 | 457305 | GGCCCTGCTACTGGGGGTGGTGG |
| Chr3 | 123863990 | 454429 | TGCCCAGCAGCTGGAGGTGAGGG |
| Chr20 | 60080554 | 452874 | AGCACTGCAGATGGAGGAGGCGG |
| Chr9 | 133039176 | 451926 | GTCACTGCAGCTGGAGGAGGGGG |
| Chr20 | 60010563 | 449013 | TGCACTGCGGCCGGAGGAGGTGG |
| Chr3 | 130508525 | 447541 | GACACTGTGGCTGGAAGTGGAAG |
| Chr19 | 41220525 | 439919 | GGCAATGTGGCTGAAGGTGGGGG |
| Chr22 | 35746283 | 439510 | GACACTAGGGCAGGAGGTGGAGG |
| Chr6 | 51500473 | 434313 | GACACAGTGGCTGGAGGTGTGGG |
| Chr15 | 60790562 | 425666 | GGCACTGCAACTGGAAGTGATGG |
| Chr13 | 2769410 | 423491 | GGCACTGGGGTTGGAGGTGGGGG |
| Chr9 | 5020591 | 417491 | TGCACTGCAGCTGCAGGTGGAGG |
| Chr19 | 38616186 | 415646 | GGCACTGAGACTGGGGGTGGGGG |
| Chr22 | 30130865 | 413438 | GGCTGTGCGGCCAGAGGTGGAGG |
| Chr8 | 144997514 | 411333 | AACACTGCGGCTGCAGCTGGAGG |
| Chr10 | 45317434 | 409344 | GGCTCTGCAGCTGTAGGAGGAGG |
| Chr2 | 241640854 | 407399 | GGGGCTGCGGCCGGAGGTGGTGG |
| Chr20 | 37471343 | 403424 | AGCACTGTGCCTGGGGGTGGGGG |
| Chr10 | 127971444 | 401650 | GGAACTGGGGCTGGGGGTGGGGG |
| Chr8 | 11479079 | 399039 | GGCCCTGCAGCTGGAGATGGAAG |
| Chr15 | 71686928 | 397419 | TGCTCTGCGGCAGGAGGAGGAGG |
| Chr12 | 54977735 | 395702 | GACACTGCTCTGGGGGTGGGGG |
| Chr20 | 24376057 | 393677 | GGCACTGAGACCAGAGGTGGTGG |
| Chr5 | 177676326 | 392871 | GCCACTGTGGCTGGAGGTGGGGA |
| Chr3 | 23651530 | 387632 | GGCACAGCAGGTGGAGGTGGAGG |
| Chr7 | 110143151 | 367129 | GCCACTGCAGCTAGAGGTGGAGG |
| Chr2 | 25348467 | 384216 | GGAACTGTGGCTGGAGGTGGCAG |
| Chr19 | 56125854 | 376148 | GGCCCAGCGGCGGGAGGTGGGGG |
| Chr10 | 1285239 | 374554 | GGCCCTTCGGCTGGAGGTGGCAG |
| Chr8 | 119227146 | 370348 | GGCACAATGGCTGGAGGTGAAGG |
| Chr20 | 45343011 | 363311 | GGCACTGAGGGTGGAGGTGGGGG |
| Chr5 | 3606830 | 361575 | GACACAACGGCAGGAGGTGGCGG |

TABLE 12-continued

| | | | |
|---|---|---|---|
| Chr10 | 126752487 | 353759 | GGCACTGCAGCCTGGGGGTGGGG |
| Chr20 | 61810739 | 352160 | GTCACTGCGGCTGCAGATGGCGG |
| Chr22 | 41620073 | 346404 | GGGCATGCGGCTGGAAGTGGTGG |
| Chr8 | 20854500 | 341030 | GGCACTGGGGCTGGAGGTGGGGG |
| Chr22 | 49132903 | 339625 | AGCACAGCAGCTGCAGGTGGGGG |
| Chr1 | 230193260 | 336660 | GACTCTGCAGCTGAAGGTGGGGG |
| Ch11 | 118950336 | 326013 | GTCACTGAGGCTGGAGTGGAGGG |
| Chr20 | 22805414 | 318568 | AGCACTGTTACAGGAGGTGGGGG |
| Chr6 | 158452369 | 317681 | AGCTCTGTGGCTGGAGGTGTGAG |
| Chr19 | 46887174 | 316408 | GAGGCTGCGGCTGGGGGTGGAGG |
| Chr22 | 43766275 | 308603 | AGCACTGCGCTTGGGGGTGGGGG |
| Chr15 | 34081546 | 306434 | AGCACTGTAGCAAGAGGTGGAGG |
| Chr3 | 53375995 | 305643 | GGCTCTGAGGCCAGAGGTGGTGG |
| Chr10 | 77103120 | 304242 | GGCATCACGGCTGGAGGTGGAGG |
| Chr10 | 73435248 | 302892 | GTAACTGCGGCTGGCGGTGGTGG |
| Chr5 | 96338759 | 300204 | AGCACTGGGGATGGAGGTGTAGG |
| Chr1 | 44397932 | 298786 | AGAACTGCTGCTGGAGGTGGTGG |
| Chr5 | 1832938 | 286492 | GGCTCTGTGGCCGGAGGAGGCGG |
| Chr6 | 160517881 | 283538 | GGCACTGCTGCTGGGGGTGGTGG |
| Chr9 | 140205577 | 281021 | GGCCCTGGGGCTGGAGGTGTTGG |
| Chr6 | 33950129 | 273481 | GGCTCTGAGGCTGGTGGTGGGGG |
| Chr1 | 53336192 | 264545 | GGCACGCGGCTGGGAGGTGGAGG |
| Chr3 | 128301954 | 259163 | TGCACTGCAGCTGGGGCTGGAGG |
| Chr12 | 104739609 | 258159 | CCTTCTGCGGCTGGAAGTGGTGG |
| Chr10 | 60003488 | 256317 | GGCACGCGGCTGGGAGGTGGAGG |
| Chr17 | 69519133 | 253054 | AGCAATACGGATGGAGGTGGAGG |
| Chr2 | 152827915 | 251661 | GGCACTTCGGTTGGGGGTGGGGG |
| Chr5 | 41803379 | 250222 | TGCACTGCGGGCGGAGGCGGCGG |
| Chr3 | 10418956 | 250189 | GGCTCCGCAGCTGGAGGTGGGGG |
| Chr7 | 139631 | 249296 | TGCACCGCGGCTGGGGCTGGAGG |
| Chr16 | 22690928 | 242892 | TCCACTGAGGCTGGGGGTGGTGG |
| Chr11 | 65326667 | 242757 | CTGGCAGCGGCTGGGGGTGGGGG |
| ChrX | 70836550 | 231845 | GGCCATGCGGCTGGTGGTGGTGG |
| Chr13 | 88900992 | 229015 | CACACTGCAGCTGGAGGTGGTGG |
| Chr12 | 104234592 | 228650 | CTGCCTGCGGCTGGGGGTGTGGG |
| Chr17 | 75429280 | 226119 | GACACCACGGCTGGAGATGGTGG |
| Chr14 | 101945036 | 224127 | GGGACTGCAACTGGAGGTGGGGG |
| Chr9 | 74103955 | 220510 | GGCACTGCAGCAGGGGATGGGGG |
| Chr3 | 9039864 | 218073 | GGCTCTGTAGCTGGGGGTGGTGG |
| Chr1 | 204463911 | 208882 | GGCGCTGCGGCTGGAGCCGGCGG |
| Chr2 | 8817154 | 207325 | TGCACAGCGGATGGAGGGGGGGG |
| Chr17 | 40693639 | 204010 | GGCACTGCAGGCAGGAGGTGAGT |
| ChrX | 152805653 | 201320 | GCCACTGAGGCCGGAGGTGGAGA |
| Chr6 | 41374185 | 201307 | GGGCACGCGGCTGGAGGAGGGGG |
| Chr2 | 6961256 | 200536 | AGCTCTGCGGCAGGAGTTGGAGG |
| Chr10 | 13692637 | 199091 | GGCACTGGGCTGGGAGGAGGGGG |
| Chr17 | 75325331 | 196964 | GGCCCTGCAGCTGGAGAGGGAGG |
| Chr7 | 43256545 | 196365 | TACACTGCAGCTGGGAGTGGTGG |
| Chr14 | 88773031 | 195053 | AGCACTGGGGCTGGGGGAGGGGG |
| Chr14 | 63796588 | 194350 | GACACTAAGGCTGGAGGTGGGGA |
| Chr17 | 42152617 | 190730 | TGCACTGCAGCTGGGGGTCGGGG |
| Chr7 | 29233956 | 187308 | GCCACTGGGGCTGGAGGGGGAGG |
| ChrX | 104846030 | 178315 | CAGCTCTGCGCTGGAGGAGGGGG |
| Chr4 | 19769425 | 177335 | AGCTCTGCTGCTGGAGGAGGTGG |
| Chr3 | 52035832 | 174753 | GGCACTGAATCTGGAGGTGGGGG |
| Chr7 | 55344186 | 172714 | ATCACTGCGCCTGGTGGTGGGGG |
| Chr17 | 73501168 | 169547 | GCACCTGCGGCCAGGGGTGGGGG |
| Chr9 | 136602370 | 168438 | GGCACTGGGGCAGGAGATGGGGG |
| Chr16 | 88716134 | 167431 | AGCACGGCAGCTGGAGGAGGGGG |
| Chr14 | 95761249 | 163668 | GGCACTCTGGCTGGAGCTGGGGG |
| Chr6 | 151886088 | 161687 | GGCCCTGCTGCTGGAGAAGGTGG |
| Chr10 | 36109441 | 159071 | GGCATTGCTGCTGGTGGTGGTGG |
| Chr1 | 228559256 | 158331 | GCACCGCGTGCTGGAGGAGGAGG |
| Chr21 | 36453434 | 155062 | AGCTCTGCTATTGGAGGTGGAGG |
| Chr9 | 19933045 | 151459 | AGCCCTGGGGCAGGAGGTGGGGG |
| Chr7 | 150498859 | 149636 | GCTGCTGCGGCTGGAGGTGGGGA |
| Chr16 | 1072626 | 147810 | GGCCCTGCAGCAGGGGGTGGAGG |
| Chr5 | 41968123 | 147631 | GGAAGTGCGGCAGGAGGTGGAGG |
| Chr2 | 45247404 | 143408 | GACACCGTGACTGGAGGTGGAGG |
| Chr18 | 60646595 | 142546 | GCAGCTGCGGCTGGAGCTGAGGG |
| Chr1 | 18954894 | 141715 | GGAACTGTGCTGGGAGGTGGAGG |
| Chr2 | 231467380 | 141358 | GGCACTGCAGCTGGGGGTTGGTG |
| Chr4 | 7686554 | 132791 | AACACTGGGGCTGGTGGTGGTGG |
| Chr17 | 25735157 | 130579 | TGCACTCCGACTGGAAGTGGTGG |
| Chr2 | 149402504 | 130567 | TGCACTGAGGAAGGAGGTGGAGG |
| Chr12 | 53453557 | 128079 | TGGACTGCGGCTGGAGAGGGAGG |
| Chr17 | 29815563 | 126311 | GGCGCTGCGGCCGGAGGTGGGGC |
| Chr8 | 145730111 | 126139 | GGCACATGGGCTGGGGGTGGGGG |
| Chr12 | 55427953 | 124563 | GGCACTGAGAAAGGAGGTGGAGG |
| Chr19 | 32836900 | 123779 | TGCCCTGCAGCTGGGGGTGGGGG |

TABLE 12-continued

| | | | |
|---|---|---|---|
| Chr20 | 49771524 | 121173 | TGCACTGCAGATGGTAGGTGGGG |
| Chr17 | 38478448 | 121131 | GGCACCTTGGCTGAAGGTGGGGG |
| Chr3 | 128169624 | 120130 | ACCACTGTGGCTGGCAGGTGGTG |
| Chr1 | 12259808 | 117998 | AGCACTGCAGCGGGAGGTGAGAG |
| Chr7 | 157443393 | 117892 | GGCACTGGGTCTGAAGGTGGAGG |
| Chr17 | 31790791 | 112013 | TGCACTGCAGCTGGGGGCAGAGG |
| Chr12 | 101718339 | 106833 | GGCACTCTGGCTGGACGTGGTGG |
| Chr8 | 1241128 | 105778 | GGCACTGTTGCTGGAGGAGGCAG |
| Chr13 | 27530813 | 105452 | GGCACTGCTGACTAGGGGTGGTG |
| Chr16 | 49777696 | 102520 | TGCACTGCGACTGGAGGGAGAGG |
| Chr3 | 193847797 | 101152 | GCACTGCAAACTGGAGGTGGGGG |
| Chr20 | 60174571 | 98694 | CCCACTGTGGCTGGAGGTGTGGG |
| Chr8 | 145543672 | 97195 | AGCCCTGCGGCCGGGGGAGGCGG |
| Chr3 | 49055364 | 96343 | GGGACTGCGGCTGGAGGTGGGAA |
| Chr4 | 156491955 | 94045 | TTCACTGTGGCTGGAGGTGGGGA |
| Chr2 | 3610377 | 86281 | AGCACTATGGATAGAGGTGGAGG |
| Chr9 | 138465751 | 86247 | TACACTGCGGCCGGGAGTGGTGG |
| Chr16 | 26710087 | 84876 | TGCACTGAAGCTGGAGGTGGAGA |
| Chr9 | 35349204 | 81775 | AGTACTGCGGCTGGGCGTGGTGG |
| Chr22 | 18663160 | 81182 | AGCACTAGGGCAGGAGATGGGGG |
| Chr18 | 75260893 | 81143 | GACACTGAGGCTGGAAGAGGTGG |
| Chr12 | 90804707 | 79601 | GGCATGCGGCTGGGAGGTGGAGG |
| Chr6 | 167276293 | 78532 | CGTTCTGCGGCGGGAGGTGGCGG |
| Chr7 | 17979718 | 76594 | GCACTGGCAGCCGGAGGTGGTGG |
| Chr17 | 64544877 | 76045 | GGCAGGGCGGCTGGAGGAGGTGG |
| Chr10 | 132972512 | 75938 | AGCACTGGGGCAGGAGGGTGGTG |
| Chr1 | 229619193 | 73977 | TTGCATGCGGCTGGAAGTGGTGG |
| Chr6 | 36761680 | 73537 | CCCACTGGGCTGGAGGTGGGGG |
| Chr14 | 77678312 | 73330 | CAGACTGCAGCTGGTAGGTGGTG |
| Chr11 | 3159715 | 69407 | GGCAGTGCAGCTGGAGGCAGGGG |
| ChrX | 26910569 | 68725 | GGCTCTGCCACTGGAGGGGGTGG |
| Chr20 | 61989531 | 68404 | GACACTGAGGCTGGAGGTCTGGG |
| Chr1 | 2933843 | 66266 | GGCCCTGAGACTGCAGCTGGAGG |
| Chr15 | 77121510 | 65980 | AGCACTGTGGATGGAGTTGGAGG |
| Chr9 | 11158273 | 65661 | CTTCCTACGGCAGGAGGTGGGGG |
| Chr3 | 16815640 | 63432 | CGCACTGGGGCTGCAGGTGGAGG |
| Chr6 | 159190938 | 59673 | GGCCCTGCAGCTGGAGGAGGAGA |
| Chr2 | 71786040 | 58033 | AGCACTGCAGTGAGAGGTGGAGG |
| Chr10 | 128864484 | 56269 | GACACCGCAGCTGGGGGCGGCGG |
| Chr7 | 48144881 | 56266 | AGCACTGGGGCTGGAGCTAGAGG |
| Chr16 | 50334859 | 51736 | GGTTCTGCGGTTGGGGGTGGGGG |
| Chr15 | 25425088 | 51134 | GGCTCTGCATTTGGAGGTGTGCG |
| Chr17 | 176302 | 50056 | TGCACTGTGGCTGGAGATGGGGG |
| Chr16 | 1029978 | 49426 | GGCACTGCAGACGGAGGTGTGGG |
| Chr13 | 29913424 | 47868 | GACACTGCTGCTGGAGAGTGGAG |
| Chr16 | 89469252 | 46847 | GGCACTGCGGGAGGAGGTGGGCG |
| Chr6 | 157547859 | 45175 | AGAACTGGGGCTGGGGGTGGGGG |
| Chr20 | 56668028 | 44304 | GGGCCTGCAGCTGGGGGTGGGGG |
| Chr16 | 784113349 | 43989 | GGTACAGTGGCTGGAGGTGGAAG |
| Chr5 | 177928896 | 43690 | CCCACTGCGGGTGGAGGTGGAAG |
| ChrX | 101411055 | 43362 | CGCAGTGCGGCAGGAGGGTGGGG |
| Chr11 | 20409041 | 42805 | AACCCTGCGGCAGGAGGAGGCGG |
| Chr14 | 99286477 | 42026 | GATACTGGGGCTGGGGGTGGAGG |
| Chr11 | 78127585 | 41787 | TGCACTGCAGCTGGAGGCAACGG |
| Chr1 | 183596713 | 40667 | GCACTTGCTGCTGGAGGAGTAGG |
| Chr11 | 17538892 | 40520 | TGCACTGCGGTCAGGAGGAGGCG |
| Chr22 | 18854922 | 35903 | AGCACTAGGGCAGGAGATGGGGG |
| Chr12 | 21742959 | 33984 | AGCCCTGCTACTGGGGGTGGGGG |
| Chr8 | 144781302 | 33431 | GACACTGCAGCTGGAGGTGGGGT |
| Chr2 | 59012462 | 33083 | TGCACTGCAACTGGGGGTGGCAG |
| Chr1 | 908980 | 33024 | GACCCTGCGGTGGGAGGTGGCGG |
| Chr15 | 43601412 | 31873 | GGCCCTGAGGCAGGAAGTGGGGG |
| Chr1 | 176665050 | 31488 | ACCACTGAGGATGGGGGTGGAGG |
| Chr20 | 19620239 | 31159 | CGCACTGGGGCTGCAGGTGGAGG |
| Chr5 | 171087054 | 30547 | GGGACTGCAGCTGGAGGTGGAGG |
| Chr15 | 26125549 | 30509 | CAAACTGCAGCTGGAGATGGGAG |
| Chr12 | 114150540 | 29438 | CTGACTGCAGCTGGAGGTGGAGA |
| Chr7 | 157889941 | 28995 | GGCACTGGGAAGGAGGTGGAGG |
| Chr22 | 44625614 | 28747 | GACACTGCTACTGGAGGCTGGGG |
| Chr18 | 60805450 | 27656 | GCACTGGCGGCTGGAGGTGGTGG |
| Chr22 | 18743056 | 27487 | AGCACTAGGGCAGGAGATGGGGG |
| Chr12 | 130859964 | 25960 | GAGAATGCGGATGGAGGTGGTGG |
| Chr14 | 24740271 | 25491 | GGCACTGCCACTGGGGGTGAGGG |
| Chr5 | 54469282 | 25319 | GCCACCGCGGCAGGAGGCGGAGG |
| Chr4 | 6094150 | 25223 | GAGCCTGCGGCTGCAGGTGGGTG |

TABLE 12-continued

| | HBB | | |
|---|---|---|---|
| Chr | Position | DNA cleavage Score | DNA seq at a cleavage sites |
| Chr12 | 124803834 | 1411410 | GCTGCCCCACAGGGCAGCAAAGG |
| Chr15 | 46598129 | 1107004 | GTTGCCCCTCAGGACAGTACAGG |
| Chr22 | 17230623 | 974499 | TGTGCCCCACAGAGCACTAAGGG |
| Chr9 | 104595883 | 923681 | TCAGCCCCACAGGGCAGTAAGGG |
| Chr17 | 8370253 | 877014 | TTGCTCCCACAGGGCAGTAAACG |
| Chr14 | 94585327 | 837168 | ATGGCCCCACAAGGCAGAAATGG |
| Chr11 | 5248215 | 818187 | CTTGCCCCACAGGGCAGTAACGG |
| Chr12 | 93549202 | 583920 | ATTGCCCCACGGGGCAGTGACGG |
| Chr1 | 177593980 | 229317 | TCTACCCCACATGGCAGTAATGG |
| ChrX | 75006257 | 165922 | GTGGCCCCACAGGGCAGGAATGG |
| Chr6 | 50041372 | 142026 | TCTGCCCCACATGGCAGTAATGA |
| Chr6 | 23709579 | 114576 | GAAGCCCTACAGGGCAGCAATGG |
| Chr2 | 121715240 | 97571 | GTGTCCCCACAGGGCAGGAAAGG |
| Chr8 | 24931381 | 97489 | AGTGCCACACACAGCAGTAAGGG |
| Chr14 | 36889538 | 53050 | GTTATCCCACAGGACAGTGAGGG |
| Chr1 | 17346702 | 51982 | CGGTCCCCACAGGGTCAGTAAGG |
| Chr20 | 39992928 | 49369 | AGTGGCCCCAGGGCAGTGAGGG |
| Chr10 | 95791920 | 47520 | ACTCTCCCACAAGGCAGTAAGGG |
| Chr4 | 148531374 | 37943 | GTTACCTCACAGAGCAGAAAGGG |
| Chr5 | 53613387 | 32279 | TCACCCCACAGGCCAGTAAAGG |

GUIDE-seq and other methods require a filtering step that removes about 90% of the detection sites that lack homology to the on-target site, but the multiplex Digenome-seq does not filter sites but are aligned based on edit distance. The 964 sites were clearly divided into 11 groups. Furthermore, each of the 11 groups for in vitro cleavage site was has a high homology to one of 11 target sequences. Accordingly, a de novo motif or sequence logo, obtained by comparing sequences within each group, matched the target sequence at almost all nucleotide sites (FIG. 15a).

The results show that although it is less than the protospacer-adjacent motif (PAM) sequence and the PAM-proximal 10-nt "seed" site recognized by Cas9, the 10-nt site of the 5'-end at the 23-nt target sequence contributes to the specificity of RGEN. Further, it was identified that all sites except one of the 964 sites cleaved by the 11 RGEN have the PAM sequence of 5'-NGG-3' or the sequences similar to PAM of 5'-NNG-3'/5'-NGN-3'. Accordingly, the multiple Digenome-seq can be used to accurately find in vitro cleavage sites without program searches for homologous sequences and is simple, can be applied to a plurality of programmable nucleases, and has many advantages as compared to the other known methods such as GUIDE-seq and HTGTS.

Figure 15B:
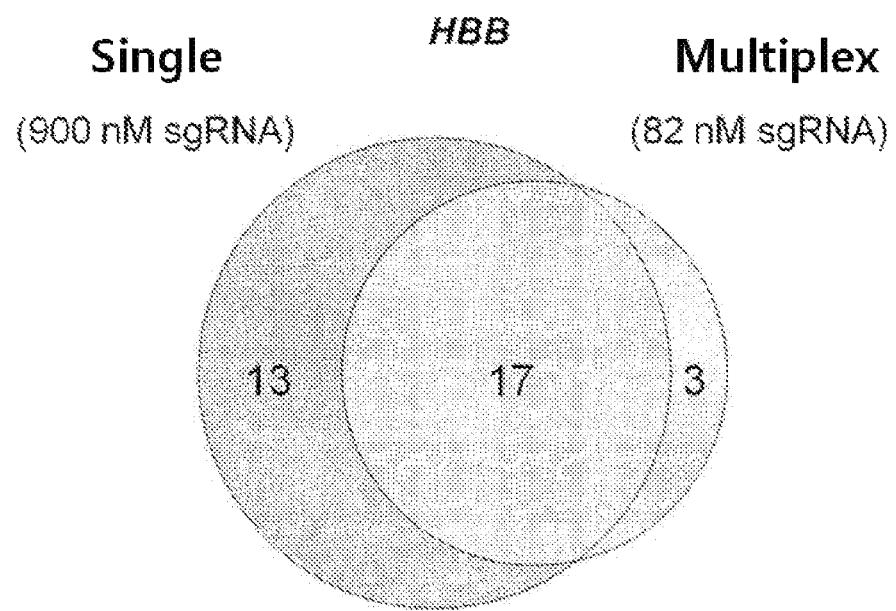
Figure 15C:
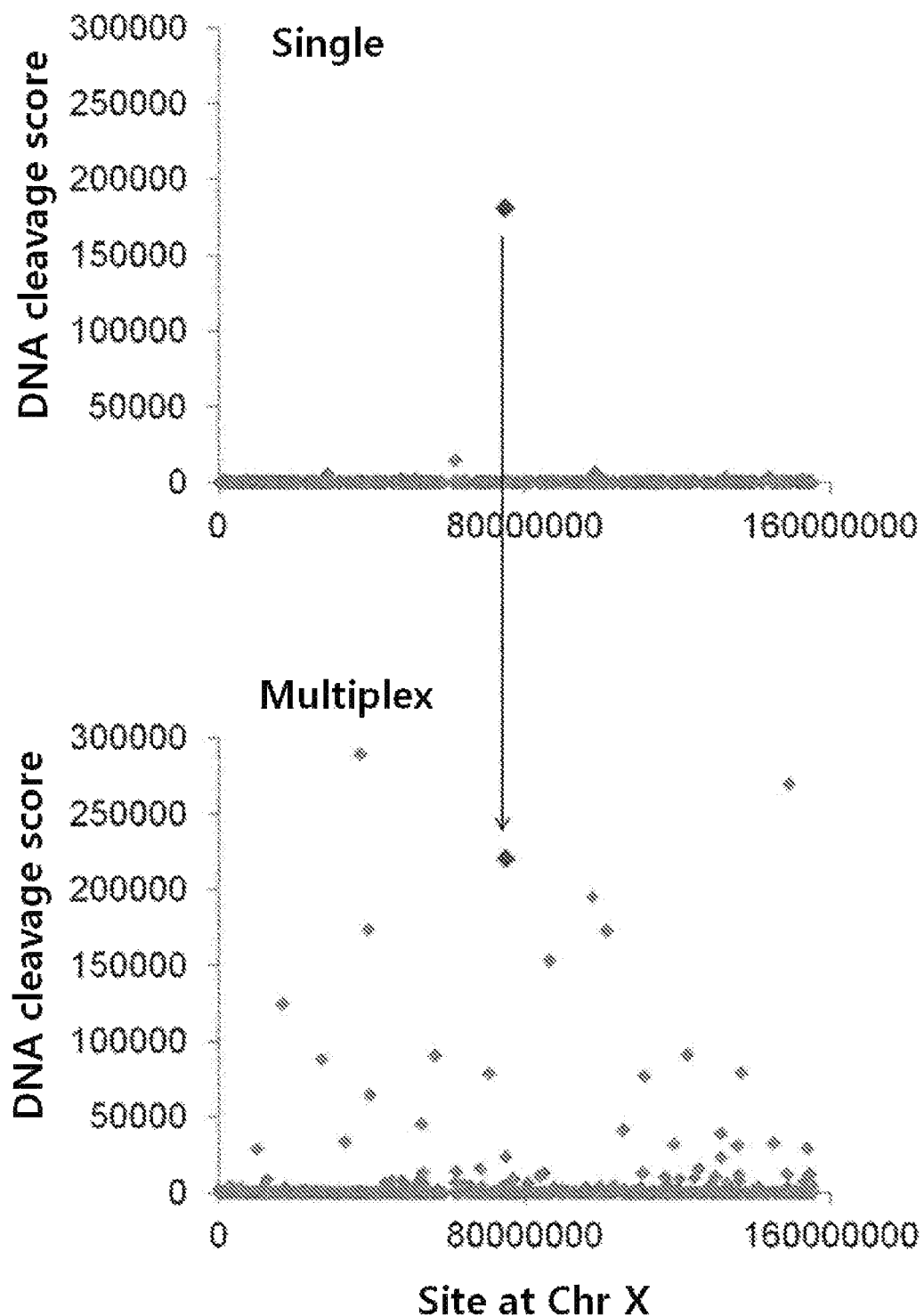
Figure 16A:
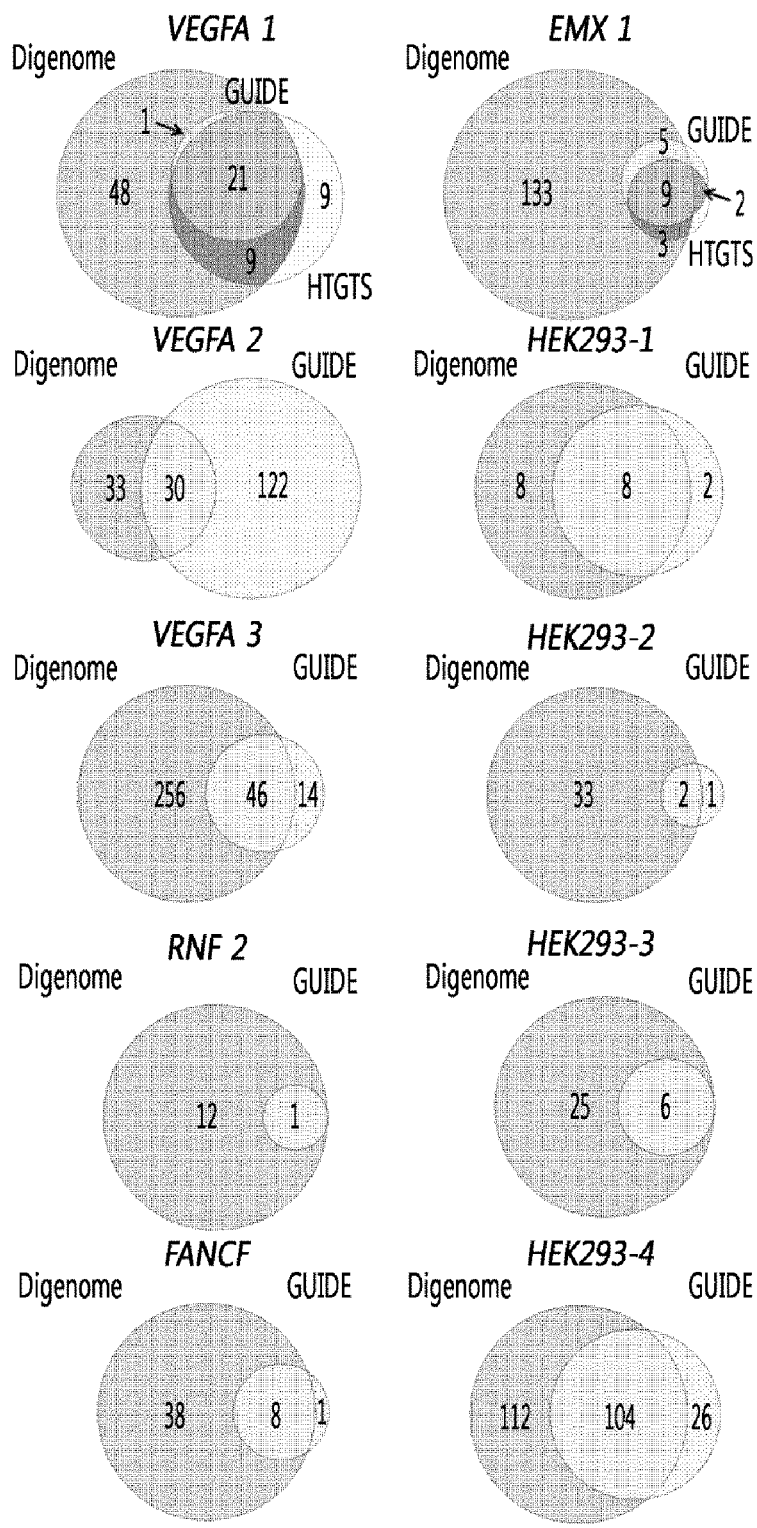
FIG. 16 illustrates an analysis of the sites identified by the multiplex Digenome-seq. (a) The number of sites identified by Digenome-seq, GUIDE-seq, and HTGTS is shown in a Venn diagram. (b) It illustrates the percentage of sites identified by Digenome-seq according to the total number of mismatches (top) and the number of mismatches in a seed region (bottom). (c) The number of sites with mismatches less than or equal to 6 nucleotides in the human genome and the number of sites identified by Digenome-seq are shown by a scatterplot (top). 11 RGEN on-target sites were divided into two groups of G1 (less than 13,000 sites with a mismatch of less than or equal to 6 nucleotides in the human genome) and G2 (greater than or equal to 16,000 sites with a mismatch of less than or equal to 6 nucleotides in the human genome) (bottom). The error bar represents the SEM. P values were calculated by Student's t-test. (d) The number of sites identified by GUIDE-seq and the number of sites identified by Digenome-seq are shown by a scatterplot.
Figure 16C:
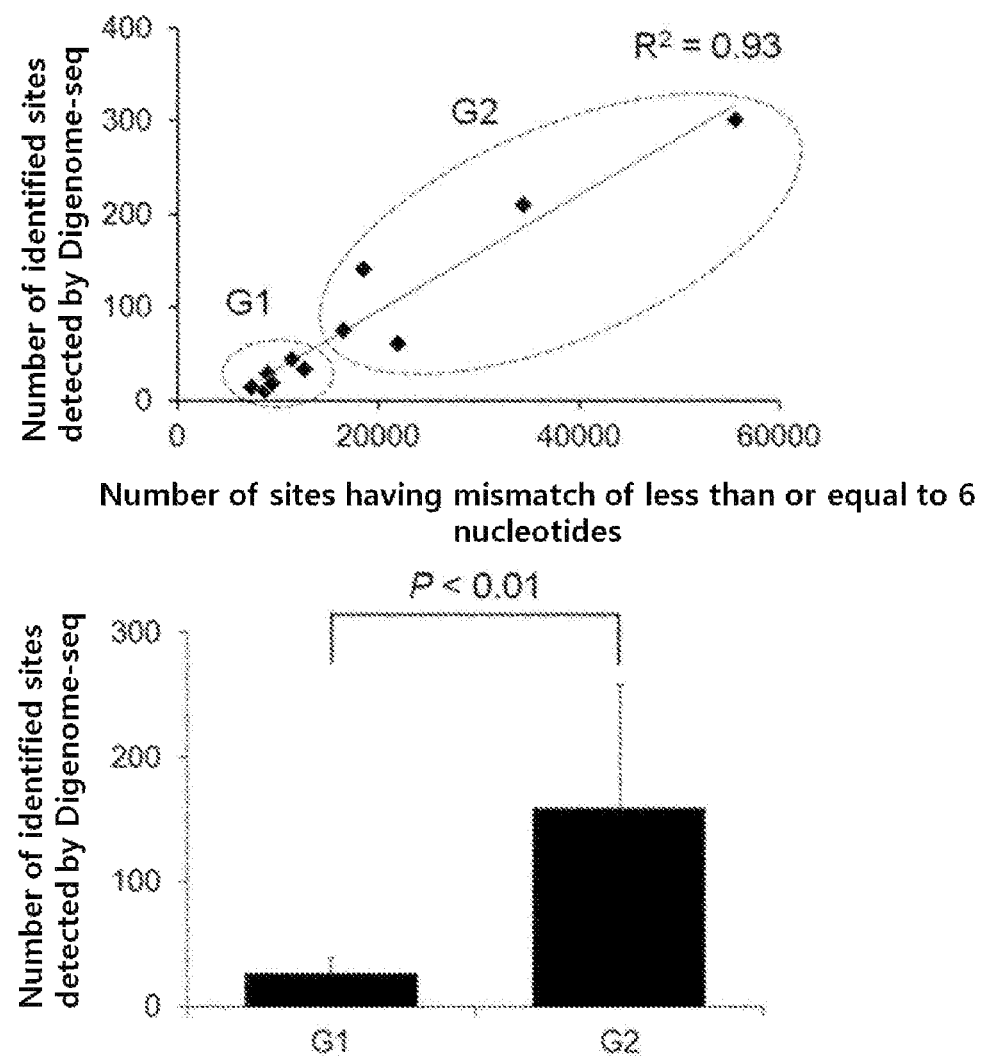

Next, it was identified whether each sgRNA was capable of cleaving on-target and off-target sites. 17 sites (=57%) of 30 sites cleaved by treatment with Cas9 (300 nM) at a high concentration (900 nM) of HBB-specific sgRNA were detected at the time of performing the multiplex Digenome-seq using the same sgRNA as low concentration (82 nM) (FIGS. 15b and 16c). These results suggest that each of 11 sgRNAs can direct Cas9 to their on-target and off-target sites independently of each other, and it can be understood that Digenome-seq has complexity.

EXPERIMENTAL EXAMPLE 8

In vitro Cleavage Site

The 11 sgRNAs showed a wide range of specificities on a genomic scale; The number of cleavage sites per sgRNA in the human genome ranged from 13 to 302 (FIG. 16a and Tables 3 to 12). As expected, all of the on-target sites identified in the human genome using the Cas-OFFinder, and each on-target site and the most of the sites having one or two nucleotides were detected when the multiplex Digenome-seq was performed (FIG. 16b). However, few sites with three or more nucleotide mismatches were detected. That is, the ratio of sites detected by Digenome-seq decreased exponentially as the number of nucleotide mismatches increased from 3 to 6 (FIG. 16b). In addition, the sites with two or more nucleotide mismatches in the seed region were not cleaved in vitro than positions with zero or one mismatch (P<0.01, Student's t-test).

Figure 17:
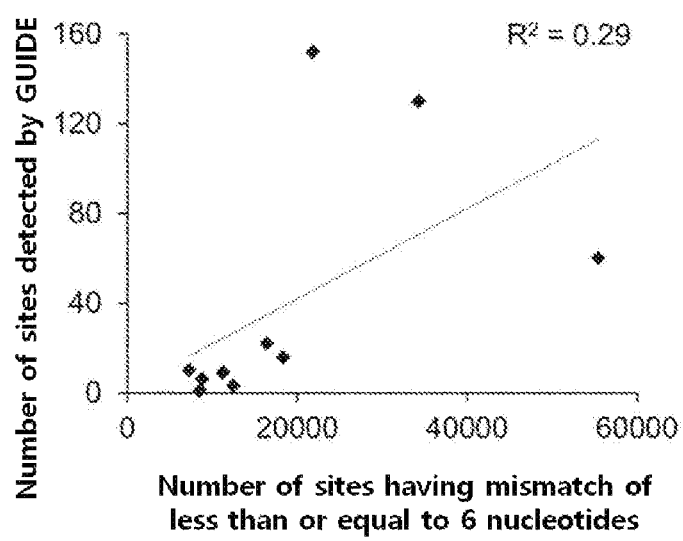
FIG. 17 illustrates the lack of correlation between the number of GUIDE-seq positive sites and the number of homologous sites with a mismatch of less than or equal to 6 nucleotides in the human genome.
Figure 18:
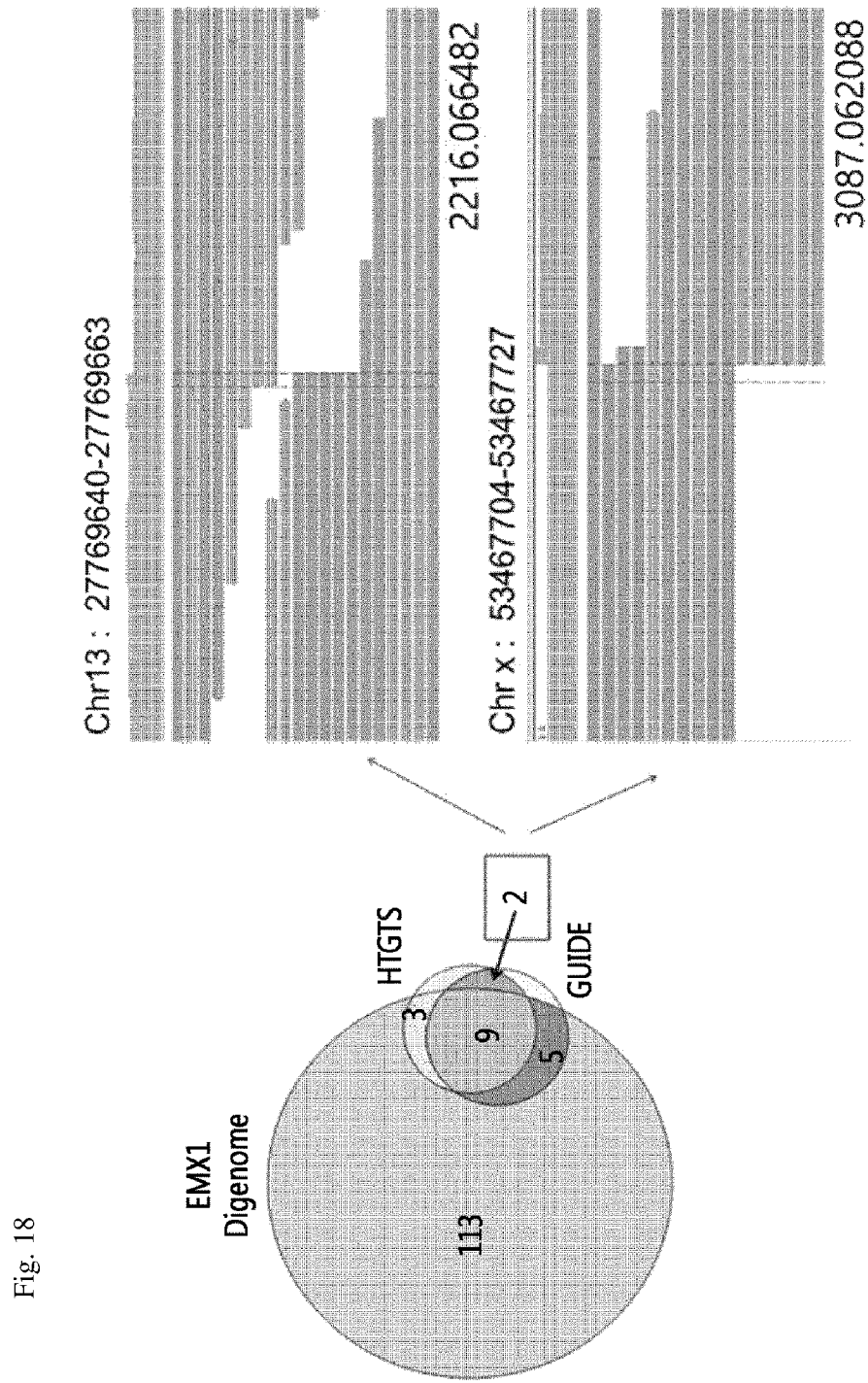
FIG. 18 illustrates two EMX1 off-target sites that are identified by HTGTS and GUIDE-seq but are not identified by Digenome-seq.

On the other hand, it was identified that the number of sites detected with Digenome-seq and the number of homologous sites (defined as "orthogonality") having a nucleotide mismatch of 6 or less in the human genome had a significant correlation ($R^2$=0.93) (FIG. 16c). That is, 5 sgRNAs with 16,000 or more of homologous sites in the human genome cleave 63 or more (161 on average per sgRNA) in vitro, whereas 6 sgRNAs with 13,000 or less of homologous sites cleave 46 or less in vitro (28 on average per sgRNA), and thus is relatively more specific (P<0.01, Student's test) (FIG. 16c). The results are different from the lack of correlation ($R^2$=0.29) observed between the number of GUIDE-seq positive sites and the orthogonality of the on-target site for the human genome (FIG. 17). However, the 5 most specific sgRNAs identified as GUIDE-seq, which cleave 10 or fewer sites in the cells, were consistent with the most specific sgRNA identified by Digenome-seq.

The results suggest that certain sites in the human genome where there are fewer than 13,000 nucleotide mismatches with 6 homologous sites or less and no homologous sites with 2 nucleotide mismatches or less are desirable to minimize off-target effects. In this regard, 368 sites (=21.5%) among the 1715 targetable sites including the 5'-NGG-3' PAM sequence correspond to the above concept for 4 genes tested in the present disclosure (Table 13).

TABLE 13

| Gene | Exon | No. of PAM (NGG)-containing sites | No. of sites with no homologous sites harboring 0 or 1 mismatch in the human genome & No. of sites with fewer than 13,000 homologous sites harboring up to 6 mismatches |
|---|---|---|---|
| VEGFA | Exon1 | 235 | 79 |
|  | Exon2 | 8 | 0 |
|  | Exon3 | 26 | 18 |
|  | Exon4 | 6 | 0 |
|  | Exon5 | 1 | 0 |
|  | Exon6 | 14 | 5 |
|  | Exon7 | 8 | 4 |
|  | Exon8 | 252 | 34 |
|  | Total | 550 | 140 |
| EMX1 | Exon1 | 238 | 73 |
|  | Exon2 | 29 | 8 |
|  | Exon3 | 245 | 37 |
|  | Total | 512 | 118 |
| FANCF | Exon1 | 373 | 90 |
|  | Total | 373 | 90 |
| RNF2 | Exon1 | 50 | 12 |
|  | Exon2 | 4 | 0 |
|  | Exon3 | 8 | 0 |
|  | Exon4 | 14 | 0 |
|  | Exon5 | 21 | 0 |
|  | Exon6 | 10 | 0 |
|  | Exon7 | 173 | 8 |
|  | Total | 280 | 20 |
|  | Total | 1715 | 368 |

EXPERIMENTAL EXAMPLE 9

Digenome-Seq. vs. Other Methods

Figure 16D:
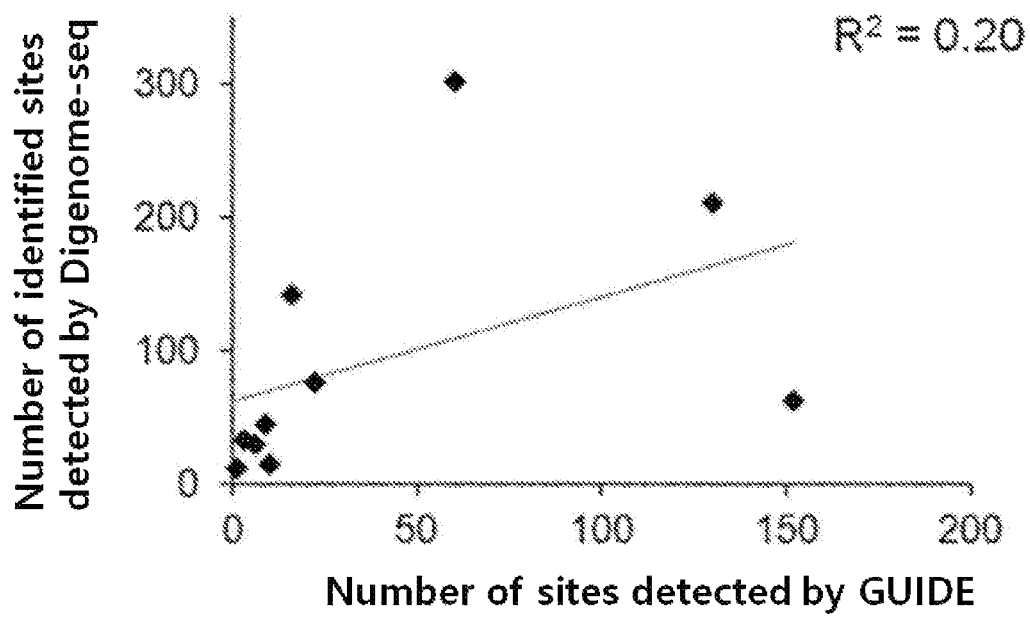

On average, the multiplex Digenome-seq successfully identified 80±8% of the sites detected by the conventional GUIDE-seq (FIG. 16a). For example, all sites detected with GUIDE-seq using three sgRNAs specific for VEGFA1, RNF2, and HEK293-3 were also identified as Digenome-seq. In addition, the multiplex Digenome-seq detected 703 new sites (70 averages per sgRNA) that were not detected by GUIDE-seq (FIG. 16A). As a result, GUIDE-seq detected 25±6% of the sites detected by multiplex Digenome-seq. RNF2 specific sgRNA is a good example showing the advantages of Digenome-seq. Previous studies have done two independent GUIDE-seq analyzes, but could not detect off-target sites for this sgRNA. However, Digenome-seq identified 12 cleavage sites in addition to the on-target site. Furthermore, a lack of correlation ($R^2$=0.20) was observed between the number of Digenome-seq positive sites and the number of GUIDE-positive sites (FIG. 16d).

Digenome-seq can obtain more off-target site candidates than GUIDE-seq for 9 of the 10 sgRNAs, but this is not a comprehensive result. That is, HBB sgRNA was not analyzed by GUIDE-seq. Overall, GUIDE-seq detected a total of 168 sites that were not detected in Digenome-seq.

On the other hand, HTGTS was also performed for two sgRNAs targeting VEGFA 1 and EMX1 sites (FIG. 16a). Most of the sites detected by at least one of the other two methods (GUIDE-seq and HTGTS) (31 of 40 in VEGFA 1 and 17 of 19 in EMX1) were also investigated as Digenome-seq, but 9 of VEGFA and 2 of EMX1 were not detected. It is because that some sites are artifact results by PCR primers or false positives arising from naturally occurring DSBs, which are the inherent limitations of GUIDE-seq and HTGTS. However, the two EMX1 off-target sites commonly found in this position, most commonly in the other two methods, are sgRNAs having a low sequencing depth (FIG. 18) or a low concentration (82 nM) at the specific site, and thus were not identified in the multiplex Digenome-seq. This problem could be overcome by performing WGS multiple times to increase the average sequencing depth and merging with sequence read obtained by using sgRNA of a high concentration in a single analysis.

VEGFA 2 specific sgRNAs are the only exception to the rule that Digenome-seq can detect more candidate sites than GUIDE-seq. That is, GUIDE-seq identified 122 sites that were not detected in Digenome-seq. The target sequence is an uncommon sequence consisting of cytosine stretch. Multiple sequence reads obtained with WGS at homopolymer sites could be removed from the mapping program. On the other hand, GUIDE-seq will be able to detect these positions using PCR to amplify the detected oligonucleotide sites.

Figure 19:
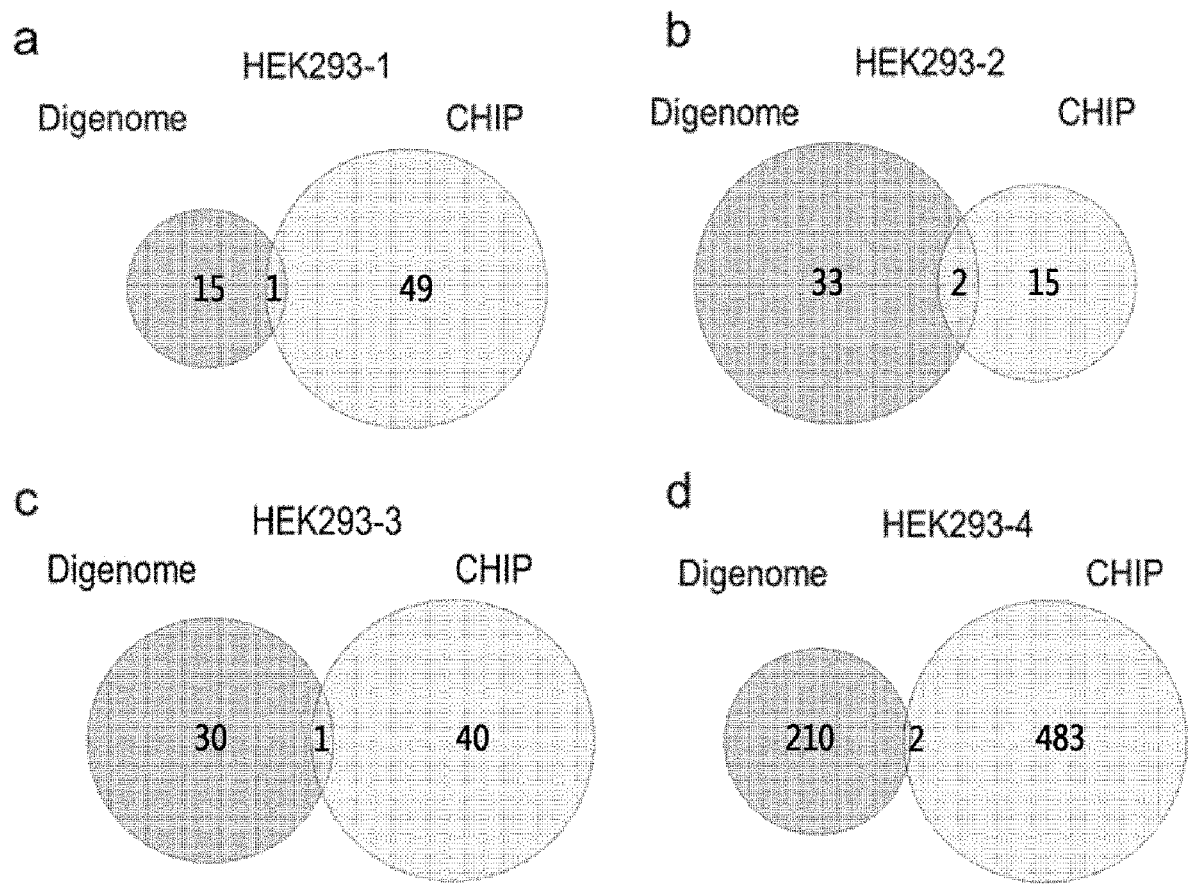
FIG. 19 illustrates the number of sites identified by Digenome-seq and CHIP-seq as a Venn diagram.

Next, the cleavage sites identified in the present disclosure were compared with those detected with ChiP-seq (chromatin immunoprecipitation sequencing). First, ChiP-seq was performed on the four sgRNAs used in the present disclosure. DCas9 did not bind to the majority of the Cas9-cleavage sites (288, 98%) identified as Digenome-seq (FIG. 19). The results show that DNA binding of Cas9 is a concept separated from DNA cleavage, and ChiP-seq using dCas9 is useful for examining the specificity of dCas9-based transcription factors and epigenome regulators, but it is inappropriate to analyze the genomic scale specificity of Cas9 RGEN.

EXPERIMENTAL EXAMPLE 10

Identification of Intracellular Off-Target Site

Next, using the next-generation sequencing (NGS) platform, it was identified whether each sgRNA and Cas9 protein for some sites of the sites (Table 14 to Table 23) identified in Digenome-seq and GUIDE-seq induces off-target indels in human cells.

TABLE 14

|  |  | Digenome only | Digenome and GUIDE | GUIDE only |
|---|---|---|---|---|
| VEGFA1 | Total captured sites | 57 | 22 | 0 |
|  | Number of NGS-tested sites | 15 | 22 | 0 |
|  | Number of validated sites | 6 | 20 | 0 |
| VEGFA2 | Total captured sites | 33 | 30 | 122 |
|  | Number of NGS-tested sites | 8 | 22 | 14 |
|  | Number of validated sites | 0 | 22 | 10 |

TABLE 14-continued

|  |  | Digenome only | Digenome and GUIDE | GUIDE only |
|---|---|---|---|---|
| VEGFA3 | Total captured sites | 256 | 46 | 14 |
|  | Number of NGS-tested sites | 18 | 27 | 9 |
|  | Number of validated sites | 4 | 22 | 5 |
| EMχ1 | Total captured sites | 129 | 14 | 2 |
|  | Number of NGS-tested sites | 16 | 12 | 2 |
|  | Number of validated sites | 3 | 9 | 2 |
| FANCF | Total captured sites | 38 | 8 | 1 |
|  | Number of NGS-tested sites | 8 | 8 | 1 |
|  | Number of validated sites | 1 | 8 | 0 |
| RNF2 | Total captured sites | 12 | 1 | 0 |
|  | Number of NGS-tested sites | 12 | 1 | 0 |
|  | Number of validated sites | 2 | 1 | 0 |
| HEK1 | Total captured sites | 8 | 8 | 2 |
|  | Number of NGS-tested sites | 3 | 8 | 2 |
|  | Number of validated sites | 1 | 7 | 2 |
| HEK2 | Total captured sites | 33 | 2 | 1 |
|  | Number of NGS-tested sites | 16 | 2 | 1 |
|  | Number of validated sites | 1 | 2 | 0 |
| HEK3 | Total captured sites | 25 | 6 | 0 |
|  | Number of NGS-tested sites | 14 | 6 | 0 |
|  | Number of validated sites | 2 | 6 | 0 |
| HEK4 | Total captured sites | 112 | 104 | 26 |
|  | Number of NGS-tested sites | 17 | 24 | 16 |
|  | Number of validated sites | 1 | 19 | 4 |
| Total | Total captured sites | 703 | 241 | 168 |
|  | Number of NGS-tested sites | 127 | 132 | 45 |
|  | Number of validated sites | 21 | 116 | 23 |

TABLE 15

VEGFA1

|  |  |  |  | Indel frequencey (%) | | |
|---|---|---|---|---|---|---|
|  | Chromosome | Location | DNA seq at a Cleavage sites | (-) RGEN | (+) RGEN | Validation |
| On-Target | Chr6 | 43737290 | GGGTGGGGGGAGTTTGCTCCAGG | 0.01% | 21.77% | validated |
| VEGFA1_02 | Chr15 | 65637537 | GGATGGAGGGAGTTTGCTCCTGG | 0.01% | 25.28% | validated |
| VEGFA1_03 | Chr5 | 706159 | GAGGGTGGGGAGTTTACTCCTGG | 0.01% | 0.09% | validated |
| VEGFA1_04 | Chr1 | 99347651 | GGGGAGGGGAAGTTTGCTCCTGG | 0.01% | 13.84% | validated |
| VEGFA1_05 | Chr12 | 1968077 | CGGGGGAGGGAGTTTGCTCCTGG | 0.00% | 11.73% | validated |
| VEGFA1_06 | Chr22 | 37215276 | GGGTGGGGGGAGTTTGCCCCAGG | 0.09% | 1.03% | validated |
| VEGFA1_07 | Chr17 | 32986325 | GGGGGTGGGGACTTTGCTCCAGG | 0.04% | 0.02% | Invalidated |
| VEGFA1_08 | Chr12 | 26641302 | AGTTTGGGGGAGTTTGCCCCAGG | 0.12% | 0.12% | Invalidated |
| VEGFA1_09 | Chr1 | 233157354 | GGAGGAGGGAGTCTGCTCCAGG | 0.01% | 0.05% | validated |
| VEGFA1_10 | Chr10 | 124731416 | AGCTGGAGGGAGTTTGCCCCAGG | 0.13% | 0.26% | validated |
| VEGFA1_11 | Chr12 | 131690199 | GGGAGGGTGGAGTTTGCTCCTGG | 0.00% | 6.70% | validated |
| VEGFA1_12 | Chr11 | 71497119 | AGGAAGGAGGAGTTAGCTCCTGG | 0.00% | 0.02% | Invalidated |
| VEGFA1_13 | Chr17 | 39796328 | TAGTGGAGGGAGCTTGCTCCTGG | 0.00% | 16.90% | validated |
| VEGFA1_14 | Chr4 | 8453803 | GAGTGGGTGGAGTTTGCTACAGG | 0.01% | 0.13% | validated |
| VEGFA1_15 | Chr9 | 93925190 | GGGGGTGGGGAGCATGCTCCAGG | 0.01% | 0.02% | validated |
| VEGFA1_16 | Chr3 | 125633992 | AGGAAGGAGGAGTTAGCTCCTGG | 0.02% | 0.01% | Invalidated |
| VEGFA1_17 | Chr16 | 8763213 | AAGTAAGGGAAGTTTGCTCCTGG | 0.01% | 0.01% | Invalidated |
| VEGFA1_18 | Chr20 | 56175356 | AGGGAGGAGGAATTTGCTCCAGG | 0.00% | 0.72% | validated |
| VEGFA1_19 | Chr15 | 93140401 | GGGGGAGGGAAGTTTCCTCCAGG | 0.02% | 0.01% | Invalidated |
| VEGFA1_20 | Chr3 | 128284321 | AGGTGGTGGGAGCTTGTTCCTGG | 0.00% | 0.14% | validated |
| VEGFA1_21 | Chr5 | 32945275 | GCGTGGGGGGTGTTTGCTCCCGG | 0.03% | 1.00% | validated |
| VEGFA1_22 | Chr6 | 14316373 | GTGGGGGTAGAGTTTGCTCCAGG | 0.02% | 6.10% | validated |
| VEGFA1_23 | Chr13 | 25202812 | GGTTGAGGGAGTCTGCTCCAGG | 0.01% | 0.17% | validated |
| VEGFA1_24 | Chr5 | 139263024 | TTGGGGGGCAGTTTGCTCCAGG | 2.33% | 7.19% | validated |
| VEGFA1_25 | Chr2 | 95056645 | GGGTGGGGAGAGTTTCTTCCTGG | 0.00% | 0.00% | Invalidated |

TABLE 15-continued

VEGFA1

| | Chromosome | Location | DNA seq at a Cleavage sites | Indel frequencey (%) | | Validation |
|---|---|---|---|---|---|---|
| | | | | (−)RGEN | (+)RGEN | |
| VEGFA1_26 | Chr3 | 195871254 | GGTGGGGGAGAGCTAGCTCCGGG | 0.00% | 0.20% | validated |
| VEGFA1_27 | Chr11 | 3445204 | AGGAAGGAGGAGTTAGCTCCTGG | 0.02% | 0.04% | validated |
| VEGFA1_28 | ChrX | 19185601 | GGGAGGGGAGAGTTTGTTCCAGG | 0.01% | 0.02% | Invalidated |
| VEGFA1_29 | Chr11 | 67574262 | AGGAAGGAGGAGTTAGCTCCTGG | 0.01% | 0.73% | validated |
| VEGFA1_30 | Chr17 | 47317539 | CTGGTGGGGGAGCTTGCTCCAGG | 1.64% | 4.14% | validated |
| VEGFA1_31 | Chr22 | 19698483 | GAGGGGGAGCAGTTTGCTCCAGG | 0.01% | 0.56% | validated |
| VEGFA1_32 | Chr21 | 37116659 | AAGTGGGAAGAGTTTGTTCCAGG | 0.03% | 0.01% | Invalidated |
| VEGFA1_33 | Chr11 | 117481206 | GGGCAAGGGGAGGTTGCTCCTGG | 0.01% | 0.35% | validated |
| VEGFA1_34 | Chr5 | 56172079 | GGTGGGGGTGGGTTTGCTCCTGG | 0.00% | 3.94% | validated |
| VEGFA1_35 | Chr1 | 33543285 | GGGTGGGTGGAGTTTGCTACTGG | 0.00% | 0.30% | validated |
| VEGFA1_36 | Chr6 | 28483353 | AAGTGGGAGGAGACTGCTCCAGG | 0.01% | 0.02% | Invalidated |
| VEGFA1_37 | Chr22 | 33219333 | AGGTCGGGGAGTTAGATCCCGG | 0.01% | 0.02% | Invalidated |

TABLE 16

VEGFA2

| | Chromosome | Location | DNA seq at a Cleavage sites | Indel frequency (%) | | Validation |
|---|---|---|---|---|---|---|
| | | | | (−)RGEN | (+)RGEN | |
| On-Target | Chr5 | 43738562 | GACCCCCTCCACCCCGCCTCCGG | 0.00% | 96.41% | validated |
| VEGFA2_02 | Chr11 | 31817483 | GGGCCCCTCCACCCCGCCTCTGG | 0.04% | 2.50% | validated |
| VEGFA2_03 | Chr5 | 6715119 | CTACCCCTCCACCCCGCCTCCGG | 0.00% | 6.24% | validated |
| VEGFA2_04 | Chr17 | 4358752 | TACCCCCCACACCCCGCCTCTGG | 0.01% | 0.74% | validated |
| VEGFA2_05 | Chr9 | 27338875 | GACCCCTCCCACCCCGACTCCGG | 0.00% | 0.87% | validated |
| VEGFA2_06 | Chr18 | 21359559 | GCCCCCACCCACCCCGCCTCTGG | 0.00% | 34.17% | validated |
| VEGFA2_07 | ChrX | 118355483 | GTCCTCCACCACCCCGCCTCTGG | 0.00% | 0.05% | validated |
| VEGFA2_08 | Chr2 | 242214607 | ATTCCCCCCACCCCGCCTCAGG | 0.78% | 5.77% | validated |
| VEGFA2_09 | Chr9 | 103599549 | ACACCCCCCACCCCGCCTCAGG | 0.00% | 3.35% | validated |
| VEGFA2_10 | Chr15 | 56563429 | TGCCCCCCCACCCCACCTCTGG | 0.03% | 3.82% | validated |
| VEGFA2_11 | Chr11 | 71948805 | GCTTCCCTCCACCCCGCATCCGG | 0.01% | 0.44% | validated |
| VEGFA2_12 | Chr17 | 40044757 | TGCCCCTCCCACCCCGCCTCTGG | 0.00% | 0.77% | validated |
| VEGFA2_13 | Chr10 | 116294256 | CCCCACCCCCACCCCGCCTCAGG | 0.15% | 53.43% | validated |
| VEGFA2_14 | Chr10 | 135149948 | CGCCCTCCCCACCCCGCCTCCGG | 0.01% | 5.44% | validated |
| VEGFA2_15 | Chr3 | 140398801 | CAACCCCCCACCCCGCTTCAGG | 0.03% | 1.38% | validated |
| VEGFA2_17 | Chr12 | 28025095 | CATTCCCCCCACCCCACCTCAGG | 0.03% | 16.64% | validated |
| VEGFA2_18 | Chr10 | 72538216 | CAGTCCCCCCACCCCACCTCTGG | 0.01% | 0.57% | validated |
| VEGFA2_19 | Chr9 | 131706582 | AGCGAACCCCACCCCGCCTCTGG | 0.01% | 0.06% | validated |
| VEGFA2_22 | Chr19 | 13122189 | GCCCCCACCACCCCACCTCGGG | 0.00% | 1.86% | validated |
| VEGFA2_33 | Chr2 | 12744776 | GACACACCCCACCCCACCTCAGG | 0.01% | 0.39% | validated |

TABLE 16-continued

VEGFA2

| | Chromosome | Location | DNA seq at a Cleavage sites | Indel frequency (%) | | Validation |
|---|---|---|---|---|---|---|
| | | | | (-)RGEN | (+)RGEN | |
| VEGFA2_34 | Chr13 | 100545989 | CCCCCCCCCCCCCCCGCCTCAGG | 4.45% | 13.82% | validated |
| VEGFA2_39 | Chr4 | 35537628 | CTCCCCACCCACCCCGCCTCAGG | 0.00% | 69.10% | validated |
| VEGFA2_40 | Chr12 | 101603788 | GCCAGCCCTCACCCCGCCTCGGG | 0.00% | 0.00% | Invalidated |
| VEGFA2_42 | Chr5 | 10662454 | CCCTCTCCACCCCCACCCTCTGG | 0.00% | 0.00% | Invalidated |
| VEGFA2_43 | Chr15 | 13492458 | TCCGCCCCCACCCCACCTCCGG | 0.04% | 0.03% | Invalidated |
| VEGFA2_44 | Chr1 | 111850503 | TAAATCCTCCACCCCACCTCAGG | 0.01% | 0.00% | Invalidated |
| VEGFA2_48 | Chr6 | 167929803 | GCTGTCTCCCACCCCGCCTCAGG | 0.00% | 0.01% | Invalidated |
| VEGFA2_50 | Chr17 | 29983010 | CATCTTCCCCACCCCGCCTCTGG | 0.24% | 0.26% | Invalidated |
| VEGFA2_51 | Chr14 | 75098723 | CCTCACCCCCACCCCACCTGTGG | 0.00% | 0.00% | Invalidated |
| VEGFA2_54 | Chr20 | 25240252 | CCCACACCCCACCCCACCTCCGG | 0.00% | 0.01% | Invalidated |

TABLE 17

VEGFA3

| | Chromosome | Location | DNA seq at a Cleavage sites | Indel frequency (%) | | Validation |
|---|---|---|---|---|---|---|
| | | | | (-)RGEN | (+)RGEN | |
| On-Target | Chr6 | 43737471 | GGTGAGTGAGTGTGTGCGTGTGG | 0.01% | 41.86% | validated |
| VEGFA3_02 | Chr14 | 65569159 | AGTGAGTGAGTGTGTGTGTGGGG | 0.28% | 35.20% | validated |
| VEGFA3_03 | Chr5 | 69440959 | AGAGAGTGAGTGTGTGCATGAGG | 0.00% | 18.71% | validated |
| VEGFA3_04 | Chr6 | 115434676 | TGTGGGTGAGTGTGTGCGTGAGG | 0.01% | 30.88% | validated |
| VEGFA3_05 | Chr22 | 37662824 | GCTGAGTGAGTGTATGCGTGTGG | 0.00% | 24.48% | validated |
| VEGFA3_06 | Chr11 | 68851139 | GGTGAGTGAGTGCGTGCGGGTGG | 1.79% | 11.15% | validated |
| VEGFA3_07 | Chr10 | 98760588 | GTTGAGTGAATGTGTGCGTGAGG | 0.00% | 19.92% | validated |
| VEGFA3_08 | Chr3 | 193993884 | AGTGAATGAGTGTGTGTGTGTGG | 0.40% | 23.67% | validated |
| VEGFA3_09 | Chr14 | 62078773 | TGTGAGTAAGTGTGTGTGTGTGG | 0.57% | 20.05% | validated |
| VEGFA3_10 | Chr19 | 40561867 | ACTGTGTGAGTGTGTGCGTGAGG | 0.02% | 0.72% | validated |
| VEGFA3_11 | Chr20 | 20178284 | AGTGTGTGAGTGTGTGCGTGTGG | 0.25% | 34.56% | validated |
| VEGFA3_12 | Chr9 | 23824554 | TGTGGGTGAGTGTGTGCGTGAGA | 0.00% | 0.32% | validated |
| VEGFA3_14 | Chr14 | 105029032 | GGTGAGTGAGTGTGTGTGTGAGG | 0.03% | 2.39% | validated |
| VEGFA3_15 | Chr19 | 47732492 | CTGGAGTGAGTGTGTGTGTGTGG | 0.01% | 0.00% | Invalidated |
| VEGFA3_16 | Chr9 | 18733635 | AGCGAGTGAGTGTGTGTGTGGGG | 0.20% | 32.70% | validated |
| VEGFA3_17 | Chr2 | 73317050 | GGTGAGTCAGTGTGTGAGTGAGG | 2.29% | 2.56% | Invalidated |
| VEGFA3_18 | Chr4 | 58326608 | AGTGAGTGAGTGAGTGAGTGAGG | 0.02% | 0.00% | Invalidated |
| VEGFA3_19 | Chr6 | 48997805 | GTAGAGTGAGTGTGTGTGTGTGG | 0.45% | 5.11% | validated |
| VEGFA3_20 | Chr14 | 74353497 | AGCGAGTGGGTGTGTGCGTGGGG | 0.01% | 12.60% | validated |
| VEGFA3_21 | Chr22 | 49740001 | GGTGTGTGAGTGTGTGTGTGTGG | 0.45% | 2.89% | validated |
| VEGFA3_23 | Chr16 | 84032646 | GGTGAATGAGTGTGTGCTCTGGG | 0.01% | 0.58% | validated |

TABLE 17-continued

VEGFA3

| | Chromosome | Location | DNA seq at a Cleavage sites | Indel frequency (%) | | Validation |
|---|---|---|---|---|---|---|
| | | | | (-)RGEN | (+)RGEN | |
| VEGFA3_24 | Chr10 | 5749657 | AGTGAGTATGTGTGTGTGGGG | 1.31% | 1.56% | validated |
| VEGFA3_27 | Chr4 | 62067619 | GATGAGTGTGTGTGTGTGAGG | 0.45% | 0.36% | Invalidated |
| VEGFA3_29 | Chr2 | 230506241 | GGTGAGCAAGTGTGTGTGTGG | 0.46% | 61.82% | validated |
| VEGFA3_31 | Chr17 | 33323259 | TGTGAGTGAGTATGTACATGTGG | 0.00% | 0.01% | Invalidated |
| VEGFA3_32 | Chr7 | 51294279 | AGTGAGTAAGTGAGTGAGTGAGG | 0.00% | 0.00% | Invalidated |
| VEGFA3_34 | Chr16 | 73585925 | AATGAGTGAGTGTGTGTGTGA | 0.77% | 0.97% | Invalidated |
| VEGFA3_36 | Chr2 | 18696225 | AGTGAGAAAGTGTGTGCATGCGG | 0.00% | 0.16% | validated |
| VEGFA3_37 | Chr19 | 5660674 | TGTGAGTGAGTGAGTGAATGTGG | 0.05% | 0.18% | validated |
| VEGFA3_39 | Chr10 | 67387984 | GGTGTGTGAGTGTGTGCATGTTG | 0.22% | 0.23% | Invalidated |
| VEGFA3_40 | Chr12 | 114752937 | TGTGAGTGAGTGTGTGCATGTGA | 0.32% | 0.36% | Invalidated |
| VEGFA3_41 | Chr14 | 98442534 | GGTGAGTGTGTGTGTGAGTGTGG | 0.00% | 0.00% | Invalidated |
| VEGFA3_42 | Chr19 | 15569487 | TGTGTGAGTGAGTGTGTGTGTGG | 0.07% | 0.22% | validated |
| VEGFA3_43 | Chr5 | 34452076 | TGTGTGAGTGTGTGTGTGCGTGG | 0.18% | 0.13% | Invalidated |
| VEGFA3_44 | ChrX | 41726218 | GGTGAGTGAGTGAGTGAGTGAGG | 0.01% | 0.03% | Invalidated |
| VEGFA3_45 | Chr10 | 105307473 | TGAGTGAGTGAGTGTGTGCGTGGGG | 0.00% | 0.01% | Invalidated |
| VEGFA3_46 | Chr11 | 12159155 | TGTGTGAGTGTGTGTGTGGGGGG | 0.40% | 0.34% | Invalidated |
| VEGFA3_47 | Chr11 | 75330150 | TGTGTGTGAGTGTGTGCATGAGG | 0.30% | 0.32% | Invalidated |
| VEGFA3_48 | Chr15 | 6130265 | TGTGAGTGAATGTGTGTGTGTGG | 0.15% | 0.25% | Invalidated |
| VEGFA3_49 | Chr16 | 73286082 | CATGAGTGGGTGTGTGCGTGGAG | 0.03% | 0.03% | Invalidated |
| VEGFA3_50 | Chr19 | 40596585 | GGACTGTGAGTGTGTGCGTGAGG | 0.01% | 0.00% | Invalidated |
| VEGFA3_52 | Chr2 | 183092036 | AGTGTGTGAGTGTGTGCCTGTGG | 0.01% | 0.07% | validated |
| VEGFA3_53 | Chr20 | 2650069 | GGTGTATGAGTGTGTGCGTCGGA | 1.26% | 1.30% | Invalidated |
| VEGFA3_54 | Chr3 | 10207131 | GGTGTGTGTGTGTGTGTGTGTGG | 0.10% | 0.09% | Invalidated |
| VEGFA3_55 | Chr5 | 98946319 | GGTGTAGTGGTGTGTGCTTGTGG | 0.00% | 0.00% | Invalidated |
| VEGFA3_56 | Chr6 | 39025642 | GGTGTGTGAGTGTGTGCATTGGG | 0.00% | 0.09% | validated |

TABLE 18

EMX1

| | Chromosome | Location | DNA seq at a Cleavage sites | Indel frequency (%) | | Validation |
|---|---|---|---|---|---|---|
| | | | | (-)RGEN | (+)RGEN | |
| On-Target | Chr2 | 73160999 | GAGTCCGAGCAGAAGAAGAAGGG | 0.23% | 61.61% | validated |
| EMX1_02 | Chr5 | 45359067 | GAGTTAGAGCAGAAGAAGAAAGG | 0.02% | 47.11% | validated |
| EMX1_03 | Chr15 | 44109764 | GAGTCTAAGCAGAAGAAGAAGAG | 0.42% | 39.41% | validated |
| EMX1_04 | Chr2 | 219845073 | GAGGCCGAGCAGAAGAAGACGG | 0.01% | 6.38% | validated |
| EMX1_05 | Chr8 | 128801260 | GAGTCCTAGCAGGAGAAGAAGAG | 0.03% | 6.67% | validated |
| EMX1_06 | Chr5 | 146833190 | GAGCCGGAGCAGAAGAAGGAGGG | 0.03% | 0.78% | validated |
| EMX1_07 | Chr1 | 23720518 | AAGTCCGAGGAGAGGAAGAAAGG | 0.03% | 0.06% | Invalidated |

TABLE 18-continued

EMX1

| | Chromosome | Location | DNA seq at a Cleavage sites | Indel frequency (%) | | Validation |
|---|---|---|---|---|---|---|
| | | | | (-)RGEN | (+)RGEN | |
| EMX1_08 | Chr6 | 9118799 | ACGTCTGAGCAGAAGAAGAATGG | 0.03% | 0.75% | validated |
| EMX1_09 | Chr15 | 100292479 | AAGTCCCGGCAGAGGAAGAAGGG | 0.01% | 0.09% | validated |
| EMX1_10 | Chr10 | 58846729 | GAGCACGAGCAAGAGAAGAAGGG | 0.00% | 0.00% | Invalidated |
| EMX1_11 | Chr2 | 218378108 | GAGTCTAAGCAGGAGAATAAAGG | 0.06% | 0.14% | validated |
| EMX1_12 | Chr3 | 55590185 | TCATCCAAGCAGAAGAAGAAGAG | 0.45% | 0.51% | Invalidated |
| EMX1_15 | Chr14 | 48332120 | GAGTCCCAGCAAAAGAAGAAAAG | 0.05% | 0.03% | Invalidated |
| EMX1_16 | Chr1 | 113741471 | GAGGTAGAGCAGAAGAAGAAGCG | 0.06% | 0.06% | Invalidated |
| EMX1_17 | Chr1 | 231750743 | GAGTCAGAGCAAAAGAAGTAGTG | 0.00% | 0.00% | Invalidated |
| EMX1_18 | Chr1 | 234492664 | GAAGTAGAGCAGAAGAAGAAGCG | 0.07% | 0.06% | Invalidated |
| EMX1_19 | Chr2 | 172374203 | GAAGTAGAGCAGAAGAAGAAGCG | 0.07% | 0.07% | Invalidated |
| EMX1_20 | Chr11 | 62355273 | GAATCCAAGCAGAAGAAGAGAAG | 0.02% | 0.13% | validated |
| EMX1_21 | Chr3 | 16077518 | GAGGCAGAGAGAAAGAAGAAAGG | 0.01% | 0.01% | Invalidated |
| EMX1_22 | Chr1 | 33606480 | GAGCCTGAGCAGAAGGAGAAGGG | 0.01% | 0.06% | validated |
| EMX1_23 | Chr1 | 221522625 | GAGTTTGAGTAGAAGAAGAAGAG | 0.72% | 0.70% | Invalidated |
| EMX1_24 | Chr3 | 34042974 | GAGTTCAAGCAGAGAAGAAAGGG | 1.09% | 1.10% | Invalidated |
| EMX1_25 | Chr4 | 44522977 | AAGTCTGAGAAGAAGAAGAAAGA | 0.02% | 0.03% | Invalidated |
| EMX1_26 | Chr4 | 87256692 | GAGTAAGAGAAGAAGAAGAAGGG | 0.08% | 0.09% | Invalidated |
| EMX1_28 | Chr15 | 51546878 | AAGTCAGAGGAGAAGAAGAAGGG | 0.26% | 0.47% | validated |
| EMX1_30 | Chr17 | 54421043 | GAGTCCCAGGAGAAGAAGAGAGG | 0.01% | 0.01% | Invalidated |
| EMX1_31 | Chr19 | 24250503 | GAGTCCAAGCAGTAGAGGAAGGG | 0.01% | 0.02% | Invalidated |
| EMX1_33 | Chr20 | 665399 | AAGTCCAGACAGAAGAAGAAGGA | 0.11% | 0.14% | Invalidated |

TABLE 19

FANCF

| | Chromosome | Location | DNA seq at a Cleavage sites | Indel frequency (%) | | Validation |
|---|---|---|---|---|---|---|
| | | | | (-)RGEN | (+)RGEN | |
| On-Target | Chr11 | 22647338 | GGAATCCCTTCTGCAGCACCTGG | 0.06% | 54.37% | validated |
| FANCF_02 | Chr16 | 8707528 | GGAACCCCGTCTGCAGCACCAGG | 0.05% | 27.79% | validated |
| FANCF_03 | Chr10 | 43410031 | GGAGTCCCTCCTACAGCACCAGG | 0.01% | 5.41% | validated |
| FANCF_04 | Chr17 | 78923978 | AGAGGCCCCTCTGCAGCACCAGG | 0.01% | 3.09% | validated |
| FANCF_05 | ChrX | 86355180 | ACCATCCCTCCTGCAGCACCAGG | 0.02% | 0.35% | validated |
| FANCF_06 | Chr10 | 73463136 | TGAATCCCATCTCCAGCACCAGG | 0.01% | 0.34% | validated |
| FANCF_07 | Chr10 | 37953200 | GGAGTCCCTCCTACAGCACCAGG | 0.01% | 2.75% | validated |
| FANCF_08 | Chr16 | 49671025 | GGAGTCCCTCCTGCAGCACCTGA | 0.00% | 0.82% | validated |
| FANCF_11 | Chr16 | 28615201 | GGCTTCCCTTCTGCAGCCCCAGG | 0.11% | 0.12% | Invalidated |
| FANCF_12 | Chr11 | 66475045 | GGAACACCTTCTGCAGCTCCAGG | 0.00% | 0.07% | validated |

TABLE 19-continued

FANCF

| | Chromosome | Location | DNA seq at a Cleavage sites | Indel frequency (%) | | Validation |
|---|---|---|---|---|---|---|
| | | | | (−)RGEN | (+)RGEN | |
| FANCF_15 | Chr17 | 39675789 | GGGAGTCCATCTGCAGCACCAGG | 0.01% | 0.02% | Invalidated |
| FANCF_16 | Chr17 | 34955068 | GGGTCCGCTTCTGCAGCACCTGG | 0.00% | 0.00% | Invalidated |
| FANCF_17 | Chr17 | 3980376 | GGAACCCCTCTGCAGCTTCTGG | 0.00% | 0.00% | Invalidated |
| FANCF_18 | Chr13 | 109802140 | AAAATACCTTCTGCAGTACCAGG | 0.02% | 0.01% | Invalidated |
| FANCF_19 | Chr12 | 115467806 | AGGGTCCCTTCTGCAGCCCCTGG | 0.04% | 0.06% | Invalidated |
| FANCF_21 | Chr12 | 2719895 | ACACTCCCTTCTGCAGCACCATG | 0.00% | 0.01% | Invalidated |

TABLE 20

HEK293-1

| | Chromosome | Location | DNA seq at a Cleavage sites | Indel frequency (%) | | Validation |
|---|---|---|---|---|---|---|
| | | | | (−)RGEN | (+)RGEN | |
| On-Target | Chr9 | 110103705 | GGGAAAGACCCAGCATCCGTGGG | 0.04% | 48.67% | validated |
| HEK1_02 | Chr1 | 201992441 | GGGAAAGTCCCAGCATCCTTTGG | 0.05% | 42.76% | validated |
| HEK1_03 | Chr8 | 21121524 | GGGAAGGACCCAGCATCCTGGGG | 0.01% | 21.48% | validated |
| HEK1_04 | Chr9 | 129512088 | GGGAAATACCCAGCATCCAATGG | 0.01% | 1.81% | validated |
| HEK1_05 | Chr8 | 48879627 | GAGAAAAGCCCAGCATCCTTAGG | 0.02% | 0.25% | validated |
| HEK1_06 | Chr22 | 47970525 | GGAAAAGACCAAGCATCAGTGGG | 0.00% | 0.06% | validated |
| HEK1_07 | Chr13 | 31633478 | ATGAAAGACCCAGCATCCATTGA | 0.00% | 0.01% | Invalidated |
| HEK1_08 | Chr10 | 123094947 | GGGAAAAGCCCAGCATCCCTTGG | 1.62% | 17.98% | validated |
| HEK1_14 | Chr12 | 5555206 | GGAGAAAGACCAGCATCCATAGG | 0.00% | 0.01% | Invalidated |
| HEK1_15 | Chr11 | 75956264 | TTATAAGACCCAGCATCCGTAAG | 0.01% | 0.09% | validated |
| HEK1_16 | Chr10 | 86303625 | TGGAAAGAAACAGCATCCGTACG | 0.00% | 0.01% | Invalidated |

TABLE 21

HEK293-2

| | Chromosome | Location | DNA seq at a Cleavage sites | Indel frequency (%) | | Validation |
|---|---|---|---|---|---|---|
| | | | | (−)RGEN | (+)RGEN | |
| On-Target | Chr5 | 87240614 | GAACACAAAGCATAGACTGCGGG | 0.01% | 59.05% | validated |
| HEK2_02 | Chr4 | 90522184 | GAACACAATGCATAGATTGCCGG | 0.01% | 16.33% | validated |
| HEK2_04 | Chr4 | 53536210 | GAATACTAAGCATAGACTCCAGG | 0.01% | 0.03% | Invalidated |
| HEK2_05 | Chr11 | 128508577 | GAATTCAAAGCATAGATTGCAGG | 0.00% | 0.01% | Invalidated |
| HEK2_06 | Chr13 | 113428467 | CAATACAAAGGATAGACTGCAGG | 0.01% | 0.02% | Invalidated |
| HEK2_07 | Chr20 | 97641 | GAATTCAAAGCATAGATTGCAGG | 0.01% | 0.01% | Invalidated |
| HEK2_08 | ChrX | 36949815 | GAAAACAAAACATAGAGTGCTGG | 0.00% | 0.00% | Invalidated |

TABLE 21-continued

HEK293-2

| | Chromosome | Location | DNA seq at a Cleavage sites | Indel frequency (%) (−)RGEN | (+)RGEN | Validation |
|---|---|---|---|---|---|---|
| HEK2_09 | Chr1 | 77190507 | TCACACAAACCATAGACTGAGGG | 0.00% | 0.00% | Invalidated |
| HEK2_10 | Chr5 | 126365455 | CCACACCAAGCATAGACTTCTGG | 0.00% | 0.01% | Invalidated |
| HEK2_11 | Chr5 | 131174461 | AAATACAATGCATAGACTGCTAG | 0.53% | 0.52% | Invalidated |
| HEK2_12 | Chr6 | 139353018 | CCAAACAAAACATAGACTGCTGG | 0.00% | 0.01% | Invalidated |
| HEK2_13 | Chr9 | 290158 | AAACATAAAGAATAGACTGCAAG | 0.00% | 0.00% | Invalidated |
| HEK2_16 | Chr18 | 22360702 | GGAATCAAAGCACAGACTGCAGG | 0.00% | 0.00% | Invalidated |
| HEK2_17 | Chr18 | 56307003 | AAGAACAAAACATAGACTGCAGG | 0.01% | 0.04% | validated |
| HEK2_19 | Chr20 | 23101380 | ATACACAGAGCAAAGACTGCAGG | 0.00% | 0.00% | Invalidated |
| HEK2_20 | Chr9 | 97332609 | GTAATTAAAGCACAGACTGCTGG | 0.00% | 0.00% | Invalidated |
| HEK2_21 | Chr2 | 19844956 | AACTCCAAAGCATATACTGCTGG | 0.01% | 0.01% | Invalidated |
| HEK2_22 | Chr15 | 55377019 | GAGCGATAAGCACAGACTGCTGG | 0.00% | 0.00% | Invalidated |

TABLE 22

HEK293-3

| | Chromosome | Location | DNA seq at a Cleavage sites | Indel frequency (%) (−)RGEN | (+)RGEN | Validation |
|---|---|---|---|---|---|---|
| On-Target | Chr9 | 110184637 | GGCCCAGACTGAGCACGTGATGG | 0.01% | 66.99% | validated |
| HEK3_02 | Chr1 | 34163192 | ATTCTAGACTGAGCACGTGCAAG | 0.01% | 0.02% | validated |
| HEK3_03 | Chr11 | 134582415 | GGCGCAGACAGAGCACGTGACGA | 0.00% | 0.00% | Invalidated |
| HEK3_04 | Chr1 | 47005705 | AGCTCAGACTGAGCAAGTGAGGG | 0.01% | 15.23% | validated |
| HEK3_05 | Chr10 | 131593121 | GAGCCAGAATGAGCACGTGAGGG | 0.00% | 1.17% | validated |
| HEK3_06 | Chr15 | 79749931 | CACCCAGACTGAGCACGTGCTGG | 0.00% | 33.14% | validated |
| HEK3_07 | Chr6 | 103918240 | AAATAAGACTGAGCACGTGGTGG | 0.01% | 0.02% | Invalidated |
| HEK3_08 | Chr7 | 66968042 | GACACAGACCGGGCACGTGAGGG | 0.01% | 0.15% | validated |
| HEK3_09 | ChrX | 114764149 | AGACCAGACTGAGCAAGAGAGGG | 0.01% | 0.20% | validated |
| HEK3_10 | Chr15 | 35402774 | CCTAAAGACTGAGCAAGTGAAGG | 0.01% | 0.01% | Invalidated |
| HEK3_11 | Chr9 | 137039236 | CAGCCAGACAGAGCACGTGGAGG | 0.02% | 0.02% | Invalidated |
| HEK3_12 | Chr6 | 79958440 | AACAAAGACTGAGCACGTTAGGG | 0.01% | 0.01% | Invalidated |
| HEK3_13 | Chr2 | 130402896 | GACCCAGAATGAGCACAAAGGG | 0.10% | 0.10% | Invalidated |
| HEK3_14 | Chr2 | 97163211 | CCCATGGACTGAGCACATGAAGG | 0.06% | 0.08% | Invalidated |
| HEK3_15 | Chr10 | 22896606 | GAAGGAGACTGAGCATGTGAGGG | 0.00% | 0.00% | Invalidated |
| HEK3_16 | Chr8 | 20947875 | TCTCCAGACTGAGCCCATGAGGG | 0.04% | 0.03% | Invalidated |
| HEK3_17 | Chr2 | 240026760 | GGCTCAGACTGAGCACCTGAGAG | 0.01% | 0.11% | validated |
| HEK3_18 | Chr14 | 102917106 | CTCGGAGACTGACCACGTGAGGG | 0.04% | 0.05% | Invalidated |
| HEK3_19 | Chr10 | 23135503 | ACTCCAGACTGAGCAACTGAGGG | 0.01% | 0.01% | Invalidated |
| HEK3_20 | ChrX | 16605309 | TTCCCAGACAAAGCACGCGAAGG | 2.25% | 2.14% | Invalidated |

TABLE 23

HEK293-4

| | Chromosome | Location | DNA seq at a Cleavage sites | Indel frequence (%) (−)RGEN | (+)RGEN | Validation |
|---|---|---|---|---|---|---|
| On-Target | Chr20 | 31349773 | GGCACTGCGGCTGGAGGTGGGGG | 0.00% | 82.90% | validated |
| HEK4_02 | Chr19 | 33382081 | GGCTCTGCGGCTGGAGGGGGTGG | 0.14% | 2.84% | validated |
| HEK4_03 | Chr10 | 126694875 | GGCACGACGGCTGGAGGTGGGGG | 0.06% | 11.61% | validated |
| HEK4_04 | Chr15 | 41044242 | GGCGCTGCGGCGGGAGGTGGAGG | 0.02% | 5.25 | validated |
| HEK4_05 | Chr6 | 160517881 | GGCACTGCTGCTGGGGGTGGTGG | 0.15% | 5.38% | validated |
| HEK4_06 | Chr13 | 27629410 | GGCACTGGGGTTGGAGGTGGGGG | 0.02% | 2.15% | validated |
| HEK4_07 | Chr20 | 45353011 | GGCACTGAGGGTGGAGGTGGGGG | 0.02% | 1.55% | validated |
| HEK4_08 | Chr20 | 1151854 | GGCACTGTGGCTGCAGGTGGAGG | 0.01% | 1.44% | validated |
| HEK4_10 | Chr4 | 56815199 | GGCAATGCGGCTGGAGGCGGAGG | 0.02% | 11.90% | validated |
| HEK4_11 | Chr20 | 60010563 | TGCACTGCGGCCGGAGGAGGTGG | 0.01% | 2.83% | validated |
| HEK4_12 | Chr10 | 77103120 | GGCATCACGGCTGGAGGTGGAGG | 0.04% | 5.09% | validated |
| HEK4_13 | Chr19 | 36616166 | GGCACTGAGACTGGGGGTGGGGG | 0.02% | 17.00% | validated |
| HEK4_14 | Chr13 | 39262929 | AGCAGTGCGGCTAGAGGTGGTGG | 0.03% | 12.34% | validated |
| HEK4_15 | Chr10 | 13692537 | GGCACTGGGGCTGGGGAGGGGG | 0.14% | 0.25% | Invalidated |
| HEK4_16 | Chr7 | 54561438 | AGGACTGCGGCTGGGGGTGGTGG | 0.24% | 8.72% | validated |
| HEK4_17 | Chr19 | 41220525 | GGCAATGTGGCTGAAGGTGGGGG | 0.01% | 0.66% | validated |
| HEK4_18 | Chr20 | 50895671 | GGCACAGCAGCTGGAGGTGCTGG | 0.02% | 0.59% | validated |
| HEK4_19 | Chr1 | 171018460 | GCCACTGGGGCTGGGGGTGGGGG | 0.25% | 2.32% | validated |
| HEK4_20 | Chr17 | 176302 | TGCACTGTGGCTGGAGATGGGGG | 0.01% | 1.02% | validated |
| HEK4_21 | Chr13 | 86900992 | CACACTGCAGCTGGAGGTGGTGG | 0.55% | 0.80% | validated |
| HEK4_25 | Chr16 | 89469252 | GGCACTGCGGGAGGAGGTGGGCG | 0.06% | 0.09% | Invalidated |
| HEK4_31 | Chr14 | 24740271 | GGCACTGCCACTGGGGGTGAGGG | 0.40% | 0.45% | Invalidated |
| HEK4_41 | Chr10 | 1285239 | GGCCCTTCGGCTGGAGGTGGCAG | 0.02% | 0.01% | Invalidated |
| HEK4_42 | Chr10 | 60003458 | GGCACGCGGCTGGGAGGTGGAGG | 0.07% | 0.07% | Invalidated |
| HEK4_43 | Chr12 | 90804707 | GGCATGCGGCTGGGAGGTGGAGG | 0.03% | 0.03% | Invalidated |
| HEK4_45 | Chr15 | 75532142 | GCACCTGCGGCTGGAGGTGGCAG | 0.02% | 0.01% | Invalidated |
| HEK4_46 | Chr1 | 2933843 | GGCCCTGAGACTGCAGCTGGAGG | 0.01% | 0.02% | Invalidated |
| HEK4_48 | Chr3 | 16515640 | CGCACTGGGGCTGCAGGTGGAGG | 0.66% | 0.74% | Invalidated |
| HEK4_50 | Chr4 | 156491955 | TTCACTGTGGCTGGAGGTGGGGA | 0.12% | 0.10% | Invalidated |
| HEK4_51 | Chr5 | 41968123 | GGAAGTGCGGCAGGAGGTGGAGG | 0.02% | 0.02% | Invalidated |
| HEK4_52 | Chr5 | 177928896 | CCCACTGCGGGTGGAGGTGGAAG | 0.01% | 0.02% | Invalidated |
| HEK4_53 | Chr6 | 33950129 | GGCTCTGAGGCTGGTGGTGGGGG | 0.46% | 0.42% | Invalidated |
| HEK4_54 | Chr6 | 159190938 | GGCCCTGCAGCTGGAGGAGGAGA | 0.06% | 0.05% | Invalidated |
| HEK4_55 | Chr7 | 157869941 | GGCACTGGGGAAGGAGGTGGAGG | 1.81% | 1.90% | Invalidated |
| HEK4_56 | Chr8 | 1241128 | GGCACTGTTGCTGGAGGAGGCAG | 0.01% | 0.00% | Invalidated |
| HEK4_57 | Chr8 | 11479079 | GGCCCTGCAGCTGGAGATGGAAG | 0.67% | 0.72% | Invalidated |
| HEK4_58 | Chr8 | 145730111 | GGCACATGGGCTGGGGGTGGGGG | 0.06% | 0.07% | Invalidated |

TABLE 23-continued

HEK293-4

|  | Chromosome | Location | DNA seq at a Cleavage sites | Indel frequence (%) | | Validation |
|---|---|---|---|---|---|---|
|  |  |  |  | (−)RGEN | (+)RGEN |  |
| HEK4_59 | Chr10 | 36109441 | GGCATTGCTGCTGGTGGTGGTGG | 0.00% | 0.00% | Invalidated |
| HEK4_60 | Chr10 | 127971444 | GGAACTGGGGCTGGGGGTGGGGG | 0.01% | 0.20% | validated |

Indels were detected above the background noise level caused by sequencing errors at 116 sites (=88%) of the 132 sites commonly detected in Digenome-seq and GUIDE-seq. On the other hand, most of the locations detected in Digenome-seq and only in GUIDE-seq were not identified by targeting deep sequencing. On the other hand, the most of the sites detected only in Digenome-seq and GUIDE-seq did not identify indels by targeting deep sequencing. That is, 21 (=17%) of the 127 sites detected only in the Digenome-seq and 23 (=51%) of the 45 sites detected only in the GUIDE-seq induced indels above the noise level. It was identified that both of the two methods are not general methods. In most of the validated sites, the indel frequency was less than 1%, much lower than that identified at the corresponding on-target site. For example, RNF2-targeted sgRNAs induced indels at the on-target site and two off-target sites validated in the present disclosure, which showed frequencies of 68%, 0.25%, and 0.09%, respectively (FIG. 20). It can be seen that indels can be induced at a frequency lower than the noise level (0.001% to 4% depending on the site) at sites that are not identified in NGS.

Figure 21C:
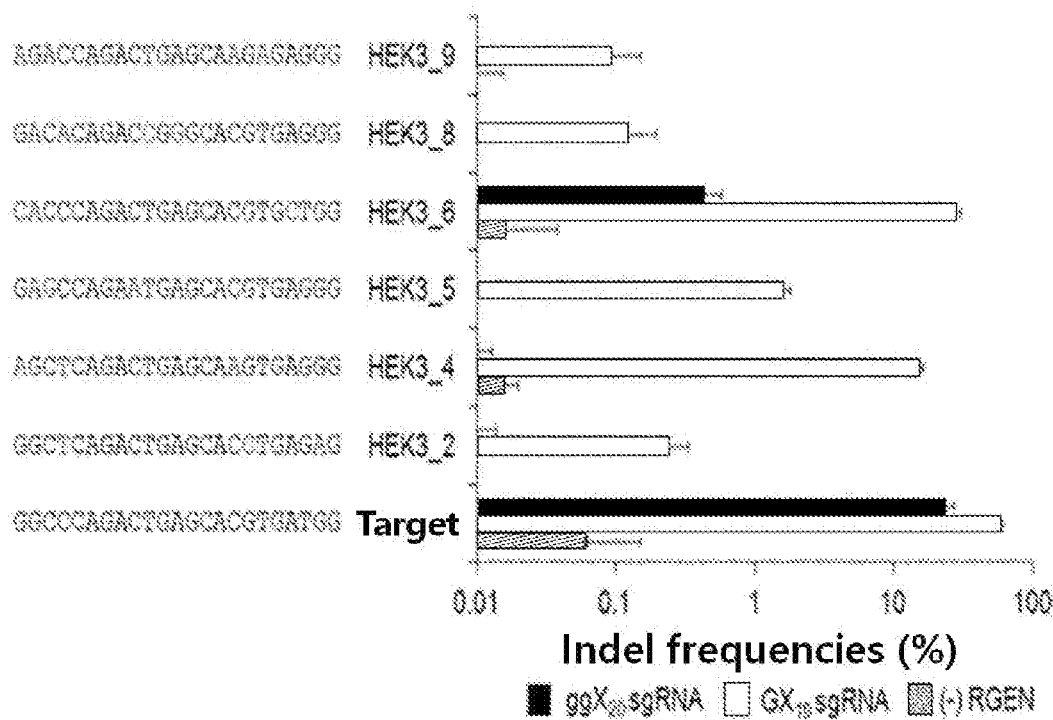
FIG. 21 identifies the indel frequencies using targeted deep sequencing at off-target sites. (a) It mimetically illustrates a general sgRNA ($gX_{19}$ sgRNA) and a modified sgRNA ($ggX_{20}$ sgRNA). (b-d) It illustrates the indel frequencies at on-target and off-target sites of (b) EMX1, (c) HEK293-3, and (d) RNF2 sgRNA validated by NGS. (e-g) It illustrates the specificity ratios calculated by dividing the indel frequencies at on-target sites of (e) EMX1, (f) HEK293-3, and (g) RNF2 sgRNA into the indel frequencies at off-target sites.
Figure 21D:
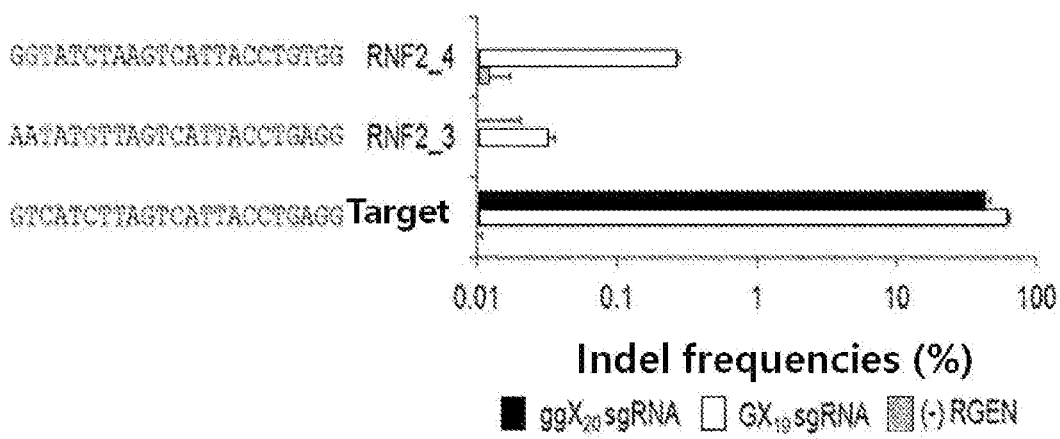

In order to reduce off-target effects, sgRNA (referred to as $ggX_{20}$ sgRNA) including two guanines was additionally used at the 5' end (FIG. 21a). The modified sgRNA was 598 times more specific than the corresponding $GX_{19}$ sgRNA (FIGS. 21b-22g). RNF2-specific $ggX_{20}$ sgRNA did not detect off-target indels above the noise level (FIG. 21d).

EXPERIMENTAL EXAMPLE 11

Indel Frequency at an Off-Target Site

Figure 22A:
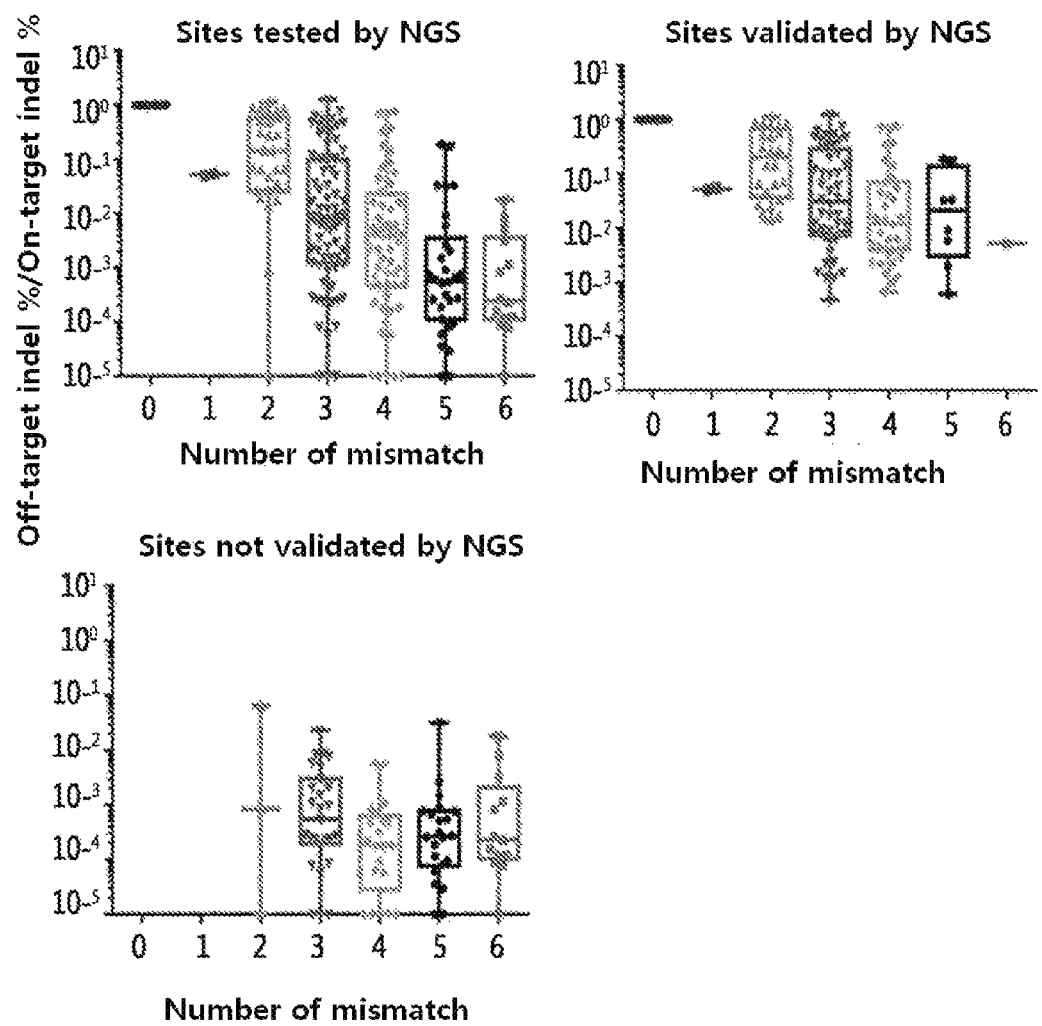
FIG. 22 illustrates an analysis of off-target sites that are validated by NGS and off-target sites that are not validated by NGS. (a-c) It illustrates a relative indel frequency (log scale) plot at off-target sites according to a mismatch shown in (a) the entire 20-nt sequence or (b and c) 10-nt seed sequence. The sites (a) identified by NGS were divided into two groups of a validated site (b) and invalidated site (c).
Figure 22B:
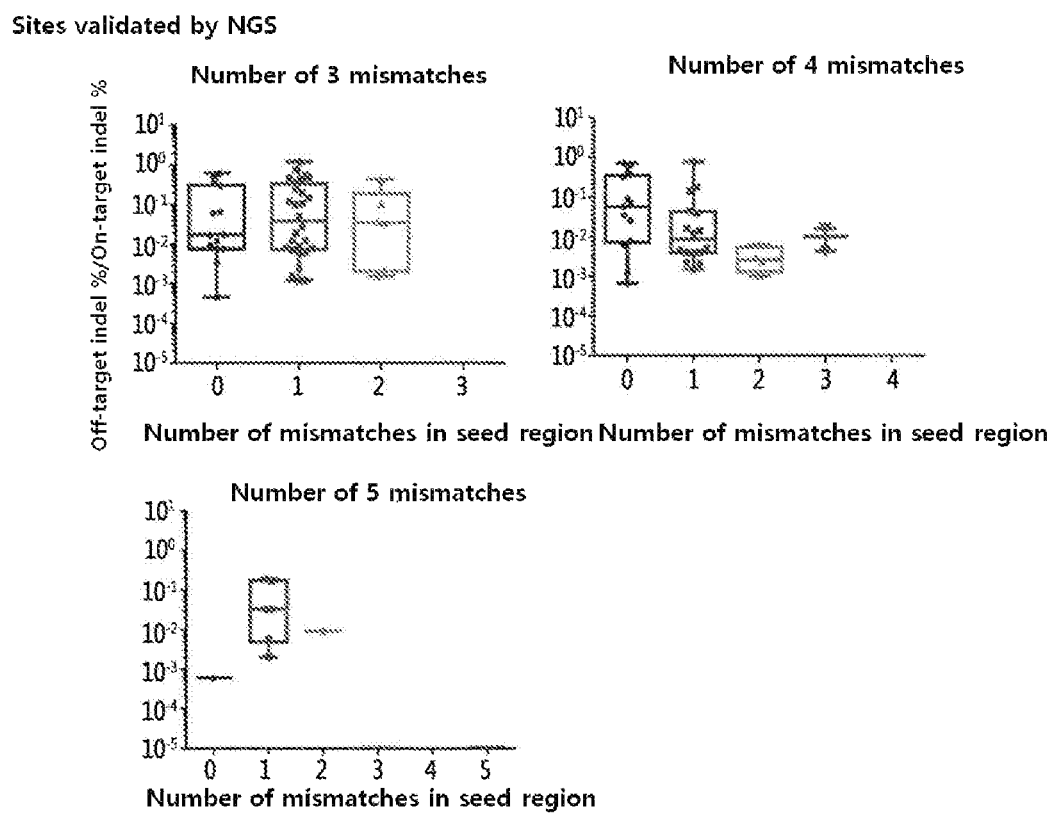
Figure 22C:
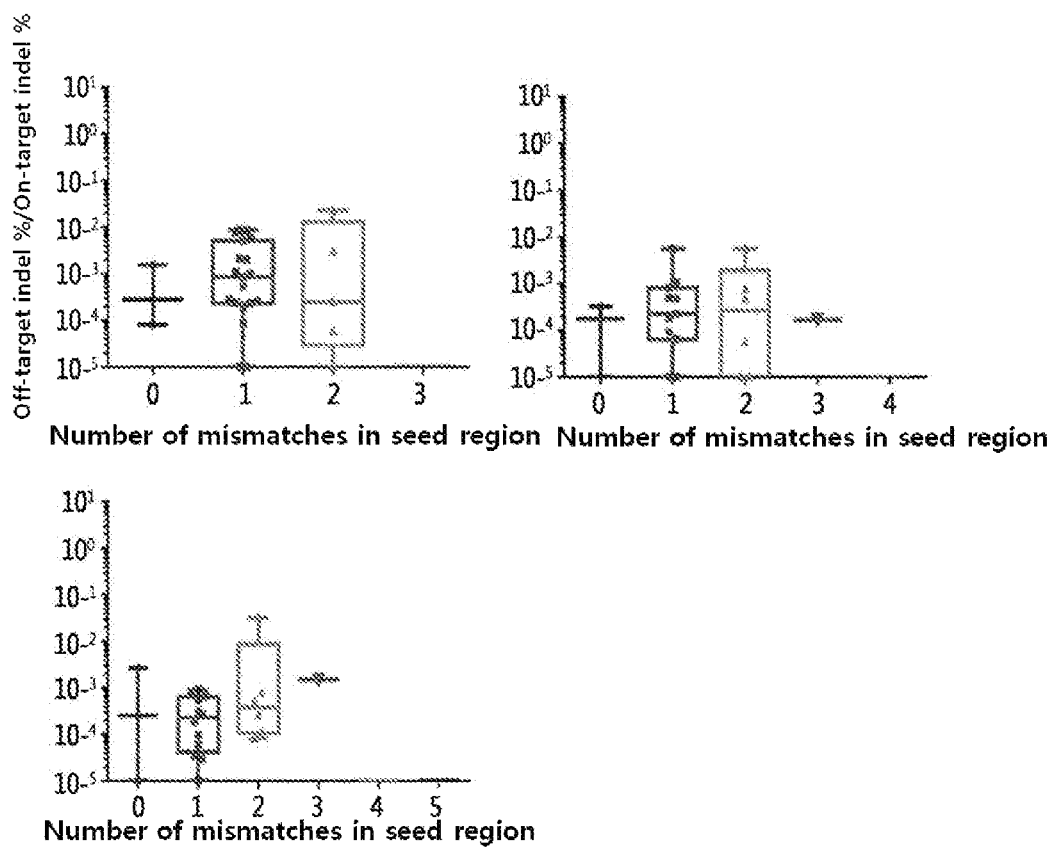

The indel frequency at off-target sites validated by NGS (=160) and non-validated off-target sites (=144) were specially used to identify off-target effects. It was identified that the number of mismatch nucleotide and off-target sites with a nucleotide mismatch of 2 or less in the plot of indel frequency of on-target sites and off-target sites were found to be effectively cleaved intracellularly (average indel frequency=5.38%), and that are not well cleaved in case of having 3 or more nucleotide mismatches (average indel frequency=0.14% or less) (FIG. 22A). The indel frequency was 60 ±7% at an on-target site. At validated or unvalidated sites, nucleotide mismatches were distributed almost evenly in the PAM-distal and PAM-proximal regions. The validated or unvalidated sites with 3 or more nucleotide mismatches were as important as PAM-distal sites (FIGS. 22b and 23c). That is, at a site having 0 or 1 nucleotide mismatch at the seed site, the indel frequency was as low as the site having 2 or more mismatches.

The results show that the number of potential off-target sites in a genome, the ratio of sites identified by Digenome-seq (FIG. 16a), and the off-target scores (Table 24) calculated from the average indelible frequency of the site (FIG. 20a) were calculated.

TABLE 24

Calculation of off-target scores on EMX1 target sequences (5'-GAGTCCGAGCAGAAGAAGAANGG-3') in human genomes

| Number of mismatch nucleotide | Number of mismatch nucleotide at the seed site | Number of potential off-target sites[a] | Ratio identified by Digenome-seq[b] | Average indelible frequency[c] | Number of potential off-target sites X Ratio identified by Digertome-seq X Average indelible frequency |
|---|---|---|---|---|---|
| 0 | — | 1 | 1.0 | 0.0 | 0.0 |
| 1 or 2 | — | 1 | 1.0 | 0.15 | 0.15 |
| 3 | 0 | 7 | 0.56 | 0.030 | 0.12 |
|  | 1 | 7 | 0.44 | 0.0077 | 0.024 |
|  | 2 | 4 | 0.12 | 0.0030 | 0.0014 |
|  | 3 | 0 | 0.0020 | 0.00010 | 0.0 |
| 4 | 0 | 68 | 0.22 | 0.030 | 0.45 |
|  | 1 | 73 | 0.062 | 0.0039 | 0.018 |
|  | 2 | 115 | 0.010 | 0.00088 | 0.0010 |
|  | 3 | 16 | 0.0013 | 0.00088 | 0.000018 |
|  | 4 | 4 | 0.0 | 0.0 | 0.0 |
| 5 | 0 | 136 | 0.010 | 0.00067 | 0.00091 |
|  | 1 | 674 | 0.010 | 0.00067 | 0.0045 |
|  | 2 | 888 | 0.0015 | 0.00067 | 0.00089 |

TABLE 24-continued

Calculation of off-target scores on EMX1 target sequences (5'-GAGTCCGAGCAGAAGAAGAANGG-3') in human genomes

| Number of mismatch nucleotide | Number of mismatch nucleotide at the seed site | Number of potential off-target sites[a] | Ratio identified by Digenome-seq[b] | Average indelible frequency[c] | Number of potential off-target sites X Ratio identified by Digertome-seq X Average indelible frequency |
|---|---|---|---|---|---|
| | 3 | 521 | 0.00025 | 0.00067 | 0.000087 |
| | 4 | 91 | 0.0 | 0.0 | 0.0 |
| | 5 | 3 | 0.0 | 0.0 | 0.0 |
| 6 | 0 | 426 | 0.0067 | 0.00026 | 0.00074 |
| | 1 | 2641 | 0.0017 | 0.00026 | 0.0012 |
| | 2 | 5673 | 0.000047 | 0.00026 | 0.000069 |
| | 3 | 4954 | 0.000047 | 0.00026 | 0.000061 |
| | 4 | 1846 | 0.0 | 0.0 | 0.0 |
| | 5 | 197 | 0.0 | 0.0 | 0.0 |
| | 6 | 10 | 0.0 | 0.0 | 0.0 |
| | | | | off-target score: | 0.77 |

[a]Obtained by using Cas-OFFinder
[b]Identified as shown in FIG. 16b
[c]Identified by targeted deep sequencing (FIG. 22a).

To summarize the above results, the present inventors have developed a Digenome-seq method capable of detecting the off-target site of the programmable nuclease, which is highly reproducible compared to other conventional methods, and is configured to easily detect off-target sites. Furthermore, the present inventors developed an in vitro DNA cleavage scoring system and developed an enhanced Digenome-seq that can reduce false positive and false negative site numbers using sgRNA transcribed from a plasmid template rather than a synthetic oligonucleotide double strand. In addition, a multiplex Digenome-seq was performed by cleaving genomic DNA with 11 sgRNA mixtures, and an average of 70 additional cleavage sites per sgRNA, which were not detected in GUIDE-seq, were identified. Off-target indels were induced in many of these sites in RGEN-transformed human cells. Thus, by examining the indel frequency, the number of nucleotide mismatches, and the site of mismatches in hundreds of off-target sites, it was identified that the PAM-distal region in the RGEN specificity is as important as the seed region. In addition, it has been identified that sites having two or more nucleotide mismatches at the seed site are not cleaved in vitro compared to the case where the total mismatch nucleotide number is none or one.

EXPERIMENTAL EXAMPLE 12

Large Scale Multiplex Digenome-Seq

The present inventors tried to identify whether off-target sites can be efficiently detected even in case of expanding the target of the multiplex Digenome-seq on a large scale.

Specifically, the multiplex Digenome-seq was performed for each different 100 on-target sites. Even if on-target sites were expanded to 100, off-target sites for the 100 targets could be efficiently detected through Digenome-seq.

In this regard, after fining the sites having 6 or less of nucleotide mismatch(es) with respect to an on-target sites through a computer program, this portion was classified as a cleavage site by RGEN and non-cleavage site. Next, the difference between the sequence of the cleavage site and the sequence of the non-cleavage site was analyzed through machine learning based on the neural network, and a program capable of predicting the off-target site with respect to the on-target site was produced. It was found that a larger number of off-target sites can be detected in comparison with other programs (crop-it) that have been developed through the program (FIG. 23).

EXPERIMENTAL EXAMPLE 13

Digenome-Seq for ZFN

Furthermore, the present inventors also tried to detect off-target sites of ZFN instead of RGEN by the same approach.

Figure 24A:
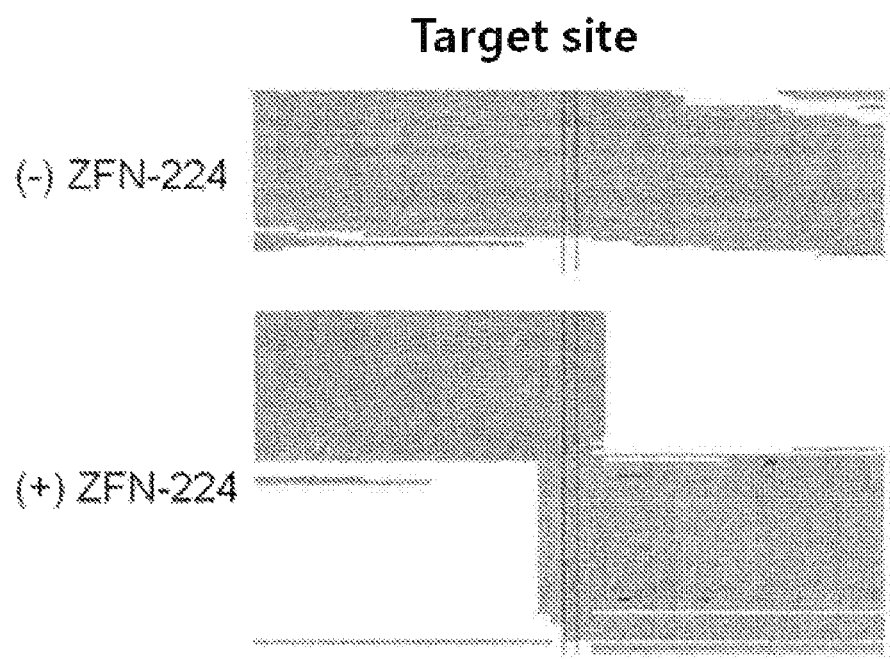
FIG. 24 illustrates the off-target effect of ZFN (zinc finger nuclease) through the Digenome-seq on a genomic scale. (a) It is the representative IGV photograph of on-target sites before and after ZFN-224 treatment. (b) It illustrates a Circos plot showing in vitro DNA cleavage score on a genomic scale of untreated genome DNA (red), DNA cleaved with ZFN-224 (WT Fokl) (green), and DNA cleaved with ZFN-224 (KK/EL Fold) (blue) (c-d) It illustrates a sequence logo obtained using off-target candidate sites in ZFN-224 (WT Fold) or ZFN-224 (KK/EL Fokl).
Figure 24B:
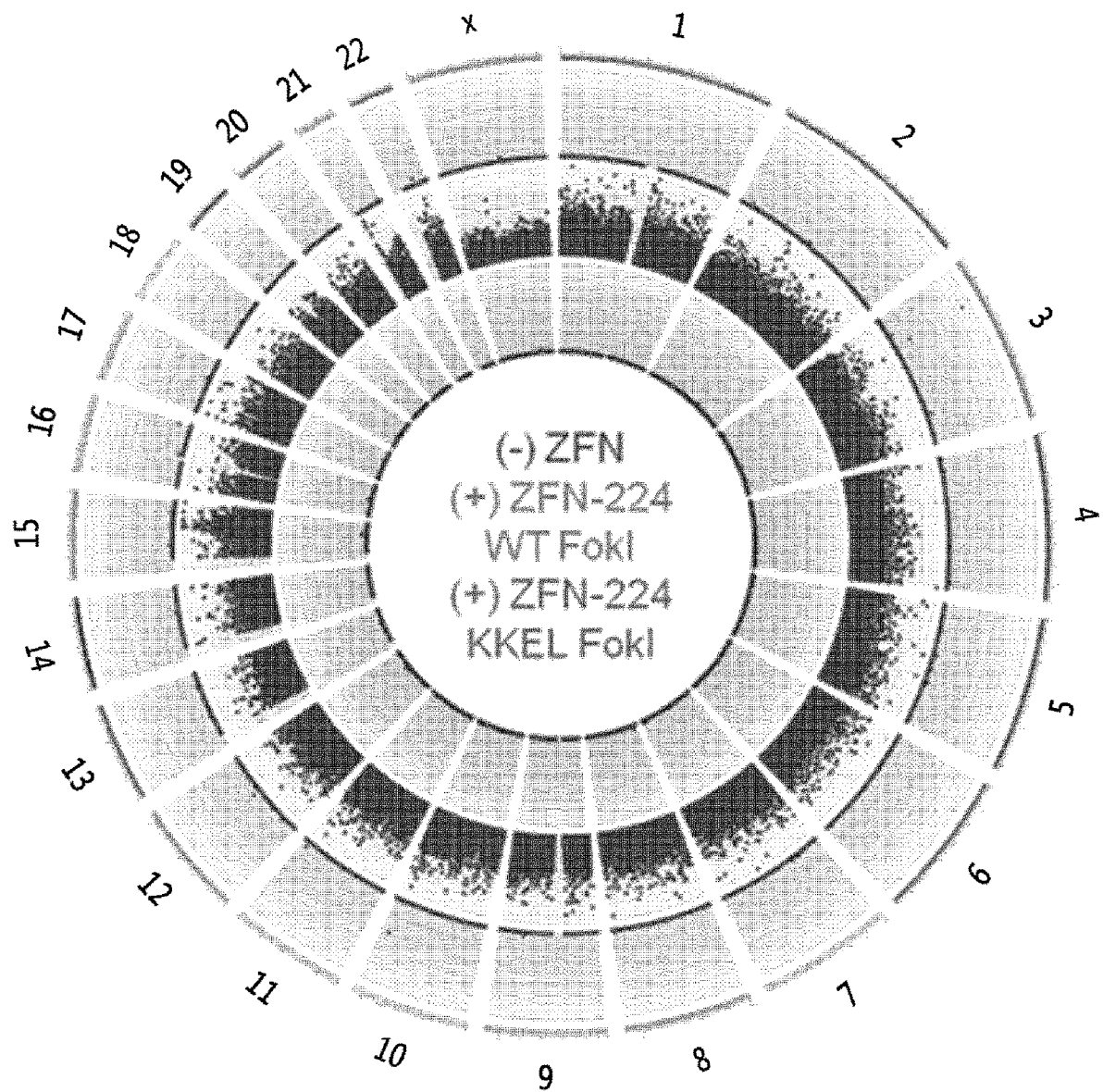
Figure 24D:
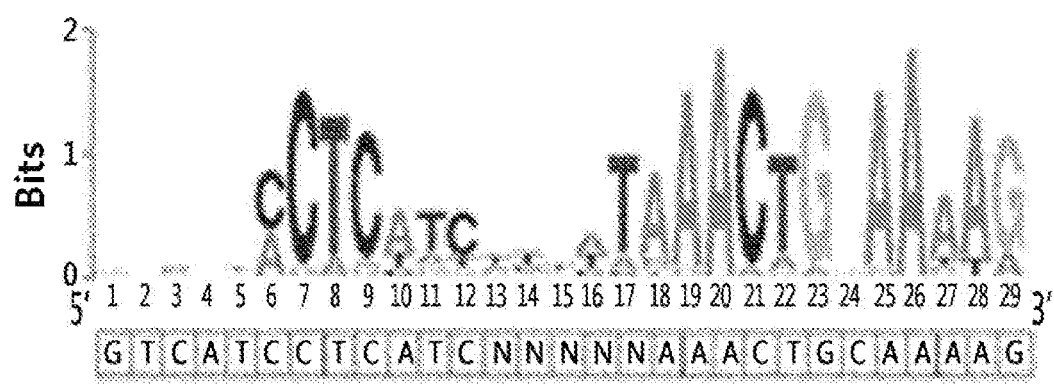

Like RGEN, ZFN protein was treated by cell-free genomic DNA isolated in vitro and then WGS was performed. In the case of ZFN, it was identified that vertical alignment occurred when the on-target site was observed through the IGV (FIG. 24a), and a cleavage score was given on the entire genomic scale (FIG. 24b). It was identified that the sequence logo obtained by comparing the DNA sequence around the cleavage site in vitro coincides with the target sequence at most sites (FIG. 24c and FIG. 24d).

Targeted deep sequencing was performed after transformation through ZFN for a portion of the on-target site and off-target site candidates resulting from Digenome-seq that has 4 or less nucleotide mismatch regions (Table 25).

TABLE 25

| | 1st | | 2nd | |
|---|---|---|---|---|
| | (−) ZFN | (+) ZFN | (−) ZFN | (+) ZFN |
| ZFN-224_01 | 0.004% | 5.690% | 0.002% | 5.920% |
| ZFN-224_02 | 0.000% | 4.057% | 0.000% | 4.240% |
| ZFN-224_03 | 0.000% | 1.940% | 0.000% | 1.866% |
| ZFN-224_04 | 0.006% | 0.055% | 0.015% | 0.038% |

TABLE 25-continued

|  | 1st | | 2nd | |
| --- | --- | --- | --- | --- |
|  | (−) ZFN | (+) ZFN | (−) ZFN | (+) ZFN |
| ZFN-224_05 | 0.000% | 0.218% | 0.000% | 0.218% |
| ZFN-224_06 | 0.000% | 0.678% | 0.009% | 0.717% |
| ZFN-224_07 | 0.000% | 0.162% | 0.014% | 0.151% |
| ZFN-224_08 | 0.000% | 0.084% | 0.003% | 0.086% |
| ZFN-224_10 | 0.007% | 0.107% | 0.004% | 0.110% |
| ZFN-224_11 | 0.000% | 0.075% | 0.003% | 0.042% |
| ZFN-224_12 | 0.000% | 0.179% | 0.019% | 0.163% |
| ZFN-224_14 | 0.016% | 0.094% | 0.040% | 0.130% |
| ZFN-224_17 | 0.022% | 0.169% | 0.016% | 0.161% |
| ZFN-224_19 | 0.008% | 0.029% | 0.000% | 0.030% |
| ZFN-224_22 | 0.000% | 0.067% | 0.032% | 0.192% |
| ZFN-224_23 | 0.006% | 0.030% | 0.000% | 0.025% |
| ZFN-224_24 | 0.000% | 0.116% | 0.003% | 0.121% |
| ZFN-224_25 | 0.000% | 0.199% | 0.000% | 0.173% |
| ZFN-224_28 | 0.000% | 1.441% | 0.000% | 1.971% |
| ZFN-224_29 | 0.000% | 0.432% | 0.000% | 0.429% |
| ZFN-224_32 | 0.000% | 0.059% | 0.006% | 0.047% |
| ZFN-224_33 | 0.000% | 0.078% | 0.000% | 0.076% |
| ZFN-224_34 | 0.000% | 0.046% | 0.000% | 0.026% |
| ZFN-224_35 | 0.000% | 0.281% | 0.000% | 0.274% |
| ZFN-224_37 | 0.005% | 0.073% | 0.014% | 0.088% |
| ZFN-224_44 | 0.017% | 0.031% | 0.017% | 0.036% |
| ZFN-224_45 | 0.000% | 0.080% | 0.000% | 0.130% |
| ZFN-224_46 | 0.031% | 0.346% | 0.022% | 0.258% |
| ZFN-224_48 | 0.020% | 1.510% | 0.021% | 1.426% |
| ZFN-224_49 | 0.000% | 0.226% | 0.013% | 0.252% |
| ZFN-224_51 | 0.000% | 2.507% | 0.004% | 2.827% |
| ZFN-224_55 | 0.006% | 0.048% | 0.016% | 0.048% |
| ZFN-224_56 | 0.000% | 1.261% | 0.007% | 1.217% |
| ZFN-224_59 | 0.010% | 0.042% | 0.003% | 0.139% |
| ZFN-224_62 | 0.008% | 0.074% | 0.020% | 0.086% |

Figure 25A:
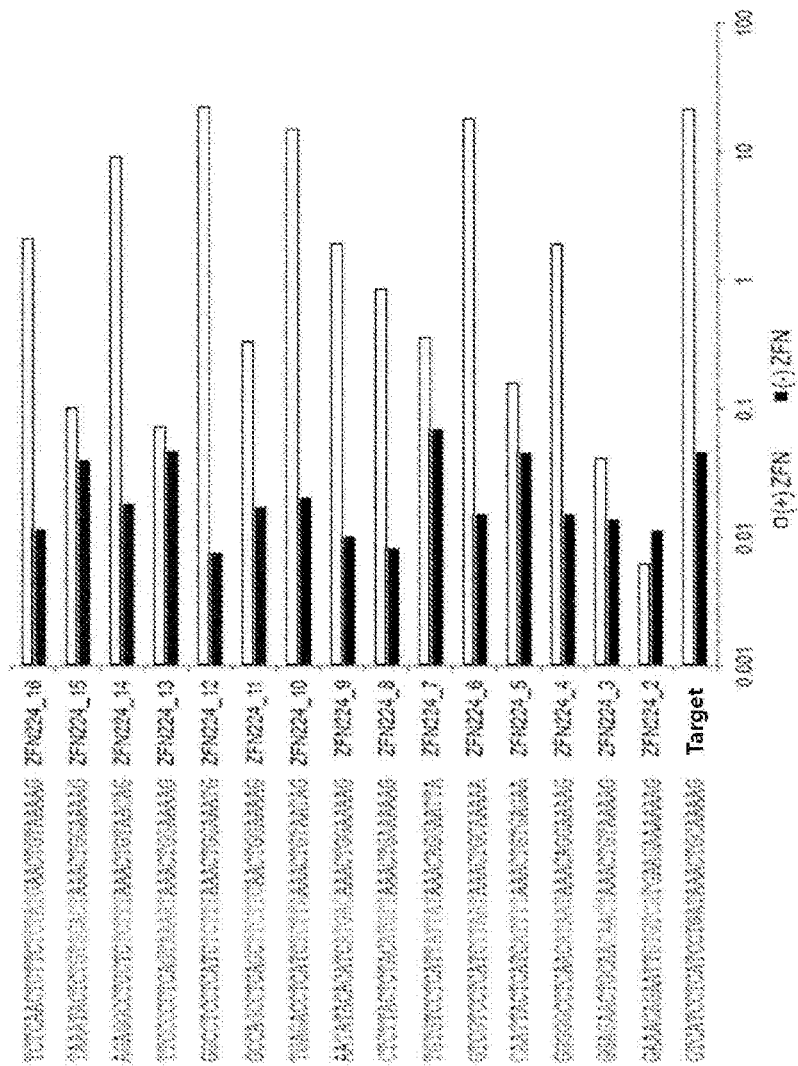
FIG. 25 illustrates the results of detecting off-target sites in Digenome-seq of ZFN. (a) Indel frequencies were measured by using targeted deep sequencing at off-target candidate sites of ZFN-224 (KK/EL Fokl). (b-c) It is a Venn diagram showing Digenome-seq, ILDV, and the numbers of (b) off-target candidate sites detected in vitro and (c) validated on-target sites.
Figure 25B:
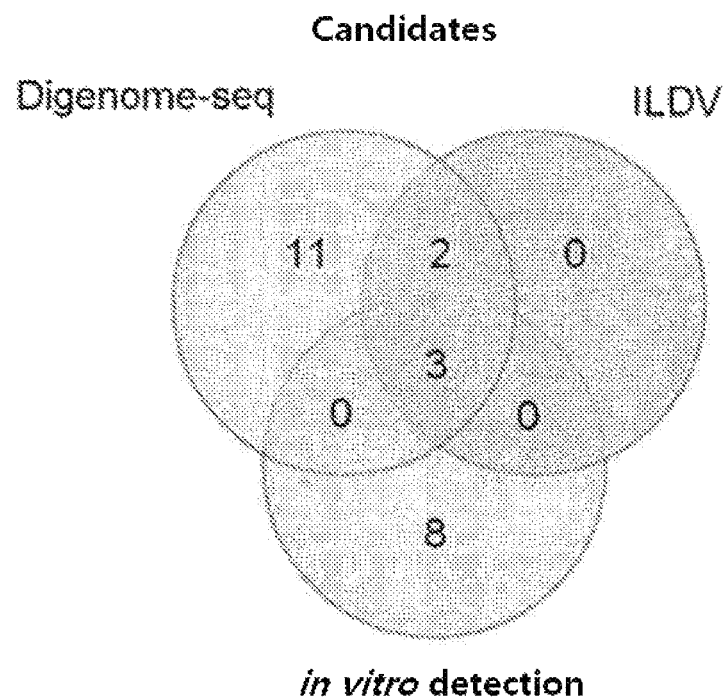
Figure 25C:
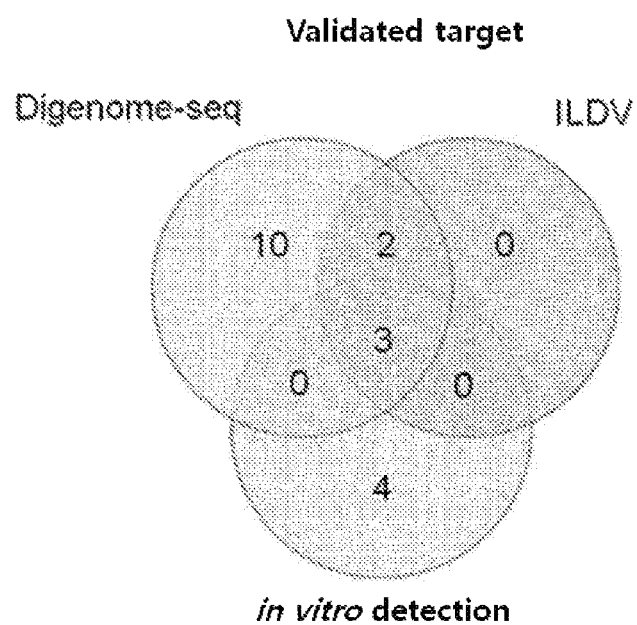

As a result, it was identified that indels were present in 35 on-target and off-target sites out of 62 off-target site candidates. Specifically, it was identified that 0.028% to 5.9% was induced (Table 25). This shows that the Digenome-seq method also predicts the off-target site of the ZFN. In the case of ZFN made by modifying (KK or EL) at the FokI site, the specificity was increased (FIG. 24). As such, a total of 16 off-target site candidates were found when Digenome-seq was performed through FokI modified ZFN. It was also identified that indels occurred at 15 of 16 off-target site candidates in cells transformed by using FokI-modified ZFN, and this indicates that a large number of off-targets sites can be found compared to the conventional other methods (ILDV, in vitro selection) (FIG. 25).

In conclusion, the above results suggest that the Digenome-seq of the present disclosure can be applied to any programmable nuclease that can have RGEN, ZFN as well as on-target and off-target sites.

As described above, it will be understood by a person having ordinary skill in the technical field to which the present disclosure pertains that the present disclosure may be embodied in other specific forms without departing from the technical spirit or essential characteristics thereof. In this regard, it should be understood that the above-described embodiments are intended to illustrate in every aspect, but are not intended to be limiting. The scope of the invention should be construed to cover all modifications and variations that come within the meaning and range, as well as equivalent concepts thereof, as defined by the appended claims rather than the foregoing description.

The invention claimed is:

1. A method for detecting an on- or off-target site in a whole genome comprising:
   (a) cleaving an isolated genomic DNA with a target-specific programmable nuclease;
   (b) performing whole genome sequencing by next generation sequencing of the cleaved DNA;
   (c) aligning forward and reverse sequence reads obtained by performing step (b) to a reference genome by mapping sequence reads to the reference genome, such that the 5' ends of the sequence reads having the same 5' end cleaved by the target-specific programmable nuclease are vertically aligned at a cleaved site showing double-peak patterns at the 5' end plot; and
   (d) determining that the cleaved site where the 5' ends of the sequence reads are vertically aligned is an off-target site using a formula as follows at each cleaved site, if C value in the formula is 100 and the calculated score in the formula is 25,000 or more:

$$\text{Score at the } i \text{ site} = \sum_{a=1}^{5} \frac{C(F_i - 1)}{D_i} \times \frac{C(R_{i-4+a} - 1)}{D_{i-4+a}} \times (F_i + R_{i-4+a} - 2) +$$

$$\sum_{a=1}^{5} \frac{C(R_{i-1} - 1)}{D_{i-1}} \times \frac{C(F_{i-3+a} - 1)}{D_{i-3+a}} \times (R_{i-a} + F_{i-3+a} - 2)$$

$F_i$: Number of forward sequence reads starting at the $i$ site $R_i$: Number of reverse sequence reads starting at the $i$ site $D_i$: Sequencing depth at the $i$ site $C$: Arbitrary constant 2. The method according to claim 1, wherein the genomic DNA is isolated from cells expressing or not expressing the target-specific programmable nuclease.

3. The method according to claim 1, further comprising determining a site where two or more sequence reads corresponding to Watson strand and Crick strand are separately aligned vertically as an off-target site.

4. The method according to claim 1, further comprising determining a site where 20% or more of sequence reads is vertically aligned and the number of sequence reads having the same 5' end in each of the Watson and Creek strands is 10 or more as an off-target site.

5. The method according to claim 1, wherein the isolated genomic DNA is isolated from cells expressing a programmable nuclease, and further comprising determining an off-target effect by identifying indels (insertion and deletion) at an off-target site of the DNA.

6. The method according to claim 5, wherein the indels are identified by performing a mutant detection using T7E1 analysis on the off-target site and Cel-I enzyme, or targeted deep sequencing.

7. The method according to claim 1, wherein the off-target site has one or more nucleotide mismatch(es) to the target site.

8. The method according to claim 1, wherein the off-target site has 1 to 6 nucleotide mismatch(es) to the target site.

9. The method according to claim 1, wherein the programmable nuclease is a mixture of programmable nucleases for 2 or more targets.

10. The method according to claim 9, further comprising classifying the off-target site according to the edit distance to the on-target site.

11. The method according to claim 1, wherein the programmable nuclease is a mixture of programmable nucleases for 2 to 100 targets.

12. The method according to claim 1, wherein the programmable nuclease is selected from(Original) the group consisting of meganuclease, ZFN (zinc finger nuclease), TALEN (transcription activator-like effector nuclease), RGEN (RNA-guided engineered nuclease), and Cpf1.

13. The method according to claim 12, wherein RGEN comprises a guide RNA binding specifically to a sequence of a target gene and Cas protein.

14. The method according to claim 13, wherein the guide RNA is transcribed from an oligonucleotide double strand or a plasmid template.

15. The method according to claim 13, wherein the guide RNA is a dual RNA comprising a crRNA and a tracrRNA or a single chain guide RNA.

16. The method according to claim 13, wherein the Cas protein is Cas9 protein or a variant of Cas9 protein.

17. The method according to claim 13, wherein the Cas protein is derived from one selected from the group consisting of a genus *Streptococcus*, a genus *Neisseria*, a genus *Pasteurella*, a genus *Francisella*, and a genus *Campylobacter*.

18. The method according to claim 12, wherein the meganuclease is selected from the group consisting of I-Scel, I-Ceul, PI-Pspl and PI-Scel.

19. The method according to claim 12, wherein the Cpf1 is derived from one selected from the group consisting of *CandidatusPaceibacter*, *Lachnospira* genus, *Butyrivibrio* genus, *Peregrinibacteria*, *Acidominococcus* genus, *Porphyromonas* genus, *Prevotella* genus, *Francisella* genus, *Candidatus methanoplasma*, and *Eubacterium* genus.

* * * * *

SEQUENCE LISTING

<160> NUMBER OF SEQ ID NOS: 1356

<210> SEQ ID NO 1
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1
cttgccccac agggcagtaa cgg                                              23

<210> SEQ ID NO 2
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 2
ctctgtctcg cgctgctttt ggg                                              23

<210> SEQ ID NO 3
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 3
tctaccccac atggcagtaa tgg                                              23

```
<210> SEQ ID NO 4
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 4
ggtcccggga atagcgggta agg                                              23

<210> SEQ ID NO 5
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 5
acagccccac agggcactag agg                                              23

<210> SEQ ID NO 6
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 6
aaagccccac agggtagtag agg                                              23

<210> SEQ ID NO 7
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 7
gctaccccac agggcattag ggg                                              23

<210> SEQ ID NO 8
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 8
gctgccccac atgacagaaa tgg                                              23

<210> SEQ ID NO 9
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 9
actcgtctcc gatatccagt tgg                                              23

<210> SEQ ID NO 10
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 10
ggtgtaaccc ggagtgacca agg                                            23

<210> SEQ ID NO 11
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 11
ggtgtaaccc ggagtgacca agg                                            23

<210> SEQ ID NO 12
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 12
gttacctcac agagcagaaa ggg                                            23

<210> SEQ ID NO 13
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 13
tatgctccag agggtagtaa tga                                            23

<210> SEQ ID NO 14
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 14
cataccccac aggtcagtaa gga                                            23

<210> SEQ ID NO 15
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 15
tctgccccac aggccaggaa ggg                                            23

<210> SEQ ID NO 16
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 16
tctgccccac atggcagtaa tga                                            23

<210> SEQ ID NO 17
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 17
tgagttctcc aatatccagt tgg                                              23

<210> SEQ ID NO 18
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 18
actgccccac agggaagtaa tag                                              23

<210> SEQ ID NO 19
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 19
tcagccccac aggtcagcaa tgg                                              23

<210> SEQ ID NO 20
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 20
ggactcctcc aatatcctgt tgg                                              23

<210> SEQ ID NO 21
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 21
gttaccccca gggaagtata gg                                               22

<210> SEQ ID NO 22
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 22
tcagccccac agggcagtaa ggg                                              23

<210> SEQ ID NO 23
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 23
```
tttgcccctc agggcagcta agg                     23

<210> SEQ ID NO 24
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 24
cctgccccac agggcaatta tgg                     23

<210> SEQ ID NO 25
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 25
catggccagg aagagaaggc tgg                     23

<210> SEQ ID NO 26
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 26
caagccccac agggcagaca ggg                     23

<210> SEQ ID NO 27
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 27
caggccccac aggacaggaa ggg                     23

<210> SEQ ID NO 28
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 28
agcccccaca gggcaggtag ggg                     23

<210> SEQ ID NO 29
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 29
cggccagatt catggcaatc agg                     23

<210> SEQ ID NO 30
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 30
ctgcccctca gggacagtat ggg                                              23

<210> SEQ ID NO 31
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 31
gatgcctcac aggacaggaa ggg                                              23

<210> SEQ ID NO 32
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 32
gctatggttc ctgaacggcc tgg                                              23

<210> SEQ ID NO 33
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 33
attgccccac ggggcagtga cgg                                              23

<210> SEQ ID NO 34
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 34
gctgccccac agggcagcaa agg                                              23

<210> SEQ ID NO 35
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 35
ttggtcaatt cgtcgcctta cgg                                              23

<210> SEQ ID NO 36
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 36
ggagccccac agggcagaga ggg                                              23
```

<210> SEQ ID NO 37
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 37
gttatcccac aggacagtga ggg                                             23

<210> SEQ ID NO 38
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 38
cttccccaat atccagtagg g                                               21

<210> SEQ ID NO 39
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 39
atggccccac aaggcagaaa tgg                                             23

<210> SEQ ID NO 40
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 40
ccagccccac agggcagtaa agc                                             23

<210> SEQ ID NO 41
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 41
gttgcccctc aggacagtac agg                                             23

<210> SEQ ID NO 42
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 42
tgtgccccac agggagtgag gg                                              22

<210> SEQ ID NO 43
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 43
gcagccccac aggtcagtga ggg                                           23

<210> SEQ ID NO 44
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 44
tgctcccaca gggcagtaaa cgg                                           23

<210> SEQ ID NO 45
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 45
aaaatacctc gttgatttcc agg                                           23

<210> SEQ ID NO 46
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 46
gttgccccac tggggagaaa agg                                           23

<210> SEQ ID NO 47
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 47
tgtgccccac aggcagtaga tg                                            22

<210> SEQ ID NO 48
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 48 ctgctcccaca gggcaggtat ggg                                          23

<210> SEQ ID NO 49
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 49
cttgcaccac agagcactaa ggg                                           23

```
<210> SEQ ID NO 50
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 50
agtggccccc agggcagtga ggg                                              23

<210> SEQ ID NO 51
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 51
tgtgccccac agagcactaa ggg                                              23

<210> SEQ ID NO 52
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 52
agtgccccac aggggagaaa tgg                                              23

<210> SEQ ID NO 53
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 53
gtggccccac agggcaggaa tgg                                              23

<210> SEQ ID NO 54
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 54
gcatccccac agggcagtat gtg                                              23

<210> SEQ ID NO 55
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 55
cttgccccac agggcagtaa cgg                                              23

<210> SEQ ID NO 56
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 56
ggtccccaca gggtcagtaa ggg                                              23

<210> SEQ ID NO 57
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 57
tctaccccac atggcagtaa tgg                                              23

<210> SEQ ID NO 58
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 58
aaagccccac agggtagtag agg                                              23

<210> SEQ ID NO 59
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 59
gctaccccac agggcattag ggg                                              23

<210> SEQ ID NO 60
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 60
gttacctcac agagcagaaa ggg                                              23

<210> SEQ ID NO 61
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 61
cataccccac aggtcagtaa gga                                              23

<210> SEQ ID NO 62
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 62
tctgccccac aggccaggaa ggg                                              23

<210> SEQ ID NO 63
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 63
gaagccctac agggcagcaa tgg                                          23

<210> SEQ ID NO 64
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 64
tctgccccac atggcagtaa tga                                          23

<210> SEQ ID NO 65
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 65
agtgccacac acagcagtaa ggg                                          23

<210> SEQ ID NO 66
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 66
tcagccccac agggcagtaa ggg                                          23

<210> SEQ ID NO 67
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 67
cctgccccac agggcaatta tgg                                          23

<210> SEQ ID NO 68
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 68
caagccccac agggcagaca ggg                                          23

<210> SEQ ID NO 69
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 69
```
caggccccac aggacaggaa ggg                                               23

<210> SEQ ID NO 70
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 70
ctgcccctca gggacagtat ggg                                               23

<210> SEQ ID NO 71
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 71
gatgcctcac aggacaggaa ggg                                               23

<210> SEQ ID NO 72
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 72
attgccccac ggggcagtga cgg                                               23

<210> SEQ ID NO 73
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 73
gctgccccac agggcagcaa agg                                               23

<210> SEQ ID NO 74
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 74
ggagccccac agggcagaga ggg                                               23

<210> SEQ ID NO 75
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 75
gttatcccac aggacagtga ggg                                               23

<210> SEQ ID NO 76
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 76
atggccccac aaggcagaaa tgg                                              23

<210> SEQ ID NO 77
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 77
gttaccacac agagcagtta agg                                              23

<210> SEQ ID NO 78
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 78
gttgcccctc aggacagtac agg                                              23

<210> SEQ ID NO 79
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 79
gcagccccac aggtcagtga ggg                                              23

<210> SEQ ID NO 80
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 80
ttgctcccac agggcagtaa acg                                              23

<210> SEQ ID NO 81
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 81
aaatccccac agggcagtaa ggc                                              23

<210> SEQ ID NO 82
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 82
agtggccccc agggcagtga ggg                                              23
```

<210> SEQ ID NO 83
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 83
tgtgccccac agagcactaa ggg                                    23

<210> SEQ ID NO 84
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 84
gtggccccac agggcaggaa tgg                                    23

<210> SEQ ID NO 85
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 85
gctgccccac agggcagcaa agg                                    23

<210> SEQ ID NO 86
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 86
gttgcccctc aggacagtac agg                                    23

<210> SEQ ID NO 87
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 87
tgtgccccac agagcactaa ggg                                    23

<210> SEQ ID NO 88
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 88
tcagccccac agggcagtaa ggg                                    23

<210> SEQ ID NO 89
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 89
ttgctcccac agggcagtaa acg                                              23

<210> SEQ ID NO 90
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 90
atggccccac aaggcagaaa tgg                                              23

<210> SEQ ID NO 91
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 91
cttgccccac agggcagtaa cgg                                              23

<210> SEQ ID NO 92
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 92
attgccccac ggggcagtga cgg                                              23

<210> SEQ ID NO 93
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 93
tctaccccac atggcagtaa tgg                                              23

<210> SEQ ID NO 94
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 94
gtggccccac agggcaggaa tgg                                              23

<210> SEQ ID NO 95
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 95
tctgccccac atggcagtaa tga                                              23

<210> SEQ ID NO 96
```

-continued

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 96
gaagccctac agggcagcaa tgg                                              23

<210> SEQ ID NO 97
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 97
gtgtccccac agggcaggaa agg                                              23

<210> SEQ ID NO 98
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 98
agtgccacac acagcagtaa ggg                                              23

<210> SEQ ID NO 99
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 99
gttatcccac aggacagtga ggg                                              23

<210> SEQ ID NO 100
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 100
cggtccccac agggtcagta agg                                              23

<210> SEQ ID NO 101
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 101
agtggccccc agggcagtga ggg                                              23

<210> SEQ ID NO 102
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 102
```
actctcccac aaggcagtaa ggg                                                23

<210> SEQ ID NO 103
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 103
gttacctcac agagcagaaa ggg                                                23

<210> SEQ ID NO 104
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 104 tcaccccac aggccagtaa agg                                                 23

<210> SEQ ID NO 105
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 105 attcccccc accccgcctc agg                                                 23

<210> SEQ ID NO 106
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 106 acacccccc accccgcctc agg                                                 23

<210> SEQ ID NO 107
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 107 cctcacccc accccacctc tgg                                                 23

<210> SEQ ID NO 108
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 108 gggccctcc accccgcctc tgg                                                 23

<210> SEQ ID NO 109
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 109
taccccccac accccgcctc tgg                                            23

<210> SEQ ID NO 110
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 110 tgccccccccc accccacctc tgg                                           23

<210> SEQ ID NO 111
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 111 cattccccccc accccacctc agg                                           23

<210> SEQ ID NO 112
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 112
taaatcctcc accccacctc agg                                            23

<210> SEQ ID NO 113
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 113
gcccccaccc accccgcctc tgg                                            23

<210> SEQ ID NO 114
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 114
gaccccctcc accccgcctc cgg                                            23

<210> SEQ ID NO 115
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 115
ccccaccccc accccgcctc agg                                            23
```

<210> SEQ ID NO 116
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 116
gagccactgc gcccggcccc cgg                                              23

<210> SEQ ID NO 117
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 117
gacccctccc accccgactc cgg                                              23

<210> SEQ ID NO 118
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 118
tgcccctccc accccgcctc tgg                                              23

<210> SEQ ID NO 119
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 119
gatcgactcc accccgcctc tgg                                              23

<210> SEQ ID NO 120
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 120
cccccccccc ccccgcctc agg                                               23

<210> SEQ ID NO 121
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 121
gccccccacc accccacctc ggg                                              23

<210> SEQ ID NO 122
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 122
ctacccctcc acccgcctc cgg                                                23

<210> SEQ ID NO 123
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 123 cagtccccc accccacctc tgg                                                23

<210> SEQ ID NO 124
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 124 tccgccccc accccacctc cgg                                                23

<210> SEQ ID NO 125
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 125
ctccccaccc acccgcctc agg                                                23

<210> SEQ ID NO 126
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 126
tcagacctcc acccgcctc agg                                                23

<210> SEQ ID NO 127
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 127
ttcaccatca accccactt cag                                                23

<210> SEQ ID NO 128
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 128
tcctttctcc accccacctc tgg                                               23

```
<210> SEQ ID NO 129
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 129
cgccctcccc accccgcctc cgg                                              23

<210> SEQ ID NO 130
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 130
ctcacccccc accccacctc tgg                                              23

<210> SEQ ID NO 131
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 131
gtcactcccc accccgcctc tgg                                              23

<210> SEQ ID NO 132
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 132
tcccgccccc accccacctc cgg                                              23

<210> SEQ ID NO 133
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 133
tgcaacctcc tccccgcctc ggg                                              23

<210> SEQ ID NO 134
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 134
agccaacccc accccgcctc tgg                                              23

<210> SEQ ID NO 135
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 135
catcttcccc accccgcctc tgg                                            23

<210> SEQ ID NO 136
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 136
ctacgctcca ccaccacctc cag                                            23

<210> SEQ ID NO 137
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 137
agtagccccc accccgcctc ggg                                            23

<210> SEQ ID NO 138
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 138
aggcccccac accccgcctc agg                                            23

<210> SEQ ID NO 139
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 139
tcactccccc accccacctc tgg                                            23

<210> SEQ ID NO 140
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 140
gcttccctcc accccgcatc cgg                                            23

<210> SEQ ID NO 141
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 141
cgtctccccc accccacctc agg                                            23

<210> SEQ ID NO 142
<211> LENGTH: 23

<212> TYPE: DNA
<213> ORGANISM: Artificial Sequence
<220> FEATURE:
<223> OTHER INFORMATION: Synthesized Sequence

<400> SEQUENCE: 142 aggcccccccc gccccgcctc agg                                      23

<210> SEQ ID NO 143
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 143
gtcgaggtcc accccgcctc agg                                       23

<210> SEQ ID NO 144
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 144
ctcccccccc tccccgcctc ggg                                       23

<210> SEQ ID NO 145
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 145
ctcccagact cctcccctc ctc                                        23

<210> SEQ ID NO 146
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 146
caaccccccc accccgcttc agg                                       23

<210> SEQ ID NO 147
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 147
cccacacccc accccacctc cgg                                       23

<210> SEQ ID NO 148
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 148
ccaccatccc accccgcctc tgg                                          23

<210> SEQ ID NO 149
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 149
gtcctccacc accccgcctc tgg                                          23

<210> SEQ ID NO 150
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 150
ctgcctcctc accccgcctc agg                                          23

<210> SEQ ID NO 151
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 151
ccctctccac ccccaccctc tgg                                          23

<210> SEQ ID NO 152
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 152
tctcccctgt accccgcctc tgg                                          23

<210> SEQ ID NO 153
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 153
ccctaccccc accccacctc agg                                          23

<210> SEQ ID NO 154
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 154
cccttccccc accccacctc cgg                                          23

<210> SEQ ID NO 155
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 155
ttctccctcc tcccgcctc ggg                                          23

<210> SEQ ID NO 156
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 156
ctcccctcca ccccagcctc cgg                                         23

<210> SEQ ID NO 157
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 157
gccagccctc accccgcctc ggg                                         23

<210> SEQ ID NO 158
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 158
gacacacccc accccacctc agg                                         23

<210> SEQ ID NO 159
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 159
cgatcctctt accccgcctc cgg                                         23

<210> SEQ ID NO 160
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 160
gctgtctccc accccgcctc agg                                         23

<210> SEQ ID NO 161
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 161
tcttctttcc accccgcctc agg                                         23
```

<210> SEQ ID NO 162
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 162
tccccttccc accccacctc cgg          23

<210> SEQ ID NO 163
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 163
caagtaatcc accccacctc agg          23

<210> SEQ ID NO 164
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 164
gccaccttcc accccacctc agg          23

<210> SEQ ID NO 165
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 165
cttcctccac cccgcagtct atg          23

<210> SEQ ID NO 166
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 166
cgcccacccc accccacctc agg          23

<210> SEQ ID NO 167
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 167
ccagctcccc accccacctc agg          23

<210> SEQ ID NO 168
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 168
ggtgtatgag tgtgtgcgtc gga                                              23

<210> SEQ ID NO 169
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 169
ggtgagtgtg tgtgtgcatg tgg                                              23

<210> SEQ ID NO 170
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 170
agagagtgag tgtgtgcatg agg                                              23

<210> SEQ ID NO 171
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 171
ggtgtagtgg tgtgtgcttg tgg                                              23

<210> SEQ ID NO 172
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 172
ggtgtgtgag tgtgtgcatt ggg                                              23

<210> SEQ ID NO 173
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 173
agtgagtgag tgagtgagtg agg                                              23

<210> SEQ ID NO 174
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 174
catgagtgag tgtgtgggtg ggg                                              23

<210> SEQ ID NO 175
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 175
ggtgagagag tgtgtgcgta gga                                          23

<210> SEQ ID NO 176
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 176
agtgagtgag tgagtgagtg agg                                          23

<210> SEQ ID NO 177
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 177
tctgagtgag tgtgggcatg ggg                                          23

<210> SEQ ID NO 178
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 178
ggtgaatgag tgtgtgctct ggg                                          23

<210> SEQ ID NO 179
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 179
gctgagtgag tgtatgcgtg tgg                                          23

<210> SEQ ID NO 180
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 180
cgtgagtgag tgtgtacctg ggg                                          23

<210> SEQ ID NO 181
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 181
```
gatgagtgag tgagtgagtg ggg 23

<210> SEQ ID NO 182
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 182
agtgagtgag tgagtggggt tgg 23

<210> SEQ ID NO 183
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 183
agtgagtgag tgtgtgtgtg ggg 23

<210> SEQ ID NO 184
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 184
agtgtgtgag tgtgtgcgtg tgg 23

<210> SEQ ID NO 185
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 185
tgtgagtgag tatgtacatg tgg 23

<210> SEQ ID NO 186
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 186
tatgagtgag tgtgtggatg agg 23

<210> SEQ ID NO 187
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 187
tgtgtgagtg tgtgtgtgcg tgg 23

<210> SEQ ID NO 188
<211> LENGTH: 23
<212> TYPE: DNA

<213> ORGANISM: Artificial Sequence
<220> FEATURE:
<223> OTHER INFORMATION: Synthesized Sequence

<400> SEQUENCE: 188
tgtgagtgag tgtgtgtatg ggg                                         23

<210> SEQ ID NO 189
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 189
ggtgagtgtg tgtgtgagtg tgg                                         23

<210> SEQ ID NO 190
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 190
ggagagcgag tgtgtgcatt tgg                                         23

<210> SEQ ID NO 191
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 191
ggtgtatgag tgtgtgtgtg agg                                         23

<210> SEQ ID NO 192
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 192
agcgagtgag tgagtgcatt ggg                                         23

<210> SEQ ID NO 193
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 193
ggtgagcaag tgtgtgtgtg tgg                                         23

<210> SEQ ID NO 194
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 194
tgtgagtgag tgtgtgcaga agg                                         23

<210> SEQ ID NO 195
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 195
ggtgagtgag tgagtgagtg agg                                        23

<210> SEQ ID NO 196
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 196
tgagagtgag tgtgtgtata tgg                                        23

<210> SEQ ID NO 197
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 197
gatgtgtgag tgtgtgcctg tgg                                        23

<210> SEQ ID NO 198
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 198
tgtgagtgag tgtgtgtgtg tga                                        23

<210> SEQ ID NO 199
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 199
tgtgggtgag tgtgtgcgtg agg                                        23

<210> SEQ ID NO 200
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 200
agcgagtgag tgtgtgtgtg ggg                                        23

<210> SEQ ID NO 201
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 201
ggtaagtgtg tgtgtgcatg tgg                                          23

<210> SEQ ID NO 202
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 202
catgagtggg tgtgtgcatt ggg                                          23

<210> SEQ ID NO 203
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 203
gtagagtgag tgtgtgtgtg tgg                                          23

<210> SEQ ID NO 204
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 204
gaagaatgag tgtgtgcttg tgg                                          23

<210> SEQ ID NO 205
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 205
ggtgtgtgag tgtgtgcatg ttg                                          23

<210> SEQ ID NO 206
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 206
tgtgagtggg tgtgtgagtg agg                                          23

<210> SEQ ID NO 207
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 207
ggtgagtagg tgtgtgtgtg ggg                                          23

```
<210> SEQ ID NO 208
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 208
ggagagtgtg tgtgtgagtg tgg                                            23

<210> SEQ ID NO 209
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 209
ggtgagcgtg tgtgtgcatg tgg                                            23

<210> SEQ ID NO 210
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 210
agtgagaaag tgtgtgcatg cgg                                            23

<210> SEQ ID NO 211
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 211
cataagtgag tgtgtgcgag tgg                                            23

<210> SEQ ID NO 212
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 212
agggagtgac tgtgtgcgtg tgg                                            23

<210> SEQ ID NO 213
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 213
tgtgagtgtg tgtgtgcatc tgg                                            23

<210> SEQ ID NO 214
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 214
ggtgaagtgg tgtgtgcctg tgg					23

<210> SEQ ID NO 215
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 215
aatgagtgag tgtgtgagtg aag					23

<210> SEQ ID NO 216
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 216
agggagtgag tgtgagagtg cgg					23

<210> SEQ ID NO 217
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 217
ggggtgagtg tgtgtgtggg ggg					23

<210> SEQ ID NO 218
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 218
tgtgagtgaa tgtgtgcata tgg					23

<210> SEQ ID NO 219
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 219
ggtgtgtgtg tgtgtgcatg tgg					23

<210> SEQ ID NO 220
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 220
ggtgtgtgag tgtgtgtgtg tgg					23

<210> SEQ ID NO 221
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 221
ctggagtgag tgtgtgtgtg tgg                                            23

<210> SEQ ID NO 222
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 222
ggagagtgag tgtgtttgtg tgg                                            23

<210> SEQ ID NO 223
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 223
tgtgtatgag tgtgtgcgtt ggg                                            23

<210> SEQ ID NO 224
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 224
aatgggtgag tgtgtgggtg ggg                                            23

<210> SEQ ID NO 225
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 225
aatgaatgaa tgtgtgcatg tgg                                            23

<210> SEQ ID NO 226
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 226
tgtgtgtgag tgtgtgcatg tgg                                            23

<210> SEQ ID NO 227
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 227
```

```
tgtgagagag agtgtgcgtg tgg                                             23

<210> SEQ ID NO 228
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 228
tgtgagtatg tgtgtgcatg tgg                                             23

<210> SEQ ID NO 229
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 229
tgtgcatgag ggtgtgtgtt ggg                                             23

<210> SEQ ID NO 230
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 230
ggtaagtatg tgtgtgcatg ggg                                             23

<210> SEQ ID NO 231
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 231
agtgagtaag tgagtgagtg agg                                             23

<210> SEQ ID NO 232
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 232
tgtgagtgaa tgagtgcatg tgg                                             23

<210> SEQ ID NO 233
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 233
agtgagtatg tgtgtgaggg tgg                                             23

<210> SEQ ID NO 234
<211> LENGTH: 23
<212> TYPE: DNA
<213> ORGANISM: Artificial Sequence
```

```
<220> FEATURE:
<223> OTHER INFORMATION: Synthesized Sequence

<400> SEQUENCE: 234
tgtgagtggg tgtgtgcatg tgg                                              23

<210> SEQ ID NO 235
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 235
ggtgtgtgtg tgtgtgtgtg tgg                                              23

<210> SEQ ID NO 236
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 236
tgtgtgagtg agtgtgtgtg tgg                                              23

<210> SEQ ID NO 237
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 237
agtgaatgag tgagtgagtg agg                                              23

<210> SEQ ID NO 238
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 238
agtgaatgag tgtgtgtgtg tgg                                              23

<210> SEQ ID NO 239
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 239
gatgtgtgag tgtgtacatg agg                                              23

<210> SEQ ID NO 240
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 240
aatgagtgag tgagtgcatg gag                                              23
```

<210> SEQ ID NO 241
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 241
agtgaatgag gctgtgcttc ggg                                            23

<210> SEQ ID NO 242
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 242
tgtgagtgtg tgtgtgcatg tgg                                            23

<210> SEQ ID NO 243
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 243
ggtgagagag tgtgtgcacg ggg                                            23

<210> SEQ ID NO 244
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 244
tgtgagtgtg tgtgtgcatg cag                                            23

<210> SEQ ID NO 245
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 245
gtgatgtgag cgtgtgtgtg tgg                                            23

<210> SEQ ID NO 246
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 246
agagagtgag tgagtgagtg tgg                                            23

<210> SEQ ID NO 247
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 247
agtgagtgaa tgagtgcata gtg                                          23

<210> SEQ ID NO 248
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 248
ggtgtgtgtg tgtgtgtgtg tgg                                          23

<210> SEQ ID NO 249
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 249
ggtgagtgag tgcgtgcggg tgg                                          23

<210> SEQ ID NO 250
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 250
ggggaatgag tgtgtgcatg gag                                          23

<210> SEQ ID NO 251
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 251
tcagaatgag tgtgtgcctg ggg                                          23

<210> SEQ ID NO 252
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 252
gggaggtgag tgcatgcgtg tgg                                          23

<210> SEQ ID NO 253
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 253
ggggtgtgag catgtgcgtg tgg                                          23

<210> SEQ ID NO 254
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 254
cgtgagtgag tgtgtggttg ggg                                              23

<210> SEQ ID NO 255
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 255
tgtgagtgaa tgtgtgtgtg tgg                                              23

<210> SEQ ID NO 256
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 256
ggtgagtgag tgtgtgtgtg agg                                              23

<210> SEQ ID NO 257
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 257
gatgagtgtg tctgtgcatg agg                                              23

<210> SEQ ID NO 258
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 258
actgagtggg tgtgtgcctg agg                                              23

<210> SEQ ID NO 259
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 259
tgtgagtaag tgtgtgtgtg tgg                                              23

<210> SEQ ID NO 260
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 260
```
agtgtgtgag agtgtgcatg tgg                                              23

<210> SEQ ID NO 261
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 261
actgtgtgag tgtgtgcgtg agg                                              23

<210> SEQ ID NO 262
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 262
tgtatgtgag tgtgtgcgtg tgg                                              23

<210> SEQ ID NO 263
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 263
aggtagtgag tgtgtgcatg ggt                                              23

<210> SEQ ID NO 264
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 264
tgtgagtgcg tgtctgtgtg tgg                                              23

<210> SEQ ID NO 265
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 265
tatgagtgtg tgtgtgagtg tgg                                              23

<210> SEQ ID NO 266
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 266
tgtgagtgag tgagtgaatg tgg                                              23

<210> SEQ ID NO 267
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 267
agtgtgtgtg tgtgtgtgtg ggg                                              23

<210> SEQ ID NO 268
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 268
tgtgagagag tgtgtgagtg tgg                                              23

<210> SEQ ID NO 269
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 269
agtgatggag tgtgtgcctg tgg                                              23

<210> SEQ ID NO 270
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 270
tgcatgtgag tgtgtgtgcg tgg                                              23

<210> SEQ ID NO 271
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 271
agagagtgtg tgtgtgcttg ggg                                              23

<210> SEQ ID NO 272
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 272
catgagtggg tgtgtgcgtg gag                                              23

<210> SEQ ID NO 273
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 273
tatgagtgtg tgtgtgaatg tgg                                              23
```

-continued

<210> SEQ ID NO 274
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 274
agagagtgtg tgtgtgtgtg tgg                                          23

<210> SEQ ID NO 275
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 275
tgtgagtgag tgtgttggtg agg                                          23

<210> SEQ ID NO 276
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 276
tatgagtgta tgtgtgcata ggg                                          23

<210> SEQ ID NO 277
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 277
ggtgtgtgtg tgtgtgtgtg tgg                                          23

<210> SEQ ID NO 278
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 278
ggtgtgtgtg tgtgtgtgtg tgg                                          23

<210> SEQ ID NO 279
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 279
agtgagtatg tgtgtgtgtg ggg                                          23

<210> SEQ ID NO 280
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 280
agggagtgag tgtgtaagtg tgg                                            23

<210> SEQ ID NO 281
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 281
tgtgagtgta tgtgtgtgtg tgg                                            23

<210> SEQ ID NO 282
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 282
tgtgagtgtg tgtgtgcatg tga                                            23

<210> SEQ ID NO 283
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 283
agagagtgag tgtgtgagtg tga                                            23

<210> SEQ ID NO 284
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 284
gatgagtgtg tgtgtgtgtg agg                                            23

<210> SEQ ID NO 285
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 285
gggtgaggaa ggtgtgcgtg gtg                                            23

<210> SEQ ID NO 286
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 286
gataagtgag tatgtgtgtg tgg                                            23

```
<210> SEQ ID NO 287
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 287
agtgagtgag tgagtgaatg agg                                              23

<210> SEQ ID NO 288
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 288
agagagagag tgtgtgcgtg tga                                              23

<210> SEQ ID NO 289
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 289
agcgagtggg tgtgtgcgtg ggg                                              23

<210> SEQ ID NO 290
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 290
agagagagag tgtgtgcacg tgg                                              23

<210> SEQ ID NO 291
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 291
tgtgagtgaa tgtgtgccag ggg                                              23

<210> SEQ ID NO 292
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 292
ggtgtgtgtg tgtgtacgtg ggg                                              23

<210> SEQ ID NO 293
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 293
tgtgtgagtg tgtgtgtggg ggg                                      23

<210> SEQ ID NO 294
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 294
tgtgcgtgag tgtgtgtatg tgg                                      23

<210> SEQ ID NO 295
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 295
cttgagtgag agtgagcgtg agg                                      23

<210> SEQ ID NO 296
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 296
ggtgtgtgtg tgtgtgtgtg tgg                                      23

<210> SEQ ID NO 297
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 297
agagagtgag tgtgtgtgtt ggg                                      23

<210> SEQ ID NO 298
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 298
agtgtgtgag tgtgtgtatg agg                                      23

<210> SEQ ID NO 299
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 299
tgagtgtgag tgtgtgcgtg ggg                                      23

<210> SEQ ID NO 300
<211> LENGTH: 23
```

<212> TYPE: DNA
<213> ORGANISM: Artificial Sequence
<220> FEATURE:
<223> OTHER INFORMATION: Synthesized Sequence

<400> SEQUENCE: 300
tgtgtgtgag tgtgtgtgtg tgg                                          23

<210> SEQ ID NO 301
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 301
tgtgggtgag tgtgtgcgtg aga                                          23

<210> SEQ ID NO 302
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 302
tgtgggtgag tgtgtgtgtg tgg                                          23

<210> SEQ ID NO 303
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 303
agcgagagag tgtgtgagtg tgg                                          23

<210> SEQ ID NO 304
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 304
ggtgtgtgtg tgtgtgcgtg cgg                                          23

<210> SEQ ID NO 305
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 305
ggtgtgtgtg tgtgtgtgtg tgg                                          23

<210> SEQ ID NO 306
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 306

```
acagagtgag tgtatgtgtg ggg                                             23
```

<210> SEQ ID NO 307
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 307

```
tggtgatgag tgtgtgtgtg tgg                                             23
```

<210> SEQ ID NO 308
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 308

```
tatgaatgtg tgtgtgcatg tgg                                             23
```

<210> SEQ ID NO 309
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 309

```
ggtgtgtgag tgagtgagtg cgg                                             23
```

<210> SEQ ID NO 310
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 310

```
ggtgtgtgtg tgtgtgtgtg tgg                                             23
```

<210> SEQ ID NO 311
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 311

```
tgtgtgtgag tgtgtgtgtg tgg                                             23
```

<210> SEQ ID NO 312
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 312

```
tgtgtgagtg agtgtgtgtg tgg                                             23
```

<210> SEQ ID NO 313
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 313
agtgagagtg tgtgtgtggg ggg                                              23

<210> SEQ ID NO 314
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 314
tgagagtgag tgtgagagtg ggg                                              23

<210> SEQ ID NO 315
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 315
tgtgagtgtg tatgtgtgtg ggg                                              23

<210> SEQ ID NO 316
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 316
ggtgtagtgg tgtgtgcctg tgg                                              23

<210> SEQ ID NO 317
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 317
tgtgtgtgtg agtgtgtgta tgg                                              23

<210> SEQ ID NO 318
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 318
tgtgtgtgag tgtgtgcatg tga                                              23

<210> SEQ ID NO 319
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 319
cgtgagtgtg tgtatgcgtg tgg                                              23
```

```
<210> SEQ ID NO 320
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 320
catgcgtgag tgtgtgcatg ggg                                              23

<210> SEQ ID NO 321
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 321
tgtgagtgag tgtgtgcatg tga                                              23

<210> SEQ ID NO 322
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 322
agtgtgtgag tgtgtgtgtg agg                                              23

<210> SEQ ID NO 323
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 323
actgagtgag tgtgagtgtg agg                                              23

<210> SEQ ID NO 324
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 324
gggtgagatg tgtgtgcatg tgg                                              23

<210> SEQ ID NO 325
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 325
ggtgtagtgg tgtgtgcctg tgg                                              23

<210> SEQ ID NO 326
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 326
tgtgtgtgag tgtgtgcatg tgg                                              23

<210> SEQ ID NO 327
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 327
agagagagag agtgtgtgtg tgg                                              23

<210> SEQ ID NO 328
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 328
gaagagtaag tgtgtgtgtg ggg                                              23

<210> SEQ ID NO 329
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 329
agtggatgag tgagtgcatg cgg                                              23

<210> SEQ ID NO 330
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 330
gtagagtgag tgtgagagtg tgg                                              23

<210> SEQ ID NO 331
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 331
agtgagtgag tgtgagcgtg aag                                              23

<210> SEQ ID NO 332
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 332
agagtgtgag tgtgtgtgtg ggg                                              23

<210> SEQ ID NO 333
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 333 gggtgtgag tgtggtgcgt gtg                                              23

<210> SEQ ID NO 334
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 334
ggtgagtgag tgtgtgcgtg tgg                                             23

<210> SEQ ID NO 335
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 335
ggtgtgtgtg tgtgtgcgtg tgg                                             23

<210> SEQ ID NO 336
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 336
tgtgagtgag tgtgtgtgtg tga                                             23

<210> SEQ ID NO 337
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 337
agtgtgtaag tgtgtgagtg ggg                                             23

<210> SEQ ID NO 338
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 338
agtgagtgtg tgtgtgtgtt ggg                                             23

<210> SEQ ID NO 339
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 339
```
agtgaatgtg tgtgtgcatg tgg    23

<210> SEQ ID NO 340
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 340
tgtgagtgcg tgtgtgtgtg tgg    23

<210> SEQ ID NO 341
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 341
tgtgagtgcg tgtgtgagtg tgg    23

<210> SEQ ID NO 342
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 342
tgtgagagag tgtgtgcatg tga    23

<210> SEQ ID NO 343
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 343
tgtgtgtgag tgtgtgtatg tgg    23

<210> SEQ ID NO 344
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 344
ggtgagtttg tgtgtgggtg tgg    23

<210> SEQ ID NO 345
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 345
ggtaaatgag tgtgaggcat ggg    23

<210> SEQ ID NO 346
<211> LENGTH: 23
<212> TYPE: DNA

<213> ORGANISM: Artificial Sequence
<220> FEATURE:
<223> OTHER INFORMATION: Synthesized Sequence

<400> SEQUENCE: 346
ggagtgtgag tgtgtgagtg cgg                                              23

<210> SEQ ID NO 347
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 347
tgtgagtgag tgcatgtgtg tgg                                              23

<210> SEQ ID NO 348
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 348
tgtgtgtgag tgtgtgtgtg tgg                                              23

<210> SEQ ID NO 349
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 349
gaagagtgag tgtgtggtgt ggg                                              23

<210> SEQ ID NO 350
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 350
gcagagtgag tgtgtgtgtt ggg                                              23

<210> SEQ ID NO 351
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 351
catgagtgtg tgtgtgagtg tgg                                              23

<210> SEQ ID NO 352
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 352
tgtgaatgag tgcgtgaatg ggg                                              23

<210> SEQ ID NO 353
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 353
agtgtgtgag tgtgtgagtg agg                                          23

<210> SEQ ID NO 354
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 354
ggtgagtcag tgtgtgagtg agg                                          23

<210> SEQ ID NO 355
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 355
ggtggatgag tgtgtgtgtg ggg                                          23

<210> SEQ ID NO 356
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 356
tgagagtgag tgtatgagtg tgg                                          23

<210> SEQ ID NO 357
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 357
tgtgtgtgag tgtgtacatg agg                                          23

<210> SEQ ID NO 358
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 358
ggtatttgag tgtgtacatg tgg                                          23

<210> SEQ ID NO 359
<211> LENGTH: 23
<212> TYPE: DNA
<213> ORGANISM: Artificial Sequence
<220> FEATURE:

```
<223> OTHER INFORMATION: Synthesized Sequence

<400> SEQUENCE: 359
actgactgag tgtgagcatg tgg                                              23

<210> SEQ ID NO 360
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 360
aatgagtgtg tgtgtgtatg ggg                                              23

<210> SEQ ID NO 361
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 361
ggtgtgtgtg tgtgtgcgtg tgg                                              23

<210> SEQ ID NO 362
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 362
gtagagtgtg tgagtgtgtg gcg                                              23

<210> SEQ ID NO 363
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 363
gatgagtgtg cgtgtgcatg agg                                              23

<210> SEQ ID NO 364
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 364
accaggtgag tgtgtgcgtg ggc                                              23

<210> SEQ ID NO 365
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 365
tgtgagtatg tgtgtgtgtg tgg                                              23
```

```
<210> SEQ ID NO 366
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 366
cctgagcgag tatgtgcatg tgg                                              23

<210> SEQ ID NO 367
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 367
ggagagtgag tgtgtgcatg tgc                                              23

<210> SEQ ID NO 368
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 368
ggtgtgtgaa tgtgtgtgtg tgg                                              23

<210> SEQ ID NO 369
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 369
agaaagtgag tgtgtgtata agg                                              23

<210> SEQ ID NO 370
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 370
agtgcatgag tgtgtatgtg agg                                              23

<210> SEQ ID NO 371
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 371
gctgagtgtg tgtgtgcgtg tag                                              23

<210> SEQ ID NO 372
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 372
ggtgagtgag cgaaggagta ggg                                        23

<210> SEQ ID NO 373
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 373
tgtgagtgtg tgtgtgagtg tgg                                        23

<210> SEQ ID NO 374
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 374
tgtgagtgta tgtgtgtgtg tgg                                        23

<210> SEQ ID NO 375
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 375
tatgagtgtg tgtgtgcacg tgg                                        23

<210> SEQ ID NO 376
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 376
tgggtgtgag tgtgtgcgtg tgg                                        23

<210> SEQ ID NO 377
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 377
tgtgagtgtg tgtgtgcgtg cgc                                        23

<210> SEQ ID NO 378
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 378
agagagagag tgtgtgtgtg tgg                                        23

<210> SEQ ID NO 379
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 379
catgagtgac tgtgtgtgtg tgg                                              23

<210> SEQ ID NO 380
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 380
ggtgtgtgtg tgtgtgtgtg ggg                                              23

<210> SEQ ID NO 381
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 381
tgtgagtgtg agtgtgtgtt ggg                                              23

<210> SEQ ID NO 382
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 382
tgtgtgtggg ggtgggggtg ggg                                              23

<210> SEQ ID NO 383
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 383
agtgagtgtg tatgtgtgtg tgg                                              23

<210> SEQ ID NO 384
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 384
aatgagtgtg tatgtgtgtg tgg                                              23

<210> SEQ ID NO 385
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 385
```
tttgagtgtg tgtgtgcatg agg         23

<210> SEQ ID NO 386
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 386
tgcgtgtgag tgtgtgcgta ggt         23

<210> SEQ ID NO 387
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 387
agagagagag tgtgtgtgtg agg         23

<210> SEQ ID NO 388
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 388
ggggtaaggg tgtgtgtgtg tgg         23

<210> SEQ ID NO 389
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 389
tgtgtgtgag cgtgtgtgtg tgg         23

<210> SEQ ID NO 390
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 390
gatgagtgag tgtgtgagtg aga         23

<210> SEQ ID NO 391
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 391
ggtgtgagag tgtgtgcgga ggc         23

<210> SEQ ID NO 392
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 392
tgtgtgtgag tgtgtgtgtg tgg                                              23

<210> SEQ ID NO 393
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 393
gatgagtttg tgtgtgtgtg ggg                                              23

<210> SEQ ID NO 394
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 394
tgtgagagaa tgtgtgcgtg tga                                              23

<210> SEQ ID NO 395
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 395
tgagagtgag agtgtgtgtg ggg                                              23

<210> SEQ ID NO 396
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 396
ggactgtgag tgtgtgcgtg agg                                              23

<210> SEQ ID NO 397
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 397
tgtgagtggg tgtgtgtgtg tgg                                              23

<210> SEQ ID NO 398
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 398
tgtgagtgtg tgtgtgggtg ggg                                              23
```

```
<210> SEQ ID NO 399
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 399
ggtgagtgag tgagtgagtg agg                                              23

<210> SEQ ID NO 400
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 400
ggtgtagtgg tgtgtgcctg tgg                                              23

<210> SEQ ID NO 401
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 401
agtgaatgag tgtgtgcatg tga                                              23

<210> SEQ ID NO 402
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 402
tgtgtatgag tgtgtgtatg cgg                                              23

<210> SEQ ID NO 403
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 403
tgtgagtggg tgtgtgggtg tgg                                              23

<210> SEQ ID NO 404
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 404
tgagtgtgag tgtgagcgtg cgg                                              23

<210> SEQ ID NO 405
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 405
tgtgaaggag tgtgtgtgtg tgg                                           23

<210> SEQ ID NO 406
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 406
attgtgtgag tgtgtgcatg tgg                                           23

<210> SEQ ID NO 407
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 407
tgtgggtgtg gatgtgtgtg tgg                                           23

<210> SEQ ID NO 408
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 408
tatgtgtgag tgtgtgcata tgg                                           23

<210> SEQ ID NO 409
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 409
tgtgggtggg tgtgtgcgtg tgg                                           23

<210> SEQ ID NO 410
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 410
gttgagtgaa tgtgtgcgtg agg                                           23

<210> SEQ ID NO 411
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 411
gggaagggag tgtgtgcatg ggg                                           23

<210> SEQ ID NO 412
```

<211> LENGTH: 23
<212> TYPE: DNA
<213> ORGANISM: Artificial Sequence
<220> FEATURE:
<223> OTHER INFORMATION: Synthesized Sequence

<400> SEQUENCE: 412
ggggaatgag tgtgtatgtg agg                                      23

<210> SEQ ID NO 413
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 413
agtgagtgtg tgtgttgcgg ggg                                      23

<210> SEQ ID NO 414
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 414
ggtgtgtgtg tgtgtgtgtg tgg                                      23

<210> SEQ ID NO 415
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 415
agagagtgtg tgtgtgtgtg tgg                                      23

<210> SEQ ID NO 416
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 416
tgagtgtgtg tgtgtgcgtg tgg                                      23

<210> SEQ ID NO 417
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 417
catgagtgtg tgtgtgcttg tgg                                      23

<210> SEQ ID NO 418
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 418
gtgagtgatg tgtgtgtgtg tgg 23

<210> SEQ ID NO 419
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 419
tgtgtgtgag tgtgtgcatg agg 23

<210> SEQ ID NO 420
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 420
tgtgtgtgag tgtgtgcccg tgg 23

<210> SEQ ID NO 421
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 421
tgtgtgtgag tgtgagtgtg tgg 23

<210> SEQ ID NO 422
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 422
agagagagag tgtgtgtgtg tgg 23

<210> SEQ ID NO 423
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 423
tgtgagtgtg tgtgtacctg ggg 23

<210> SEQ ID NO 424
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 424
ggtgtaggag tgtgtgtgtg ggg 23

<210> SEQ ID NO 425
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 425
ggtgaggtgg tgtgtgcctg tgg                                          23

<210> SEQ ID NO 426
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 426
aatgagtgag tgtgtgtgtg tga                                          23

<210> SEQ ID NO 427
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 427
ggggtgtgag tgggtgtgtg cgg                                          23

<210> SEQ ID NO 428
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 428
ggtgggtgag tgagtgagtg agg                                          23

<210> SEQ ID NO 429
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 429
agtgtatgag tgtttgcatg ggg                                          23

<210> SEQ ID NO 430
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 430
agtgagtgag tgagtgaatg tgg                                          23

<210> SEQ ID NO 431
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 431
tgtgagtgtg tgtgtgtatg tgg                                          23
```

<210> SEQ ID NO 432
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 432
ggtgtgtgag agtgtgtatg tgg                                         23

<210> SEQ ID NO 433
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 433
ggtgtgtggg tgtgtgtgtg ggg                                         23

<210> SEQ ID NO 434
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 434
gatgagtgtg tgtgtgtgtg cgg                                         23

<210> SEQ ID NO 435
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 435
tgtgagtgtg tatgtgtgtg tgg                                         23

<210> SEQ ID NO 436
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 436
tgtgtgtgtg tgtgtgtgtg tgg                                         23

<210> SEQ ID NO 437
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 437
ggtgtgtgtg tgtgtgtgtg tgg                                         23

<210> SEQ ID NO 438
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 438
tgtgtgtgag tgtgtgtgtg ggg                                              23

<210> SEQ ID NO 439
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 439
aggatgtgag tgtgtgcatg tgg                                              23

<210> SEQ ID NO 440
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 440
ggagaatagg tgtgtgcgtg ggg                                              23

<210> SEQ ID NO 441
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 441
agtgagtgtg tgtgtgaagg agg                                              23

<210> SEQ ID NO 442
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 442
gatgagtaag tgtctgagtg ggg                                              23

<210> SEQ ID NO 443
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 443
tgtgagtgtg tgtatgcgtg tga                                              23

<210> SEQ ID NO 444
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 444
tgtgtgtgag tgtgtgtgtg tgg                                              23

```
<210> SEQ ID NO 445
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 445
ggggtgtgtg tgtgtgtgtg tgg                                              23

<210> SEQ ID NO 446
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 446
agagagagag tgtgtgcaag ggg                                              23

<210> SEQ ID NO 447
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 447
gtagggtggg agtgtgtgtg tgg                                              23

<210> SEQ ID NO 448
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 448
tgtgagtggg tgtgtatgtg agg                                              23

<210> SEQ ID NO 449
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 449
ggcgagtgtg tgtgtgagtg tgg                                              23

<210> SEQ ID NO 450
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 450
gatgtgtgtg tgtgtgcgtg tgg                                              23

<210> SEQ ID NO 451
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 451
tgttagtgag tgtgtgcagg tgg                                           23

<210> SEQ ID NO 452
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 452
gatgagcgag tgtgtgtgta tgg                                           23

<210> SEQ ID NO 453
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 453
ggtgaaagag tatgtgtgtg tgg                                           23

<210> SEQ ID NO 454
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 454
ggtgtgtatg tgtggggtg tgg                                            23

<210> SEQ ID NO 455
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 455
ggtgtgagag tgtgtgagtg ggg                                           23

<210> SEQ ID NO 456
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 456
ggggtgtgtg tgtgtgtgtg tgg                                           23

<210> SEQ ID NO 457
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 457
ggtgtagtgg tgtgtgcctg tgg                                           23

<210> SEQ ID NO 458
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 458
tgtgagtgtg tgtgtgtgtg tgg                                              23

<210> SEQ ID NO 459
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 459
ggtgtgtgtg tgtgtgtgtg tgg                                              23

<210> SEQ ID NO 460
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 460
ggtgtgtgag tgtgtgtgtg tga                                              23

<210> SEQ ID NO 461
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 461
ggtatgtgag tgtgagtgtg ggg                                              23

<210> SEQ ID NO 462
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 462
ggtgtggtgg tgtgtgcgtg tgg                                              23

<210> SEQ ID NO 463
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 463
ccagaatgag tgtgtgtgtg tgg                                              23

<210> SEQ ID NO 464
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 464
```
tgtgtgtgag tatgtgtgtg tgg    23

<210> SEQ ID NO 465
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 465
tgtgagtgaa tatgtgtatg tgg    23

<210> SEQ ID NO 466
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 466
ggtatgtgag tgtgtgtata tgg    23

<210> SEQ ID NO 467
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 467
ggtgagctcg tgagtgcgtg agg    23

<210> SEQ ID NO 468
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 468
aagtgaggag tgtgtgcctg tgg    23

<210> SEQ ID NO 469
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 469
ggtgagtaag tgtgagcgta agg    23

<210> SEQ ID NO 470
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 470
gaatccaagc agaagaagag aag    23

<210> SEQ ID NO 471
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 471
gaagtagagc agaagaagaa gcg                                          23

<210> SEQ ID NO 472
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 472
gagtccgagc agaagaagaa ggg                                          23

<210> SEQ ID NO 473
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 473
gaagtagagc agaagaagaa gcg                                          23

<210> SEQ ID NO 474
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 474
gaagtagagc agaagaagaa gcg                                          23

<210> SEQ ID NO 475
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 475
gaggccgagc agaagaaaga cgg                                          23

<210> SEQ ID NO 476
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 476
aagtccgagg agaggaagaa agg                                          23

<210> SEQ ID NO 477
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 477
aagtccatgc agaagaggaa ggg                                          23

<210> SEQ ID NO 478
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 478
gagtctaagc agaagaagaa gag        23

<210> SEQ ID NO 479
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 479
gagtcctagc aggagaagaa gag        23

<210> SEQ ID NO 480
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 480
ggagtagagc agaggaagaa ggg        23

<210> SEQ ID NO 481
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 481
aagcccaagc aaatgaagaa tgg        23

<210> SEQ ID NO 482
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 482
aagcccgagc aaaggaagaa agg        23

<210> SEQ ID NO 483
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 483
aagtctgagc acaagaagaa tgg        23

<210> SEQ ID NO 484
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 484
gagtacaagc agatgaaaaa cgg                                         23

<210> SEQ ID NO 485
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 485
gagcctgagc agaaggagaa ggg                                         23

<210> SEQ ID NO 486
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 486
gagttcaagc agagaagaaa ggg                                         23

<210> SEQ ID NO 487
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 487
ccctccaagc agaagaagat gag                                         23

<210> SEQ ID NO 488
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 488
aagtctgaga agaagaagac atg                                         23

<210> SEQ ID NO 489
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 489
gagttagagc agaagaagaa agg                                         23

<210> SEQ ID NO 490
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 490
agagtagaac agaagaagga aag                                         23

<210> SEQ ID NO 491
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 491
gagtaagaga agaagaagaa ggg                                           23

<210> SEQ ID NO 492
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 492
gagcacgagc aagagaagaa ggg                                           23

<210> SEQ ID NO 493
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 493
aagtccaaaa agaagaaaaa agg                                           23

<210> SEQ ID NO 494
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 494
gagtccaagc agtagaggaa ggg                                           23

<210> SEQ ID NO 495
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 495
gagcccaaga agaagaagaa gga                                           23

<210> SEQ ID NO 496
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 496
gaggccaagc agaaaaaaaa tgg                                           23

<210> SEQ ID NO 497
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 497
```

```
cagtctgagt agaagaaaaa ggg                                              23
```

<210> SEQ ID NO 498
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 498

```
aagtcccaga agaagaaata tgg                                              23
```

<210> SEQ ID NO 499
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 499

```
gagagggagc agggagaaga agg                                              23
```

<210> SEQ ID NO 500
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 500

```
ggagtcaagg agaagaagaa gag                                              23
```

<210> SEQ ID NO 501
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 501

```
gagcccaagc acaaaagaa tgg                                               23
```

<210> SEQ ID NO 502
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 502

```
gagtcccagc aaaagaagaa aag                                              23
```

<210> SEQ ID NO 503
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 503

```
atgtccaagc agaagaagtc tgg                                              23
```

<210> SEQ ID NO 504
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 504
tagtcagagc agatgaagga aag                                      23

<210> SEQ ID NO 505
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 505
tcatccaagc agaagaagaa gag                                      23

<210> SEQ ID NO 506
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 506
gaggcagaga gaaagaagaa agg                                      23

<210> SEQ ID NO 507
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 507
gagttagagc agaaaaaaaa tgg                                      23

<210> SEQ ID NO 508
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 508
acgtctgagc agaagaagaa tgg                                      23

<210> SEQ ID NO 509
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 509
aagtcacagg agcagaaaga aga                                      23

<210> SEQ ID NO 510
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 510
gaggccaagc agaaagaaaa agg                                      23
```

<210> SEQ ID NO 511
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 511
ttatccgaga agaagaagta agg                                           23

<210> SEQ ID NO 512
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 512
gagccggagc agggagaaga agg                                           23

<210> SEQ ID NO 513
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 513
gagcctgagc aggaagaaga aga                                           23

<210> SEQ ID NO 514
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 514
tgtccaaggc aggagaagaa ggg                                           23

<210> SEQ ID NO 515
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 515
cagagagagg agcagaaaaa aga                                           23

<210> SEQ ID NO 516
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 516
caggctgagc agaaagaaga aag                                           23

<210> SEQ ID NO 517
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 517
gagtcagagc agaactagaa ggg                                          23

<210> SEQ ID NO 518
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 518
aagtccagac agaagaagaa gga                                          23

<210> SEQ ID NO 519
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 519
cagtccagca ggaagaagag agg                                          23

<210> SEQ ID NO 520
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 520
gcctccaagc agaaggagaa atg                                          23

<210> SEQ ID NO 521
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 521
gagagagagc aaaaggaaga atg                                          23

<210> SEQ ID NO 522
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 522
gaggagagca gaaagaagaa ggg                                          23

<210> SEQ ID NO 523
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 523
aagtcagaga aggaagaaga aag                                          23

<210> SEQ ID NO 524
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 524
gagccggagc agaagaagga ggg                                            23

<210> SEQ ID NO 525
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 525
atgtccaagc acaagaggaa tgg                                            23

<210> SEQ ID NO 526
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 526
gaggtagagc agaagaagaa gcg                                            23

<210> SEQ ID NO 527
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 527
gagtcccaga agaagaaaga aag                                            23

<210> SEQ ID NO 528
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 528
cctctcgagc aaaaggaaga agg                                            23

<210> SEQ ID NO 529
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 529
agttccaagc agaggaagaa ggg                                            23

<210> SEQ ID NO 530
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 530
tgctttgagc agaaagaaga aag                                         23

<210> SEQ ID NO 531
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 531
aagtaagaag agcaggaaga aga                                         23

<210> SEQ ID NO 532
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 532
tagtcctagc aagaataaga atg                                         23

<210> SEQ ID NO 533
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 533
gaatccaagc aggagaagaa gga                                         23

<210> SEQ ID NO 534
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 534
taatgagagc agaaagaaga atg                                         23

<210> SEQ ID NO 535
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 535
gacagagaag agaagaagga aga                                         23

<210> SEQ ID NO 536
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 536
aggtcagagc agaagaaaag agg                                         23

<210> SEQ ID NO 537
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 537
gcaaagagca ggaagaagaa ggg                                            23

<210> SEQ ID NO 538
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 538
gagcctgagc ggaagaggaa agg                                            23

<210> SEQ ID NO 539
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 539
taatcccaga gcaggaagaa gaa                                            23

<210> SEQ ID NO 540
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 540
agtccagagc aaaataagaa ggg                                            23

<210> SEQ ID NO 541
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 541
aagtctgaga agaagaagaa aga                                            23

<210> SEQ ID NO 542
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 542
gctaaagagc agaaggaaga agg                                            23

<210> SEQ ID NO 543
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 543
```
cagtacgagc agaggaagga aga                                              23

<210> SEQ ID NO 544
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 544
agttccaagc agaagaagca tgg                                              23

<210> SEQ ID NO 545
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 545
atggcagagc agaaagaaga aag                                              23

<210> SEQ ID NO 546
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 546
cagtccatgc agagggaaga agg                                              23

<210> SEQ ID NO 547
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 547
gcattagagc agaaggaaga agg                                              23

<210> SEQ ID NO 548
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 548
gagtcagagc aaaagaagta gtg                                              23

<210> SEQ ID NO 549
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 549
ggcagagagc agaaggaaga aag                                              23

<210> SEQ ID NO 550
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 550
aagtcagagg agaagaagaa ggg							23

<210> SEQ ID NO 551
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 551
aagtccgggc aaaagaggaa agg							23

<210> SEQ ID NO 552
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 552
gagagggagc aaaagaagga agg							23

<210> SEQ ID NO 553
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 553
cagaatgagc aggaagaaga aca							23

<210> SEQ ID NO 554
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 554
gagactgaga agaagaagaa agg							23

<210> SEQ ID NO 555
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 555
gagtcagctg agcagaagga aga							23

<210> SEQ ID NO 556
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 556
gaaggagagc agaaagaaga aag							23

<210> SEQ ID NO 557
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 557
gtttgagagc agaaggaaga aga                                               23

<210> SEQ ID NO 558
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 558
atttccaagc agagagaaga atg                                               23

<210> SEQ ID NO 559
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 559
gagtccgaga agaagaaaga aaa                                               23

<210> SEQ ID NO 560
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 560
gagtttgagt agaagaagaa gag                                               23

<210> SEQ ID NO 561
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 561
tggccagagc agaaggaaga agg                                               23

<210> SEQ ID NO 562
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 562
tgtccgaggc agtagaaaga acg                                               23

<210> SEQ ID NO 563
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 563
aagcccgagc tagaagaaat agg                                              23

<210> SEQ ID NO 564
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 564 aagggagca ggaagaagaa agg                                               23

<210> SEQ ID NO 565
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 565
aagaaggagc aggaagaaga aag                                              23

<210> SEQ ID NO 566
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 566
cactccaagt agaagaagaa aag                                              23

<210> SEQ ID NO 567
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 567
gaggcagaga gaagaaagaa ggg                                              23

<210> SEQ ID NO 568
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 568
agatccaaac agaaggaaga atg                                              23

<210> SEQ ID NO 569
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 569
cgctccgagc agaagaaaag tgg                                              23

<210> SEQ ID NO 570
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 570
agtcctgagc agaggaagga atg                                               23

<210> SEQ ID NO 571
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 571
gagtccaaga agaagaagcc agg                                               23

<210> SEQ ID NO 572
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 572
gagtcccagg agaagaagag agg                                               23

<210> SEQ ID NO 573
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 573
tgttgagagc agaaagaaga aag                                               23

<210> SEQ ID NO 574
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 574
gtccaaaggc aggagaagaa ggg                                               23

<210> SEQ ID NO 575
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 575
gagggagaga gcaggaagaa gaa                                               23

<210> SEQ ID NO 576
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 576
```
ttgttgagca ggaagaagaa tgg                                        23

<210> SEQ ID NO 577
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 577
tgtccagagc agatgaagaa tgg                                        23

<210> SEQ ID NO 578
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 578
gaatccaagc agaagaaaat gga                                        23

<210> SEQ ID NO 579
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 579
gagtcctaga aaagaagag agg                                         23

<210> SEQ ID NO 580
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 580
gagagagagc agaagaagta gag                                        23

<210> SEQ ID NO 581
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 581
aggcctgagc agaaggaaga agg                                        23

<210> SEQ ID NO 582
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 582
aagtcccggc agaggaagaa ggg                                        23

<210> SEQ ID NO 583
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 583
gagggagagc aaaagaagga aag                                             23

<210> SEQ ID NO 584
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 584
gtccatagca agaaaaagaa ggg                                             23

<210> SEQ ID NO 585
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 585
agtgcagagc agaagaagga aag                                             23

<210> SEQ ID NO 586
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 586
gaatcagagc aaaaggagaa agg                                             23

<210> SEQ ID NO 587
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 587
aagtcagagc agaaaaagag agg                                             23

<210> SEQ ID NO 588
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 588
ttctccaagc agaagaagaa gag                                             23

<210> SEQ ID NO 589
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 589
cagtccaaac agaagaggaa tgg                                             23
```

<210> SEQ ID NO 590
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 590
tggccagagc agaaggaaga aag                                              23

<210> SEQ ID NO 591
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 591
gagtcaaagc agaagaaaga acg                                              23

<210> SEQ ID NO 592
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 592
tatccaagca ggaagaagca agg                                              23

<210> SEQ ID NO 593
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 593
tgcacgagca gggagaagaa agg                                              23

<210> SEQ ID NO 594
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 594
tatttacaga gcaggaagaa gag                                              23

<210> SEQ ID NO 595
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 595
cattccaagc agaaggaaga gag                                              23

<210> SEQ ID NO 596
<211> LENGTH: 23
<212> TYPE: DNA
<213> ORGANISM: Artificial Sequence
<220> FEATURE:

```
<223> OTHER INFORMATION: Synthesized Sequence

<400> SEQUENCE: 596
taccaggagc aggaaaaaga agg                                           23

<210> SEQ ID NO 597
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 597
gagcgggagc aaaaggaaga atg                                           23

<210> SEQ ID NO 598
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 598
gtacccaagc agaaggaaga agg                                           23

<210> SEQ ID NO 599
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 599
cctgaagagc agaaggagga agg                                           23

<210> SEQ ID NO 600
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 600
gtctgagcag aaaggaagaa ggg                                           23

<210> SEQ ID NO 601
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 601
gaagtcagac agaagaagaa gag                                           23

<210> SEQ ID NO 602
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 602
gagaaagagc agaaggaaga agt                                           23
```

```
<210> SEQ ID NO 603
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 603
gagtctaagc aggagaataa agg                                              23

<210> SEQ ID NO 604
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 604
ggtccagaga gaaagaagaa agg                                              23

<210> SEQ ID NO 605
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 605
aaatccaacc agaagaagaa agg                                              23

<210> SEQ ID NO 606
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 606
taatccaatc agaagaagaa ggg                                              23

<210> SEQ ID NO 607
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 607
gagagaagca gaaagaagaa agg                                              23

<210> SEQ ID NO 608
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 608
gaatcccagc agaaaggaag aaa                                              23

<210> SEQ ID NO 609
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 609
atgaatgagc agaaggagga aag                                          23

<210> SEQ ID NO 610
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 610
gataccgagc taaagaagga agg                                          23

<210> SEQ ID NO 611
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 611
gaagaggagc agaaggagga agg                                          23

<210> SEQ ID NO 612
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 612
acctgggagc aggaaaaaga agg                                          23

<210> SEQ ID NO 613
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 613
gtctcccctt ctgcagcacc agg                                          23

<210> SEQ ID NO 614
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 614 ggaatcccctt ctgcagcacc tgg                                         23

<210> SEQ ID NO 615
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 615
tgaatcccat ctccagcacc agg                                          23

<210> SEQ ID NO 616
<211> LENGTH: 23
```

<212> TYPE: DNA
<213> ORGANISM: Artificial Sequence
<220> FEATURE:
<223> OTHER INFORMATION: Synthesized Sequence

<400> SEQUENCE: 616
ggagtccctc ctacagcacc agg        23

<210> SEQ ID NO 617
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 617
ggagtccctc ctacagcacc agg        23

<210> SEQ ID NO 618
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 618
gtctcccctt ctgcagcacc agg        23

<210> SEQ ID NO 619
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 619
ggaaccccgt ctgcagcacc agg        23

<210> SEQ ID NO 620
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 620
ggagtccctc ctgcagcacc tga        23

<210> SEQ ID NO 621
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 621
tgaatcctaa ctgcagcacc agg        23

<210> SEQ ID NO 622
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 622

```
gtctcccctt ctgcagcacc agg                                              23
```

<210> SEQ ID NO 623
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 623

```
tccatcccta ctgccagcac cag                                              23
```

<210> SEQ ID NO 624
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 624

```
ggaacaccTT ctgcagctcc agg                                              23
```

<210> SEQ ID NO 625
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 625

```
accctccctt ctgcaggcac cgg                                              23
```

<210> SEQ ID NO 626
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 626

```
ctctgtcctt ctgcagcacc tgg                                              23
```

<210> SEQ ID NO 627
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 627

```
gggagtccat ctgcagcacc agg                                              23
```

<210> SEQ ID NO 628
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 628

```
ggaatccctt ctacagcatc ctg                                              23
```

<210> SEQ ID NO 629
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 629
ggaatatctt ctgcagcccc agg        23

<210> SEQ ID NO 630
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 630
agggtccctt ctgcagcccc tgg        23

<210> SEQ ID NO 631
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 631
accatccctc ctgcagcacc agg        23

<210> SEQ ID NO 632
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 632
actttatctt ctgcagcacc tgg        23

<210> SEQ ID NO 633
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 633
atcctttctt ctgcagcacc tgg        23

<210> SEQ ID NO 634
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 634 acactcccctt ctgcagcacc atg        23

<210> SEQ ID NO 635
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 635
ggcttccctt ctgcagcccc agg        23

```
<210> SEQ ID NO 636
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 636
tgtattcctt ctgcaggcac cag                                        23

<210> SEQ ID NO 637
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 637
cctgctgctt ctgcagcacc tgg                                        23

<210> SEQ ID NO 638
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 638
aaaatccctt ccgcagcacc tag                                        23

<210> SEQ ID NO 639
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 639
aatattccct ctgcagcacc agg                                        23

<210> SEQ ID NO 640
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 640
accatttctt ctgcagcacc tgg                                        23

<210> SEQ ID NO 641
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 641
gggtccgctt ctgcagcacc tgg                                        23

<210> SEQ ID NO 642
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 642
aggaatccta ctgcagcacc cag                                          23

<210> SEQ ID NO 643
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 643
ttactcactt ctgcaggcac ctg                                          23

<210> SEQ ID NO 644
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 644
ccactccttt ctgcagcacc cgg                                          23

<210> SEQ ID NO 645
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 645 ggaacccct ctgcagcttc tgg                                           23

<210> SEQ ID NO 646
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 646
cattttcttt ctgcagcacc tgg                                          23

<210> SEQ ID NO 647
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 647
agaggcccct ctgcagcacc agg                                          23

<210> SEQ ID NO 648
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 648
tttcctgctt ctgcagcacc agg                                          23

<210> SEQ ID NO 649
```

```
<210> SEQ ID NO 649
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 649 gcccctcct ctgcagcacc tgg                                              23

<210> SEQ ID NO 650
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 650
ctcctccctc ctgcagcacc tgg                                             23

<210> SEQ ID NO 651
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 651 aaaataccttt ctgcagtacc agg                                            23

<210> SEQ ID NO 652
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 652
ctactgactt ctgcagcacc tgg                                             23

<210> SEQ ID NO 653
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 653
agctcccatt ctgcagcacc cgg                                             23

<210> SEQ ID NO 654
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 654
agttccccat ctgcagcacc agg                                             23

<210> SEQ ID NO 655
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 655
```
ctcatccctt ctgcagcccc agg 23

<210> SEQ ID NO 656
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 656
gccccctgct ctgcagcacc cgg 23

<210> SEQ ID NO 657
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 657
acctgccttc tggcagcacc agg 23

<210> SEQ ID NO 658
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 658
actgtcattt ctgcagcacc tgg 23

<210> SEQ ID NO 659
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 659
gtcatcttag tcattacctg agg 23

<210> SEQ ID NO 660
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 660
atcaccttag ccattaccag ggg 23

<210> SEQ ID NO 661
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 661
attattttag tcattacctt tgg 23

<210> SEQ ID NO 662
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 662
cgtgcattag tcattacctg agg                                          23

<210> SEQ ID NO 663
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 663
acttatttag tcattacctg tag                                          23

<210> SEQ ID NO 664
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 664
gtaatattag tcattaccgg tgg                                          23

<210> SEQ ID NO 665
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 665
taacacatag tcactacctg gtg                                          23

<210> SEQ ID NO 666
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 666
aatatgttag tcattacctg agg                                          23

<210> SEQ ID NO 667
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 667
atgcttcttg tcattacctt ggg                                          23

<210> SEQ ID NO 668
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 668
acttcagtag tcattaccta ggg                                          23
```

<210> SEQ ID NO 669
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 669
ggtatctaag tcattacctg tgg                                          23

<210> SEQ ID NO 670
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 670
catctaatag taattacctg ggg                                          23

<210> SEQ ID NO 671
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 671
gtcatcttag tcattactga gg                                           22

<210> SEQ ID NO 672
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 672
gggaaagtcc cagcatcctt tgg                                          23

<210> SEQ ID NO 673
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 673
gggaaagacc cagcatccgt ggg                                          23

<210> SEQ ID NO 674
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 674
ggaaaagacc aagcatcagt ggg                                          23

<210> SEQ ID NO 675
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 675
gggaaggacc cagcatcctg ggg                                    23

<210> SEQ ID NO 676
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 676
gggaaatacc cagcatccaa tgg                                    23

<210> SEQ ID NO 677
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 677
gggaaaagcc cagcatccct tgg                                    23

<210> SEQ ID NO 678
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 678
tggaaagaaa cagcatccgt acg                                    23

<210> SEQ ID NO 679
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 679
ttataagacc cagcatccgt aag                                    23

<210> SEQ ID NO 680
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 680
ggagaaagac cagcatccat agg                                    23

<210> SEQ ID NO 681
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 681
gggaaatccc cagcatctct agg                                    23

```
<210> SEQ ID NO 682
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 682
ggaaagtaca cagcatccat cgg                                             23

<210> SEQ ID NO 683
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 683
ggggaagacc cagcaccctt ggg                                             23

<210> SEQ ID NO 684
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 684
atgaaagacc cagcatccat tga                                             23

<210> SEQ ID NO 685
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 685
aggattcccc aagcatccgt ggg                                             23

<210> SEQ ID NO 686
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 686
gagaaaagcc cagcatcctt agg                                             23

<210> SEQ ID NO 687
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 687
gggaatacac cagcatccgt aga                                             23

<210> SEQ ID NO 688
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 688
gaacacaaag catagactgc ggg                                              23

<210> SEQ ID NO 689
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 689
gaacacaatg catagattgc cgg                                              23

<210> SEQ ID NO 690
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 690
aacacaaaga catagaccac tgg                                              23

<210> SEQ ID NO 691
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 691
tacacacaag cacagactgc agg                                              23

<210> SEQ ID NO 692
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 692
aactccaaag catatactgc tgg                                              23

<210> SEQ ID NO 693
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 693
agaacacatg catagactgc tag                                              23

<210> SEQ ID NO 694
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 694
gaattcaaag catagattgc agg                                              23

<210> SEQ ID NO 695
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 695
aaatacaatg catagactgc tag                                              23

<210> SEQ ID NO 696
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 696
tacacaaaac ataagactgc tgg                                              23

<210> SEQ ID NO 697
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 697
gaattcaaag catagattgc agg                                              23

<210> SEQ ID NO 698
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 698
gaatactaag catagactcc agg                                              23

<210> SEQ ID NO 699
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 699
caatacaaag gatagactgc agg                                              23

<210> SEQ ID NO 700
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 700
ggaatcaaag cacagactgc agg                                              23

<210> SEQ ID NO 701
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 701
```
gaaaacaaaa catagagtgc tgg                                              23

<210> SEQ ID NO 702
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 702
actatataag catagactgt tgg                                              23

<210> SEQ ID NO 703
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 703
ccacaccaag catagacttc tgg                                              23

<210> SEQ ID NO 704
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 704
taaacactaa catagactgc agg                                              23

<210> SEQ ID NO 705
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 705
aagaacaaaa catagactgc agg                                              23

<210> SEQ ID NO 706
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 706
gtaaacaaag catagactga ggg                                              23

<210> SEQ ID NO 707
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 707
ctcctaaagc attagactgc agg                                              23

<210> SEQ ID NO 708
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 708
ggtacacaat aatagactgc agg                                              23

<210> SEQ ID NO 709
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 709
cctacagaag catagactgc agg                                              23

<210> SEQ ID NO 710
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 710
ccaaacaaaa catagactgc tgg                                              23

<210> SEQ ID NO 711
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 711
attaagatag catagactgc agg                                              23

<210> SEQ ID NO 712
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 712
tcacacaaac catagactga ggg                                              23

<210> SEQ ID NO 713
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 713
aacaagtatg catagactgc tgg                                              23

<210> SEQ ID NO 714
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 714
gtaattaaag cacagactgc tgg                                              23
```

<210> SEQ ID NO 715
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 715
tgtgtaagag catagactgc tgg                                              23

<210> SEQ ID NO 716
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 716
atacacagag caaagactgc agg                                              23

<210> SEQ ID NO 717
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 717
gaacacagta catagactgg cag                                              23

<210> SEQ ID NO 718
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 718
aaacataaag aatagactgc aag                                              23

<210> SEQ ID NO 719
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 719
tactctatat catagactgc tgg                                              23

<210> SEQ ID NO 720
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 720
tgattgagtg catagactgc tgg                                              23

<210> SEQ ID NO 721
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 721
agtatagcag catagactgc agg                                              23

<210> SEQ ID NO 722
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 722
gagcgataag cacagactgc tgg                                              23

<210> SEQ ID NO 723
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 723
cacccagact gagcacgtgc tgg                                              23

<210> SEQ ID NO 724
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 724
gagccagaat gagcacgtga ggg                                              23

<210> SEQ ID NO 725
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 725
agctcagact gagcaagtga ggg                                              23

<210> SEQ ID NO 726
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 726
gacacagacc gggcacgtga ggg                                              23

<210> SEQ ID NO 727
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 727
ggcccagact gagcacgtga tgg                                              23

<210> SEQ ID NO 728
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 728
ggcgcagaca gagcacgtga cga                                           23

<210> SEQ ID NO 729
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 729
agaccagact gagcaagaga ggg                                           23

<210> SEQ ID NO 730
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 730
atatcagact gagcaccgtg agg                                           23

<210> SEQ ID NO 731
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 731
aaataagact gagcacgtgg tgg                                           23

<210> SEQ ID NO 732
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 732
agccagactg aggcaagtga ggg                                           23

<210> SEQ ID NO 733
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 733
aggccagact gaacacgatg agg                                           23

<210> SEQ ID NO 734
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 734
```
cctaaagact gagcaagtga agg                                               23

<210> SEQ ID NO 735
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 735
cagccagaca gagcacgtgg agg                                               23

<210> SEQ ID NO 736
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 736
aacaaagact gagcacgtta ggg                                               23

<210> SEQ ID NO 737
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 737
gacccagaat gagcacaaaa ggg                                               23

<210> SEQ ID NO 738
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 738
attctagact gagcacgtgc aag                                               23

<210> SEQ ID NO 739
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 739
cccatggact gagcacatga agg                                               23

<210> SEQ ID NO 740
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 740
tggccagact gagctcgtga gtg                                               23

<210> SEQ ID NO 741
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 741
gaaggagact gagcatgtga ggg                                      23

<210> SEQ ID NO 742
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 742
tctccagact gagcccatga ggg                                      23

<210> SEQ ID NO 743
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 743
ggaccaggct gagcacatgg agg                                      23

<210> SEQ ID NO 744
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 744
aagccagact gagcacgttc agg                                      23

<210> SEQ ID NO 745
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 745
ggtcatcact gagcacgtga ggt                                      23

<210> SEQ ID NO 746
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 746
ggctcagact gagcacctga gag                                      23

<210> SEQ ID NO 747
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 747
attccagaat gagcacatga agg                                      23
```

<210> SEQ ID NO 748
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 748
acccaagaca gagcacgtgg agg                                        23

<210> SEQ ID NO 749
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 749
tcccagaact aagcacgtga atg                                        23

<210> SEQ ID NO 750
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 750
ctcggagact gaccacgtga ggg                                        23

<210> SEQ ID NO 751
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 751
actccagact gagcaactga ggg                                        23

<210> SEQ ID NO 752
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 752
ttcccagaca aagcacgcga agg                                        23

<210> SEQ ID NO 753
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 753
aaccagactg gagcacgtgg tgg                                        23

<210> SEQ ID NO 754
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 754
gcacctgcgg ctggaggtgg cag                                           23

<210> SEQ ID NO 755
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 755
ggcactgctg ctagaggtgc agg                                           23

<210> SEQ ID NO 756
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 756
agcactgtgg ctgggggagg ggg                                           23

<210> SEQ ID NO 757
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 757
ggcaatgcgg ctggaggcgg agg                                           23

<210> SEQ ID NO 758
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 758
ggctctgcgt ccggaggtga gag                                           23

<210> SEQ ID NO 759
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 759
gccacagcgg ccggaggtgg cag                                           23

<210> SEQ ID NO 760
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 760
ggcacagcag ctggaggtgc tgg                                           23

```
<210> SEQ ID NO 761
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 761
ggctcttcgg ctggaggtag cgg                                               23

<210> SEQ ID NO 762
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 762
ggcgctgcgg cgggaggtgg agg                                               23

<210> SEQ ID NO 763
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 763
agcactgtgg ctgggggagg cgg                                               23

<210> SEQ ID NO 764
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 764
ggtacagcgg ctgggggagg cgg                                               23

<210> SEQ ID NO 765
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 765
ggcactgcgg cagggaggag ggg                                               23

<210> SEQ ID NO 766
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 766
ggccctgcgg ctggagatat ggg                                               23

<210> SEQ ID NO 767
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 767
agcactgcag ctgggagtgg agg                                    23

<210> SEQ ID NO 768
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 768
ggcactgcgg gtggaggcgg ggg                                    23

<210> SEQ ID NO 769
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 769
ggcacgacgg ctggaggtgg ggg                                    23

<210> SEQ ID NO 770
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 770
ggctctgtgg ctggaggagg tgg                                    23

<210> SEQ ID NO 771
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 771
ggccctgctg ctggaggtgc tgg                                    23

<210> SEQ ID NO 772
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 772
gacacctcgg ctggaggtgc agg                                    23

<210> SEQ ID NO 773
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 773
agcagtgcgg ctagaggtgg tgg                                    23

<210> SEQ ID NO 774
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 774
ggctctgcgg ctggaggggg tgg                                    23

<210> SEQ ID NO 775
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 775
ggcactgtgg ctgcaggtgg agg                                    23

<210> SEQ ID NO 776
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 776
cagactgcgg caggggtgg cgg                                     23

<210> SEQ ID NO 777
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 777
gccactgcga ctggaggagg ggg                                    23

<210> SEQ ID NO 778
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 778
aggactgcgg ctgggggtgg tgg                                    23

<210> SEQ ID NO 779
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 779
ggcacttcag ctggaggcag agg                                    23

<210> SEQ ID NO 780
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 780
```

```
gacactgagg caggaggtgg ggg                                              23

<210> SEQ ID NO 781
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 781
ggcactgcgg ctggaggtgg ggg                                              23

<210> SEQ ID NO 782
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 782
gccactgggg ctggggtgg ggg                                               23

<210> SEQ ID NO 783
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 783
ggccctgcta ctgggggtgg tgg                                              23

<210> SEQ ID NO 784
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 784
tgcccagcag ctggaggtga ggg                                              23

<210> SEQ ID NO 785
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 785
agcactgcag atggaggagg cgg                                              23

<210> SEQ ID NO 786
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 786
gtcactgcag ctggaggagg ggg                                              23

<210> SEQ ID NO 787
<211> LENGTH: 23
<212> TYPE: DNA
<213> ORGANISM: Artificial Sequence
```

```
<220> FEATURE:
<223> OTHER INFORMATION: Synthesized Sequence

<400> SEQUENCE: 787
tgcactgcgg ccggaggagg tgg                                              23

<210> SEQ ID NO 788
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 788
gacactgtgg ctggaagtgg aag                                              23

<210> SEQ ID NO 789
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 789
ggcaatgtgg ctgaaggtgg ggg                                              23

<210> SEQ ID NO 790
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 790
gacactaggg caggaggtgg agg                                              23

<210> SEQ ID NO 791
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 791
gacacagtgg ctggaggtgt ggg                                              23

<210> SEQ ID NO 792
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 792
ggcactgcaa ctggaagtga tgg                                              23

<210> SEQ ID NO 793
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 793
ggcactgggg ttggaggtgg ggg                                              23
```

```
<210> SEQ ID NO 794
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 794
tgcactgcag ctgcaggtgg agg                                              23

<210> SEQ ID NO 795
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 795
ggcactgaga ctggggtgg ggg                                               23

<210> SEQ ID NO 796
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 796
ggctgtgcgg ccagaggtgg agg                                              23

<210> SEQ ID NO 797
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 797
aacactgcgg ctgcagctgg agg                                              23

<210> SEQ ID NO 798
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 798
ggctctgcag ctgtaggagg agg                                              23

<210> SEQ ID NO 799
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 799
ggggctgcgg ccggaggtgg tgg                                              23

<210> SEQ ID NO 800
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 800
agcactgtgc ctgggggtgg ggg                                                  23

<210> SEQ ID NO 801
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 801
ggaactgggg ctgggggtgg ggg                                                  23

<210> SEQ ID NO 802
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 802
ggccctgcag ctggagatgg aag                                                  23

<210> SEQ ID NO 803
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 803
tgctctgcgg caggaggagg agg                                                  23

<210> SEQ ID NO 804
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 804
gacactgcct ctgggggtgg ggg                                                  23

<210> SEQ ID NO 805
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 805
ggcactgaga ccagaggtgg tgg                                                  23

<210> SEQ ID NO 806
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 806
gccactgtgg ctggaggtgg gga                                                  23

<210> SEQ ID NO 807

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 807
ggcacagcag gtggaggtgg agg                                              23

<210> SEQ ID NO 808
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 808
gccactgcag ctagaggtgg agg                                              23

<210> SEQ ID NO 809
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 809
ggaactgtgg ctggaggtgg cag                                              23

<210> SEQ ID NO 810
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 810
ggcccagcgg cgggaggtgg ggg                                              23

<210> SEQ ID NO 811
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 811
ggcccttcgg ctggaggtgg cag                                              23

<210> SEQ ID NO 812
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 812
ggcacaatgg ctggaggtga agg                                              23

<210> SEQ ID NO 813
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 813
```
ggcactgagg gtggaggtgg ggg 23

<210> SEQ ID NO 814
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 814
gacacaacgg caggaggtgg cgg 23

<210> SEQ ID NO 815
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 815
ggcactgcag cctggggtg ggg 23

<210> SEQ ID NO 816
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 816
gtcactgcgg ctgcagatgg cgg 23

<210> SEQ ID NO 817
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 817
gggcatgcgg ctggaagtgg tgg 23

<210> SEQ ID NO 818
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 818
ggcactgggg ctggagacgg ggg 23

<210> SEQ ID NO 819
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 819
agcacagcag ctgcaggtgg ggg 23

<210> SEQ ID NO 820
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 820
gactctgcag ctgaaggtgg ggg                                              23

<210> SEQ ID NO 821
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 821
gtcactgagg ctggagtgga ggg                                              23

<210> SEQ ID NO 822
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 822
agcactgtta caggaggtgg ggg                                              23

<210> SEQ ID NO 823
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 823
agctctgtgg ctggaggtgt gag                                              23

<210> SEQ ID NO 824
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 824
gaggctgcgg ctggggggtgg agg                                             23

<210> SEQ ID NO 825
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 825
agcactgcgc ttgggggtgg ggg                                              23

<210> SEQ ID NO 826
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 826
agcactgtag caagaggtgg agg                                              23
```

<210> SEQ ID NO 827
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 827
ggctctgagg ccagaggtgg tgg                                          23

<210> SEQ ID NO 828
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 828
ggcatcacgg ctggaggtgg agg                                          23

<210> SEQ ID NO 829
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 829
gtaactgcgg ctggcggtgg tgg                                          23

<210> SEQ ID NO 830
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 830
agcactgggg atggaggtgt agg                                          23

<210> SEQ ID NO 831
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 831
agaactgctg ctggaggtgg tgg                                          23

<210> SEQ ID NO 832
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 832
ggctctgtgg ccggaggagg cgg                                          23

<210> SEQ ID NO 833
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 833
ggcactgctg ctgggggtgg tgg                                    23

<210> SEQ ID NO 834
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 834
ggccctgggg ctggaggtgt tgg                                    23

<210> SEQ ID NO 835
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 835
ggctctgagg ctggtggtgg ggg                                    23

<210> SEQ ID NO 836
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 836
ggcacgcggc tgggaggtgg agg                                    23

<210> SEQ ID NO 837
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 837
tgcactgcag ctggggctgg agg                                    23

<210> SEQ ID NO 838
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 838
ccttctgcgg ctggaagtgg tgg                                    23

<210> SEQ ID NO 839
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 839
ggcacgcggc tgggaggtgg agg                                    23

```
<210> SEQ ID NO 840
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 840
agcaatacgg atggaggtgg agg                                              23

<210> SEQ ID NO 841
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 841
ggcacttcgg ttggggtgg ggg                                               23

<210> SEQ ID NO 842
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 842
tgcactgcgg gcggaggcgg cgg                                              23

<210> SEQ ID NO 843
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 843
ggctccgcag ctggaggtgg ggg                                              23

<210> SEQ ID NO 844
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 844
tgcaccgcgg ctggggctgg agg                                              23

<210> SEQ ID NO 845
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 845
tccactgagg ctggggtgg tgg                                               23

<210> SEQ ID NO 846
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 846
ctggcagcgg ctggggtgg ggg                                        23

<210> SEQ ID NO 847
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 847
ggccatgcgg ctggtggtgg tgg                                       23

<210> SEQ ID NO 848
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 848
cacactgcag ctggaggtgg tgg                                       23

<210> SEQ ID NO 849
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 849
ctgcctgcgg ctgggggtgt ggg                                       23

<210> SEQ ID NO 850
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 850
gacaccacgg ctggagatgg tgg                                       23

<210> SEQ ID NO 851
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 851
gggactgcaa ctggaggtgg ggg                                       23

<210> SEQ ID NO 852
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 852
ggcactgcag cagggatgg ggg                                        23

<210> SEQ ID NO 853
<211> LENGTH: 23

-continued

<212> TYPE: DNA
<213> ORGANISM: Artificial Sequence
<220> FEATURE:
<223> OTHER INFORMATION: Synthesized Sequence

<400> SEQUENCE: 853
ggctctgtag ctgggggtgg tgg                                    23

<210> SEQ ID NO 854
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 854
ggcgctgcgg ctggagccgg cgg                                    23

<210> SEQ ID NO 855
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 855
tgcacagcgg atggaggggg ggg                                    23

<210> SEQ ID NO 856
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 856
ggcactgcag gcaggaggtg agt                                    23

<210> SEQ ID NO 857
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 857
gccactgagg ccggaggtgg aga                                    23

<210> SEQ ID NO 858
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 858
gggcacgcgg ctggaggagg ggg                                    23

<210> SEQ ID NO 859
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 859
agctctgcgg caggagttgg agg                                              23

<210> SEQ ID NO 860
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 860
ggcactgggg ctgggggagg ggg                                              23

<210> SEQ ID NO 861
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 861
ggccctgcag ctggagaggg agg                                              23

<210> SEQ ID NO 862
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 862
tacactgcag ctgggagtgg tgg                                              23

<210> SEQ ID NO 863
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 863
agcactgggg ctgggggagg ggg                                              23

<210> SEQ ID NO 864
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 864
gacactaagg ctggaggtgg gga                                              23

<210> SEQ ID NO 865
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 865
tgcactgcag ctgggggtcg ggg                                              23

<210> SEQ ID NO 866
<211> LENGTH: 23
<212> TYPE: DNA
<213> ORGANISM: Artificial Sequence -continued

```
<220> FEATURE:
<223> OTHER INFORMATION: Synthesized Sequence

<400> SEQUENCE: 866
gccactgggg ctggagggg agg                                        23

<210> SEQ ID NO 867
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 867
cagctctgcg ctggaggagg ggg                                       23

<210> SEQ ID NO 868
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 868
agctctgctg ctggaggagg tgg                                       23

<210> SEQ ID NO 869
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 869
ggcactgaat ctggaggtgg ggg                                       23

<210> SEQ ID NO 870
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 870
atcactgcgc ctggtggtgg ggg                                       23

<210> SEQ ID NO 871
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 871
gcacctgcgg ccagggtgg ggg                                        23

<210> SEQ ID NO 872
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 872
ggcactgggg caggagatgg ggg                                       23
```

<210> SEQ ID NO 873
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 873
agcacggcag ctggaggagg ggg                                           23

<210> SEQ ID NO 874
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 874
ggcactctgg ctggagctgg ggg                                           23

<210> SEQ ID NO 875
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 875
ggccctgctg ctggagaagg tgg                                           23

<210> SEQ ID NO 876
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 876
ggcattgctg ctggtggtgg tgg                                           23

<210> SEQ ID NO 877
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 877
gcaccgcgtg ctggaggagg agg                                           23

<210> SEQ ID NO 878
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 878
agctctgcta ttggaggtgg agg                                           23

<210> SEQ ID NO 879
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 879
agccctgggg caggaggtgg ggg                                          23

<210> SEQ ID NO 880
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 880
gctgctgcgg ctggaggtgg gga                                          23

<210> SEQ ID NO 881
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 881
ggccctgcag caggggtgg agg                                           23

<210> SEQ ID NO 882
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 882
ggaagtgcgg caggaggtgg agg                                          23

<210> SEQ ID NO 883
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 883
gacaccgtga ctggaggtgg agg                                          23

<210> SEQ ID NO 884
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 884
gcagctgcgg ctggagctga ggg                                          23

<210> SEQ ID NO 885
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 885
ggaactgtgg ctggggatgg ggg                                          23

<210> SEQ ID NO 886
```

```
<210> SEQ ID NO 886
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 886
ggcactgcag ctgggggttg gtg                                              23

<210> SEQ ID NO 887
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 887
aacactgggg ctggtggtgg tgg                                              23

<210> SEQ ID NO 888
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 888
tgcactccga ctggaagtgg tgg                                              23

<210> SEQ ID NO 889
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 889
tgcactgagg aaggaggtgg agg                                              23

<210> SEQ ID NO 890
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 890
tggactgcgg ctggagaggg agg                                              23

<210> SEQ ID NO 891
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 891
ggcgctgcgg ccggaggtgg ggc                                              23

<210> SEQ ID NO 892
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 892
```
ggcacatggg ctgggggtgg ggg                                           23

<210> SEQ ID NO 893
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 893
ggcactgaga aaggaggtgg agg                                           23

<210> SEQ ID NO 894
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 894
tgccctgcag ctgggggtgg ggg                                           23

<210> SEQ ID NO 895
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 895
tgcactgcag atggtaggtg ggg                                           23

<210> SEQ ID NO 896
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 896
ggcaccttgg ctgaaggtgg ggg                                           23

<210> SEQ ID NO 897
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 897
accactgtgg ctggcaggtg gtg                                           23

<210> SEQ ID NO 898
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 898
agcactgcag cgggaggtga gag                                           23

<210> SEQ ID NO 899
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 899
ggcactgggt ctgaaggtgg agg                                               23

<210> SEQ ID NO 900
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 900
tgcactgcag ctgggggcag agg                                               23

<210> SEQ ID NO 901
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 901
ggcactctgg ctggacgtgg tgg                                               23

<210> SEQ ID NO 902
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 902
ggcactgttg ctggaggagg cag                                               23

<210> SEQ ID NO 903
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 903
ggcactgctg actagggtg gtg                                                23

<210> SEQ ID NO 904
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 904
tgcactgcga ctggagggag agg                                               23

<210> SEQ ID NO 905
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 905
gcactgcaaa ctggaggtgg ggg                                               23
```

```
<210> SEQ ID NO 906
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 906
cccactgtgg ctggaggtgt ggg                                               23

<210> SEQ ID NO 907
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 907
agccctgcgg ccgggggagg cgg                                               23

<210> SEQ ID NO 908
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 908
gggactgcgg ctggaggtgg gaa                                               23

<210> SEQ ID NO 909
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 909
ttcactgtgg ctggaggtgg gga                                               23

<210> SEQ ID NO 910
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 910
agcactatgg atagaggtgg agg                                               23

<210> SEQ ID NO 911
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 911
tacactgcgg ccgggagtgg tgg                                               23

<210> SEQ ID NO 912
<211> LENGTH: 23
<212> TYPE: DNA
<213> ORGANISM: Artificial Sequence
<220> FEATURE:
```

<223> OTHER INFORMATION: Synthesized Sequence

<400> SEQUENCE: 912
tgcactgaag ctggaggtgg aga                                           23

<210> SEQ ID NO 913
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 913
agtactgcgg ctgggcgtgg tgg                                           23

<210> SEQ ID NO 914
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 914
agcactaggg caggagatgg ggg                                           23

<210> SEQ ID NO 915
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 915
gacactgagg ctggaagagg tgg                                           23

<210> SEQ ID NO 916
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 916
ggcatgcggc tgggaggtgg agg                                           23

<210> SEQ ID NO 917
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 917
cgttctgcgg cgggaggtgg cgg                                           23

<210> SEQ ID NO 918
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 918
gcactggcag ccggaggtgg tgg                                           23

```
<210> SEQ ID NO 919
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 919
ggcagggcgg ctggaggagg tgg                                            23

<210> SEQ ID NO 920
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 920
agcactgggg caggagggtg gtg                                            23

<210> SEQ ID NO 921
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 921
ttgcatgcgg ctggaagtgg tgg                                            23

<210> SEQ ID NO 922
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 922
cccactgggg ctggaggtgg ggg                                            23

<210> SEQ ID NO 923
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 923
cagactgcag ctggtaggtg gtg                                            23

<210> SEQ ID NO 924
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 924
ggcagtgcag ctggaggcag ggg                                            23

<210> SEQ ID NO 925
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 925
ggctctgcca ctggagggg tgg                                          23

<210> SEQ ID NO 926
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 926
gacactgagg ctggaggtct ggg                                         23

<210> SEQ ID NO 927
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 927
ggccctgaga ctgcagctgg agg                                         23

<210> SEQ ID NO 928
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 928
agcactgtgg atggagttgg agg                                         23

<210> SEQ ID NO 929
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 929
cttcctacgg caggaggtgg ggg                                         23

<210> SEQ ID NO 930
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 930
cgcactgggg ctgcaggtgg agg                                         23

<210> SEQ ID NO 931
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 931
ggccctgcag ctggaggagg aga                                         23

<210> SEQ ID NO 932
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 932
agcactgcag tgagaggtgg agg                                           23

<210> SEQ ID NO 933
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 933
gacaccgcag ctggggcgg cgg                                            23

<210> SEQ ID NO 934
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 934
agcactgggg ctggagctag agg                                           23

<210> SEQ ID NO 935
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 935
ggttctgcgg ttggggtgg ggg                                            23

<210> SEQ ID NO 936
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 936
ggctctgcat ttggaggtgt gcg                                           23

<210> SEQ ID NO 937
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 937
tgcactgtgg ctggagatgg ggg                                           23

<210> SEQ ID NO 938
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 938
```
ggcactgcag acggaggtgt ggg                                          23

<210> SEQ ID NO 939
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 939
gacactgctg ctggagagtg gag                                          23

<210> SEQ ID NO 940
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 940
ggcactgcgg gaggaggtgg gcg                                          23

<210> SEQ ID NO 941
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 941
agaactgggg ctggggtgg ggg                                           23

<210> SEQ ID NO 942
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 942
gggcctgcag ctggggtgg ggg                                           23

<210> SEQ ID NO 943
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 943
ggtacagtgg ctggaggtgg aag                                          23

<210> SEQ ID NO 944
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 944
cccactgcgg gtggaggtgg aag                                          23

<210> SEQ ID NO 945
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 945
cgcagtgcgg caggagggtg ggg                                        23

<210> SEQ ID NO 946
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 946
aaccctgcgg caggaggagg cgg                                        23

<210> SEQ ID NO 947
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 947
gatactgggg ctgggggtgg agg                                        23

<210> SEQ ID NO 948
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 948
tgcactgcag ctggaggcaa cgg                                        23

<210> SEQ ID NO 949
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 949
gcacttgctg ctggaggagt agg                                        23

<210> SEQ ID NO 950
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 950
tgcactgcgg tcaggaggag gcg                                        23

<210> SEQ ID NO 951
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 951
agcactaggg caggagatgg ggg                                        23
```

```
<210> SEQ ID NO 952
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 952
agccctgcta ctgggggtgg ggg                                            23

<210> SEQ ID NO 953
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 953
gacactgcag ctggaggtgg ggt                                            23

<210> SEQ ID NO 954
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 954
tgcactgcaa ctgggggtgg cag                                            23

<210> SEQ ID NO 955
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 955
gaccctgcgg tgggaggtgg cgg                                            23

<210> SEQ ID NO 956
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 956
ggccctgagg caggaagtgg ggg                                            23

<210> SEQ ID NO 957
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 957
accactgagg atgggggtgg agg                                            23

<210> SEQ ID NO 958
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 958
cgcactgggg ctgcaggtgg agg                                           23

<210> SEQ ID NO 959
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 959
gggactgcag ctggggatgg ggg                                           23

<210> SEQ ID NO 960
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 960
caaactgcag ctggagatgg gag                                           23

<210> SEQ ID NO 961
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 961
ctgactgcag ctggaggtgg aga                                           23

<210> SEQ ID NO 962
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 962
ggcactgggg aaggaggtgg agg                                           23

<210> SEQ ID NO 963
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 963
gacactgcta ctggaggctg ggg                                           23

<210> SEQ ID NO 964
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 964
gcactggcgg ctgggagtgg tgg                                           23

<210> SEQ ID NO 965

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 965
agcactaggg caggagatgg ggg                                              23

<210> SEQ ID NO 966
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 966
gagaatgcgg atggaggtgg tgg                                              23

<210> SEQ ID NO 967
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 967
ggcactgcca ctgggggtga ggg                                              23

<210> SEQ ID NO 968
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 968
gccaccgcgg caggaggcgg agg                                              23

<210> SEQ ID NO 969
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 969
gagcctgcgg ctgcaggtgg gtg                                              23

<210> SEQ ID NO 970
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 970
gctgccccac agggcagcaa agg                                              23

<210> SEQ ID NO 971
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 971
```

```
gttgcccctc aggacagtac agg                                              23

<210> SEQ ID NO 972
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 972
tgtgccccac agagcactaa ggg                                              23

<210> SEQ ID NO 973
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 973
tcagccccac agggcagtaa ggg                                              23

<210> SEQ ID NO 974
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 974
ttgctcccac agggcagtaa acg                                              23

<210> SEQ ID NO 975
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 975
atggccccac aaggcagaaa tgg                                              23

<210> SEQ ID NO 976
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 976
cttgccccac agggcagtaa cgg                                              23

<210> SEQ ID NO 977
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 977
attgccccac ggggcagtga cgg                                              23

<210> SEQ ID NO 978
<211> LENGTH: 23
<212> TYPE: DNA
```

```
<213> ORGANISM: Artificial Sequence
<220> FEATURE:
<223> OTHER INFORMATION: Synthesized Sequence

<400> SEQUENCE: 978
tctaccccac atggcagtaa tgg                                              23

<210> SEQ ID NO 979
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 979
gtggccccac agggcaggaa tgg                                              23

<210> SEQ ID NO 980
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 980
tctgccccac atggcagtaa tga                                              23

<210> SEQ ID NO 981
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 981
gaagccctac agggcagcaa tgg                                              23

<210> SEQ ID NO 982
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 982
gtgtccccac agggcaggaa agg                                              23

<210> SEQ ID NO 983
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 983
agtgccacac acagcagtaa ggg                                              23

<210> SEQ ID NO 984
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 984
gttatcccac aggacagtga ggg                                              23
```

-continued

<210> SEQ ID NO 985
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 985
cggtccccac agggtcagta agg                                             23

<210> SEQ ID NO 986
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 986
agtggccccc agggcagtga ggg                                             23

<210> SEQ ID NO 987
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 987
actctcccac aaggcagtaa ggg                                             23

<210> SEQ ID NO 988
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 988
gttacctcac agagcagaaa ggg                                             23

<210> SEQ ID NO 989
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 989 tcaccccac aggccagtaa agg                                              23

<210> SEQ ID NO 990
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 990
gggtgggggg agtttgctcc agg                                             23

<210> SEQ ID NO 991
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 991
ggatggaggg agtttgctcc tgg                                           23

<210> SEQ ID NO 992
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 992
gagggtgggg agtttactcc tgg                                           23

<210> SEQ ID NO 993
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 993
ggggagggga agtttgctcc tgg                                           23

<210> SEQ ID NO 994
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 994
cgggggaggg agtttgctcc tgg                                           23

<210> SEQ ID NO 995
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 995 gggtggggg agtttgcccc agg                                            23

<210> SEQ ID NO 996
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 996
gggggtgggg actttgctcc agg                                           23

<210> SEQ ID NO 997
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 997 agtttgggg agtttgcccc agg                                            23

```
<210> SEQ ID NO 998
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 998
ggaggagggg agtctgctcc agg                                               23

<210> SEQ ID NO 999
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 999
agctggaggg agtttgcccc agg                                               23

<210> SEQ ID NO 1000
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1000
gggagggtgg agtttgctcc tgg                                               23

<210> SEQ ID NO 1001
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1001
aggaaggagg agttagctcc tgg                                               23

<210> SEQ ID NO 1002
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1002
tagtggaggg agcttgctcc tgg                                               23

<210> SEQ ID NO 1003
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1003
gagtgggtgg agtttgctac agg                                               23

<210> SEQ ID NO 1004
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 1004
gggggtgggg agcatgctcc agg                                              23

<210> SEQ ID NO 1005
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1005
aggaaggagg agttagctcc tgg                                              23

<210> SEQ ID NO 1006
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1006
aagtaaggga agtttgctcc tgg                                              23

<210> SEQ ID NO 1007
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1007
agggaggagg aatttgctcc agg                                              23

<210> SEQ ID NO 1008
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1008
gggggaggga agtttcctcc agg                                              23

<210> SEQ ID NO 1009
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1009
aggtggtggg agcttgttcc tgg                                              23

<210> SEQ ID NO 1010
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1010
gcgtgggggg tgtttgctcc cgg                                              23

<210> SEQ ID NO 1011
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 1011 gtggggtag agtttgctcc agg                                              23

<210> SEQ ID NO 1012
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1012
ggttgagggg agtctgctcc agg                                             23

<210> SEQ ID NO 1013
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1013 ttggggggc agtttgctcc tgg                                              23

<210> SEQ ID NO 1014
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1014
gggtggggag agtttcttcc tgg                                             23

<210> SEQ ID NO 1015
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1015
ggtgggggag agctagctcc ggg                                             23

<210> SEQ ID NO 1016
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1016
aggaaggagg agttagctcc tgg                                             23

<210> SEQ ID NO 1017
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1017
```

```
gggaggggag agtttgttcc agg                                                23
```

<210> SEQ ID NO 1018
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1018

```
aggaaggagg agttagctcc tgg                                                23
```

<210> SEQ ID NO 1019
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1019

```
ctggtgggg agcttgctcc agg                                                 23
```

<210> SEQ ID NO 1020
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1020

```
gaggggagc agtttgctcc agg                                                 23
```

<210> SEQ ID NO 1021
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1021

```
aagtgggaag agtttgttcc agg                                                23
```

<210> SEQ ID NO 1022
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1022

```
gggcaagggg aggttgctcc tgg                                                23
```

<210> SEQ ID NO 1023
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1023

```
ggtgggggtg ggtttgctcc tgg                                                23
```

<210> SEQ ID NO 1024
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1024
gggtgggtgg agtttgctac tgg                                    23

<210> SEQ ID NO 1025
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1025
aagtgggagg agactgctcc agg                                    23

<210> SEQ ID NO 1026
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1026
aggtcggggg agttagatcc cgg                                    23

<210> SEQ ID NO 1027
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1027 gacccccctcc acccgcctc cgg                                    23

<210> SEQ ID NO 1028
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1028
gggcccctcc acccgcctc tgg                                     23

<210> SEQ ID NO 1029
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1029 ctaccctcc accegcctc cgg                                      23

<210> SEQ ID NO 1030
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1030
taccccccac acccgcctc tgg                                     23

<210> SEQ ID NO 1031
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1031
gacccctccc accccgactc cgg                                              23

<210> SEQ ID NO 1032
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1032
gcccccaccc accccgcctc tgg                                              23

<210> SEQ ID NO 1033
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1033
gtcctccacc accccgcctc tgg                                              23

<210> SEQ ID NO 1034
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1034
attccccccc accccgcctc agg                                              23

<210> SEQ ID NO 1035
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1035 acacccccccc accccgcctc agg                                             23

<210> SEQ ID NO 1036
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1036 tgccccccccc accccacctc tgg                                             23

<210> SEQ ID NO 1037
<211> LENGTH: 23
<212> TYPE: DNA
<213> ORGANISM: Artificial Sequence
<220> FEATURE:
<223> OTHER INFORMATION: Synthesized Sequence

```
<400> SEQUENCE: 1037
gcttccctcc accccgcatc cgg                                              23

<210> SEQ ID NO 1038
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1038
tgcccctccc accccgcctc tgg                                              23

<210> SEQ ID NO 1039
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1039
ccccaccccc accccgcctc agg                                              23

<210> SEQ ID NO 1040
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1040
cgccctcccc accccgcctc cgg                                              23

<210> SEQ ID NO 1041
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1041
caaccccccc accccgcttc agg                                              23

<210> SEQ ID NO 1042
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1042 cattccccccc accccacctc agg                                             23

<210> SEQ ID NO 1043
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1043
cagtcccccc accccacctc tgg                                              23

<210> SEQ ID NO 1044
```

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1044
agccaacccc accccgcctc tgg                                            23

<210> SEQ ID NO 1045
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1045 gcccccacc accccacctc ggg                                             23

<210> SEQ ID NO 1046
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1046
gacacacccc accccacctc agg                                            23

<210> SEQ ID NO 1047
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1047
cccccccccc ccccgcctc agg                                             23

<210> SEQ ID NO 1048
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1048
ctccccaccc accccgcctc agg                                            23

<210> SEQ ID NO 1049
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1049
gccagccctc accccgcctc ggg                                            23

<210> SEQ ID NO 1050
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1050
```
ccctctccac ccccaccctc tgg                                              23

<210> SEQ ID NO 1051
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1051
tccgcccccc accccacctc cgg                                              23

<210> SEQ ID NO 1052
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1052
taaatcctcc accccacctc agg                                              23

<210> SEQ ID NO 1053
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1053
gctgtctccc accccgcctc agg                                              23

<210> SEQ ID NO 1054
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1054
catcttcccc accccgcctc tgg                                              23

<210> SEQ ID NO 1055
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1055 cctcacccccc accccacctc tgg                                             23

<210> SEQ ID NO 1056
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1056
cccacacccc accccacctc cgg                                              23

<210> SEQ ID NO 1057
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 1057
ggtgagtgag tgtgtgcgtg tgg                                             23

<210> SEQ ID NO 1058
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1058
agtgagtgag tgtgtgtgtg ggg                                             23

<210> SEQ ID NO 1059
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1059
agagagtgag tgtgtgcatg agg                                             23

<210> SEQ ID NO 1060
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1060
tgtgggtgag tgtgtgcgtg agg                                             23

<210> SEQ ID NO 1061
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1061
gctgagtgag tgtatgcgtg tgg                                             23

<210> SEQ ID NO 1062
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1062
ggtgagtgag tgcgtgcggg tgg                                             23

<210> SEQ ID NO 1063
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1063
gttgagtgaa tgtgtgcgtg agg                                             23
```

<210> SEQ ID NO 1064
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1064
agtgaatgag tgtgtgtgtg tgg                                              23

<210> SEQ ID NO 1065
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1065
tgtgagtaag tgtgtgtgtg tgg                                              23

<210> SEQ ID NO 1066
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1066
actgtgtgag tgtgtgcgtg agg                                              23

<210> SEQ ID NO 1067
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1067
agtgtgtgag tgtgtgcgtg tgg                                              23

<210> SEQ ID NO 1068
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1068
tgtgggtgag tgtgtgcgtg aga                                              23

<210> SEQ ID NO 1069
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1069
ggtgagtgag tgtgtgtgtg agg                                              23

<210> SEQ ID NO 1070
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 1070
ctggagtgag tgtgtgtgtg tgg                                              23

<210> SEQ ID NO 1071
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1071
agcgagtgag tgtgtgtgtg ggg                                              23

<210> SEQ ID NO 1072
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1072
ggtgagtcag tgtgtgagtg agg                                              23

<210> SEQ ID NO 1073
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1073
agtgagtgag tgagtgagtg agg                                              23

<210> SEQ ID NO 1074
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1074
gtagagtgag tgtgtgtgtg tgg                                              23

<210> SEQ ID NO 1075
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1075
agcgagtggg tgtgtgcgtg ggg                                              23

<210> SEQ ID NO 1076
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1076
ggtgtgtgag tgtgtgtgtg tgg                                              23

```
<210> SEQ ID NO 1077
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1077
ggtgaatgag tgtgtgctct ggg                                              23

<210> SEQ ID NO 1078
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1078
agtgagtatg tgtgtgtgtg ggg                                              23

<210> SEQ ID NO 1079
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1079
gatgagtgtg tgtgtgtgtg agg                                              23

<210> SEQ ID NO 1080
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1080
ggtgagcaag tgtgtgtgtg tgg                                              23

<210> SEQ ID NO 1081
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1081
tgtgagtgag tatgtacatg tgg                                              23

<210> SEQ ID NO 1082
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1082
agtgagtaag tgagtgagtg agg                                              23

<210> SEQ ID NO 1083
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 1083
aatgagtgag tgtgtgtgtg tga                                              23

<210> SEQ ID NO 1084
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1084
agtgagaaag tgtgtgcatg cgg                                              23

<210> SEQ ID NO 1085
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1085
tgtgagtgag tgagtgaatg tgg                                              23

<210> SEQ ID NO 1086
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1086
ggtgtgtgag tgtgtgcatg ttg                                              23

<210> SEQ ID NO 1087
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1087
tgtgagtgag tgtgtgcatg tga                                              23

<210> SEQ ID NO 1088
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1088
ggtgagtgtg tgtgtgagtg tgg                                              23

<210> SEQ ID NO 1089
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1089
tgtgtgagtg agtgtgtgtg tgg                                              23

<210> SEQ ID NO 1090
<211> LENGTH: 23

-continued

```
<212> TYPE: DNA
<213> ORGANISM: Artificial Sequence
<220> FEATURE:
<223> OTHER INFORMATION: Synthesized Sequence

<400> SEQUENCE: 1090
tgtgtgagtg tgtgtgtgcg tgg                                              23

<210> SEQ ID NO 1091
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1091
ggtgagtgag tgagtgagtg agg                                              23

<210> SEQ ID NO 1092
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1092
tgagtgtgag tgtgtgcgtg ggg                                              23

<210> SEQ ID NO 1093
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1093
tgtgtgagtg tgtgtgggg ggg                                               23

<210> SEQ ID NO 1094
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1094
tgtgtgtgag tgtgtgcatg agg                                              23

<210> SEQ ID NO 1095
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1095
tgtgagtgaa tgtgtgtgtg tgg                                              23

<210> SEQ ID NO 1096
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1096
```

-continued catgagtggg tgtgtgcgtg gag    23

<210> SEQ ID NO 1097
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1097
ggactgtgag tgtgtgcgtg agg    23

<210> SEQ ID NO 1098
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1098
gatgtgtgag tgtgtgcctg tgg    23

<210> SEQ ID NO 1099
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1099
ggtgtatgag tgtgtgcgtc gga    23

<210> SEQ ID NO 1100
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1100
ggtgtgtgtg tgtgtgtgtg tgg    23

<210> SEQ ID NO 1101
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1101
ggtgtagtgg tgtgtgcttg tgg    23

<210> SEQ ID NO 1102
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1102
ggtgtgtgag tgtgtgcatt ggg    23

<210> SEQ ID NO 1103
<211> LENGTH: 23
<212> TYPE: DNA
<213> ORGANISM: Artificial Sequence

```
<220> FEATURE:
<223> OTHER INFORMATION: Synthesized Sequence

<400> SEQUENCE: 1103
gagtccgagc agaagaagaa ggg                                          23

<210> SEQ ID NO 1104
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1104
gagttagagc agaagaagaa agg                                          23

<210> SEQ ID NO 1105
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1105
gagtctaagc agaagaagaa gag                                          23

<210> SEQ ID NO 1106
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1106
gaggccgagc agaagaaaga cgg                                          23

<210> SEQ ID NO 1107
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1107
gagtcctagc aggagaagaa gag                                          23

<210> SEQ ID NO 1108
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1108
gagccggagc agaagaagga ggg                                          23

<210> SEQ ID NO 1109
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1109
aagtccgagg agaggaagaa agg                                          23
```

<210> SEQ ID NO 1110
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1110
acgtctgagc agaagaagaa tgg                                              23

<210> SEQ ID NO 1111
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1111
aagtcccggc agaggaagaa ggg                                              23

<210> SEQ ID NO 1112
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1112
gagcacgagc aagagaagaa ggg                                              23

<210> SEQ ID NO 1113
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1113
gagtctaagc aggagaataa agg                                              23

<210> SEQ ID NO 1114
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1114
tcatccaagc agaagaagaa gag                                              23

<210> SEQ ID NO 1115
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1115
gagtcccagc aaaagaagaa aag                                              23

<210> SEQ ID NO 1116
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1116
gaggtagagc agaagaagaa gcg                                              23

<210> SEQ ID NO 1117
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1117
gagtcagagc aaaagaagta gtg                                              23

<210> SEQ ID NO 1118
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1118
gaagtagagc agaagaagaa gcg                                              23

<210> SEQ ID NO 1119
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1119
gaagtagagc agaagaagaa gcg                                              23

<210> SEQ ID NO 1120
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1120
gaatccaagc agaagaagag aag                                              23

<210> SEQ ID NO 1121
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1121
gaggcagaga gaaagaagaa agg                                              23

<210> SEQ ID NO 1122
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1122
gagcctgagc agaaggagaa ggg                                              23

<210> SEQ ID NO 1123

```
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1123
gagtttgagt agaagaagaa gag                                              23

<210> SEQ ID NO 1124
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1124
gagttcaagc agagaagaaa ggg                                              23

<210> SEQ ID NO 1125
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1125
aagtctgaga agaagaagaa aga                                              23

<210> SEQ ID NO 1126
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1126
gagtaagaga agaagaagaa ggg                                              23

<210> SEQ ID NO 1127
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1127
aagtcagagg agaagaagaa ggg                                              23

<210> SEQ ID NO 1128
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1128
gagtcccagg agaagaagag agg                                              23

<210> SEQ ID NO 1129
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1129
```
gagtccaagc agtagaggaa ggg                                              23

<210> SEQ ID NO 1130
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1130
aagtccagac agaagaagaa gga                                              23

<210> SEQ ID NO 1131
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1131
ggaatccctt ctgcagcacc tgg                                              23

<210> SEQ ID NO 1132
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1132
ggaaccccgt ctgcagcacc agg                                              23

<210> SEQ ID NO 1133
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1133
ggagtccctc ctacagcacc agg                                              23

<210> SEQ ID NO 1134
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1134
agaggcccct ctgcagcacc agg                                              23

<210> SEQ ID NO 1135
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1135
accatccctc ctgcagcacc agg                                              23

<210> SEQ ID NO 1136
<211> LENGTH: 23
<212> TYPE: DNA

```
<213> ORGANISM: Artificial Sequence
<220> FEATURE:
<223> OTHER INFORMATION: Synthesized Sequence

<400> SEQUENCE: 1136
tgaatcccat ctccagcacc agg                                              23

<210> SEQ ID NO 1137
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1137
ggagtccctc ctacagcacc agg                                              23

<210> SEQ ID NO 1138
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1138
ggagtccctc ctgcagcacc tga                                              23

<210> SEQ ID NO 1139
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1139 ggcttcccctt ctgcagcccc agg                                             23

<210> SEQ ID NO 1140
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1140
ggaacacctt ctgcagctcc agg                                              23

<210> SEQ ID NO 1141
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1141
gggagtccat ctgcagcacc agg                                              23

<210> SEQ ID NO 1142
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1142
gggtccgctt ctgcagcacc tgg                                              23
```

```
<210> SEQ ID NO 1143
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1143 ggaacccct ctgcagcttc tgg                                              23

<210> SEQ ID NO 1144
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1144 aaaataccttt ctgcagtacc agg                                            23

<210> SEQ ID NO 1145
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1145
agggtccctt ctgcagcccc tgg                                             23

<210> SEQ ID NO 1146
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1146 acactcccttt ctgcagcacc atg                                            23

<210> SEQ ID NO 1147
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1147
gggaaagacc cagcatccgt ggg                                             23

<210> SEQ ID NO 1148
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1148
gggaaagtcc cagcatcctt tgg                                             23

<210> SEQ ID NO 1149
<211> LENGTH: 23
<212> TYPE: DNA
<213> ORGANISM: Artificial Sequence
<220> FEATURE:
```

<223> OTHER INFORMATION: Synthesized Sequence

<400> SEQUENCE: 1149
gggaaggacc cagcatcctg ggg                                              23

<210> SEQ ID NO 1150
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1150
gggaaatacc cagcatccaa tgg                                              23

<210> SEQ ID NO 1151
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1151
gagaaaagcc cagcatcctt agg                                              23

<210> SEQ ID NO 1152
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1152
ggaaaagacc aagcatcagt ggg                                              23

<210> SEQ ID NO 1153
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1153
atgaaagacc cagcatccat tga                                              23

<210> SEQ ID NO 1154
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1154
gggaaaagcc cagcatccct tgg                                              23

<210> SEQ ID NO 1155
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1155
ggagaaagac cagcatccat agg                                              23

```
<210> SEQ ID NO 1156
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1156
ttataagacc cagcatccgt aag                                           23

<210> SEQ ID NO 1157
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1157
tggaaagaaa cagcatccgt acg                                           23

<210> SEQ ID NO 1158
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1158
gaacacaaag catagactgc ggg                                           23

<210> SEQ ID NO 1159
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1159
gaacacaatg catagattgc cgg                                           23

<210> SEQ ID NO 1160
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1160
gaatactaag catagactcc agg                                           23

<210> SEQ ID NO 1161
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1161
gaattcaaag catagattgc agg                                           23

<210> SEQ ID NO 1162
<211> LENGTH: 23
<212> TYPE: DNA
<213> ORGANISM: Artificial Sequence
<220> FEATURE:
<223> OTHER INFORMATION: Synthesized Sequence
```

```
<400> SEQUENCE: 1162
caatacaaag gatagactgc agg                                              23

<210> SEQ ID NO 1163
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1163
gaattcaaag catagattgc agg                                              23

<210> SEQ ID NO 1164
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1164
gaaaacaaaa catagagtgc tgg                                              23

<210> SEQ ID NO 1165
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1165
tcacacaaac catagactga ggg                                              23

<210> SEQ ID NO 1166
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1166
ccacaccaag catagacttc tgg                                              23

<210> SEQ ID NO 1167
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1167
aaatacaatg catagactgc tag                                              23

<210> SEQ ID NO 1168
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1168
ccaaacaaaa catagactgc tgg                                              23

<210> SEQ ID NO 1169
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 1169
aaacataaag aatagactgc aag                                              23

<210> SEQ ID NO 1170
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1170
ggaatcaaag cacagactgc agg                                              23

<210> SEQ ID NO 1171
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1171
aagaacaaaa catagactgc agg                                              23

<210> SEQ ID NO 1172
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1172
atacacagag caaagactgc agg                                              23

<210> SEQ ID NO 1173
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1173
gtaattaaag cacagactgc tgg                                              23

<210> SEQ ID NO 1174
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1174
aactccaaag catatactgc tgg                                              23

<210> SEQ ID NO 1175
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1175
```

```
gagcgataag cacagactgc tgg                                              23

<210> SEQ ID NO 1176
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1176
ggcccagact gagcacgtga tgg                                              23

<210> SEQ ID NO 1177
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1177
attctagact gagcacgtgc aag                                              23

<210> SEQ ID NO 1178
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1178
ggcgcagaca gagcacgtga cga                                              23

<210> SEQ ID NO 1179
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1179
agctcagact gagcaagtga ggg                                              23

<210> SEQ ID NO 1180
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1180
gagccagaat gagcacgtga ggg                                              23

<210> SEQ ID NO 1181
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1181
cacccagact gagcacgtgc tgg                                              23

<210> SEQ ID NO 1182
<211> LENGTH: 23
<212> TYPE: DNA
<213> ORGANISM: Artificial Sequence
```

```
<220> FEATURE:
<223> OTHER INFORMATION: Synthesized Sequence

<400> SEQUENCE: 1182
aaataagact gagcacgtgg tgg                                          23

<210> SEQ ID NO 1183
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1183
gacacagacc gggcacgtga ggg                                          23

<210> SEQ ID NO 1184
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1184
agaccagact gagcaagaga ggg                                          23

<210> SEQ ID NO 1185
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1185
cctaaagact gagcaagtga agg                                          23

<210> SEQ ID NO 1186
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1186
cagccagaca gagcacgtgg agg                                          23

<210> SEQ ID NO 1187
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1187
aacaaagact gagcacgtta ggg                                          23

<210> SEQ ID NO 1188
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1188
gacccagaat gagcacaaaa ggg                                          23
```

<210> SEQ ID NO 1189
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1189
cccatggact gagcacatga agg                                            23

<210> SEQ ID NO 1190
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1190
gaaggagact gagcatgtga ggg                                            23

<210> SEQ ID NO 1191
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1191
tctccagact gagcccatga ggg                                            23

<210> SEQ ID NO 1192
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1192
ggctcagact gagcacctga gag                                            23

<210> SEQ ID NO 1193
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1193
ctcggagact gaccacgtga ggg                                            23

<210> SEQ ID NO 1194
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1194
actccagact gagcaactga ggg                                            23

<210> SEQ ID NO 1195
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1195
ttcccagaca aagcacgcga agg                                                  23

<210> SEQ ID NO 1196
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1196
ggcactgcgg ctggaggtgg ggg                                                  23

<210> SEQ ID NO 1197
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1197
ggctctgcgg ctggagggggg tgg                                                 23

<210> SEQ ID NO 1198
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1198
ggcacgacgg ctggaggtgg ggg                                                  23

<210> SEQ ID NO 1199
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1199
ggcgctgcgg cgggaggtgg agg                                                  23

<210> SEQ ID NO 1200
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1200
ggcactgctg ctgggggtgg tgg                                                  23

<210> SEQ ID NO 1201
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1201
ggcactgggg ttggaggtgg ggg                                                  23

<210> SEQ ID NO 1202

```
<210> SEQ ID NO 1202
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1202
ggcactgagg gtggaggtgg ggg                                    23

<210> SEQ ID NO 1203
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1203
ggcactgtgg ctgcaggtgg agg                                    23

<210> SEQ ID NO 1204
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1204
ggcaatgcgg ctggaggcgg agg                                    23

<210> SEQ ID NO 1205
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1205
tgcactgcgg ccggaggagg tgg                                    23

<210> SEQ ID NO 1206
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1206
ggcatcacgg ctggaggtgg agg                                    23

<210> SEQ ID NO 1207
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1207
ggcactgaga ctggggtgg ggg                                     23

<210> SEQ ID NO 1208
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1208
```

-continued

| | |
|---|---|
| agcagtgcgg ctagaggtgg tgg | 23 |

<210> SEQ ID NO 1209
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1209

| | |
|---|---|
| ggcactgggg ctgggggagg ggg | 23 |

<210> SEQ ID NO 1210
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1210

| | |
|---|---|
| aggactgcgg ctggggtgg tgg | 23 |

<210> SEQ ID NO 1211
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1211

| | |
|---|---|
| ggcaatgtgg ctgaaggtgg ggg | 23 |

<210> SEQ ID NO 1212
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1212

| | |
|---|---|
| ggcacagcag ctggaggtgc tgg | 23 |

<210> SEQ ID NO 1213
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1213

| | |
|---|---|
| gccactgggg ctgggggtgg ggg | 23 |

<210> SEQ ID NO 1214
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1214

| | |
|---|---|
| tgcactgtgg ctggagatgg ggg | 23 |

<210> SEQ ID NO 1215
<211> LENGTH: 23
<212> TYPE: DNA

<213> ORGANISM: Artificial Sequence
<220> FEATURE:
<223> OTHER INFORMATION: Synthesized Sequence

<400> SEQUENCE: 1215
cacactgcag ctggaggtgg tgg                                    23

<210> SEQ ID NO 1216
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1216
ggcactgcgg gaggaggtgg gcg                                    23

<210> SEQ ID NO 1217
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1217
ggcactgcca ctggggtga ggg                                     23

<210> SEQ ID NO 1218
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1218
ggcccttcgg ctggaggtgg cag                                    23

<210> SEQ ID NO 1219
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1219
ggcacgcggc tgggaggtgg agg                                    23

<210> SEQ ID NO 1220
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1220
ggcatgcggc tgggaggtgg agg                                    23

<210> SEQ ID NO 1221
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1221
gcacctgcgg ctggaggtgg cag                                    23

<210> SEQ ID NO 1222
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1222
ggccctgaga ctgcagctgg agg                                            23

<210> SEQ ID NO 1223
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1223
cgcactgggg ctgcaggtgg agg                                            23

<210> SEQ ID NO 1224
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1224
ttcactgtgg ctggaggtgg gga                                            23

<210> SEQ ID NO 1225
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1225
ggaagtgcgg caggaggtgg agg                                            23

<210> SEQ ID NO 1226
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1226
cccactgcgg gtggaggtgg aag                                            23

<210> SEQ ID NO 1227
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1227
ggctctgagg ctggtggtgg ggg                                            23

<210> SEQ ID NO 1228
<211> LENGTH: 23
<212> TYPE: DNA
<213> ORGANISM: Artificial Sequence
<220> FEATURE:

<223> OTHER INFORMATION: Synthesized Sequence

<400> SEQUENCE: 1228
ggccctgcag ctggaggagg aga                                              23

<210> SEQ ID NO 1229
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1229
ggcactgggg aaggaggtgg agg                                              23

<210> SEQ ID NO 1230
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1230
ggcactgttg ctggaggagg cag                                              23

<210> SEQ ID NO 1231
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1231
ggccctgcag ctggagatgg aag                                              23

<210> SEQ ID NO 1232
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1232
ggcacatggg ctgggggtgg ggg                                              23

<210> SEQ ID NO 1233
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1233
ggcattgctg ctggtggtgg tgg                                              23

<210> SEQ ID NO 1234
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1234
ggaactgggg ctgggggtgg ggg                                              23

```
<210> SEQ ID NO 1235
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1235
cttgccccac agggcagtaa cgg                                              23

<210> SEQ ID NO 1236
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1236
tcagccccac agggcagtaa ggg                                              23

<210> SEQ ID NO 1237
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1237
gctgccccac agggcagcaa agg                                              23

<210> SEQ ID NO 1238
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1238
cctctcccac agggcagtaa agg                                              23

<210> SEQ ID NO 1239
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1239
cctgtcccac agggcaggaa ggg                                              23

<210> SEQ ID NO 1240
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1240
gctgccccac agggcagcaa agg                                              23

<210> SEQ ID NO 1241
<211> LENGTH: 24
<212> TYPE: DNA
<213> ORGANISM: Artificial Sequence
<220> FEATURE:
<223> OTHER INFORMATION: Synthesized Sequence
```

<400> SEQUENCE: 1241
gctgccccac agggcagcca aagg                                          24

<210> SEQ ID NO 1242
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1242
gtggccccac agggcaggaa tgg                                           23

<210> SEQ ID NO 1243
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1243
attgccccac ggggcagtga cgg                                           23

<210> SEQ ID NO 1244
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1244
gctgccccac agggcagcaa agg                                           23

<210> SEQ ID NO 1245
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1245
tcagccccac agggcagtaa ggg                                           23

<210> SEQ ID NO 1246
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1246
cttgccccac agggcagtaa cgg                                           23

<210> SEQ ID NO 1247
<211> LENGTH: 10
<212> TYPE: DNA
<213> ORGANISM: Artificial Sequence
<220> FEATURE:
<223> OTHER INFORMATION: Synthesized Sequence

<400> SEQUENCE: 1247
tggctaataa                                                          10

<210> SEQ ID NO 1248
<211> LENGTH: 20

```
<212> TYPE: DNA
<213> ORGANISM: Artificial Sequence
<220> FEATURE:
<223> OTHER INFORMATION: Synthesized Sequence

<400> SEQUENCE: 1248
tggcttagga agaaaaataa                                                   20

<210> SEQ ID NO 1249
<211> LENGTH: 6
<212> TYPE: DNA
<213> ORGANISM: Artificial Sequence
<220> FEATURE:
<223> OTHER INFORMATION: Synthesized Sequence

<400> SEQUENCE: 1249 agttct                                                                   6

<210> SEQ ID NO 1250
<211> LENGTH: 38
<212> TYPE: DNA
<213> ORGANISM: Artificial Sequence
<220> FEATURE:
<223> OTHER INFORMATION: Synthesized Sequence

<400> SEQUENCE: 1250
agtactgctc agcattacgt ggaggaacag ctgaatct                               38

<210> SEQ ID NO 1251
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1251
gctattgccc cacggggcag tgacggtac                                         29

<210> SEQ ID NO 1252
<211> LENGTH: 25
<212> TYPE: DNA
<213> ORGANISM: Artificial Sequence
<220> FEATURE:
<223> OTHER INFORMATION: Synthesized Sequence

<400> SEQUENCE: 1252
gctattgccc cacggggcag ggtac                                             25

<210> SEQ ID NO 1253
<211> LENGTH: 14
<212> TYPE: DNA
<213> ORGANISM: Artificial Sequence
<220> FEATURE:
<223> OTHER INFORMATION: Synthesized Sequence

<400> SEQUENCE: 1253
gctattgacg gtac                                                         14

<210> SEQ ID NO 1254
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 1254
```
gctattgccc cacggtac                                                         18

<210> SEQ ID NO 1255
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1255
gctattgccc cacggggcag ttgacggtac                                             30

<210> SEQ ID NO 1256
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1256
gctattgccc cacggggcag atgacggtac                                             30

<210> SEQ ID NO 1257
<211> LENGTH: 31
<212> TYPE: DNA
<213> ORGANISM: Artificial Sequence
<220> FEATURE:
<223> OTHER INFORMATION: Synthesized Sequence

<400> SEQUENCE: 1257
gttgtggccc cacagggcag gaatggcagc g                                           31

<210> SEQ ID NO 1258
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 1258
gttgtggccc cacagggcag cg                                                     22

<210> SEQ ID NO 1259
<211> LENGTH: 32
<212> TYPE: DNA
<213> ORGANISM: Artificial Sequence
<220> FEATURE:
<223> OTHER INFORMATION: Synthesized Sequence

<400> SEQUENCE: 1259
gttgtggccc cacagggcag ggaatggcag cg                                          32

<210> SEQ ID NO 1260
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1260
gttgtggccc cacagggcag aatggcagcg                                             30

<210> SEQ ID NO 1261
<211> LENGTH: 12
<212> TYPE: DNA
<213> ORGANISM: Artificial Sequence

```
<220> FEATURE:
<223> OTHER INFORMATION: Synthesized Sequence

<400> SEQUENCE: 1261
gttgtggcag cg                                                          12

<210> SEQ ID NO 1262
<211> LENGTH: 17
<212> TYPE: DNA
<213> ORGANISM: Artificial Sequence
<220> FEATURE:
<223> OTHER INFORMATION: Synthesized Sequence

<400> SEQUENCE: 1262
gttgtggaat ggcagcg                                                     17

<210> SEQ ID NO 1263
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1263
gggtgggggg agtttgcccc agg                                              23

<210> SEQ ID NO 1264
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1264
tagtggaggg agcttgctcc tgg                                              23

<210> SEQ ID NO 1265
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1265
ggatggaggg agtttgctcc tgg                                              23

<210> SEQ ID NO 1266
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1266
gggagggtgg agtttgctcc tgg                                              23

<210> SEQ ID NO 1267
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1267
cgggggaggg agtttgctcc tgg                                              23
```

<210> SEQ ID NO 1268
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1268
cccgggggga agcttgctcc agg                                    23

<210> SEQ ID NO 1269
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1269
gcgtgggggg tgtttgctcc cgg                                    23

<210> SEQ ID NO 1270
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1270
ggggagggga agtttgctcc tgg                                    23

<210> SEQ ID NO 1271
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1271
gggtgggggg agtttgctcc tgg                                    23

<210> SEQ ID NO 1272
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1272
tatgcgtggg gggtgtttgc tcccgggca                              29

<210> SEQ ID NO 1273
<211> LENGTH: 4
<212> TYPE: DNA
<213> ORGANISM: Artificial Sequence
<220> FEATURE:
<223> OTHER INFORMATION: Synthesized Sequence

<400> SEQUENCE: 1273 aggt                                                          4

<210> SEQ ID NO 1274
<211> LENGTH: 12
<212> TYPE: DNA
<213> ORGANISM: Artificial Sequence
<220> FEATURE:
<223> OTHER INFORMATION: Synthesized Sequence

```
<400> SEQUENCE: 1274
tatgcgtggg ag                                                              12

<210> SEQ ID NO 1275
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1275
tatgcgtggg gggtgtttgc ttcccgggca                                           30

<210> SEQ ID NO 1276
<211> LENGTH: 15
<212> TYPE: DNA
<213> ORGANISM: Artificial Sequence
<220> FEATURE:
<223> OTHER INFORMATION: Synthesized Sequence

<400> SEQUENCE: 1276
tatgcgtccc gggca                                                           15

<210> SEQ ID NO 1277
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 1277
tatgcgtggg gggtgtttgc a                                                    21

<210> SEQ ID NO 1278
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1278
ctgcctggag caagcttccc cccgggccc                                            29

<210> SEQ ID NO 1279
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1279
ctgcctggaa gcaagcttcc ccccgggccc                                           30

<210> SEQ ID NO 1280
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1280
ctgcctggag gcaagcttcc ccccgggccc                                           30

<210> SEQ ID NO 1281
```

```
<211> LENGTH: 28
<212> TYPE: DNA
<213> ORGANISM: Artificial Sequence
<220> FEATURE:
<223> OTHER INFORMATION: Synthesized Sequence

<400> SEQUENCE: 1281
ctgcctgagc aagcttcccc ccgggccc                                        28

<210> SEQ ID NO 1282
<211> LENGTH: 17
<212> TYPE: DNA
<213> ORGANISM: Artificial Sequence
<220> FEATURE:
<223> OTHER INFORMATION: Synthesized Sequence

<400> SEQUENCE: 1282
gaattccccc cgggccc                                                    17

<210> SEQ ID NO 1283
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1283
cagccaggag caagctccct ccactaaac                                       29

<210> SEQ ID NO 1284
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1284
cagccaggag gcaagctccc tccactaaac                                      30

<210> SEQ ID NO 1285
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 1285
aagctccctc cactaaac                                                   18

<210> SEQ ID NO 1286
<211> LENGTH: 8
<212> TYPE: DNA
<213> ORGANISM: Artificial Sequence
<220> FEATURE:
<223> OTHER INFORMATION: Synthesized Sequence

<400> SEQUENCE: 1286 cactaaac                                                              8

<210> SEQ ID NO 1287
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 1287
```
cagctccctc cactaaac                                                    18

<210> SEQ ID NO 1288
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 1288
cagcaagctc cctccactaa ac                                               22

<210> SEQ ID NO 1289
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 1289
cggtgggtgg ggggagtttg ccccaggcca                                       30

<210> SEQ ID NO 1290
<211> LENGTH: 4
<212> TYPE: DNA
<213> ORGANISM: Artificial Sequence
<220> FEATURE:
<223> OTHER INFORMATION: Synthesized Sequence

<400> SEQUENCE: 1290 acga                                                                    4

<210> SEQ ID NO 1291
<211> LENGTH: 14
<212> TYPE: DNA
<213> ORGANISM: Artificial Sequence
<220> FEATURE:
<223> OTHER INFORMATION: Synthesized Sequence

<400> SEQUENCE: 1291
cggtgggtgg ggga                                                        14

<210> SEQ ID NO 1292
<211> LENGTH: 6
<212> TYPE: DNA
<213> ORGANISM: Artificial Sequence
<220> FEATURE:
<223> OTHER INFORMATION: Synthesized Sequence

<400> SEQUENCE: 1292 aggcca                                                                  6

<210> SEQ ID NO 1293
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1293
cggtgggtgg ggggagtttg cca                                              23

<210> SEQ ID NO 1294
<211> LENGTH: 11
<212> TYPE: DNA

```
<213> ORGANISM: Artificial Sequence
<220> FEATURE:
<223> OTHER INFORMATION: Synthesized Sequence

<400> SEQUENCE: 1294
cggtgggtgc c                                                              11

<210> SEQ ID NO 1295
<211> LENGTH: 23
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (21)..(21)
<223> OTHER INFORMATION: n is a, c, g, or t

<400> SEQUENCE: 1295
cttgccccac agggcagtaa ngg                                                 23

<210> SEQ ID NO 1296
<211> LENGTH: 23
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (21)..(21)
<223> OTHER INFORMATION: n is a, c, g, or t

<400> SEQUENCE: 1296
cttgccccac agggcagtaa ngg                                                 23

<210> SEQ ID NO 1297
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 1297 gttacccca gggaagtata gg                                                   22

<210> SEQ ID NO 1298
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1298
cttgccccac agggcagtaa cgg                                                 23

<210> SEQ ID NO 1299
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 1299
cgtgccccac agggagtgag gg                                                  22

<210> SEQ ID NO 1300
<211> LENGTH: 23
```

```
<212> TYPE: DNA
<213> ORGANISM: Artificial Sequence
<220> FEATURE:
<223> OTHER INFORMATION: Synthesized Sequence

<400> SEQUENCE: 1300
cttgccccac agggcagtaa cgg                                           23

<210> SEQ ID NO 1301
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 1301
tgtgccccac aggcagtaga tg                                            22

<210> SEQ ID NO 1302
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1302
cttgccccac agggcagtaa cgg                                           23

<210> SEQ ID NO 1303
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 1303
cttccccaat atccagtagg g                                             21

<210> SEQ ID NO 1304
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1304
cttgccccac agggcagtaa cgg                                           23

<210> SEQ ID NO 1305
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1305
ggtatctaag tcattacctg tgg                                           23

<210> SEQ ID NO 1306
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1306
```

```
aatatgttag tcattacctg agg                                               23

<210> SEQ ID NO 1307
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1307
gtcatcttag tcattacctg agg                                               23

<210> SEQ ID NO 1308
<211> LENGTH: 25
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (2)..(23)
<223> OTHER INFORMATION: n is a, c, g, or t

<400> SEQUENCE: 1308
gnnnnnnnnn nnnnnnnnnn nnngg                                             25

<210> SEQ ID NO 1309
<211> LENGTH: 22
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (2)..(22)
<223> OTHER INFORMATION: n is a, c, g, or t

<400> SEQUENCE: 1309
gnnnnnnnnn nnnnnnnnnn nn                                                22

<210> SEQ ID NO 1310
<211> LENGTH: 25
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (2)..(23)
<223> OTHER INFORMATION: n is a, c, g, or t

<400> SEQUENCE: 1310
gnnnnnnnnn nnnnnnnnnn nnngg                                             25

<210> SEQ ID NO 1311
<211> LENGTH: 24
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (4)..(24)
<223> OTHER INFORMATION: n is a, c, g, or t

<400> SEQUENCE: 1311
gggnnnnnnn nnnnnnnnnn nnnn                                              24
```

```
<210> SEQ ID NO 1312
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1312
aagtcagagg agaagaagaa ggg                                                23

<210> SEQ ID NO 1313
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1313
gagcctgagc agaaggagaa ggg                                                23

<210> SEQ ID NO 1314
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1314
gaatccaagc agaagaagag aag                                                23

<210> SEQ ID NO 1315
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1315
gagtaggagc aggagaagaa gga                                                23

<210> SEQ ID NO 1316
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1316
gagtccggga aggagaagaa agg                                                23

<210> SEQ ID NO 1317
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1317
gagtctaagc aggagaataa agg                                                23

<210> SEQ ID NO 1318
<211> LENGTH: 23
<212> TYPE: DNA
<213> ORGANISM: Artificial Sequence
<220> FEATURE:
<223> OTHER INFORMATION: Synthesized Sequence
```

<400> SEQUENCE: 1318
aagtcccggc agaggaagaa ggg                                    23

<210> SEQ ID NO 1319
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1319
acgtctgagc agaagaagaa tgg                                    23

<210> SEQ ID NO 1320
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1320
gagccggagc agaagaagga ggg                                    23

<210> SEQ ID NO 1321
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1321
gagtcctagc aggagaagaa gag                                    23

<210> SEQ ID NO 1322
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1322
gaggccgagc agaagaaaga cgg                                    23

<210> SEQ ID NO 1323
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1323
gagtctaagc agaagaagaa gag                                    23

<210> SEQ ID NO 1324
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1324
gagttagagc agaagaagaa agg                                    23

<210> SEQ ID NO 1325
<211> LENGTH: 23

```
<212> TYPE: DNA
<213> ORGANISM: Artificial Sequence
<220> FEATURE:
<223> OTHER INFORMATION: Synthesized Sequence

<400> SEQUENCE: 1325
gagtccgagc agaagaagaa ggg                                          23

<210> SEQ ID NO 1326
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1326
agaccagact gagcaagaga ggg                                          23

<210> SEQ ID NO 1327
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1327
gacacagacc gggcacgtga ggg                                          23

<210> SEQ ID NO 1328
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1328
cacccagact gagcacgtgc tgg                                          23

<210> SEQ ID NO 1329
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1329
gagccagaat gagcacgtga ggg                                          23

<210> SEQ ID NO 1330
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1330
agctcagact gagcaagtga ggg                                          23

<210> SEQ ID NO 1331
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1331
```
ggctcagact gagcacctga gag                                              23

<210> SEQ ID NO 1332
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1332
ggcccagact gagcacgtga tgg                                              23

<210> SEQ ID NO 1333
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1333
ggtatctaag tcattacctg tgg                                              23

<210> SEQ ID NO 1334
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1334
aatatgttag tcattacctg agg                                              23

<210> SEQ ID NO 1335
<211> LENGTH: 23
<212> TYPE: DNA
<213> ORGANISM: Artificial Sequence
<220> FEATURE:
<223> OTHER INFORMATION: Synthesized Sequence

<400> SEQUENCE: 1335
gtcatcttag tcattacctg agg                                              23

<210> SEQ ID NO 1336
<211> LENGTH: 29
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (13)..(17)
<223> OTHER INFORMATION: n is a, c, g, or t

<400> SEQUENCE: 1336
gtcatcctca tcnnnnnaaa ctgcaaaag                                        29

<210> SEQ ID NO 1337
<211> LENGTH: 29
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (13)..(17)
<223> OTHER INFORMATION: n is a, c, g, or t

<400> SEQUENCE: 1337
cttttgcagt ttnnnnnaaa ctgcaaaag                                              29

<210> SEQ ID NO 1338
<211> LENGTH: 29
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (13)..(17)
<223> OTHER INFORMATION: n is a, c, g, or t

<400> SEQUENCE: 1338
gtcatcctca tcnnnnngat gaggatgac                                              29

<210> SEQ ID NO 1339
<211> LENGTH: 29
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (13)..(17)
<223> OTHER INFORMATION: n is a, c, g, or t

<400> SEQUENCE: 1339
gtcatcctca tcnnnnngat gaggatgac                                              29

<210> SEQ ID NO 1340
<211> LENGTH: 29
<212> TYPE: DNA
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (13)..(17)
<223> OTHER INFORMATION: n is a, c, g, or t

<400> SEQUENCE: 1340
gtcatcctca tcnnnnnaaa ctgcaaaag                                              29

<210> SEQ ID NO 1341
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1341
tctcaactct tctctatgaa ctgtaaaag                                              29

<210> SEQ ID NO 1342
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1342
taaatactct gtgcactaaa ctggaaaag                                              29

<210> SEQ ID NO 1343
<211> LENGTH: 29
<212> TYPE: DNA

```
<213> ORGANISM: Artificial Sequence
<220> FEATURE:
<223> OTHER INFORMATION: Synthesized Sequence

<400> SEQUENCE: 1343
agaggcctcc tctctttaaa ctgtaacag                              29

<210> SEQ ID NO 1344
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1344 ttcccctca gtaaaataaa ctggaaaag                               29

<210> SEQ ID NO 1345
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1345
ggcctcctca tctctttaaa ctggaaatg                              29

<210> SEQ ID NO 1346
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1346
gccagcctca gcttcttcaa ctggaaaag                              29

<210> SEQ ID NO 1347
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1347
tgagacctca tctcttaaaa ctgtaatag                              29

<210> SEQ ID NO 1348
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1348
aatatacaca tcatgacaaa ctggaaaag                              29

<210> SEQ ID NO 1349
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1349
ctcttactct acatgttaaa ctgaaaaag                              29
```

<210> SEQ ID NO 1350
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1350
tgtgtcctca ttattataaa caggaatta                              29

<210> SEQ ID NO 1351
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1351
gtcgtcctca tcttaataaa ctgcaaaaa                              29

<210> SEQ ID NO 1352
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1352
caattactca tcattttaaa ctgtgagaa                              29

<210> SEQ ID NO 1353
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1353
gggggcctca acataataaa caggaaaag                              29

<210> SEQ ID NO 1354
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1354
ggagaactgc aacaactaaa ctgtaaaag                              29

<210> SEQ ID NO 1355
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 1355
gaaacagaat tgtgtcatga agaaaaaag                              29

<210> SEQ ID NO 1356
<211> LENGTH: 29
<212> TYPE: DNA
<213> ORGANISM: Artificial Sequence
<220> FEATURE:

```
<223> OTHER INFORMATION: Synthesized Sequence

<400> SEQUENCE: 1356
gtcatcctca tcctgataaa ctgcaaaag                                        29
```